(12) United States Patent
Lee et al.

(10) Patent No.: US 11,917,914 B1
(45) Date of Patent: Feb. 27, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Yun Suk Lee, Cheonan-si (KR); Hyun Ju Song, Cheonan-si (KR); Junggeun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/355,252

(22) Filed: Jul. 19, 2023

Related U.S. Application Data

(63) Continuation of application No. 18/180,625, filed on Mar. 8, 2023, which is a continuation-in-part of
(Continued)

(30) Foreign Application Priority Data

Oct. 26, 2020 (KR) ........................ 10-2020-0139441

(51) Int. Cl.
*H10K 85/60* (2023.01)
*C07D 251/24* (2006.01)
(Continued)

(52) U.S. Cl.
CPC ....... *H10K 85/6574* (2023.02); *C07D 251/24* (2013.01); *C09K 11/06* (2013.01); *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(58) Field of Classification Search
CPC .. C07D 251/24; C07D 307/91; C07D 333/76; H10K 85/654; H10K 85/6574; H10K 85/6576
See application file for complete search history.

(56) References Cited

U.S. PATENT DOCUMENTS

2014/0367654 A1    12/2014   Kim et al.
2015/0303379 A1    10/2015   Lee et al.
(Continued)

FOREIGN PATENT DOCUMENTS

KR    10-2009-0079134 A      7/2009
KR    20150131998 A   *   11/2015   .......... C07D 401/14
(Continued)

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound capable of improving the light-emitting efficiency, stability, and lifespan of an element; an organic electronic element using same; and an electronic device thereof.

13 Claims, 2 Drawing Sheets

Related U.S. Application Data application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.

| | |
|---|---|
| *C09K 11/06* | (2006.01) |
| *H10K 50/11* | (2023.01) |
| *H10K 50/15* | (2023.01) |
| *H10K 50/16* | (2023.01) |
| *H10K 50/18* | (2023.01) |
| *H10K 101/10* | (2023.01) |
| *H10K 101/00* | (2023.01) |

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

FOREIGN PATENT DOCUMENTS

| | | | | |
|---|---|---|---|---|
| KR | 10-2016-0111780 A | | 9/2016 | |
| KR | 20180014985 A | * | 2/2018 | ............ C07D 251/24 |
| KR | 20160111780 A | * | 9/2018 | ............. C09K 11/06 |
| WO | 2017/171420 A1 | | 10/2017 | |
| WO | WO-2017171420 A1 | * | 10/2017 | ........... C07D 251/24 |
| WO | 2019/124902 A1 | | 6/2019 | |

\* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic device has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula 3. Formula 3

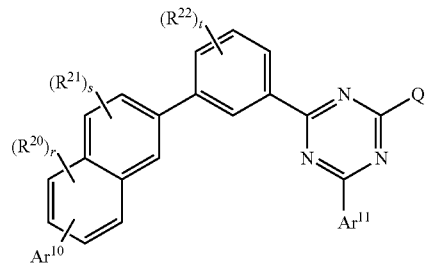

In another aspect, the present invention provides an organic electronic element comprising the compound represented by Formula 3 and an electronic device thereof.

Effects of the Invention

By using the compound according to the present invention, high luminous efficiency, low driving voltage and high heat resistance of the element can be achieved, and color purity and lifespan of the element can be greatly improved.

Figure 1:
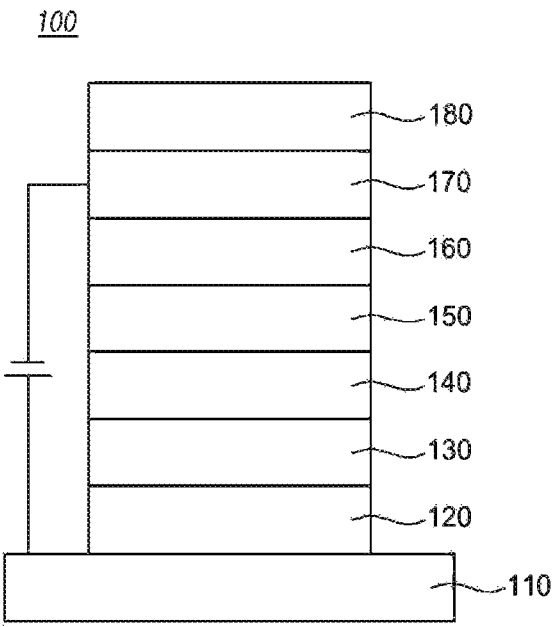
FIG. 1 to FIG. 3 are exemplary views of an organic electroluminescent device according to the present invention.

100, 200, 300: organic electronic element 110: the first electrode
120: hole injection layer 130: hole transport layer
140: emitting layer 150: electron transport layer
160: electron injection layer 170: second electrode
180: light efficiency enhancing Layer 210: buffer layer
220: emitting auxiliary layer 320: first hole injection layer
330: first hole transport layer 340: first emitting layer
350: first electron transport layer 360: first charge generation layer
361: second charge generation layer 420: second hole injection layer
430: second hole transport layer 440: second emitting layer
450: second electron transport layer CGL: charge generation layer
ST1: first stack ST2: second stack

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group.

For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

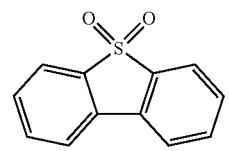 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group"

means that at least one of the substituents R, R', R" is a substituent other than hydrogen, and include those in which R and R' are bonded to each other to form a spiro compound together with the carbon to which they are bonded.

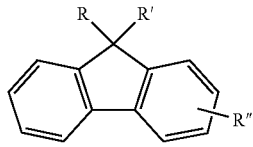

The term "Spiro compound", as used herein, has a 'Spiro union', and a spiro union means a connection in which two rings share only one atom. At this time, atoms shared in the two rings are called 'spiro atoms', and these compounds are called 'monospiro-', 'di-spiro-' and 'tri-spiro', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

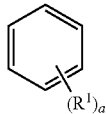

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

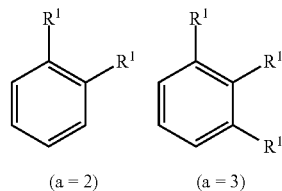

Hereinafter, a compound according to an aspect of the present invention and an organic electronic element comprising the same will be described.

The present invention provides a compound represented by Formula 2.

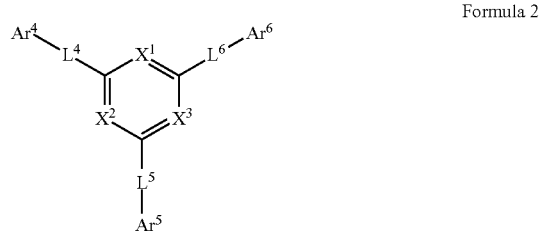

Formula 2

In Formula 2, each symbol may be defined as follows.

X1, X2 and X3 are each independently CR or N, provided that at least one of X1, X2 and X3 are N, L4, L5 and L6 are each independently selected from the group consisting of a single bond; a $C_6$-$C_{60}$ arylene group; fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; $C_1$-$C_{50}$ alkylene group; $C_2$-$C_{20}$ alkenylene group; and a $C_2$-$C_{20}$ alkynylene group;

When $L^4$, $L^5$ and $L^6$ are an arylene group, it may be preferably a $C_6$-$C_{30}$ arylene group, more preferably a $C_6$-$C_{24}$ arylene group, for example, phenylene, biphenyl, naphthalene, terphenyl, etc., When $L^4$, $L^5$ and $L^6$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $L^4$, $L^5$ and $L^6$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, When $L^4$, $L^5$ and $L^6$ are an alkylene group, it may be preferably a C1-C30 alkylene group, more preferably a $C_1$-$C_{24}$ alkylene group, $Ar^4$, $Ar^5$ and $Ar^6$ are each independently selected from the group consisting of a $C_6$-$C_{60}$ aryl group; a $C_2$-$C_{60}$ heterocyclic group including at least one heteroatom of O, N, S, Si or P; fluorenyl group; a fused ring group of a $C_6$-$C_{60}$ aromatic ring and a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ arylthio group; a $C_6$-$C_{30}$ aryloxy group; and however, at least one of $Ar^4$, $Ar^5$ and $Ar^6$ is a substituted or unsubstituted naphthyl group.

When $Ar^4$, $Ar^5$ and $Ar^6$ are an aryl group, it may be preferably a $C_6$-$C_{30}$ aryl group, and more preferably a $C_6$-$C_{24}$ aryl group, for example, it may be phenylene, biphenyl, naphthalene, terphenyl, etc, When $Ar^4$, $Ar^5$ and $Ar^6$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $Ar^4$, $Ar^5$ and $Ar^6$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $Ar^4$, $Ar^5$ and $Ar^6$ are an alkyl group, it may be preferably a $C_1$-$C_{30}$ alkyl group, and more preferably a $C_1$-$C_{24}$ alkyl group.

When $Ar^4$, $Ar^5$ and $Ar^6$ are alkoxyl groups, they may be preferably $C_1$~$C_{24}$ alkoxyl groups.

When $Ar^4$, $Ar^5$ and $Ar^6$ are an arylthio group, it may be preferably a $C_6$-$C_{24}$ arylthio group.

When $Ar^4$, $Ar^5$ and $Ar^6$ are an aryloxy group, it may be preferably a $C_6$~$C_{24}$ aryloxy group, wherein the aryl group, arylene group, heterocyclic group, fluorenyl group, fluorenylene group, fused ring group, alkyl group, alkenyl group, alkoxy group, aryloxy group and arylthio group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the present invention provides a compound wherein $L^4$, $L^5$ or $L^6$ is represented by any one of the following Formulas b-1 to b-16.

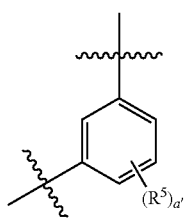

Formula b-1

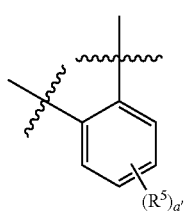

Formula b-2

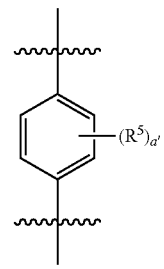

Formula b-3

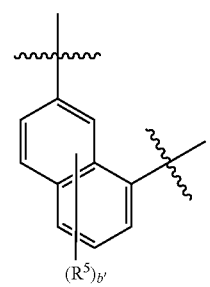

Formula b-4

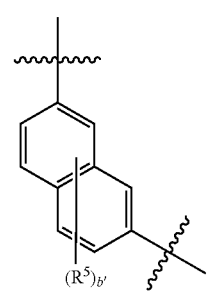

Formula b-5

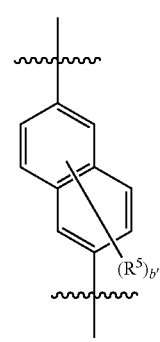

formula b-6

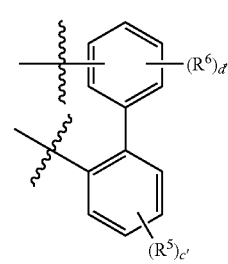

formula b-7

-continued formula b-8

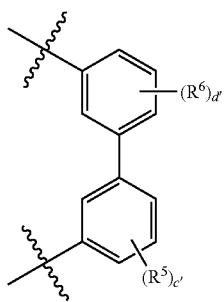

formula b-9

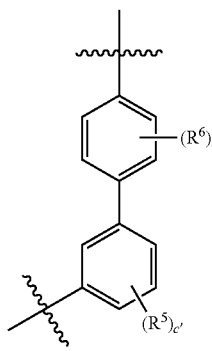

formula b-10

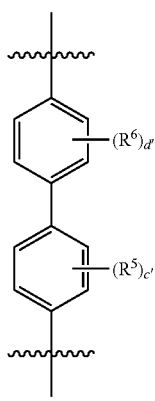

Formula b-11

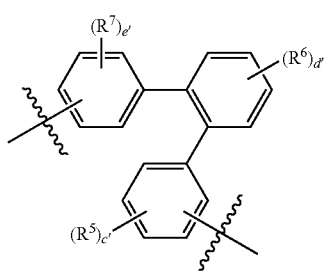

Formula b-12

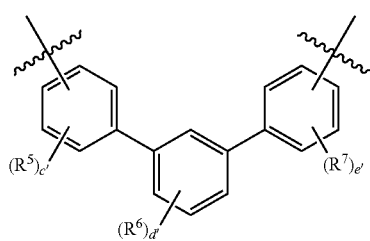

-continued

Formula b-13

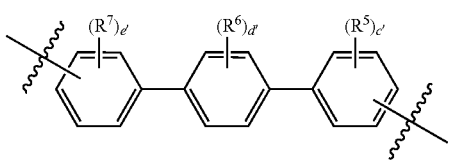

Formula b-14

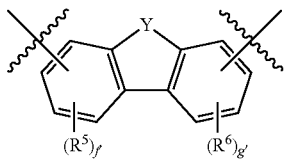

Formula b-15

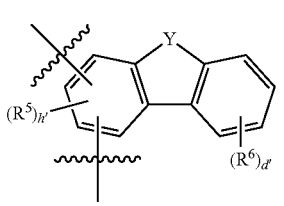

Formula b-16

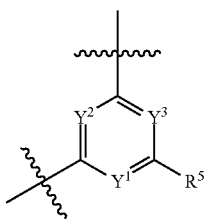

In Formula (b-1) to Formula (b-16), each symbol may be defined as follows.

1) Y is $N-L^8-Ar^7$, O, S or CR'R";
2) $L^8$ is the same as the definition of $L^4$ in Formula 2,
3) $Ar^7$ is the same as the definition of Art in Formula 2,
4) R' and R" are each independently selected from the group consisting of a hydrogen; a $C_6-C_{60}$ aryl group; fluorenyl group; a $C_2-C_{60}$ heterocyclic group including at least one heteroatom of O, N, S, Si or F; a fused ring group of a $C_3-C_{60}$ aliphatic ring and a $C_6-C_{60}$ aromatic ring; a $C_1-C_{50}$ alkyl group; a $C_2-C_{20}$ alkenyl group; a $C_2-C_{20}$ alkynyl group; a $C_1-C_{30}$ alkoxyl group; a $C_6-C_{30}$ aryloxy group; and $-L'-N(R^a)(R^b)$, or may be bonded to each other to form a ring.

When R' and R" are an aryl group, it may be preferably a $C_6-C_{30}$ aryl group, and more preferably a $C_6-C_{24}$ aryl group, for example, it may be phenylene, biphenyl, naphthalene, terphenyl, etc, When R' and R" are a heterocyclic group, it may be preferably a $C_2-C_{30}$ heterocyclic group, and more preferably a $C_2-C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When R' and R" are a fused ring group, it may be preferably a fused ring group of a $C_3-C_{30}$ aliphatic ring and a $C_6-C_{30}$ aromatic ring, more preferably a fused ring group of a $C_3-C_{24}$ aliphatic ring and a $C_6-C_{24}$ aromatic ring.

When R' and R" are an alkyl group, it may be preferably a $C_1-C_{30}$ alkyl group, and more preferably a $C_1-C_{24}$ alkyl group.

When R' and R" are alkoxyl groups, they may be preferably $C_1$~$C_{24}$ alkoxyl groups.

When R' and R" are an aryloxy group, it may be preferably a $C_6$~$C_{24}$ aryloxy group, 5) a', c', d' and e' are each independently integers from 0 to 4, b' is an integer from 0 to 6, f' and g' are independently integers from 0 to 3, and h' is an integer from 0 to 2.

6) $R^5$, $R^6$ and $R^7$ are each independently selected from the group consisting of hydrogen; deuterium; tritium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -$L^a$-N($R^c$)($R^d$), or in case a', b', c', d', e' f' g' and h' are 2 or more, $R^5$, $R^6$ and $R^7$ are each in plural being the same or different, and a plurality of $R^5$ or a plurality of $R^6$ or a plurality of $R^7$, alternatively, adjacent $R^5$ and $R^6$ or $R^6$ and $R^7$ may be bonded to each other to form an aromatic ring or a heteroaromatic ring.

Wherein $R^5$, $R^6$ and $R^7$ are an aryl group, it may be preferably a $C_6$-$C_{30}$ aryl group, and more preferably a $C_6$-$C_{24}$ aryl group, for example, it may be phenylene, biphenyl, naphthalene, terphenyl, etc, When $R^5$, $R^6$ and $R^7$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $R^5$, $R^6$ and $R^7$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^5$, $R^6$ and $R^7$ are an alkyl group, it may be preferably a $C_1$-$C_{30}$ alkyl group, and more preferably a $C_1$-$C_{24}$ alkyl group.

When $R^5$, $R^6$ and $R^7$ are alkoxyl groups, they may be preferably $C_1$~$C_{24}$ alkoxyl groups.

When $R^5$, $R^6$ and $R^7$ are an aryloxy group, it may be preferably a $C_6$~$C_{24}$ aryloxy group, 7) L' and $L^a$ are the same as the definition of $L^4$ in Formula 2, 8) $R^a$, $R^b$, $R^c$ and $R^d$ are each independently selected from the group consisting of a $C_6$-$C_{60}$ aryl group; fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

Wherein $R^a$, $R^b$, $R^c$ and $R^d$ are an aryl group, it may be preferably a $C_6$-$C_{30}$ aryl group, and more preferably a $C_6$-$C_{24}$ aryl group, for example, it may be phenylene, biphenyl, naphthalene, terphenyl, etc, When $R^a$, $R^b$, $R^c$ and $R^d$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^a$, $R^b$, Rand $R^d$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., 9) $Y^1$, $Y^2$ and $Y^3$ are independently $CR^e$ or N, provided that at least one of $Y^1$, $Y^2$ and $Y^3$ is N, 10) $R^e$ is selected from the group consisting of hydrogen; deuterium; tritium; halogen; cyano group; nitro group; a $C_6$-$C_{60}$ aryl group; fluorenyl group; a $C_2$-$C_{60}$ heterocyclic group including at least one heteroatom of O, N, S, Si or a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group;

In case $R^e$ is an aryl group, it may be preferably a $C_6$-$C_{30}$ aryl group, and more preferably a $C_6$-$C_{24}$ aryl group, for example, it may be phenylene, biphenyl, naphthalene, terphenyl, etc, In case $R^e$ is an a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., In case $R^e$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

In case $R^e$ is an alkyl group, it may be preferably a $C_1$-$C_{30}$ alkyl group, and more preferably a $C_1$-$C_{24}$ alkyl group.

When $R^e$ is an alkoxyl group, it may be preferably $C_1$-$C_{24}$ alkoxyl group.

When $R^e$ is an aryloxy group, it may be preferably a $C_6$-$C_{24}$ aryloxy group, 11) Adjacent $R^5$ and $R^e$ may be bonded to each other to form an aromatic ring or a heteroaromatic ring, 12) ~~~ indicates the position to be bonded.

Also, at least one of $Ar^4$ to $Ar^6$ in Formula 2 is represented by any one of Formula c-1 to Formula c-6.

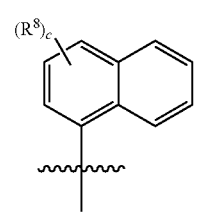

Formula c-1

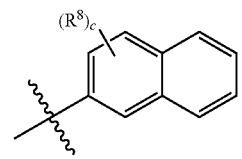

Formula c-2

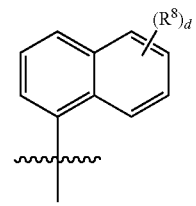

Formula c-3

-continued

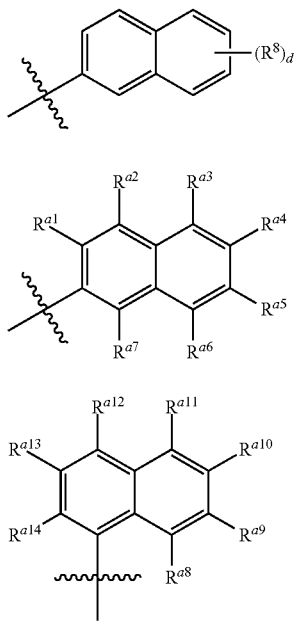

Formula c-4

Formula c-5

Formula c-6

Wherein,

1) $R^8$ and $R^{a1}$, $R^{a2}$, $R^{a3}$, $R^{a4}$, $R^{a5}$, $R^{a6}$, $R^{a7}$, $R^{a8}$, $R^{a9}$, $R^{a10}$, $R^{a11}$, $R^{a12}$, $R^{a13}$, $R^{a14}$ are each independently selected from the group consisting of a hydrogen; a $C_1$-$C_{20}$ alkyl group; a $C_6$-$C_{20}$ aryl group; a $C_6$-$C_{20}$ aryl group substituted by deuterium; fluorenyl group; and a $C_2$-$C_{20}$ heterocyclic group;

2) c is an integer from 0 to 3, d is an integer from 0 to 4.

Also, the compound represented by Formula 2 is represented by any of the following Formulas 2-1 to 2-4.

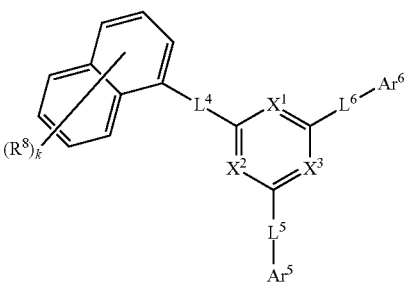

Formula 2-1

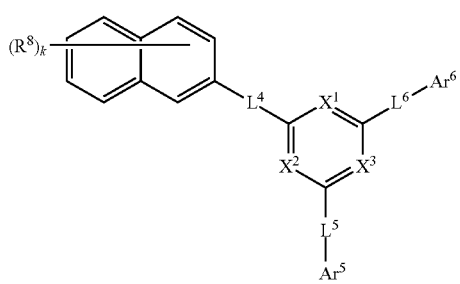

Formula 2-2

-continued

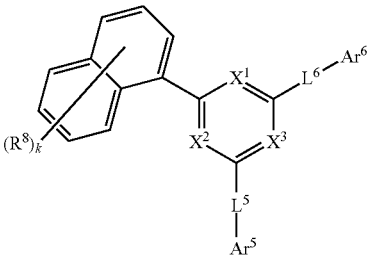

Formula 2-3

Formula 2-4

Wherein,

1) $Ar^5$, $Ar^6$, $X^1$, $X^2$, $X^3$, $L^4$, $L^5$ and $L^6$ are the same as defined in Formula 2, 2) $R^8$ is each independently selected from the group consisting of a hydrogen; a $C_1$-$C_{20}$ alkyl group; a $C_6$-$C_{20}$ aryl group; a $C_6$-$C_{20}$ aryl group substituted by deuterium; fluorenyl group; a $C_2$-$C_{20}$ heterocyclic group;

3) k is an integer of 0 to 7.

Also, the compound represented by Formula 2 is represented by any one of Formulas 2-5 to 2-8.

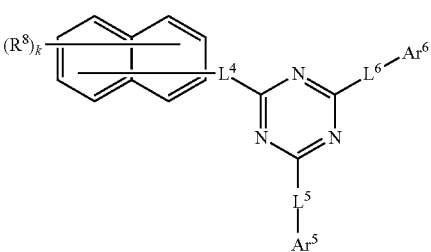

Formula 2-5

Formula 2-6

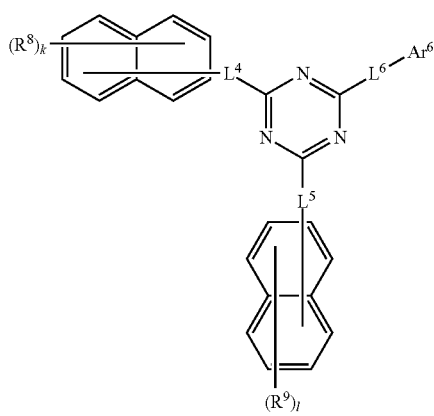

Formula 2-7

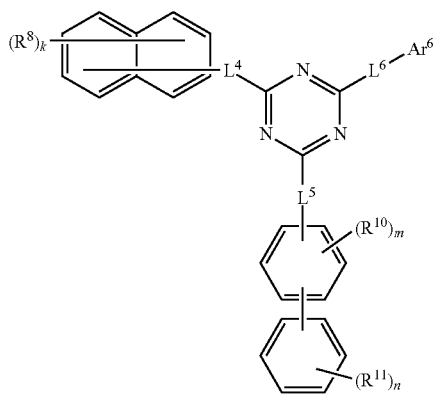

Formula 2-8

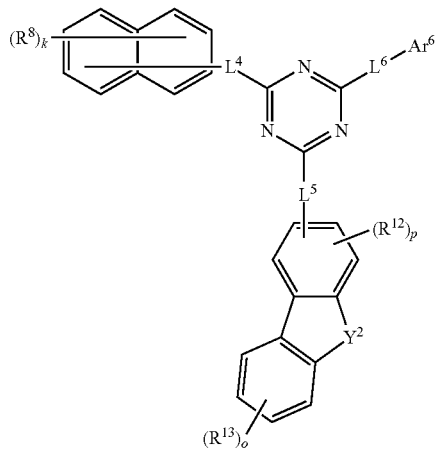

Wherein,
1) $Ar^5$, $Ar^6$, $L^4$, $L^5$ and $L^6$ are the are the same as defined in Formula 2,
2) $R^8$ is each independently selected from the group consisting of a hydrogen; a $C_1$-$C_{20}$ alkyl group; a $C_6$-$C_{20}$ aryl group; a $C_6$-$C_{29}$ aryl group substituted by deuterium; fluorenyl group; a $C_2$-$C_{29}$ heterocyclic group;
3) $R^9$, $R^{10}$, $R^{11}$, $R^{12}$ and $R^{13}$ are the same as the definition of R',
4) $Y^2$ is $CR^{14}R^{15}$, N—$Ar^7$, O or S,
5) $R^{14}$ and $R^{15}$ are the same as the definition of R',
6) $Ar^7$ is the same as the definition of $Ar^4$ in Formula 2,
7) k and l are each independently an integer of 0 to 7, m and o are each independently an integer of 0 to 4, n is an integer of 0 to 5, p is an integer of 0 to 3.

Specifically, the compound represented by Formula 2 may be any one of the following compounds.

N-1

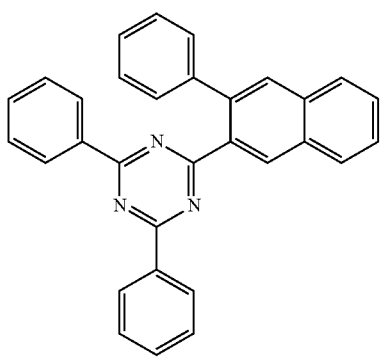

N-2

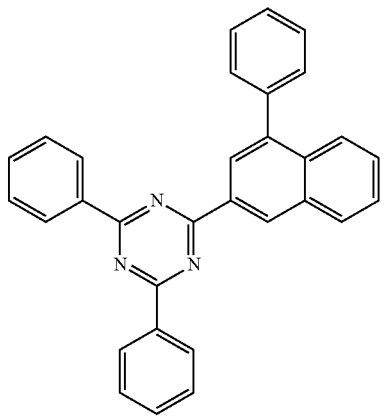

-continued
N-3
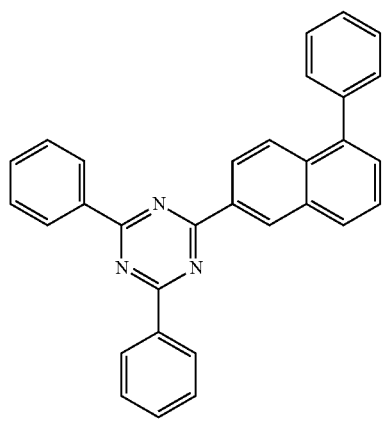
N-4
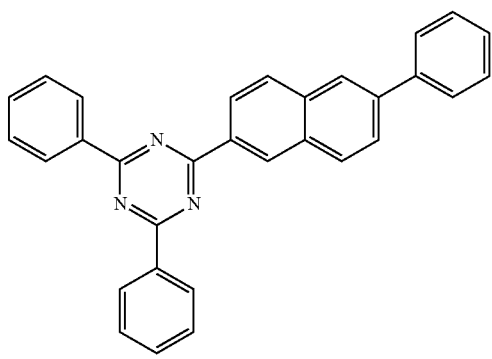
N-5
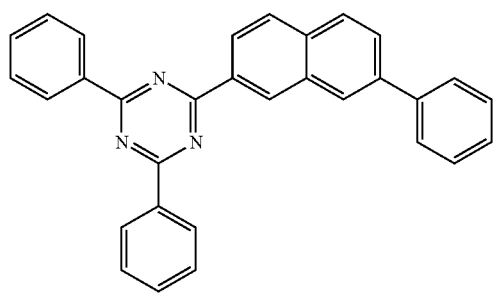
N-6
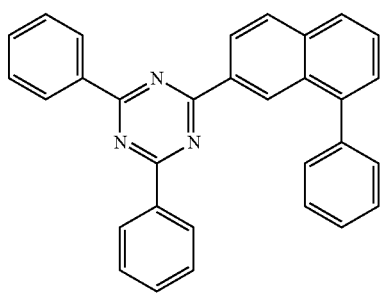
N-7
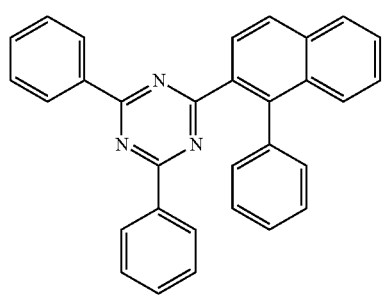
N-8
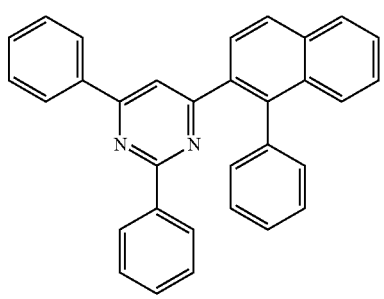
N-9
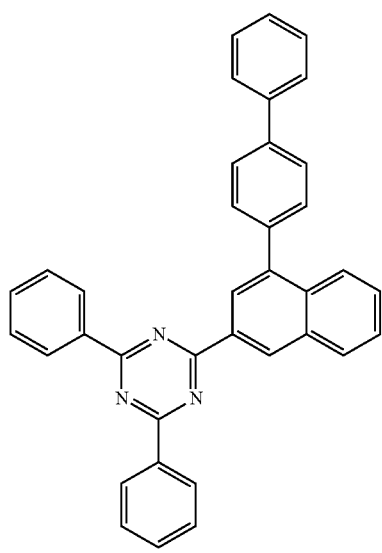
N-10
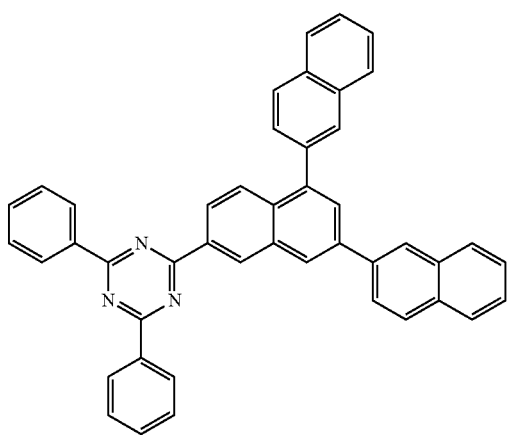

-continued
N-11
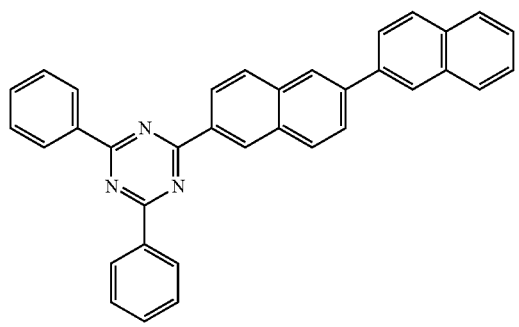
N-12
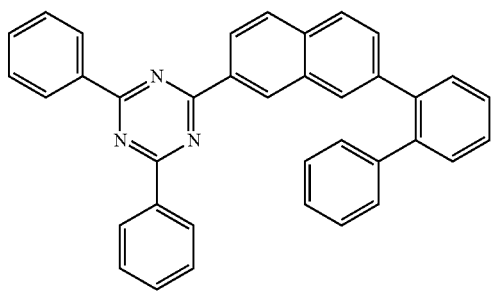
N-13
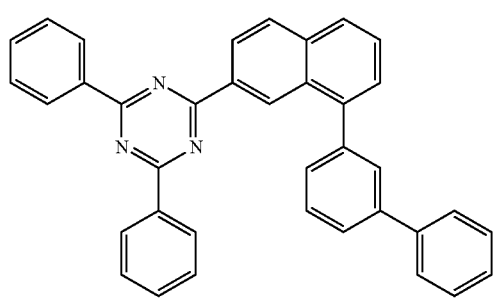
N-14
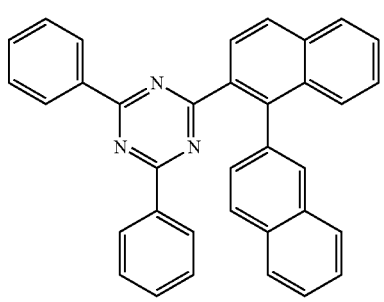
N-15
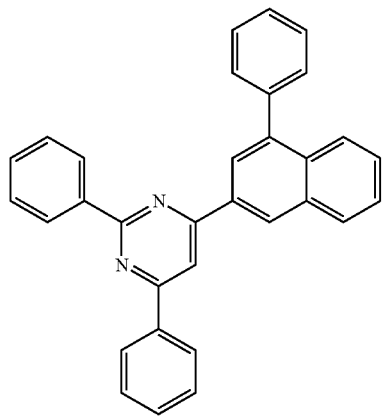
N-16
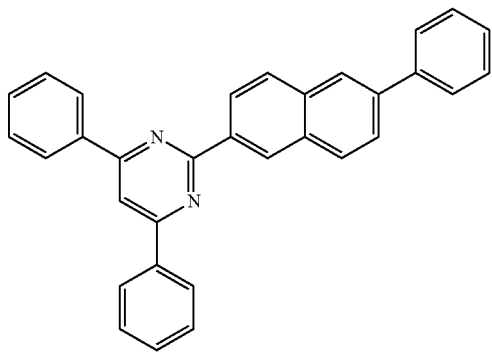
N-17
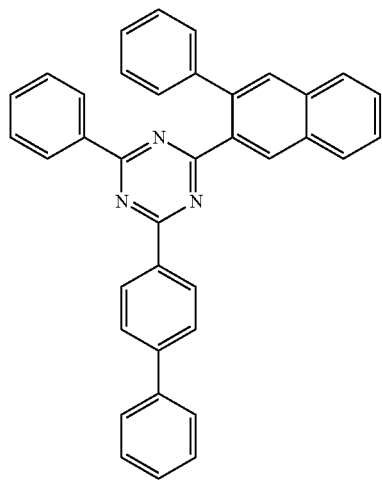
N-18
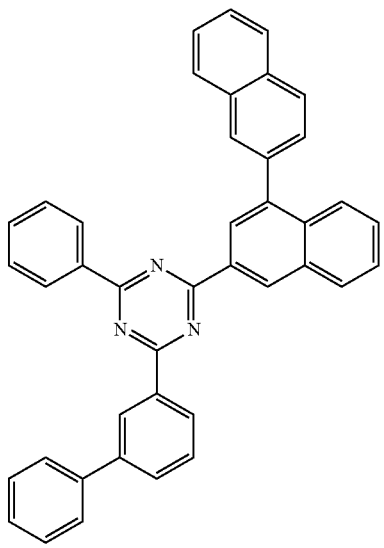

-continued
N-19
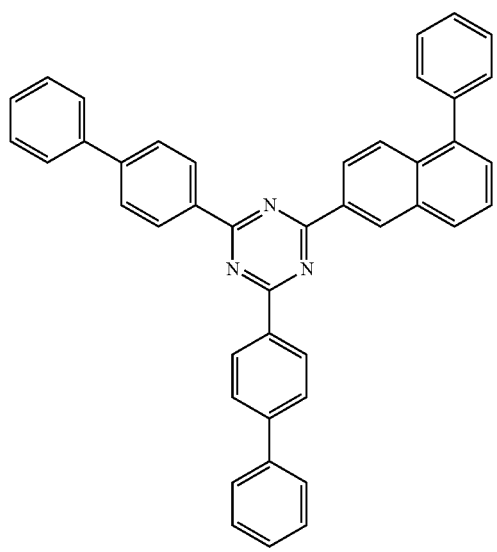
N-20
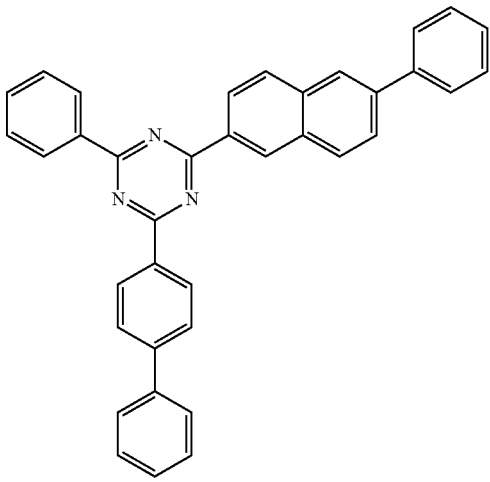
N-21
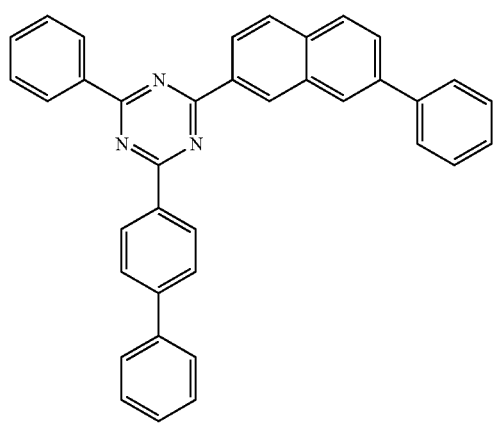
N-22
N-23
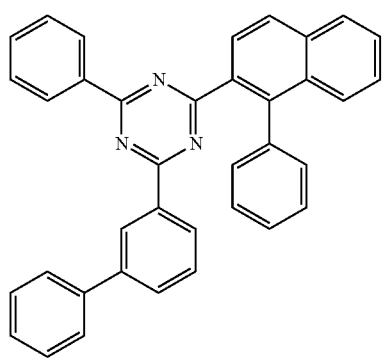
N-24
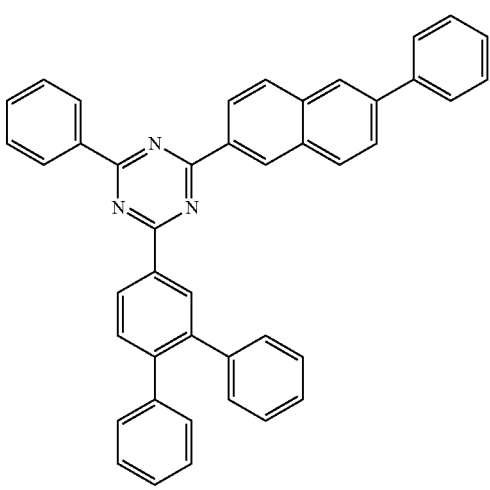

N-25 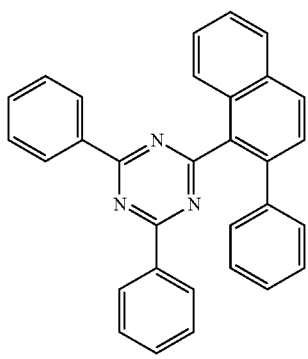
N-26 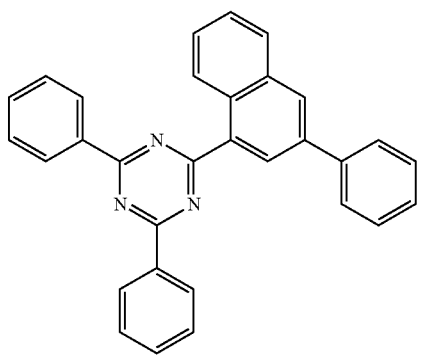
N-27 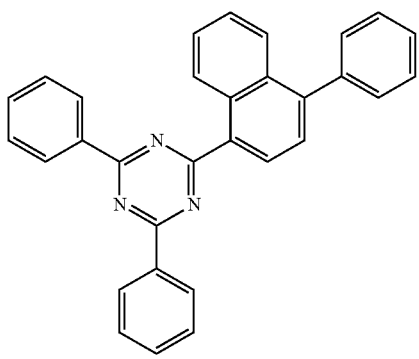
N-28 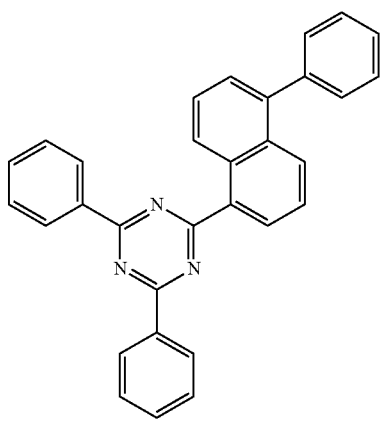
N-29 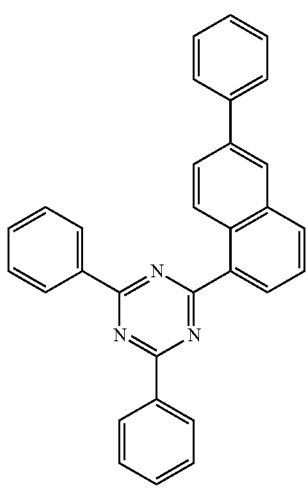
N-30 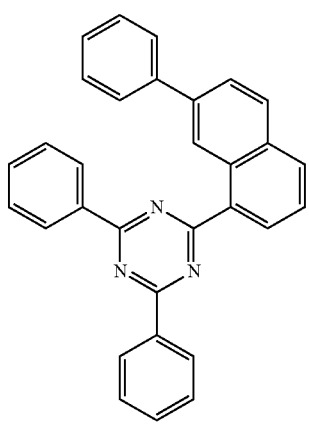
N-31 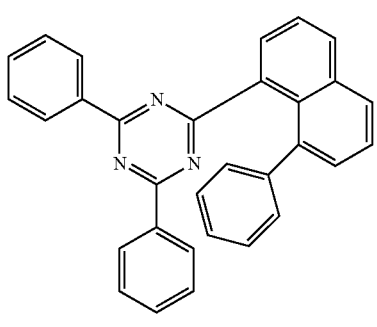
N-32 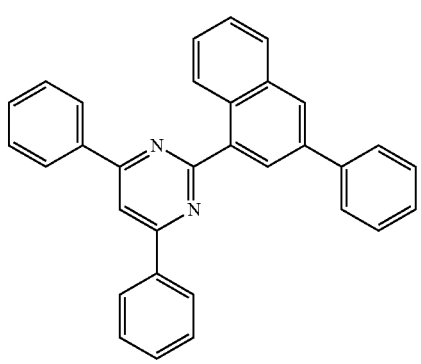

-continued
N-33
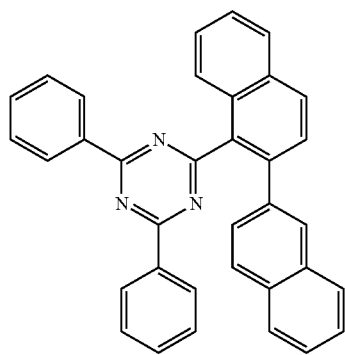
N-34
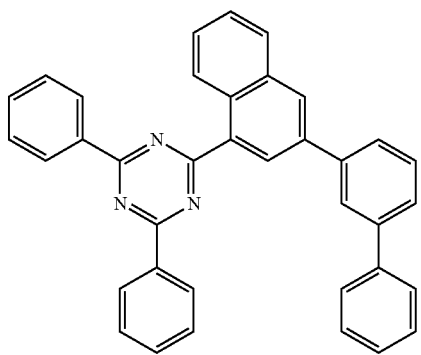
N-35
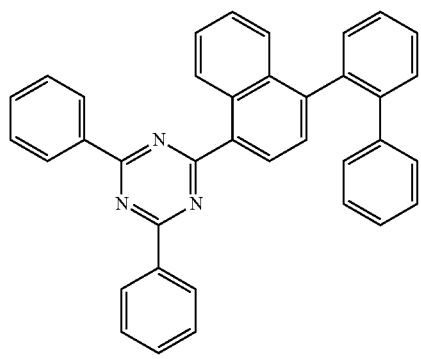
N-36
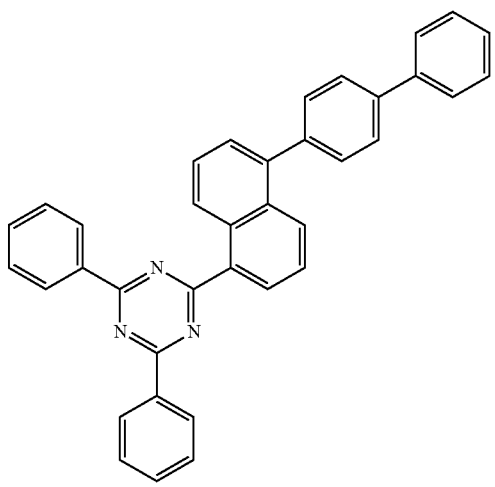
N-37
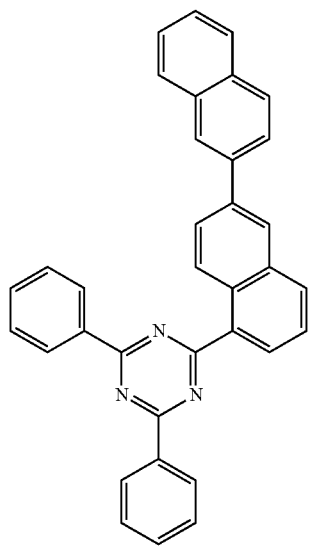
N-38
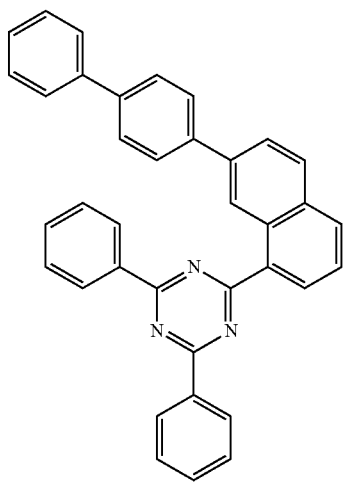

-continued
N-39
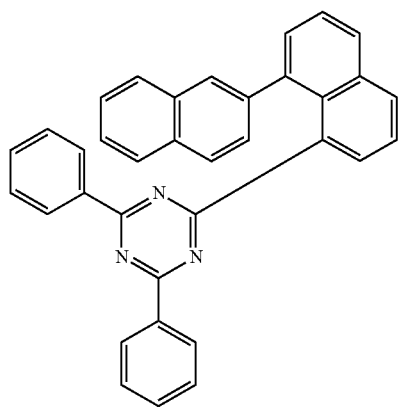
N-40
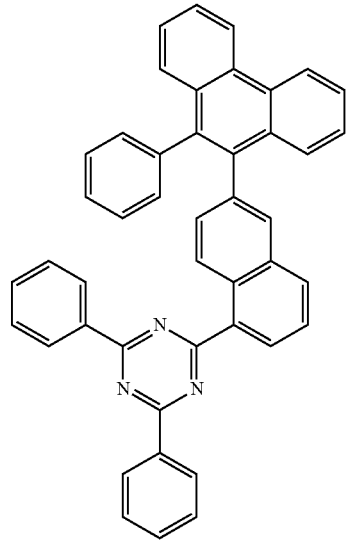
N-41
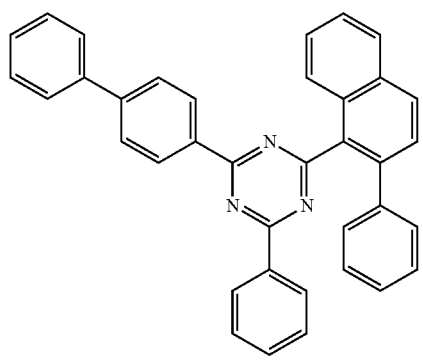
N-42
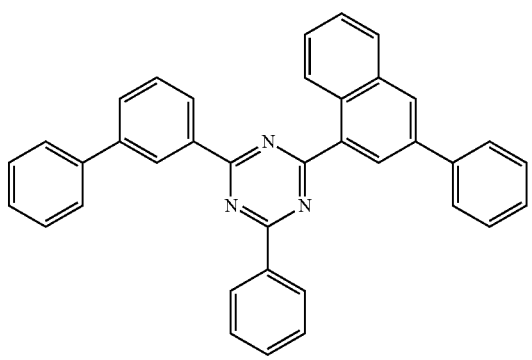
N-43
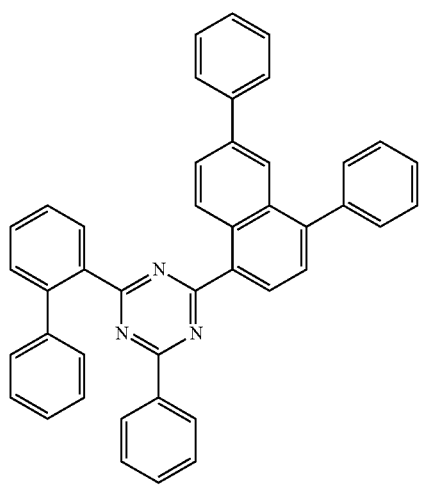
N-44
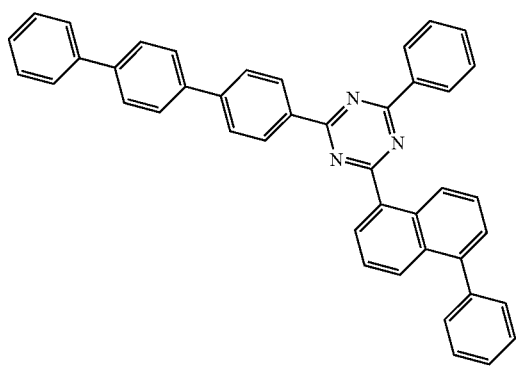

-continued
N-45
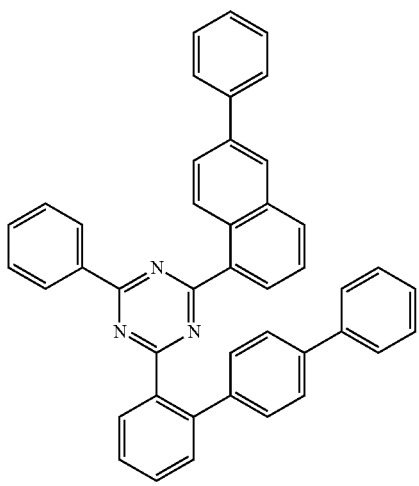
N-46
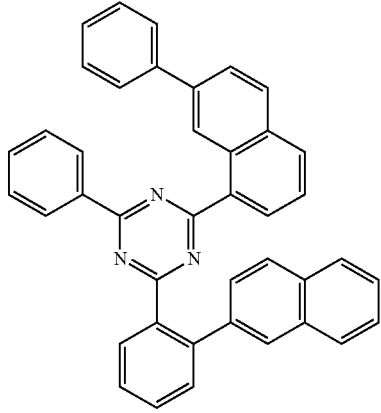
N-47
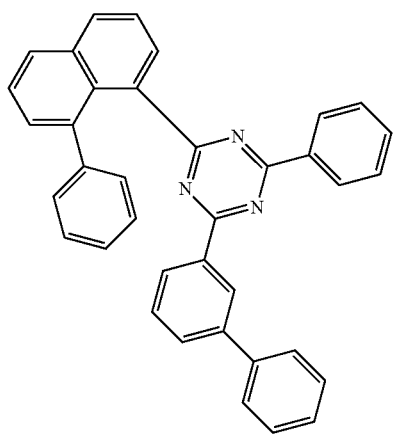
N-48
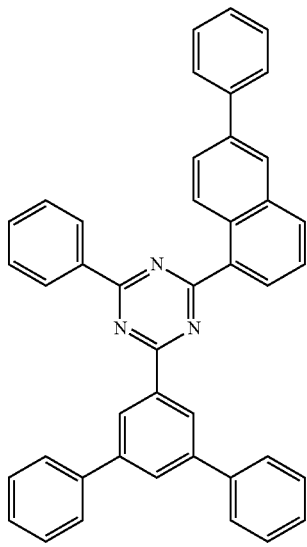
N-49
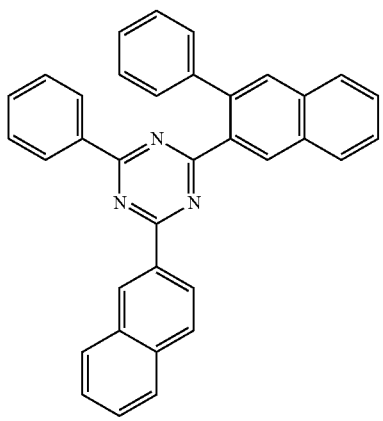
N-50
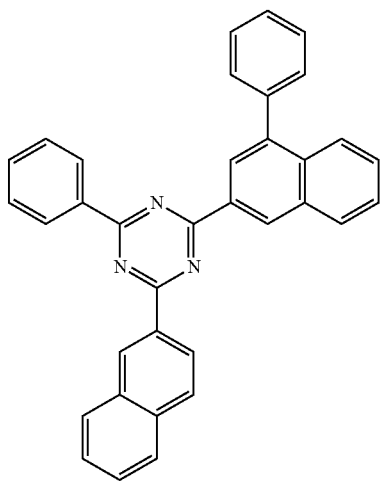

-continued
N-51
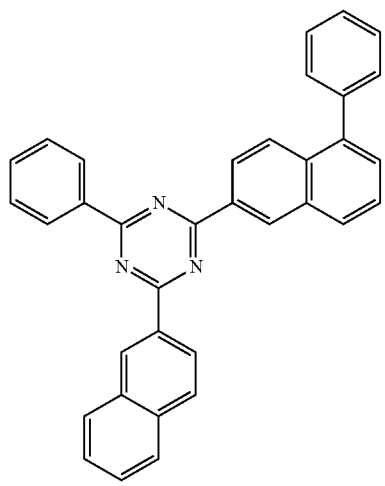
N-52
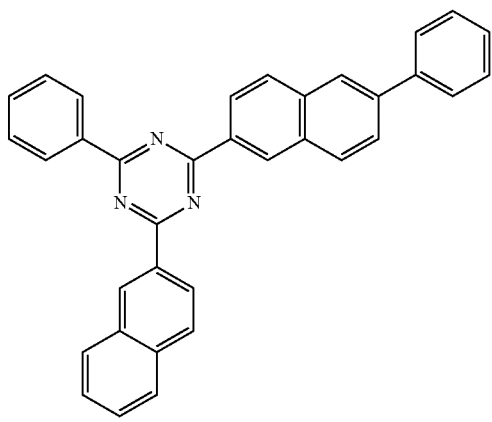
N-53
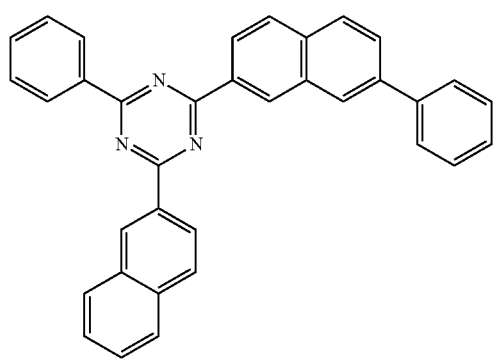
N-54
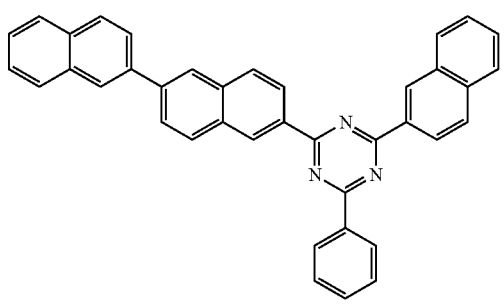
N-55
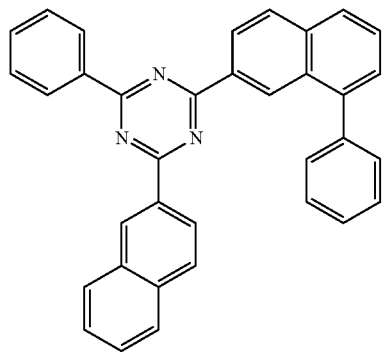
N-56
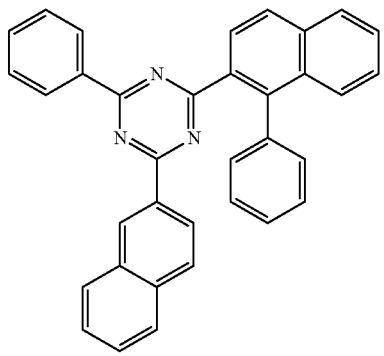
N-57
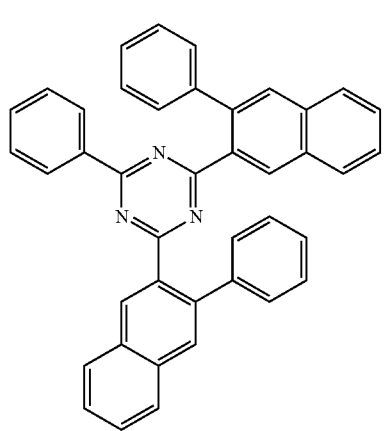
N-58
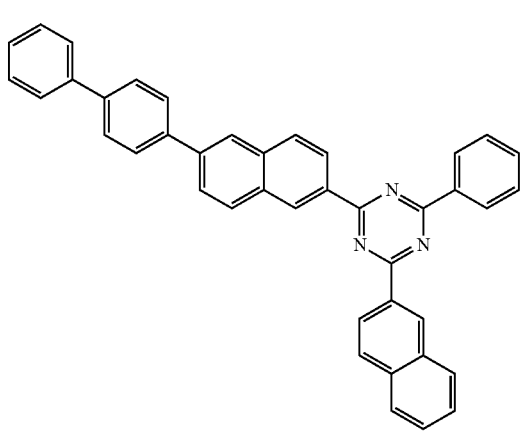

-continued
N-59
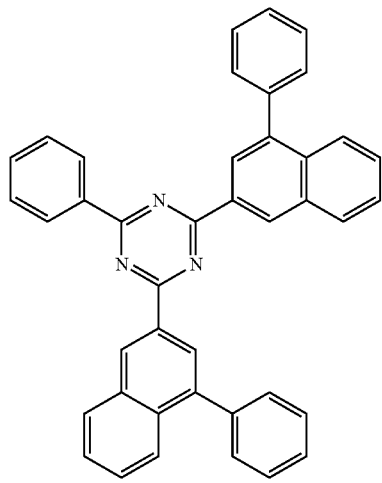
N-60
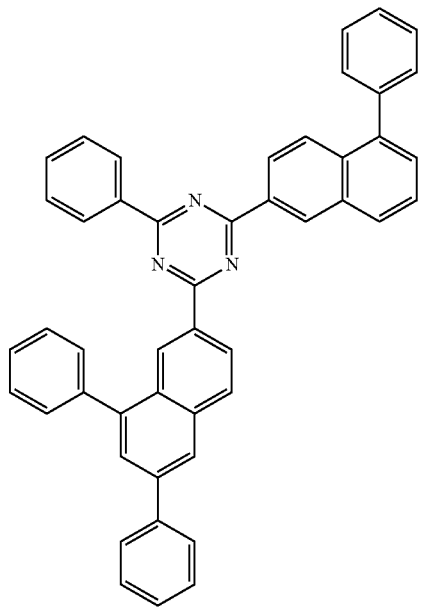
N-61
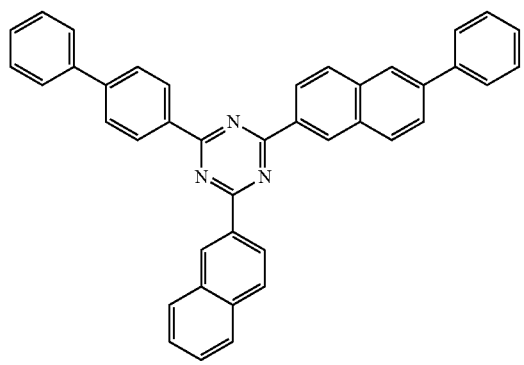
N-62
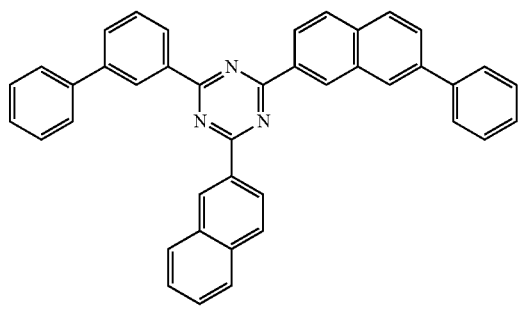
N-63
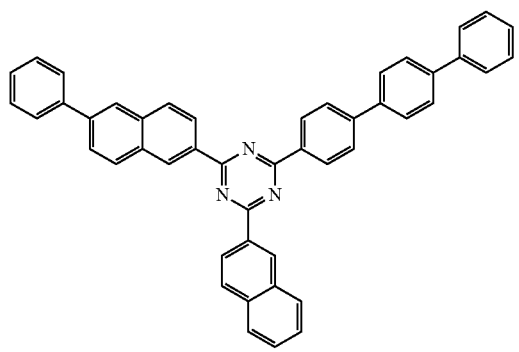
N-64
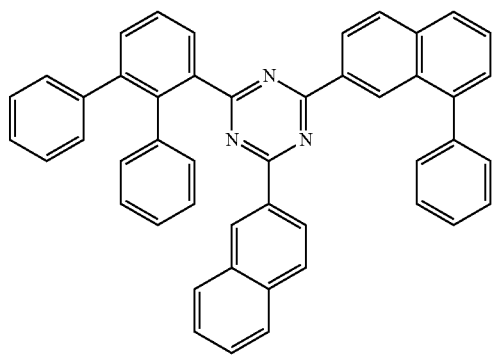

-continued
N-65
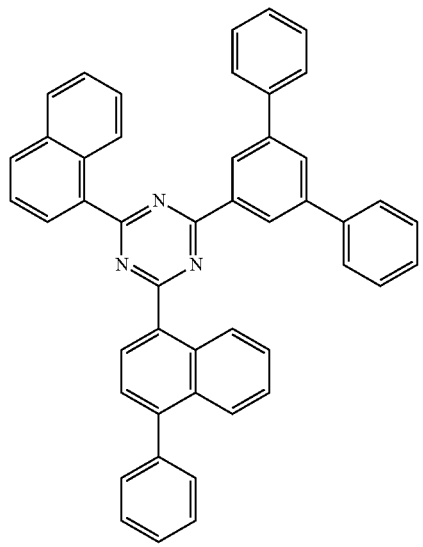
N-66
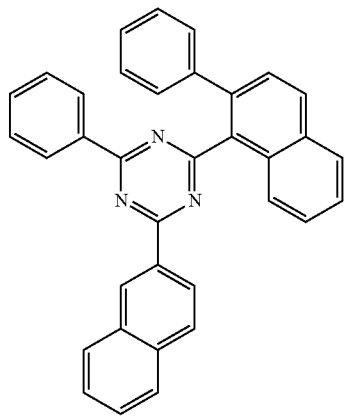
N-67
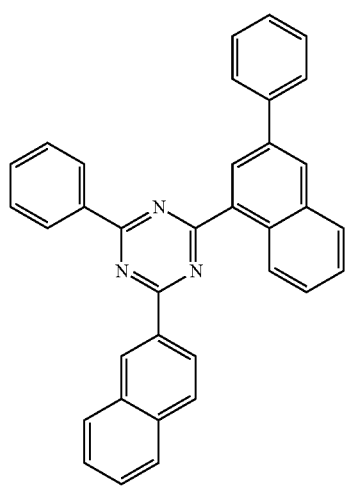
N-68
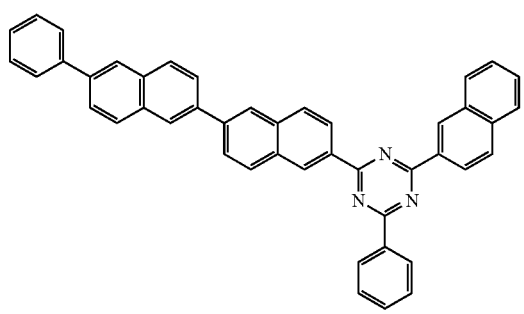
N-69
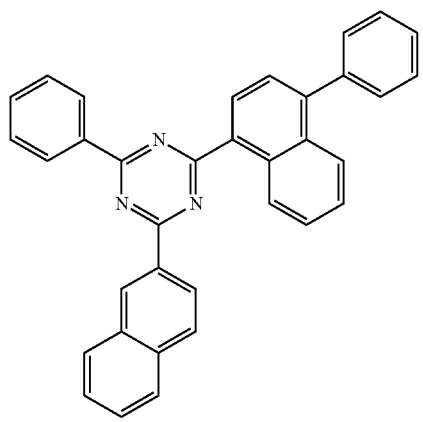
N-70
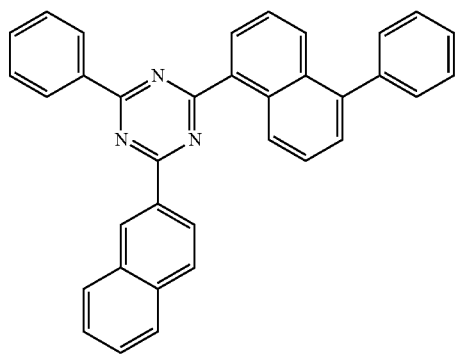

-continued
N-71
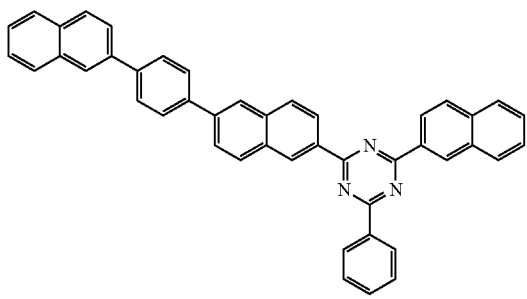
N-72
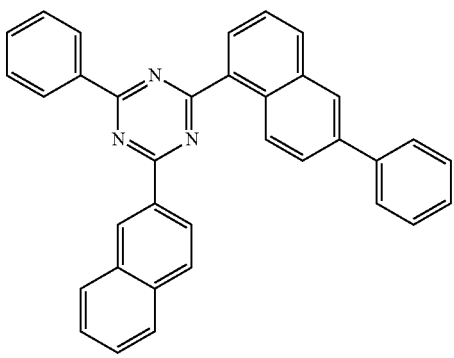
N-73
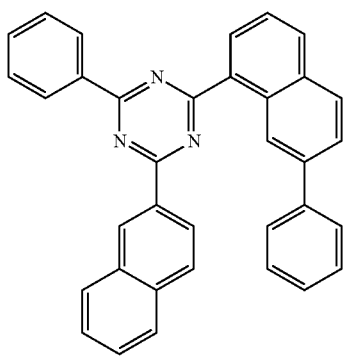
N-74
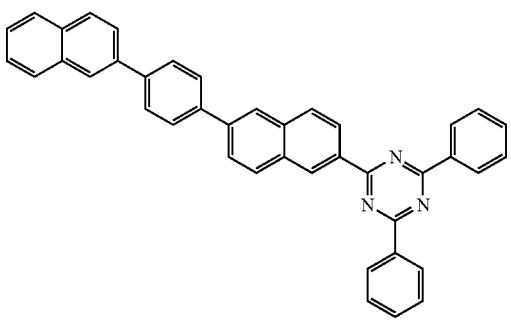
N-75
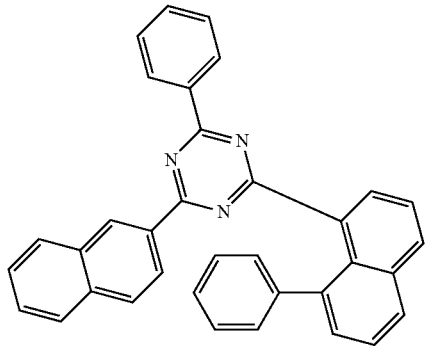
N-76
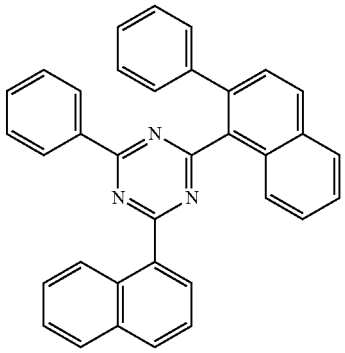
N-77
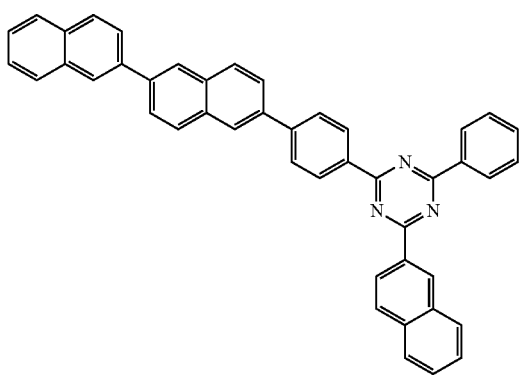
N-78
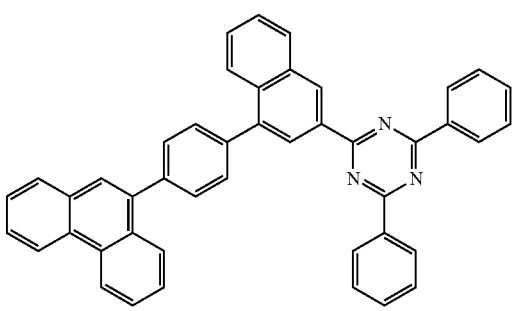

-continued
N-79
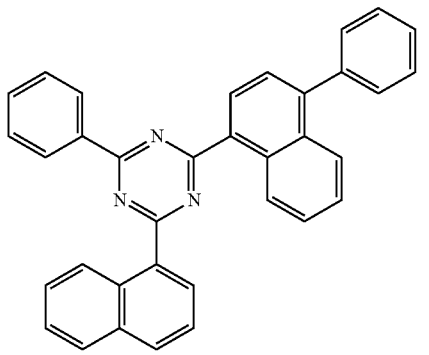
N-80
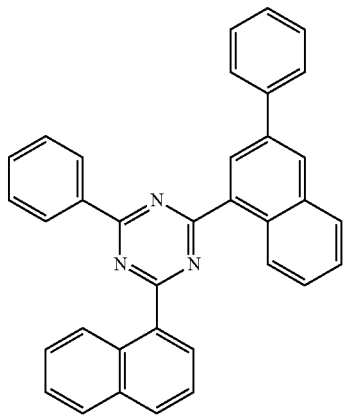
N-81
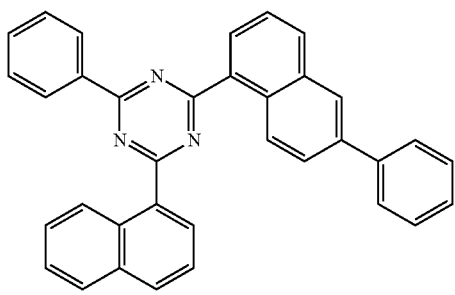
N-82
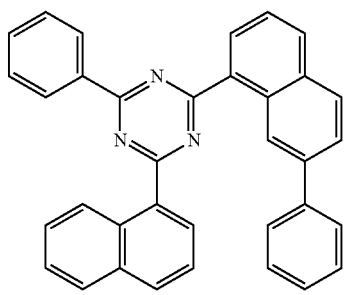
N-83
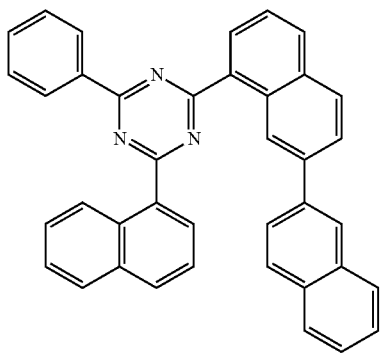
N-84
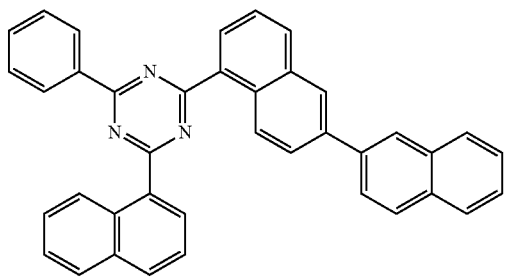
N-85
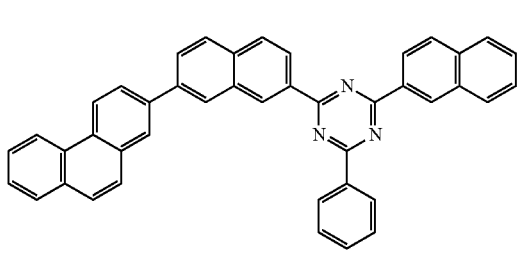
N-86
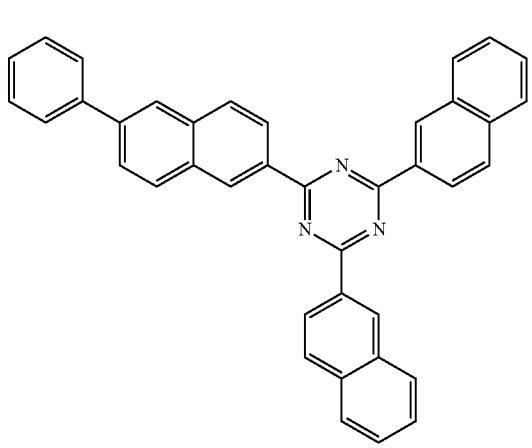

-continued
N-87
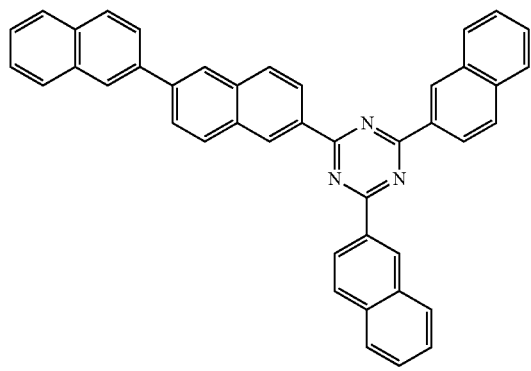
N-88
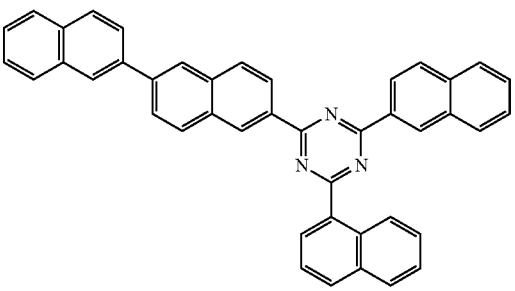
N-89
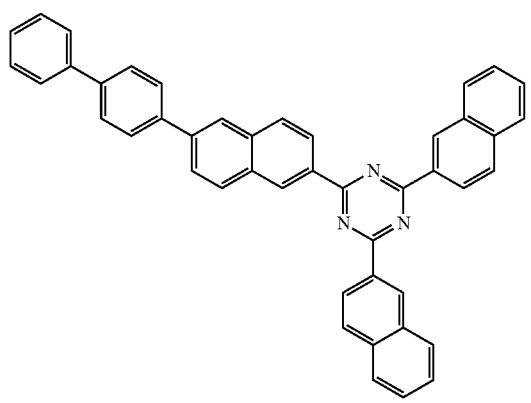
N-90
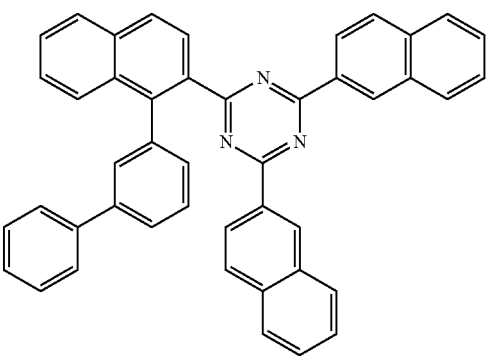
N-91
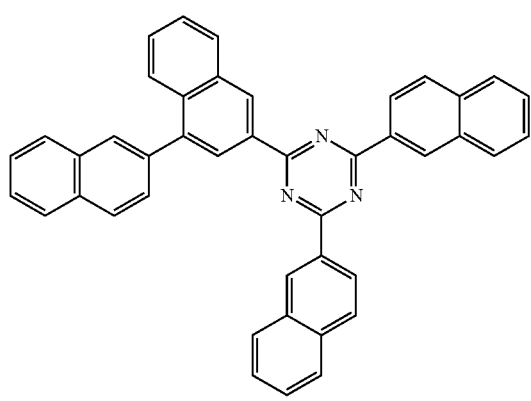
N-92
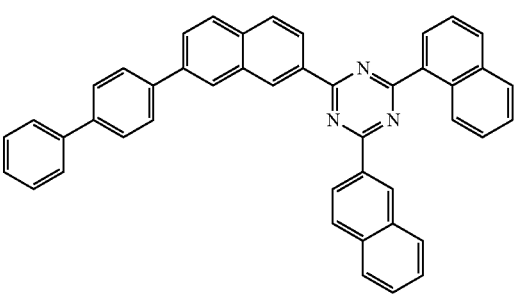
N-93
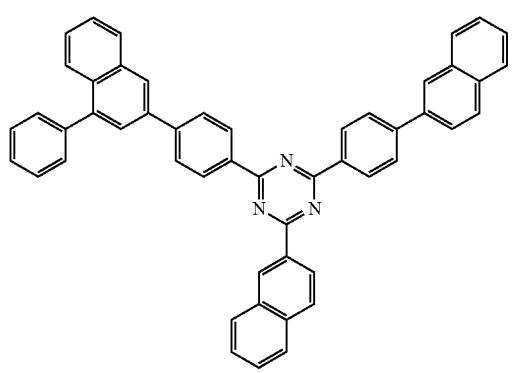
N-94
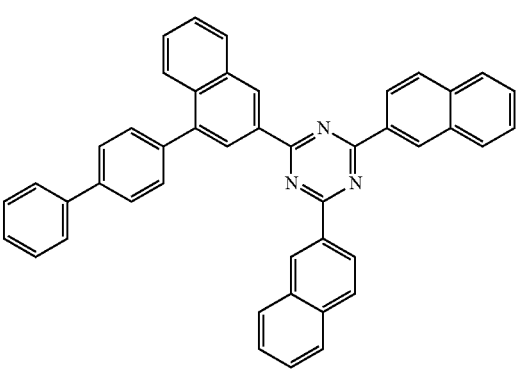

-continued
N-95
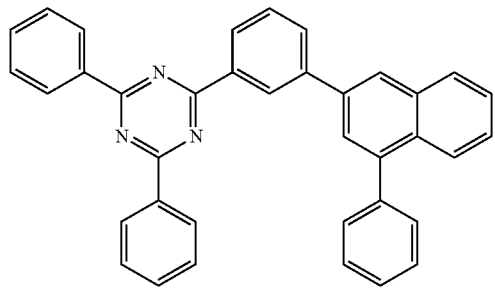
N-96
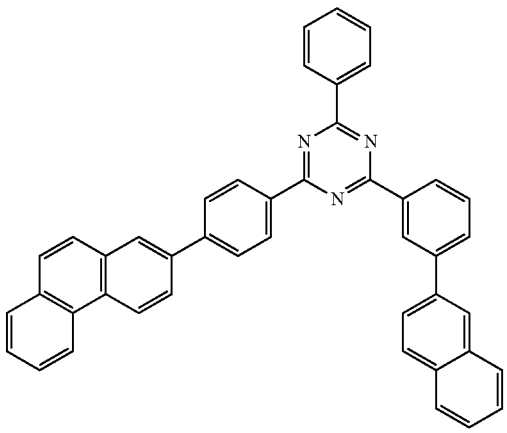
N-97
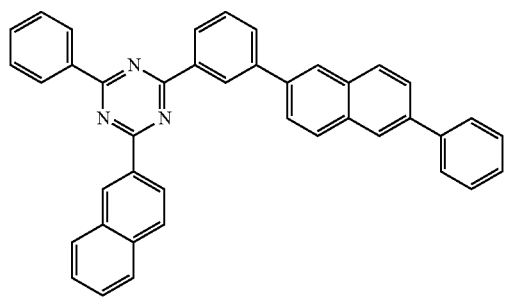
N-98
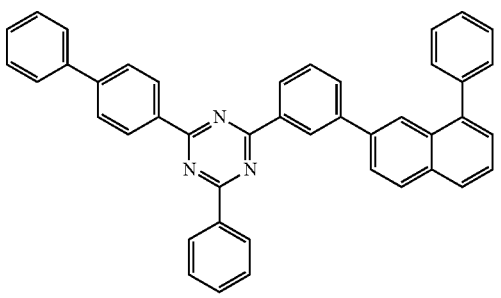
N-99
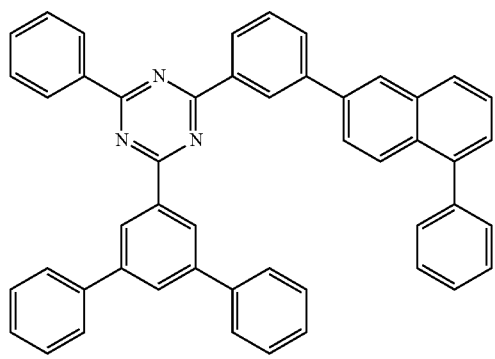
N-100
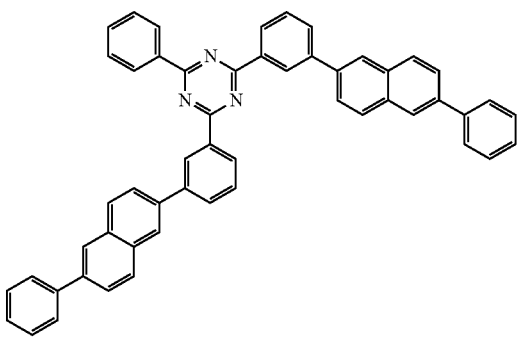
N-101
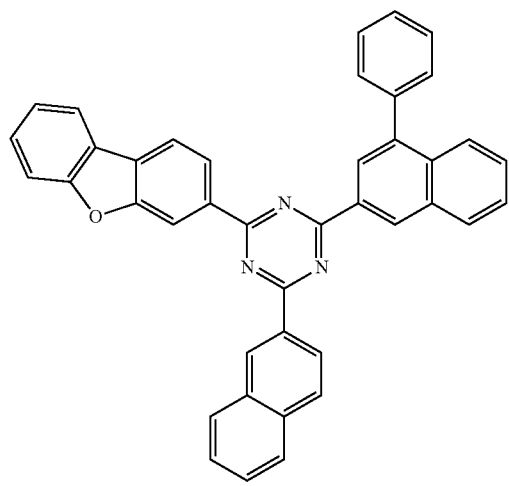
N-102
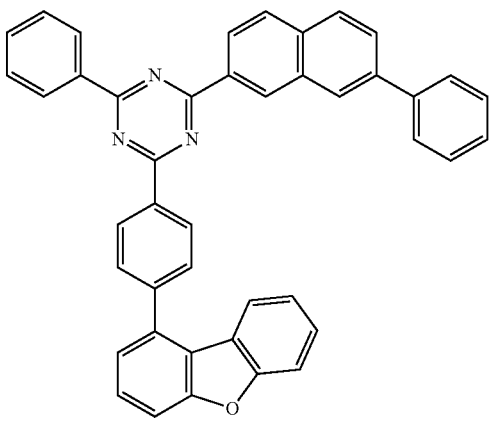

-continued
N-103
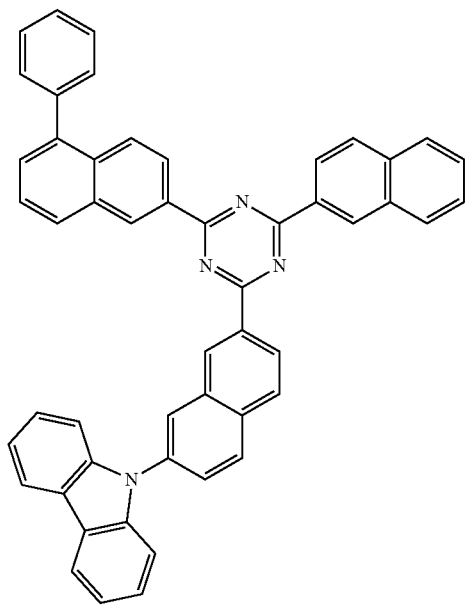
N-104
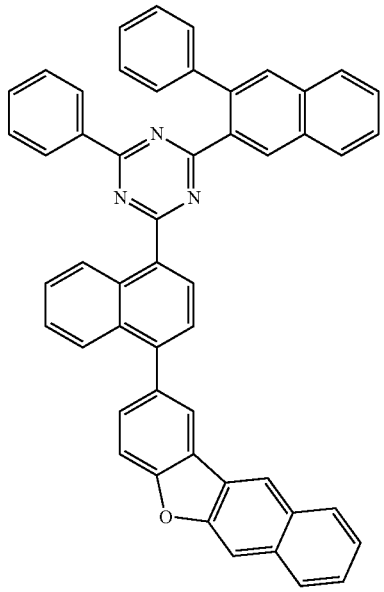
N-105
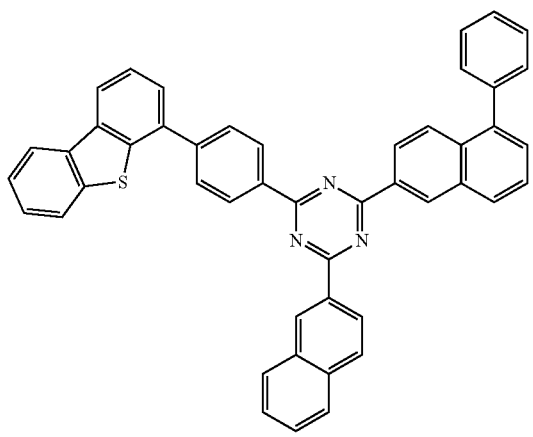
N-106
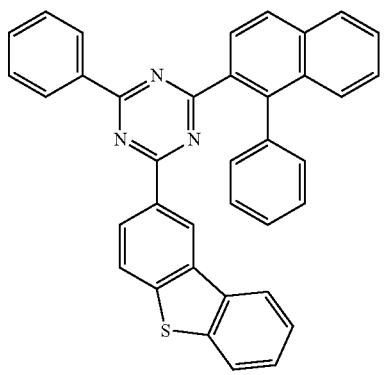
N-107
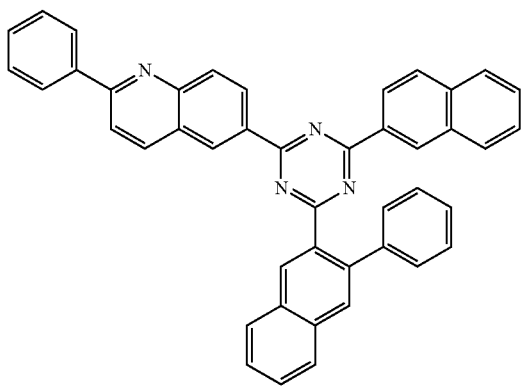
N-108
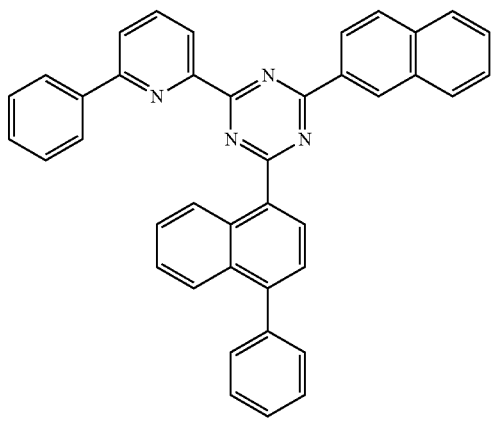

-continued
N-109
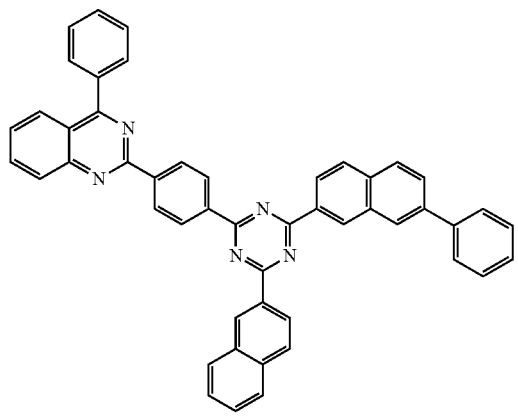
N-110
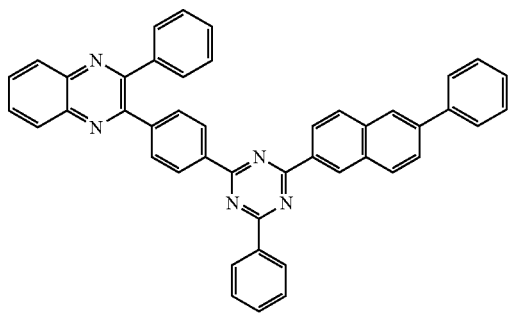
N-111
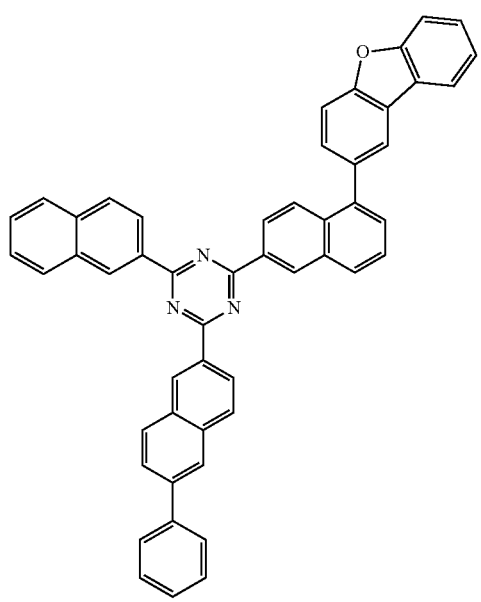
N-112
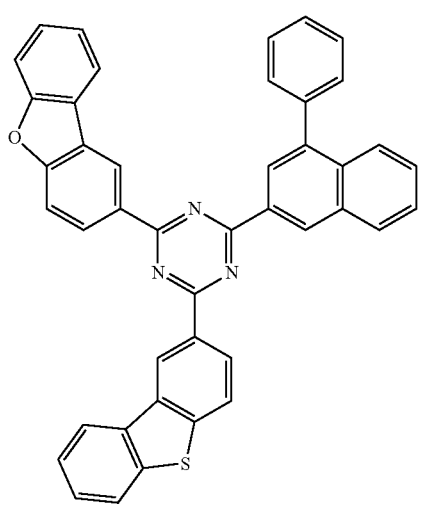
N-113
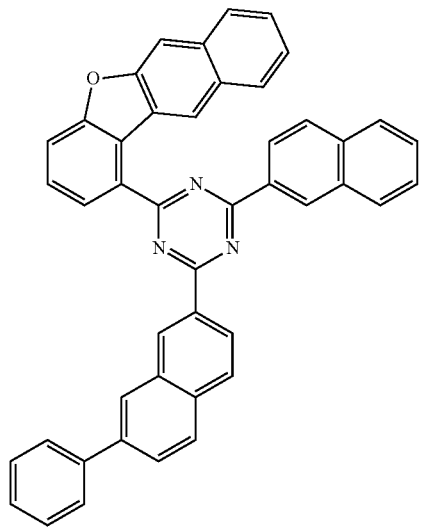
N-114
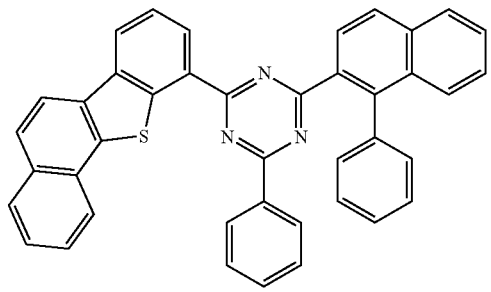

-continued
N-115
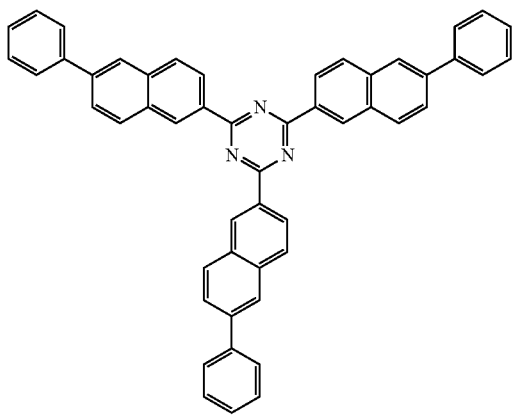
N-116
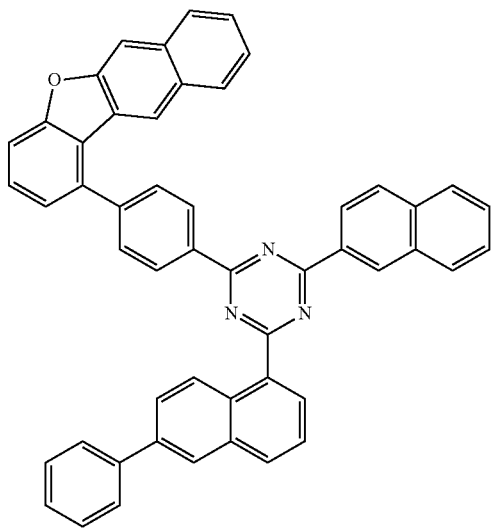
N-117
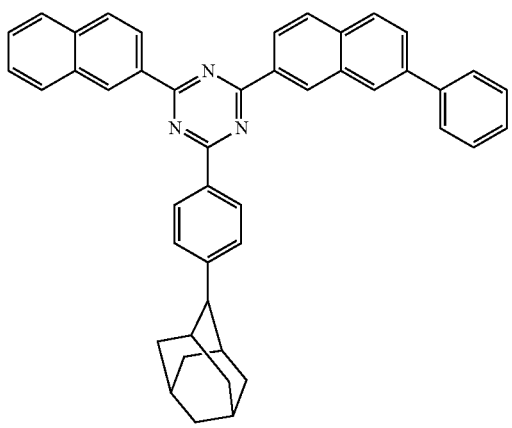
N-118
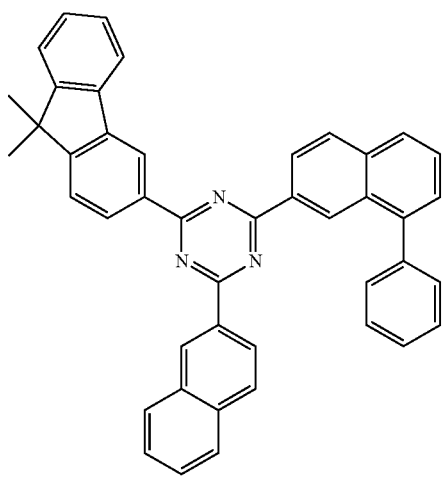
N-119
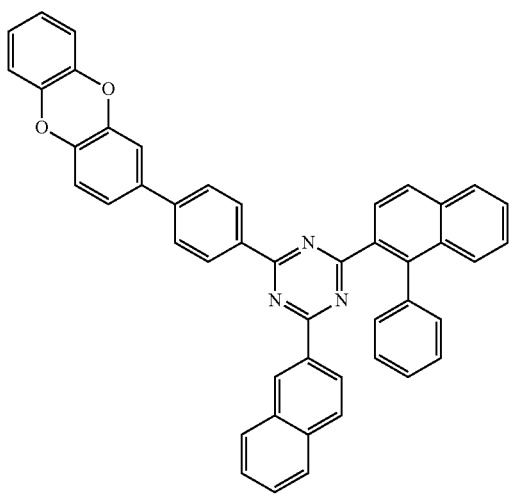
N-120
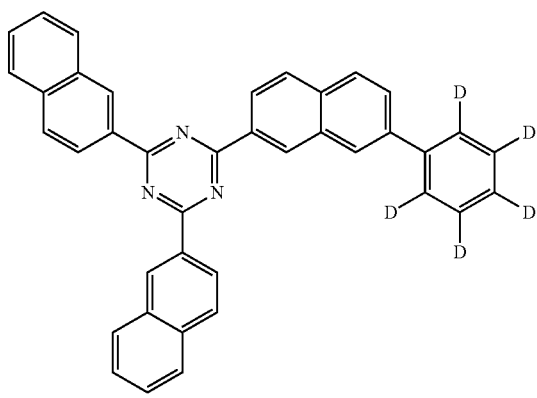

-continued
N-121
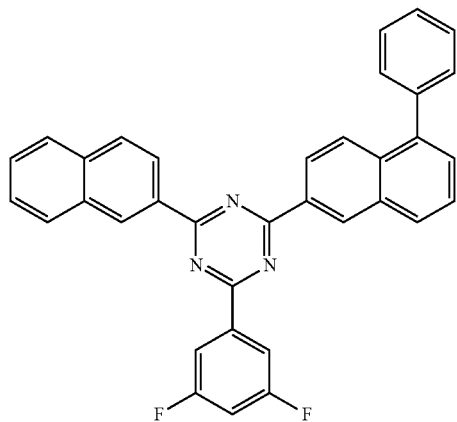
N-122
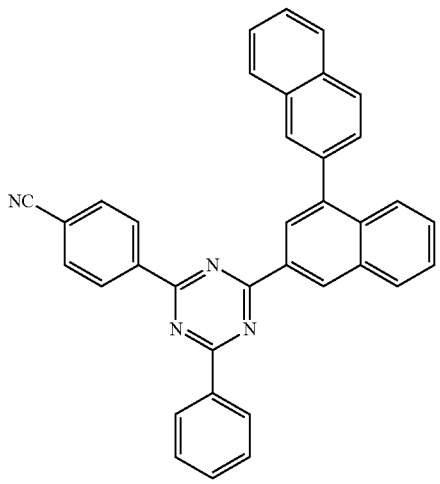
N-123
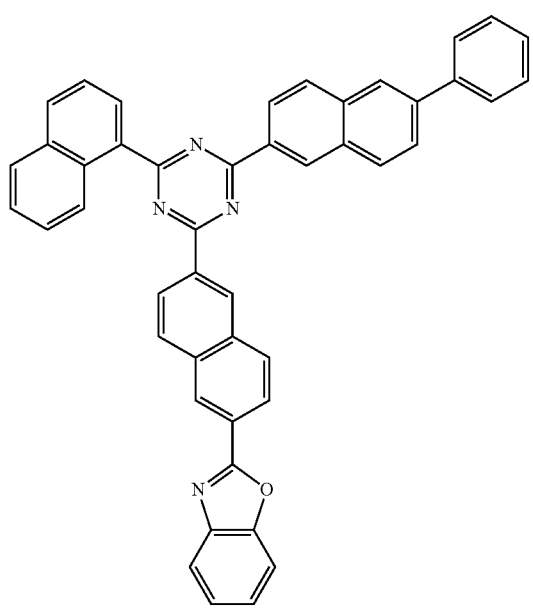
N-124
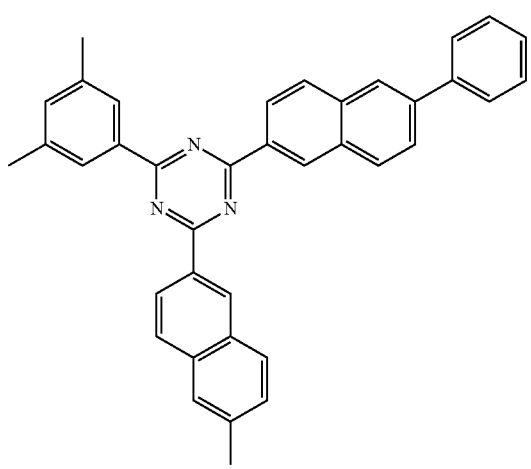
N-125
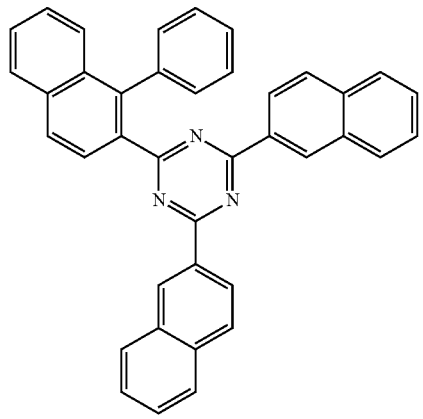
N-126
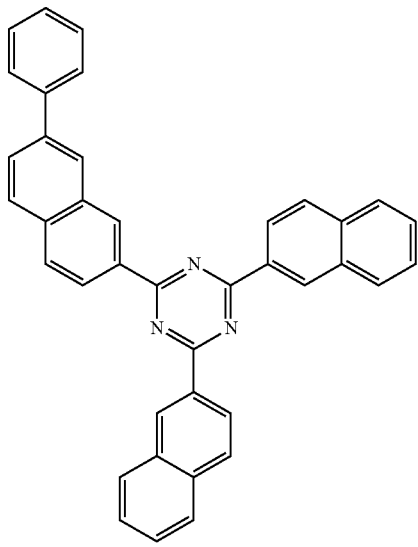

-continued
N-127
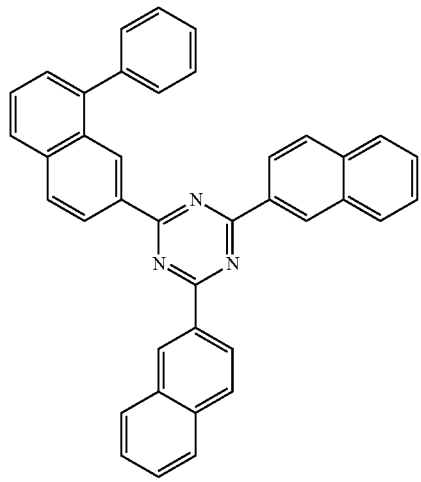
N-128
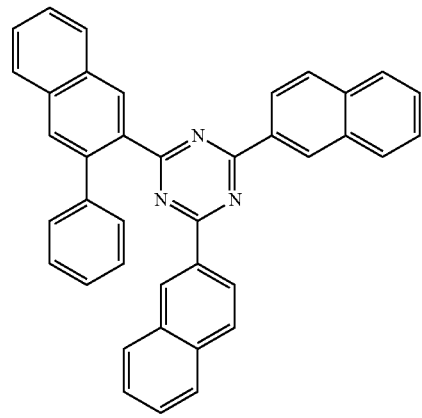
N-129
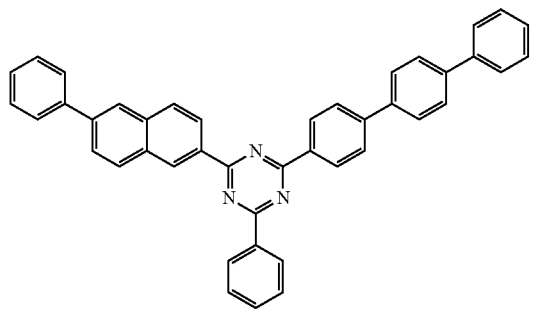
N-130
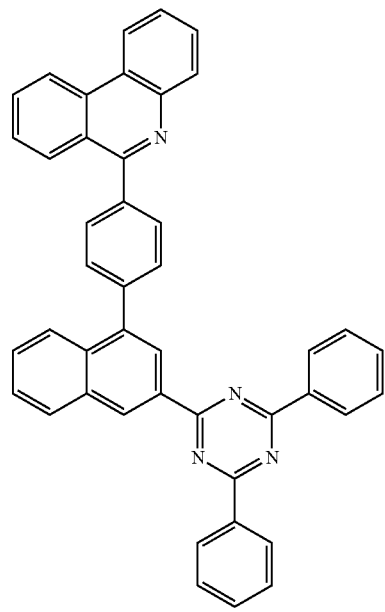
N-131
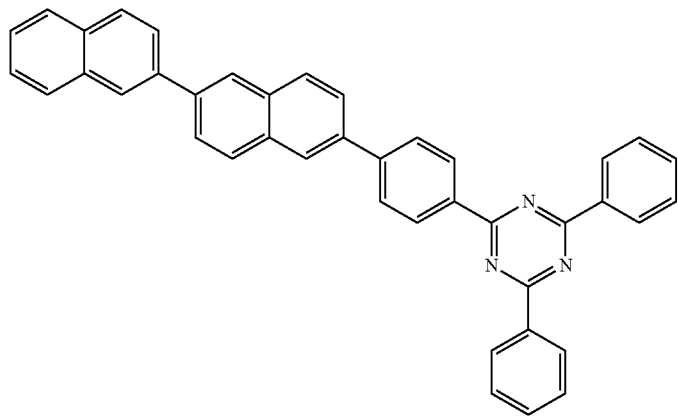

-continued
N-132
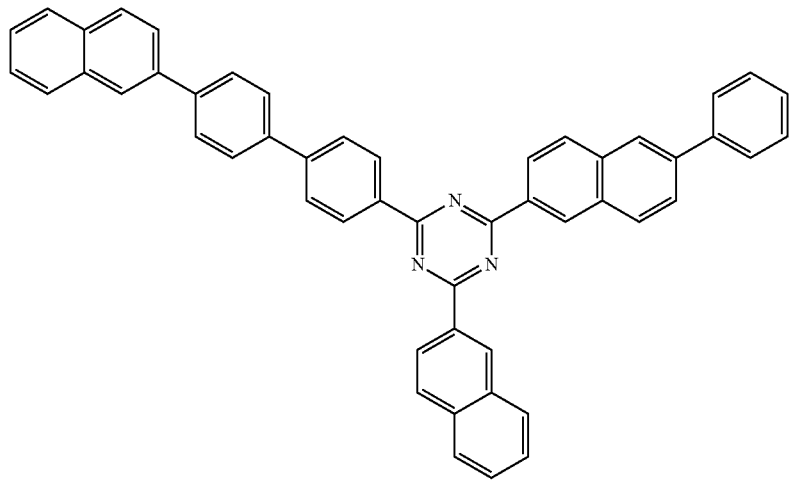
N-133                                    N-134
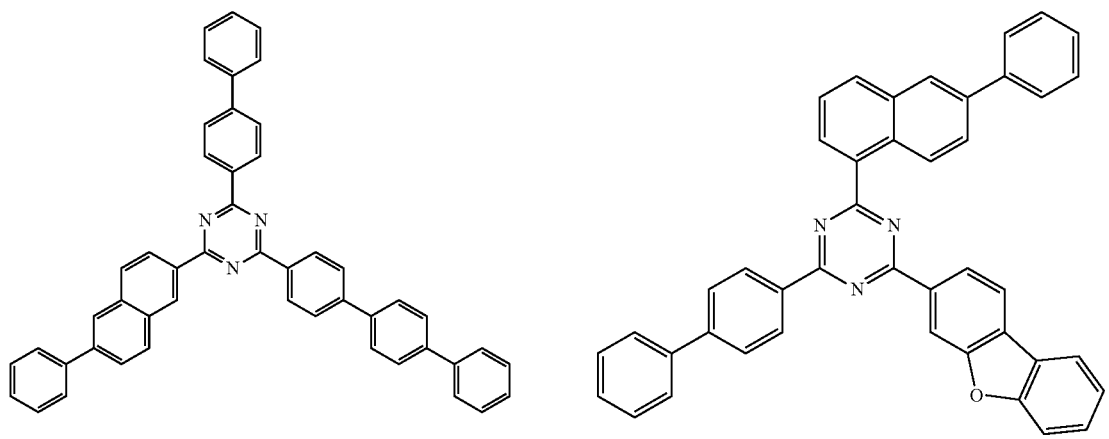
N-135                                    N-136
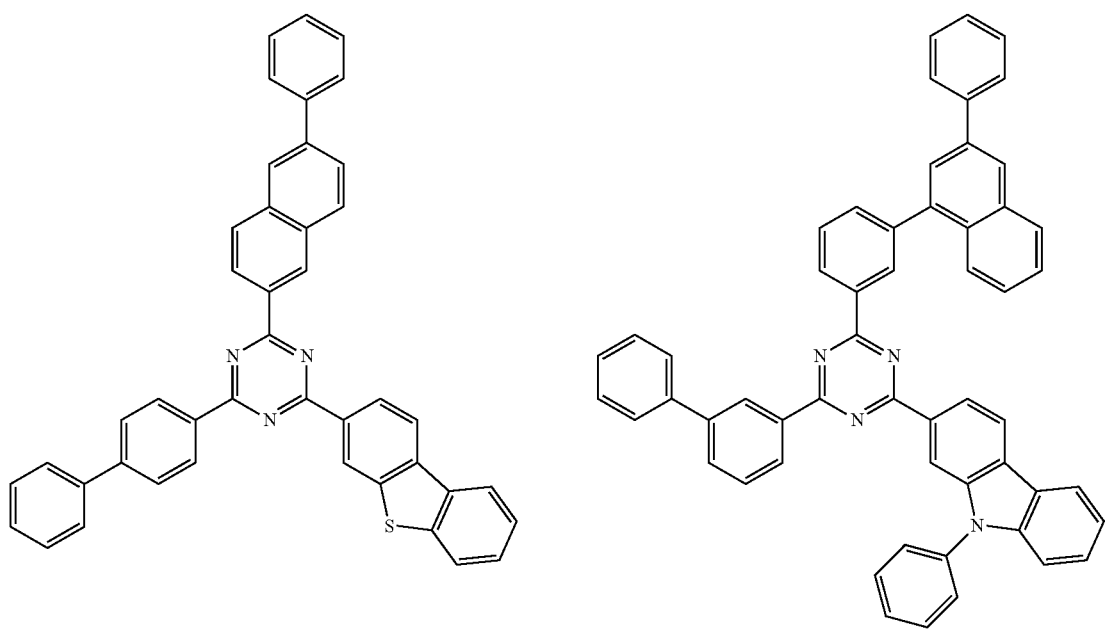

N-137
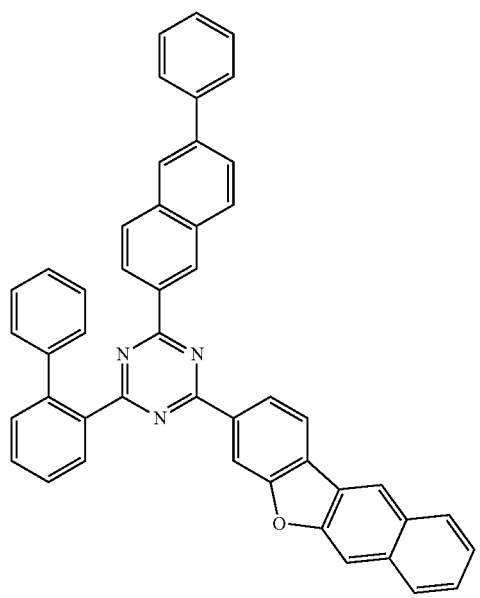
N-138
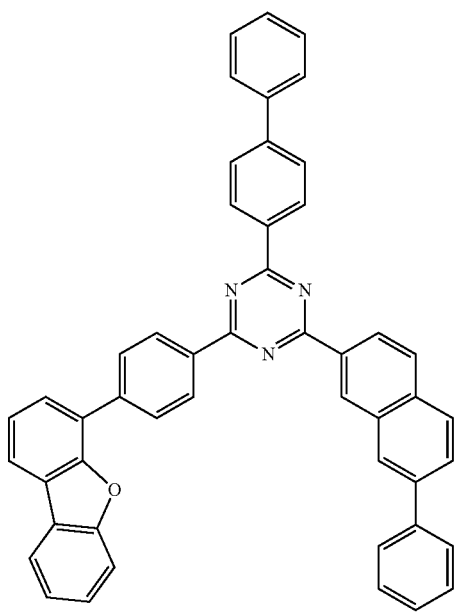
N-139
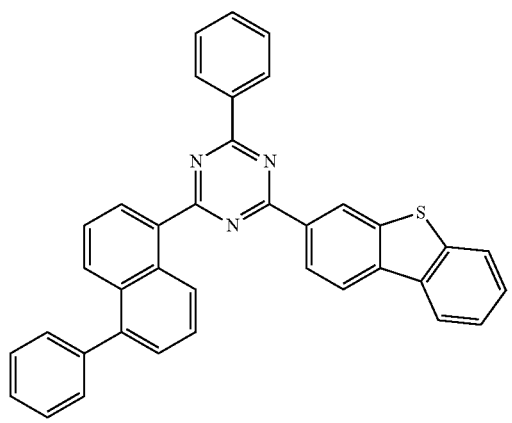
N-140
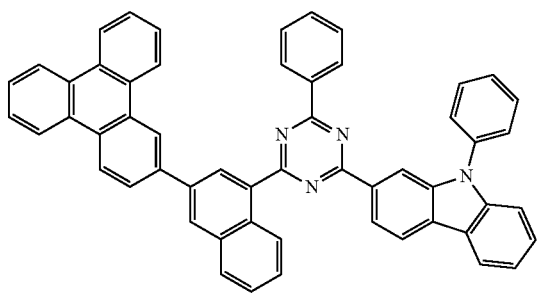

-continued
N-141
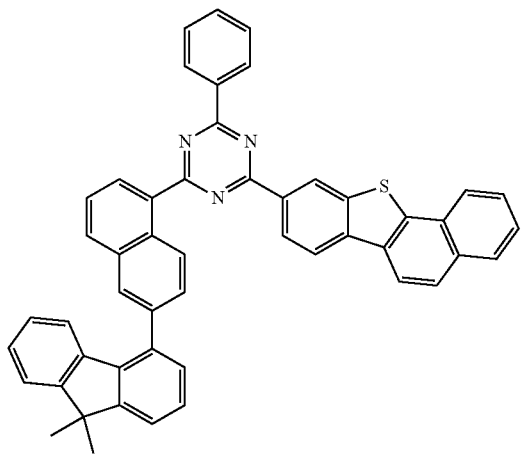
N-142
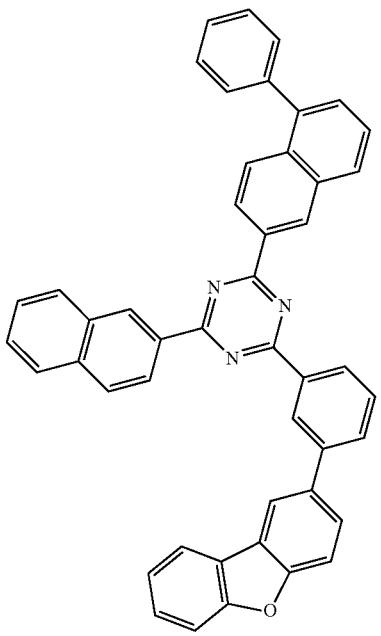
N-143
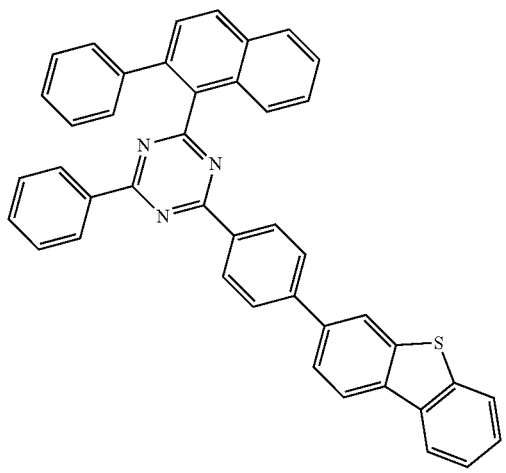
N-144
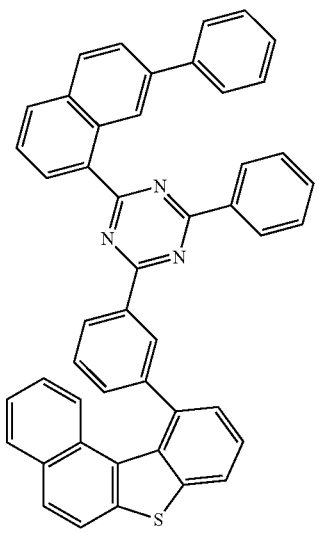
N-145
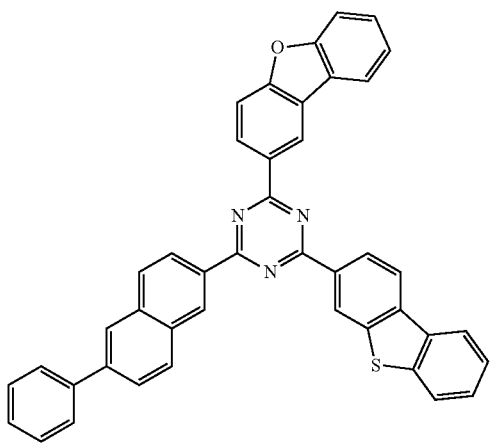
N-146
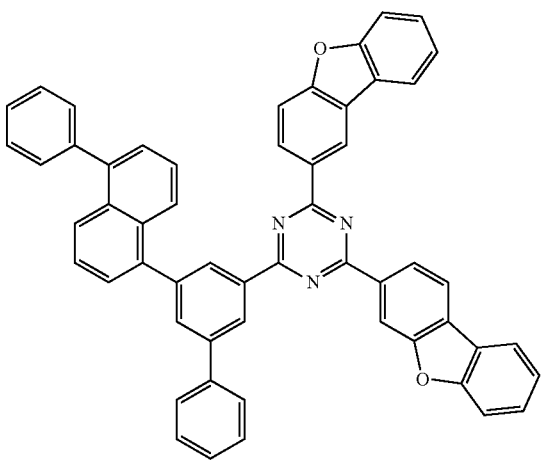

-continued
N-147
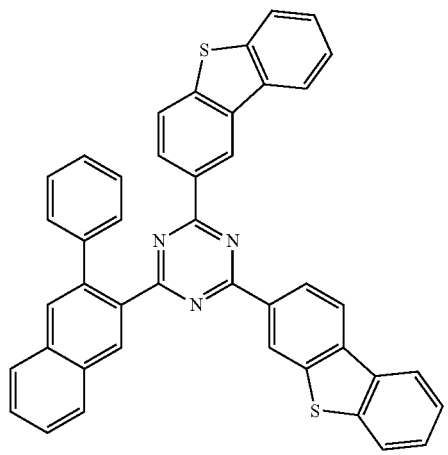
N-148
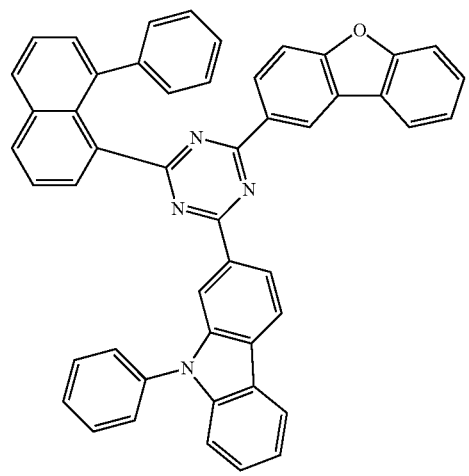
N-149
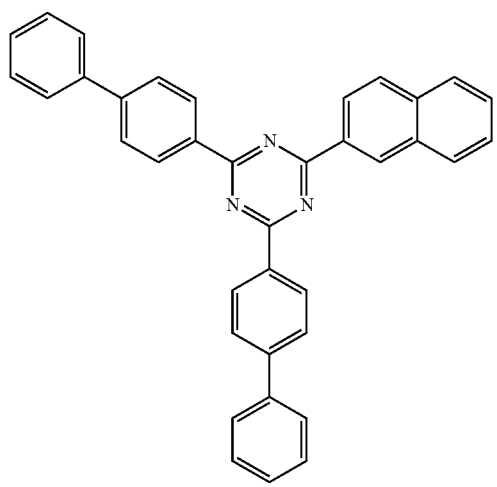
N-150
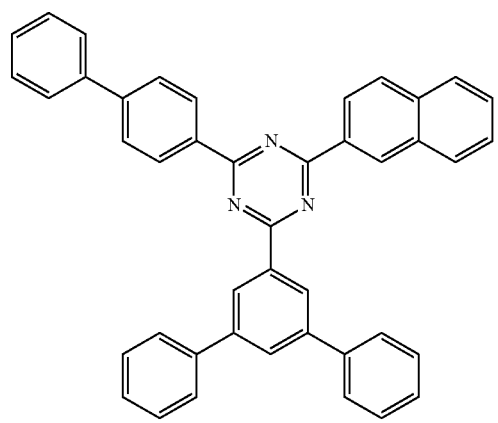
N-151
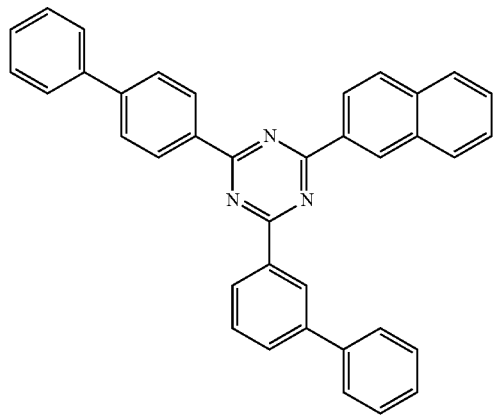
N-152
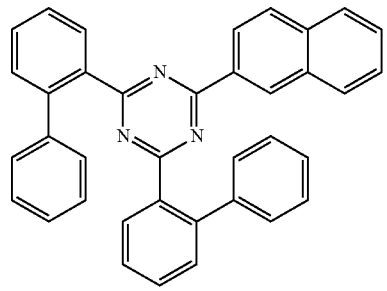

-continued
N-153
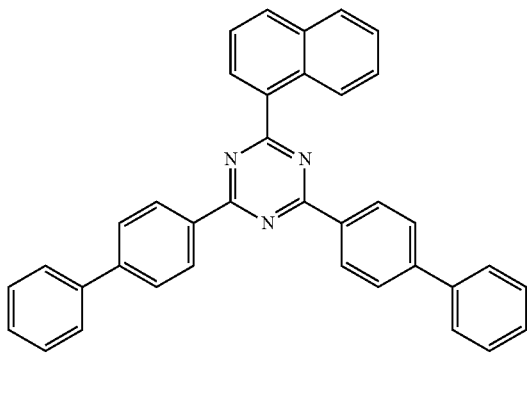
N-154
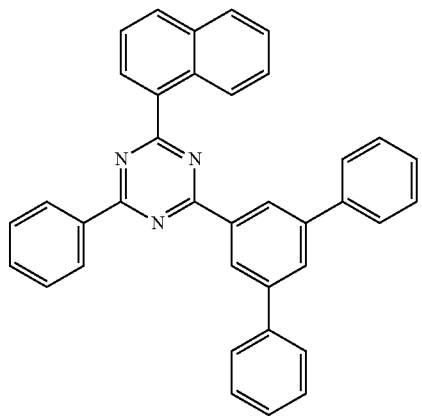
N-155
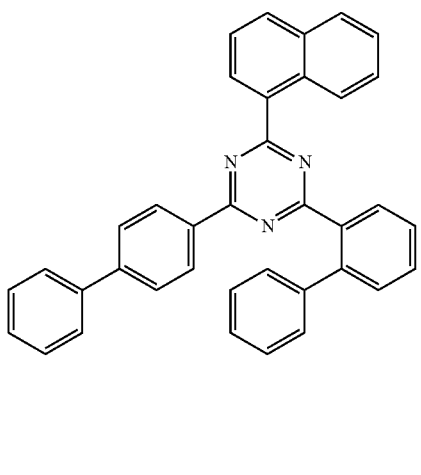
N-156
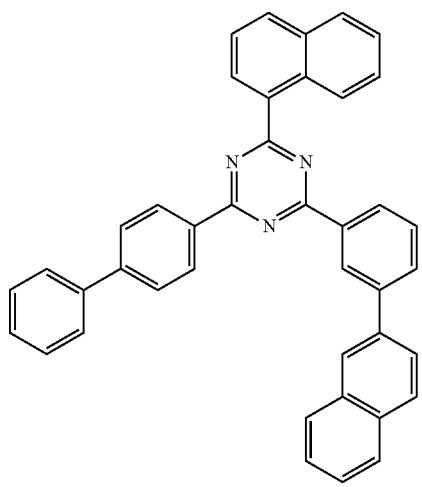
N-157
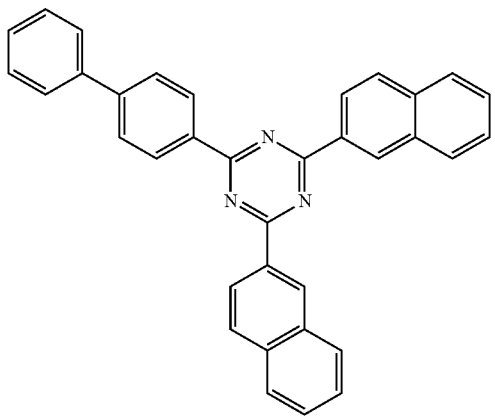
N-158
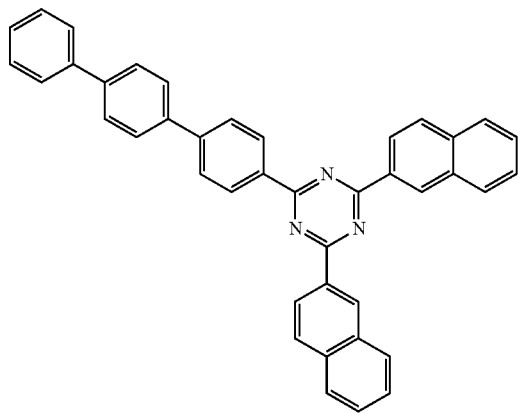

-continued
N-159
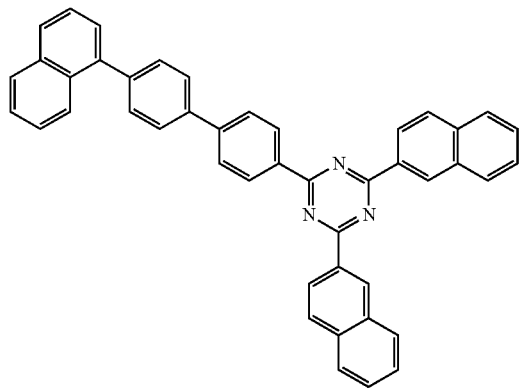
N-160
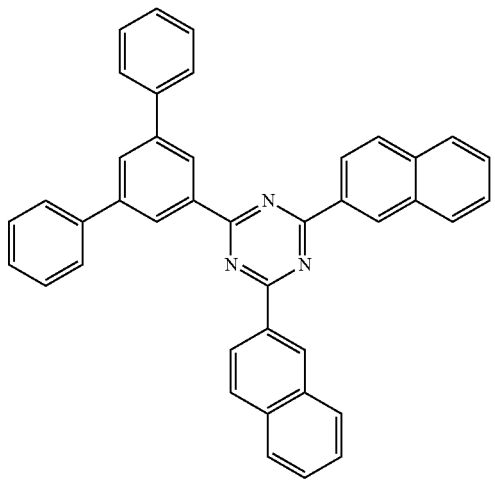
N-161
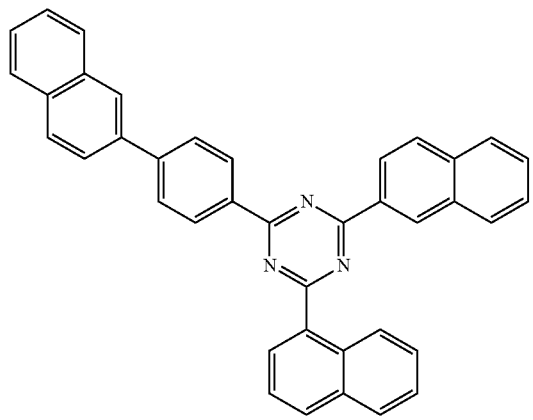
N-162
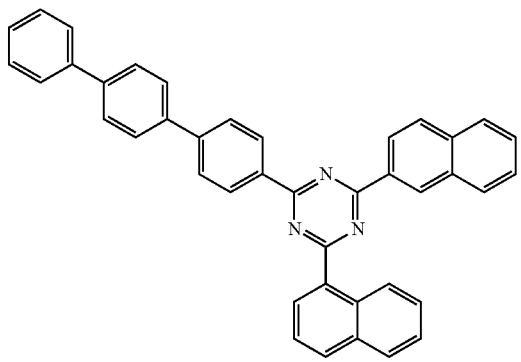
N-163
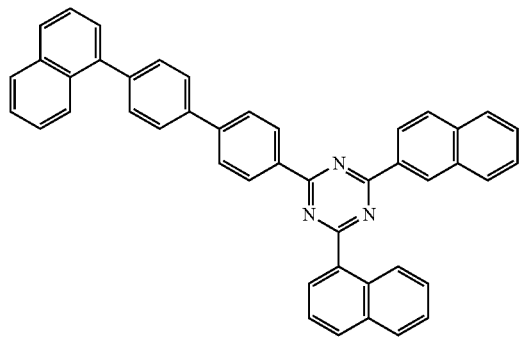
N-164
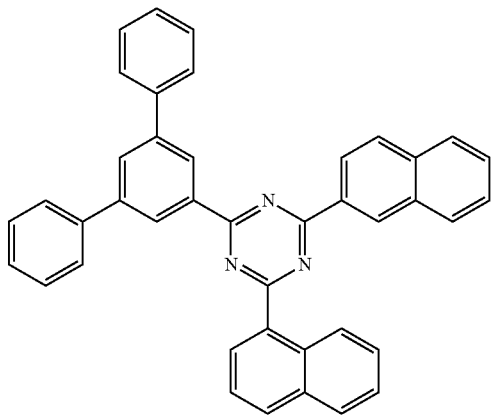

-continued
N-165
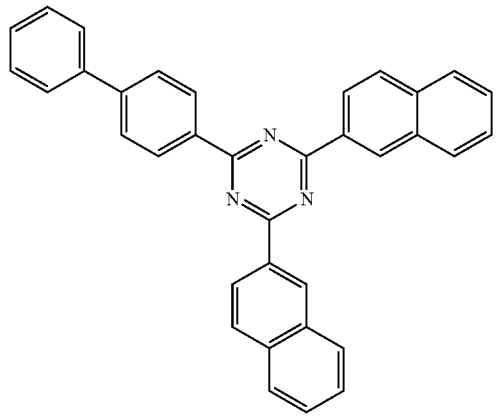
N-166
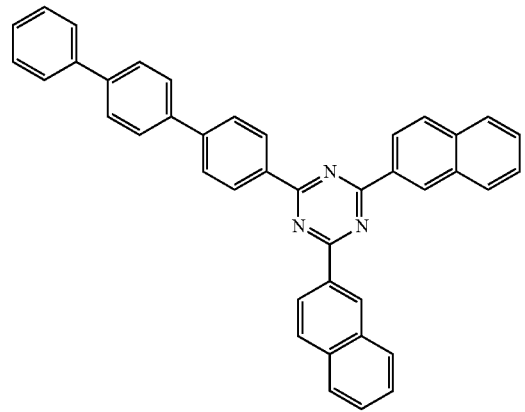
N-167
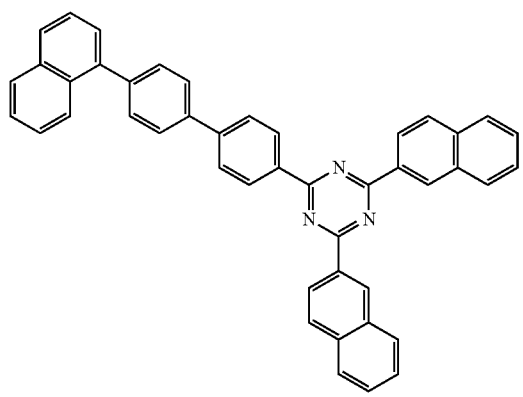
N-168
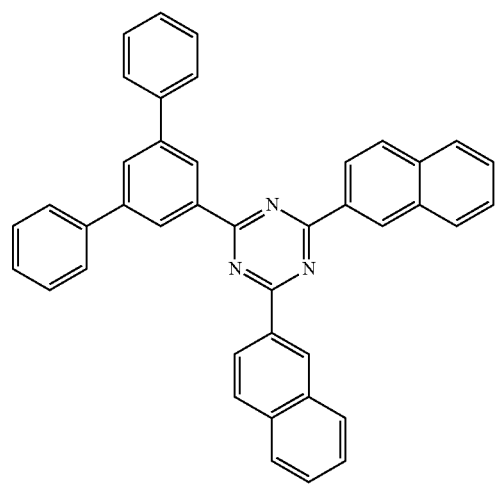
N-169
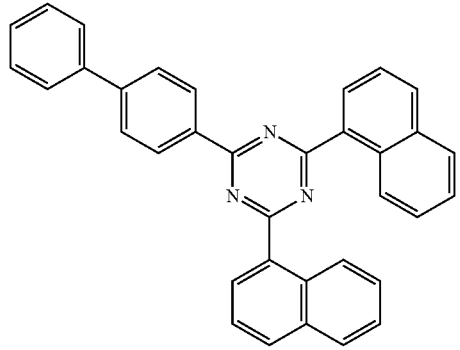
N-170
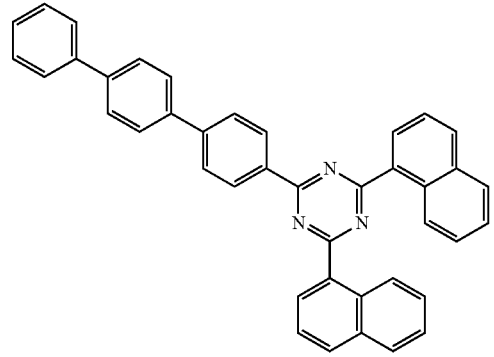

-continued
N-171
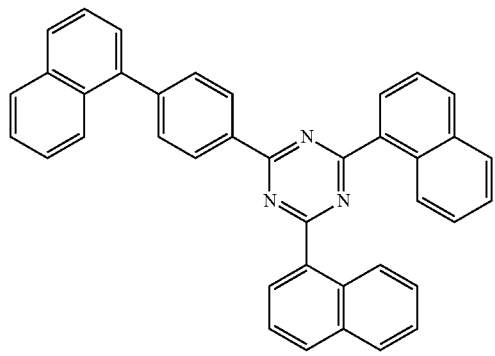
N-172
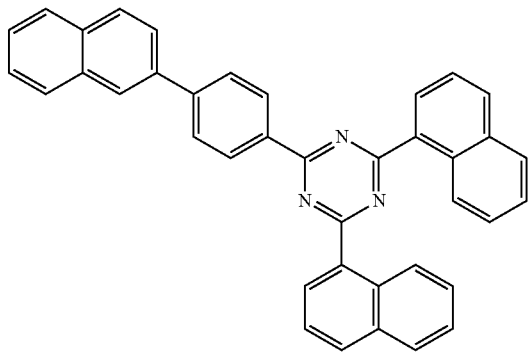
N-173
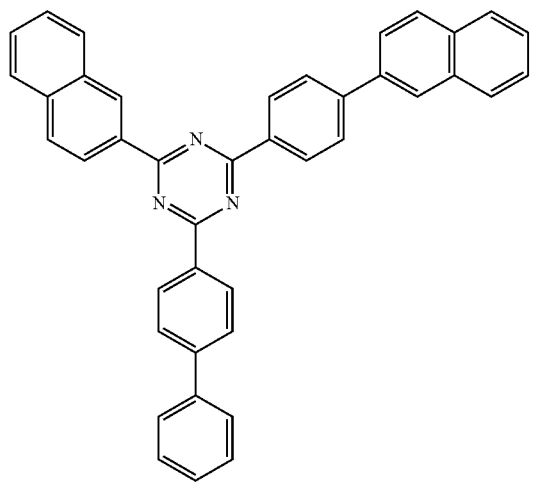
N-174
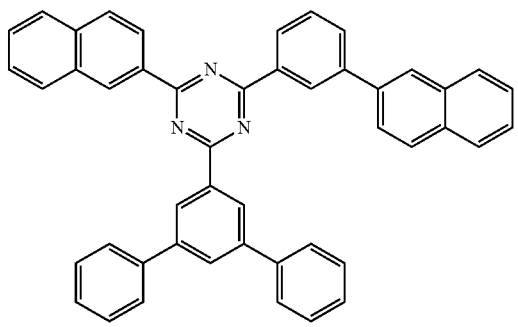
N-175
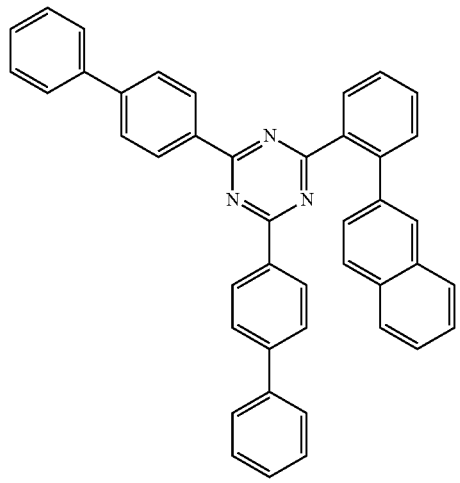
N-176
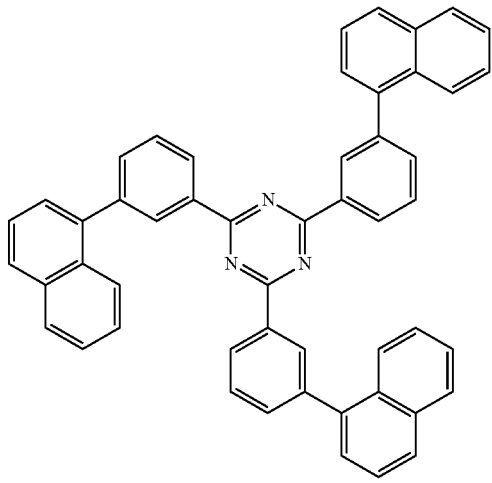

-continued
N-177
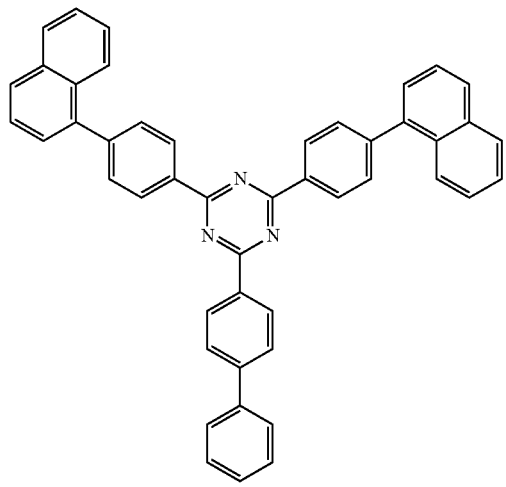
N-178
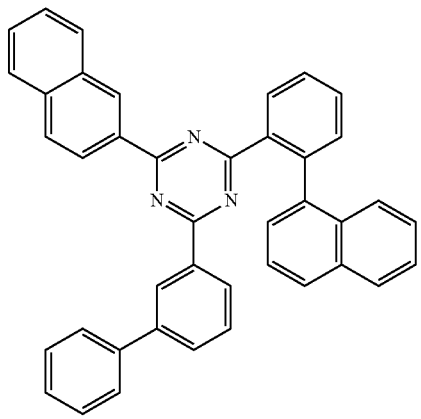
N-179
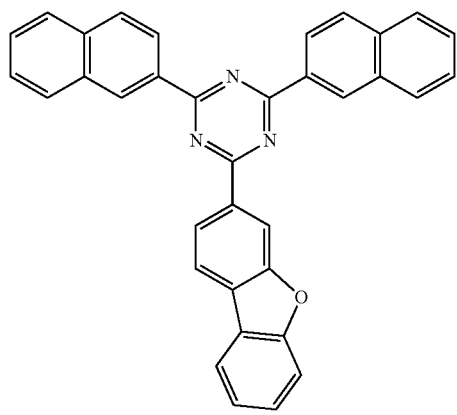
N-180
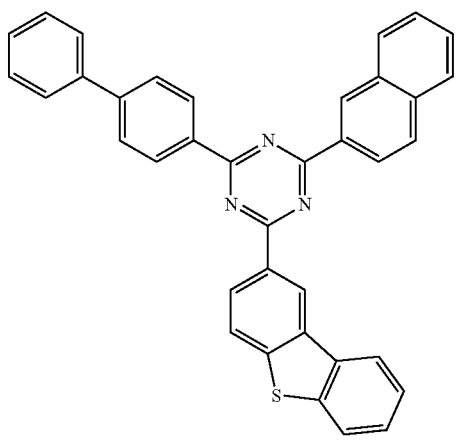
N-181
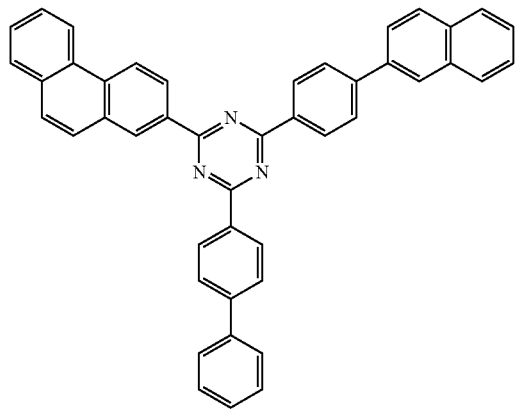
N-182
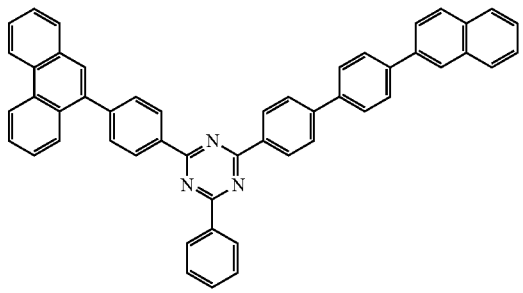

N-183

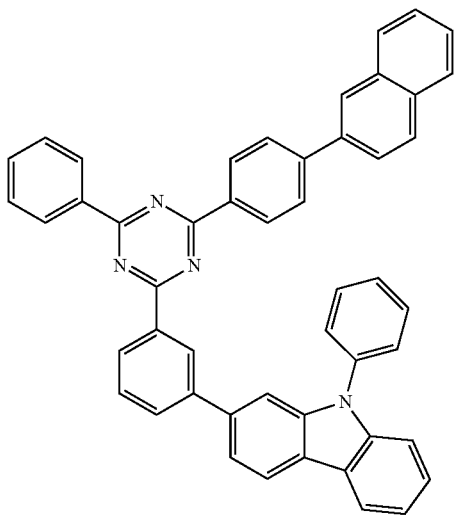

N-184

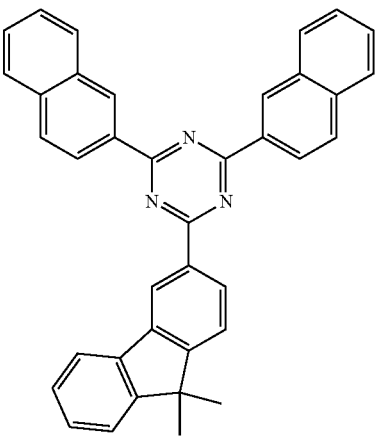

Also, Formula 2 is represented by Formula 3.

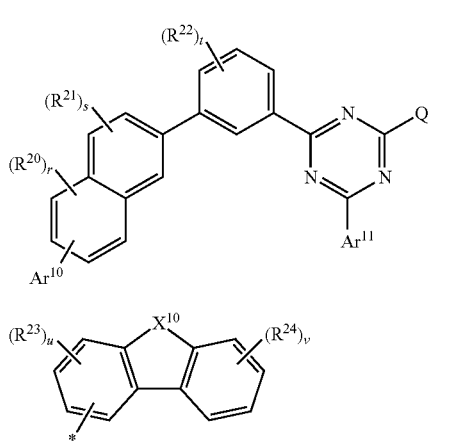

Formula 3

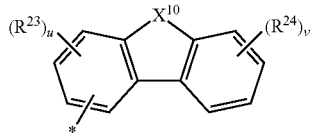

Formula Q

Wherein,

1) Q is a substituent represented by Formula Q,

2) $Ar^{10}$ is a $C_6$-$C_{60}$ aryl group; a $C_6$-$C_{60}$ aryl group substituted by deuterium;

When $Ar^{10}$ is an aryl group, it may be preferably a $C_6$-$C_{30}$ aryl group, and more preferably a $C_6$-$C_{25}$ aryl group, for example, it may be phenyl, biphenyl, naphthalene, phenanthrene, etc, 3) $Ar^{11}$ is a $C_6$-$C_{60}$ aryl group; or a $C_2$-$C_{60}$ heterocyclic group including at least one heteroatom of O, N, S, Si or P;

When $Ar^{11}$ is an aryl group, it may be preferably a $C_6$-$C_{30}$ aryl group, and more preferably a $C_6$-$C_{25}$ aryl group, for example, it may be phenyl, biphenyl, naphthalene, phenanthrene, etc, When $Ar^{11}$ is are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, naphthobenzofuran, naphthobenzothiophene, benzothienopyrimidine, benzofuropyrimidine, phenothiazine, phenylphenothiazine etc., 4) $R^{20}$, $R^{21}$ and $R^{22}$ are the same or different, and each independently hydrogen; or deuterium;

5) $R^{23}$ and $R^{24}$ are the same or different, and each independently selected from the group consisting of a hydrogen; deuterium; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; or a plurality of adjacent $R^{23}$s or a plurality of $R^{24}$s may be bonded to each other to form a ring, When $R^{23}$ and $R^{24}$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When $R^{23}$ and $R^{24}$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, naphthobenzofuran, naphthobenzothiophene, benzothienopyrimidine, benzofuropyrimidine, phenothiazine, phenylphenothiazine etc., When $R^{23}$ and $R^{24}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^{23}$ and $R^{24}$ are an alkyl group, it may be preferably a $C_1$-$C_{30}$ alkyl group, and more preferably a $C_1$-$C_{24}$ alkyl group.

When $R^{23}$ and $R^{24}$ are alkoxyl groups, they may be preferably $C_1$-$C_{24}$ alkoxyl groups.

When $R^{23}$ and $R^{24}$ are an aryloxy group, it may be preferably a $C_6$-$C_{24}$ aryloxy group, 6) $X^{10}$ is O or S, 7) r, s and u are each independently an integer of 0 to 3, t and v are each independently an integer of 0 to 4, 8) * means a position that binds to Formula (3), wherein the aryl group, heterocyclic group, fluorenyl group, aliphatic ring group, fused ring group, alkyl group, alkenyl group, alkynyl group, alkoxy group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring and a $C_6$-$C_{60}$ aromatic ring, or a $C_2$-$C_{60}$ heterocyclic group or a fused ring formed by the combination thereof.

Also, Formula 3 is represented by any one of Formulas 3-1 to 3-4.

Formula 3-1

Formula 3-2

Formula 3-3

Formula 3-4

Wherein, Q, $Ar^{10}$, $Ar^{11}$, $R^{20}$, $R^{21}$, $R^{22}$, r, s and t are the same as defined in Formula 3.

Also, Formula Q is represented by any one of the following Formula Q-1 to Formula Q-4.

Formula Q-1

Formula Q-2

Formula Q-3

Formula Q-4

Wherein, $X^{10}$, $R^{23}$, $R^{24}$, u, v and * are the same as defined in Formula Q.

Formula Q may be represented by any one of the following compounds, but is not limited thereto.

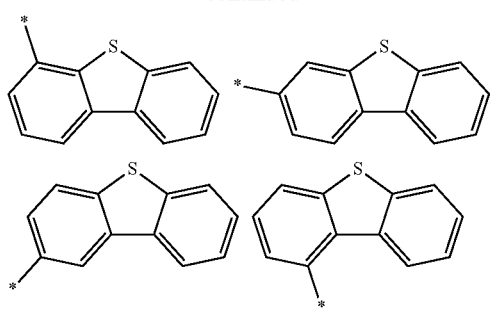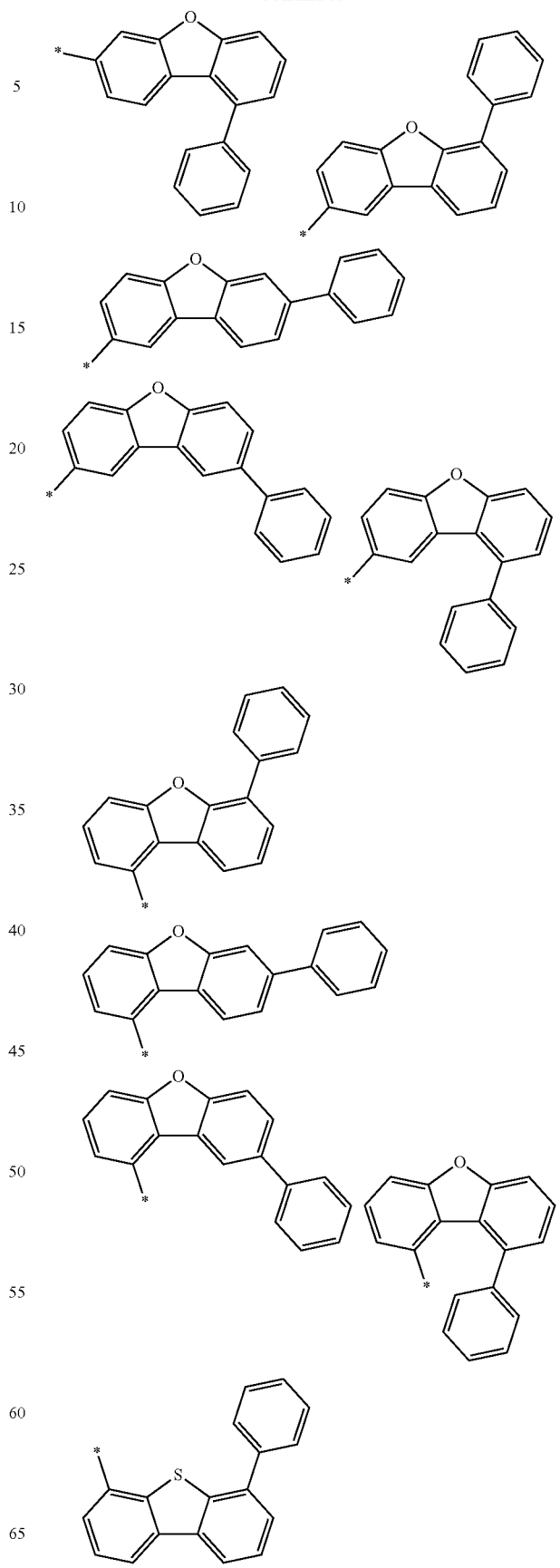

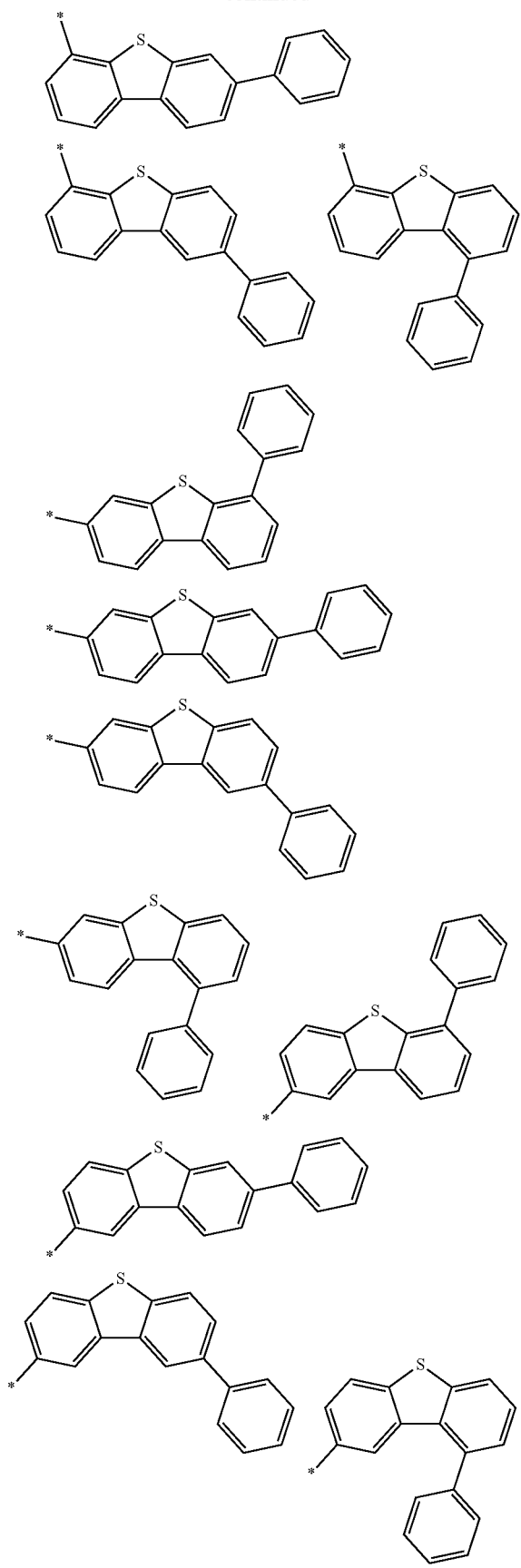
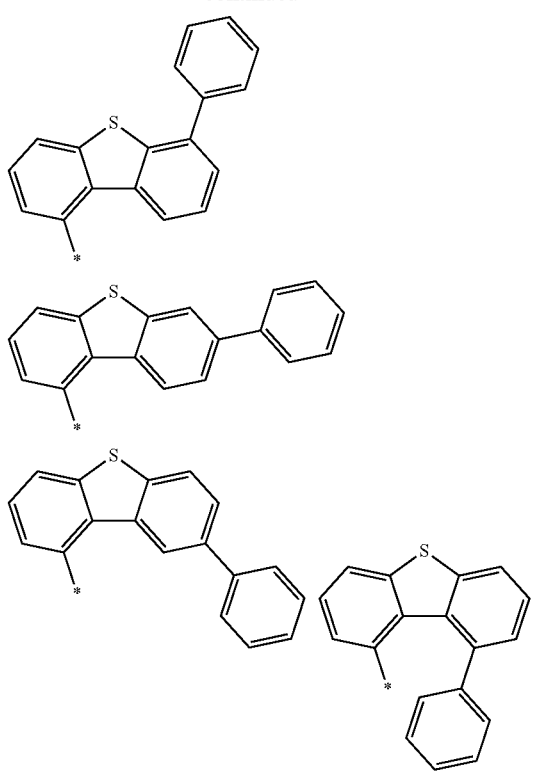
Also, Ar[10] or Ar[11] is represented by one of Formulas Ar-1 to Ar-7.
Formula Ar-1
Formula Ar-2
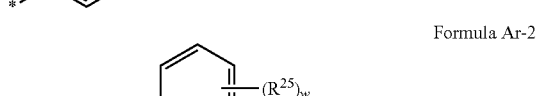
Formula Ar-3
Formula Ar-4
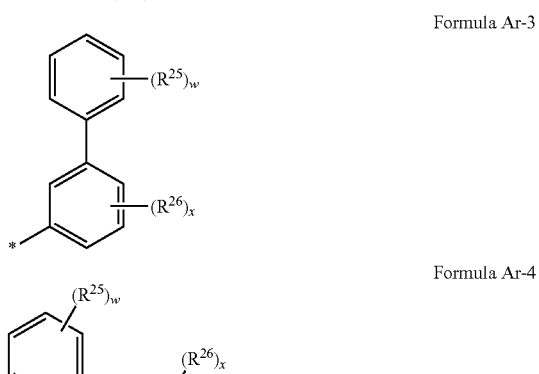

-continued

Formula Ar-5

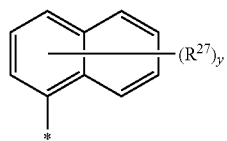

Formula Ar-6

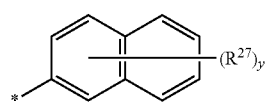

Formula Ar-7

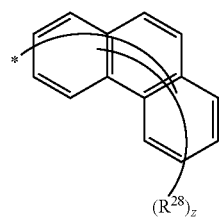

Wherein,
1) $R^{25}$, $R^{26}$, $R^{27}$ and $R^{28}$ are the same as the definition of $R^{23}$, or an adjacent plurality of $R^{25}$s, a plurality of $R^{28}$s, a plurality of $R^{27}$s, or a plurality of $R^{28}$s may be bonded to each other to form a ring,
2) w is an integer from 0 to 5, x is an integer from 0 to 4, y is an integer from 0 to 7, z is an integer from 0 to 9,
3) * means a moiety bonded to Formula 3.

Also, $Ar^{11}$ is represented by Formula Ar-8.

Formula Ar-8

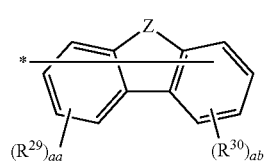

Wherein,
1) Z is O, S, $C(R^{31})(R^{32})$, $NR^{33}$ or N,
However, when Z is combined with Formula 3, it is N,
2) $R^{29}$, $R^{39}$, $R^{31}$, $R^{32}$ and $R^{33}$ are the same as definition of $R^{23}$, or an adjacent plurality of $R^{29}$s, a plurality of $R^{30}$s, a plurality of $R^{31}$s, a plurality of $R^{32}$s may be bonded to each other to form a ring,
3) aa and ab are independently integers from 0 to 4;
4) * means a moiety bonded to Formula 3.

Specifically, Formula 3 may be any one of the following compounds N 1-1 to N 1-100, but is not limited thereto.

N 1-1

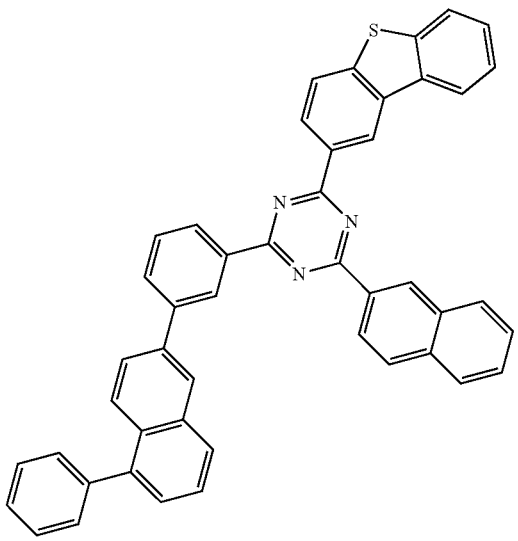

N 1-2

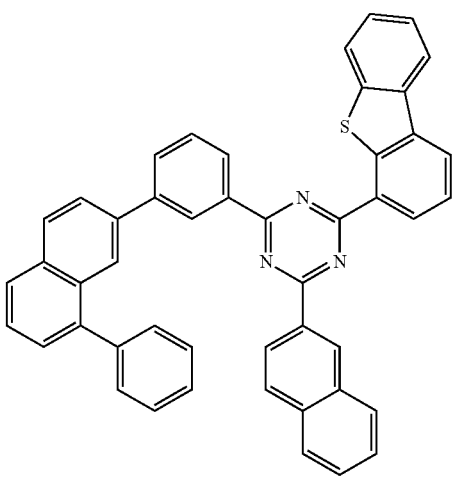

N 1-3

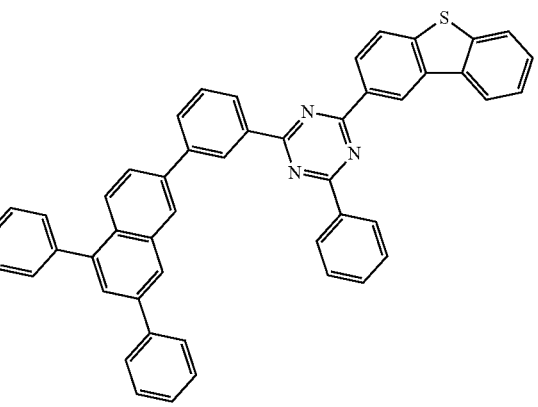

N 1-4
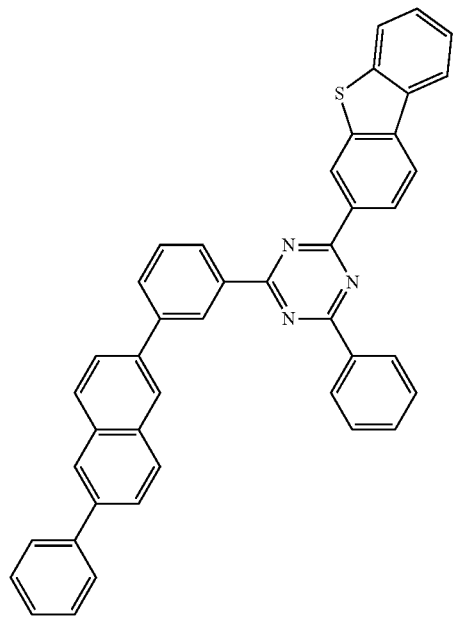
N 1-5
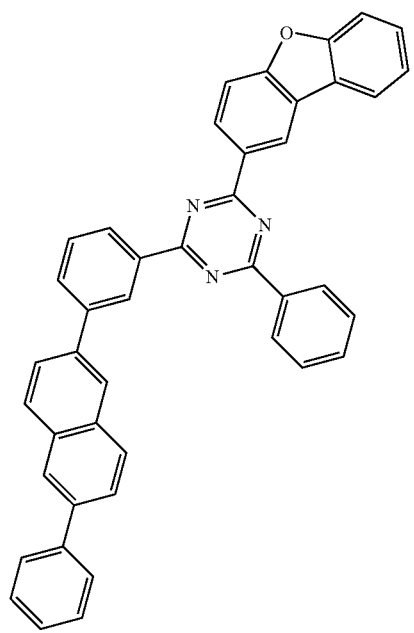
N 1-6
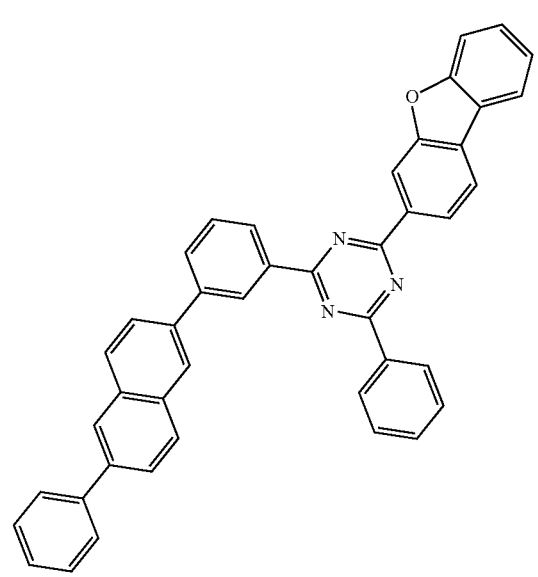
N 1-7
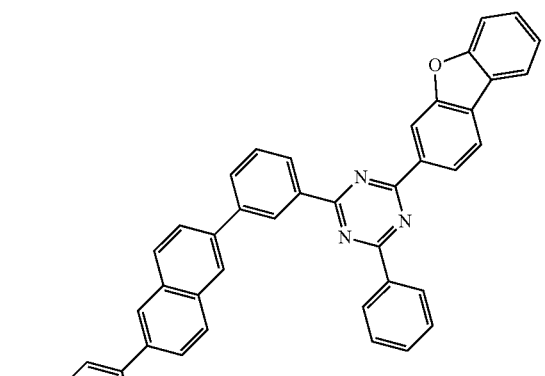
N 1-8
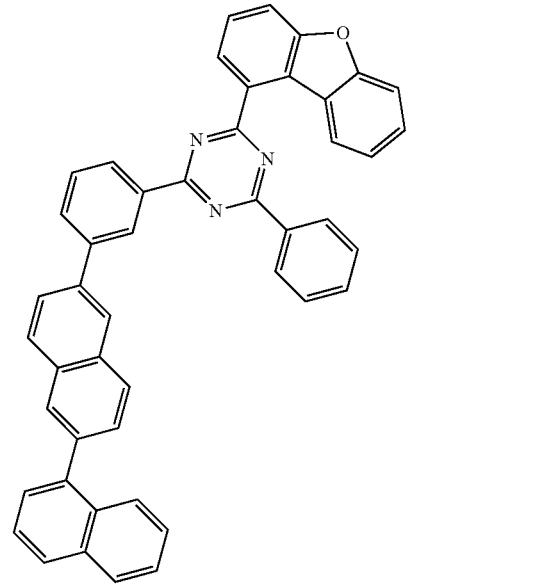

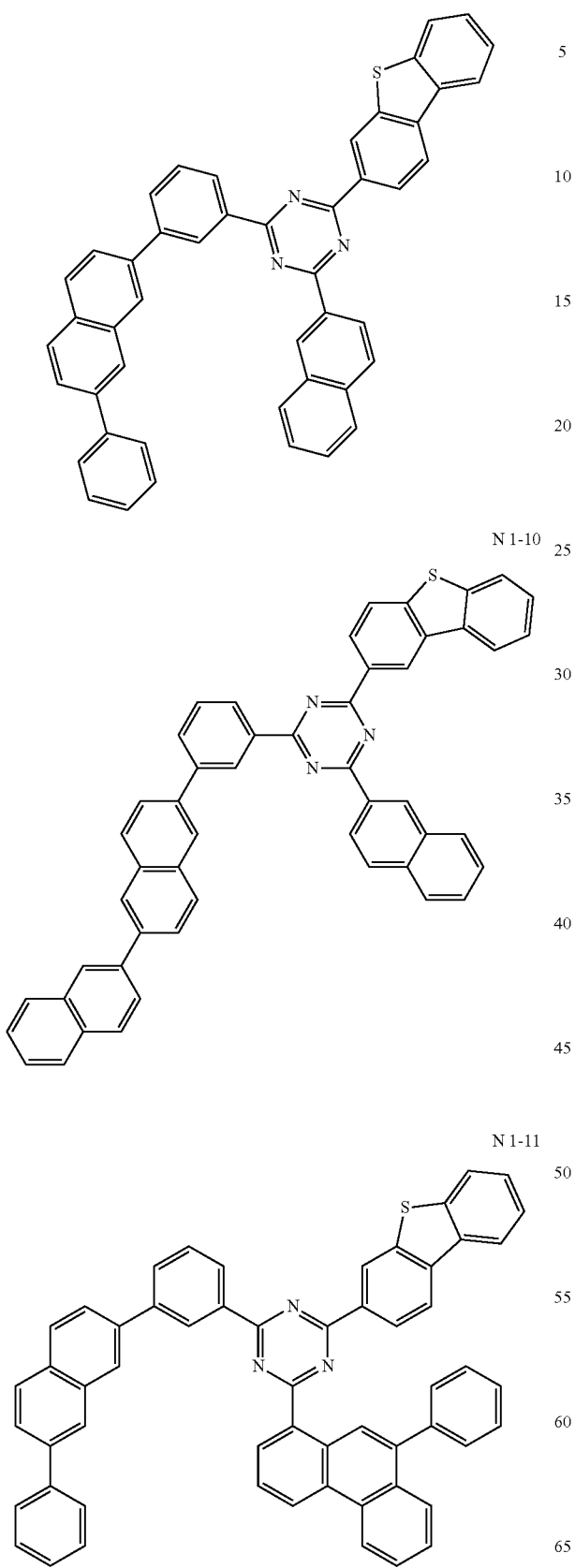
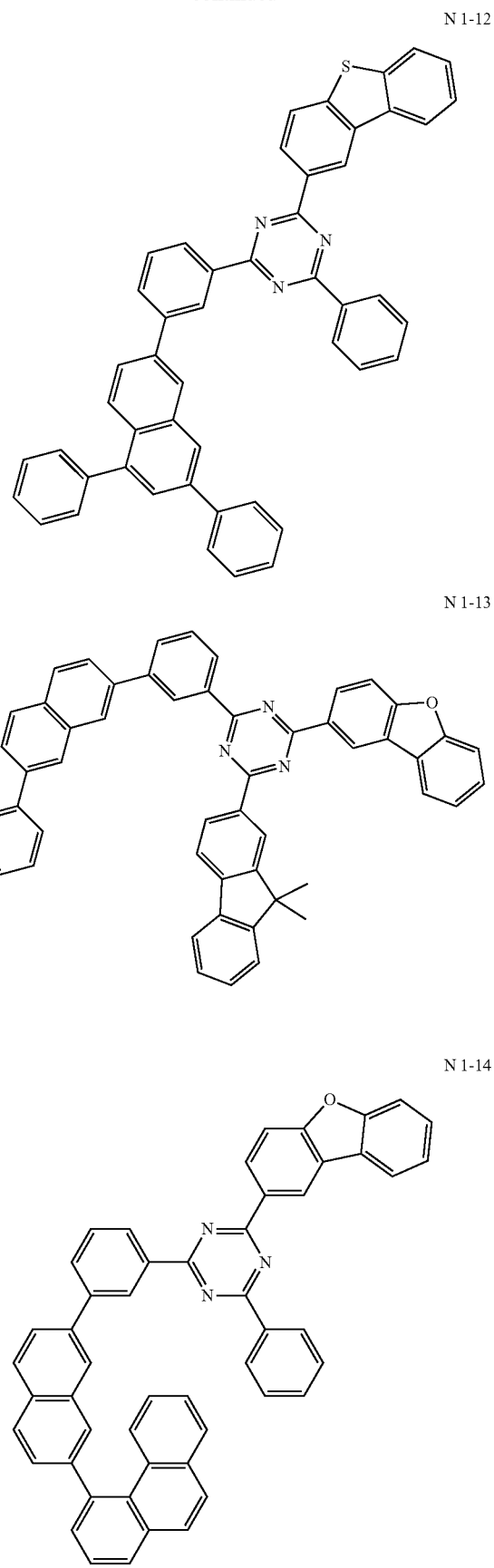

N 1-15
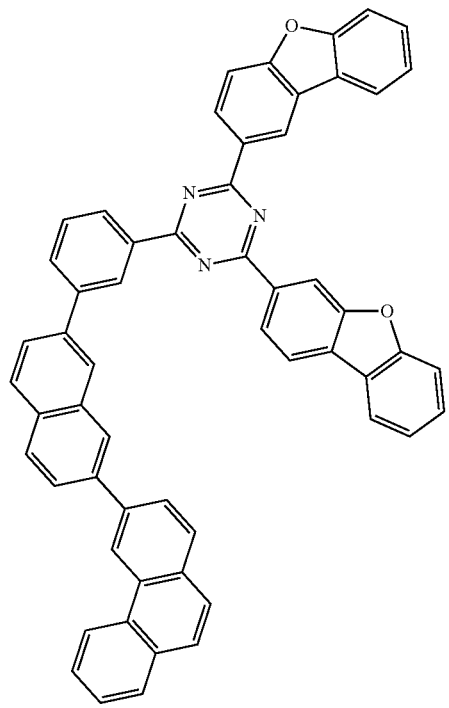
N 1-16
N 1-17
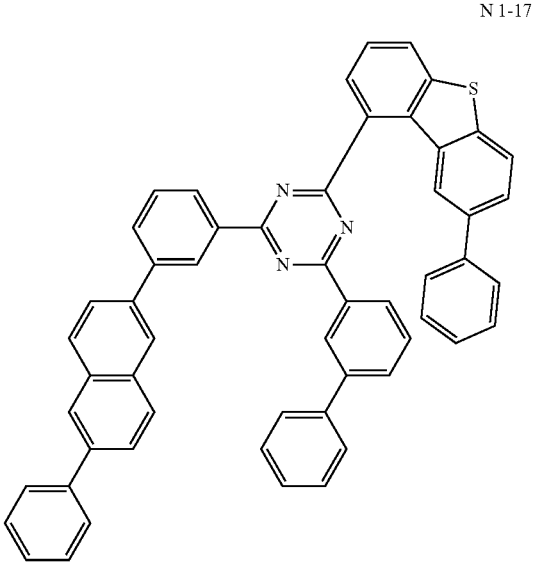
N 1-18
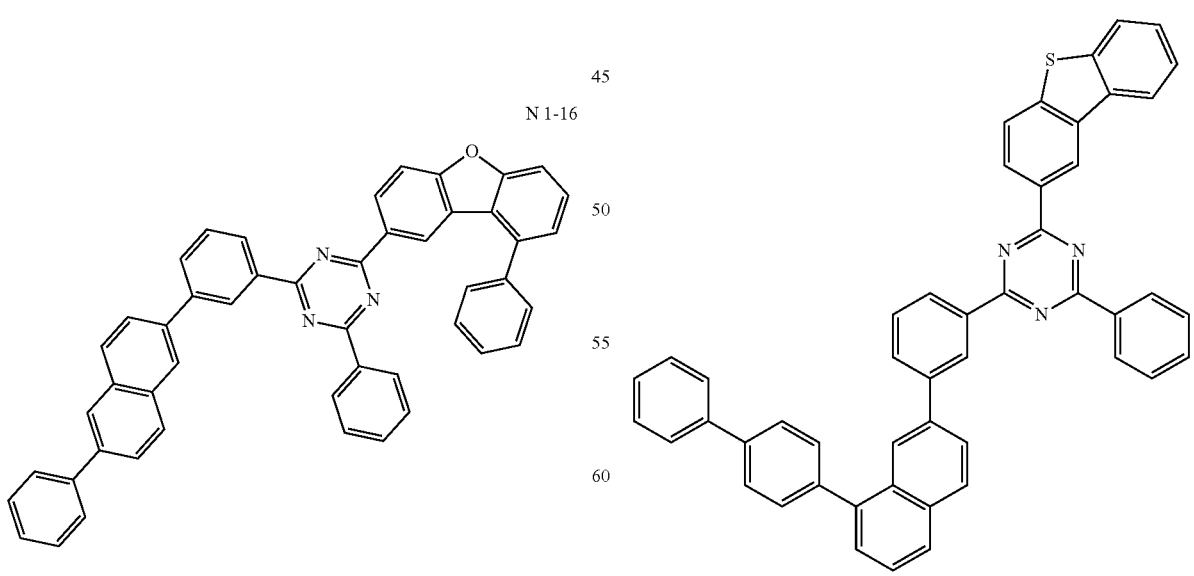

N 1-19
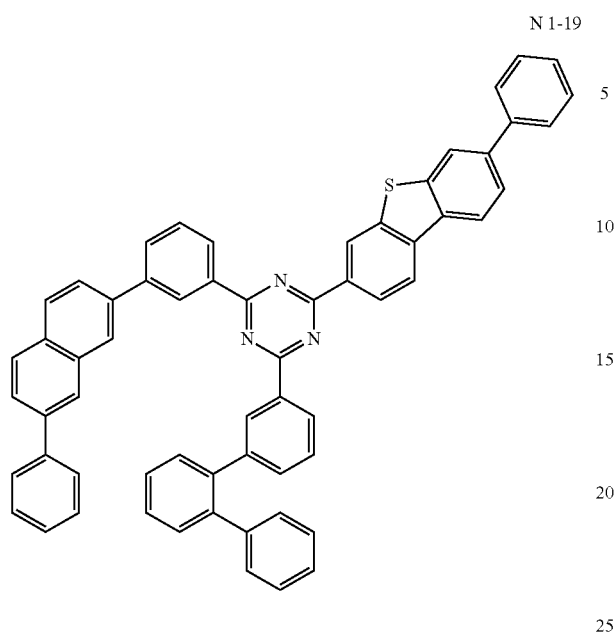
N 1-21
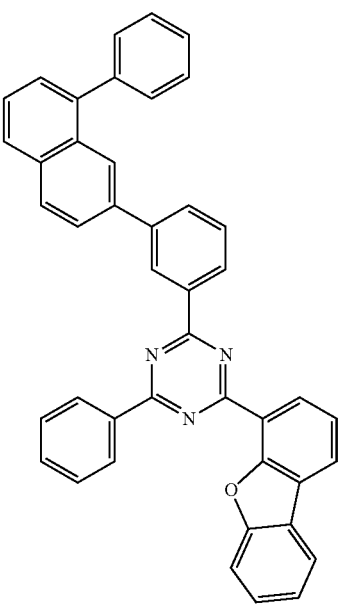
N 1-20
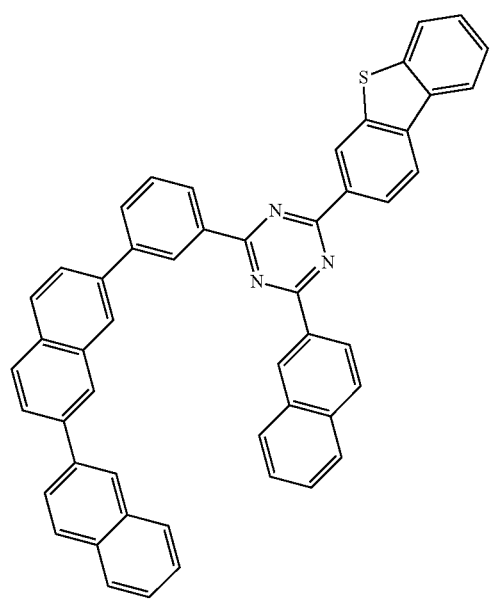
N 1-22

N 1-23
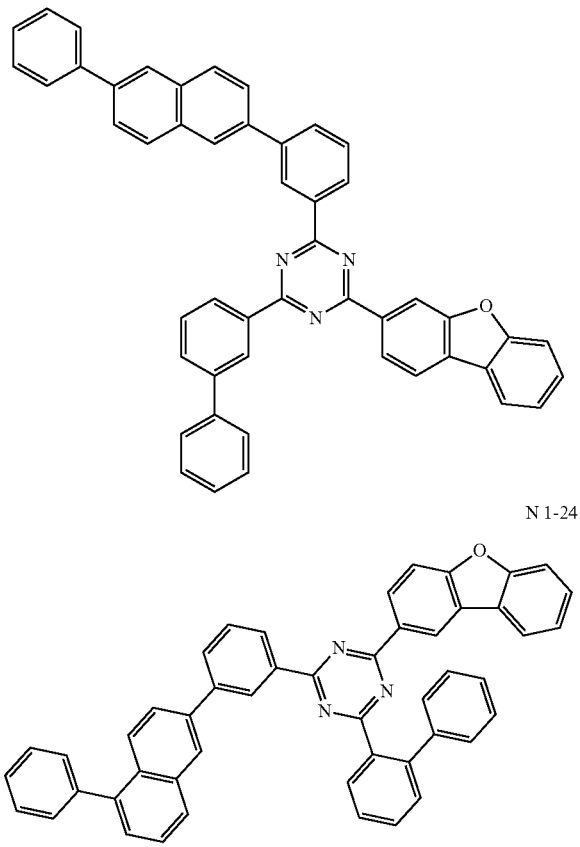
N 1-27
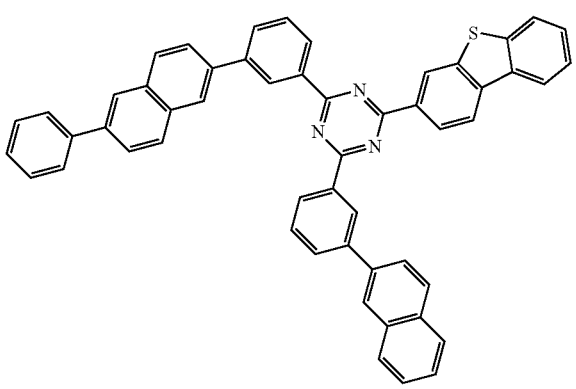
N 1-24
N 1-28
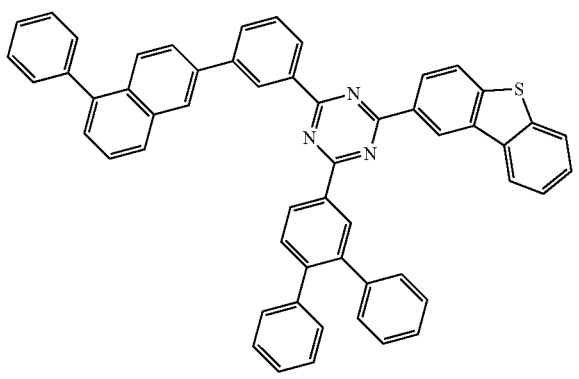
N 1-25
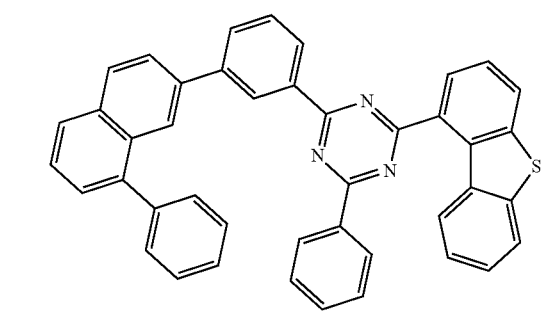
N 1-29
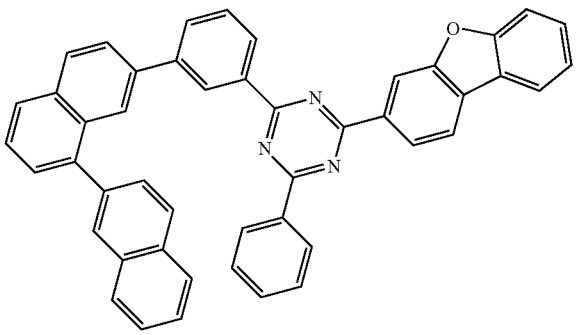
N 1-26
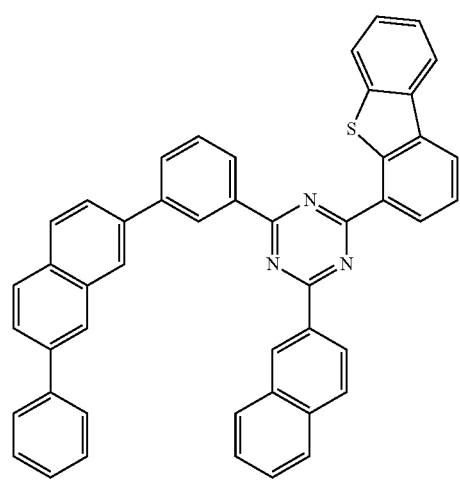
N 1-30
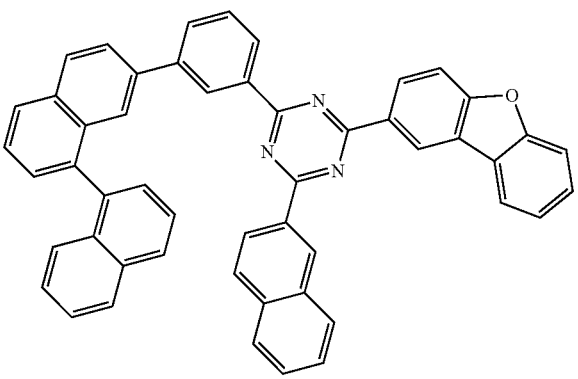

N 1-31
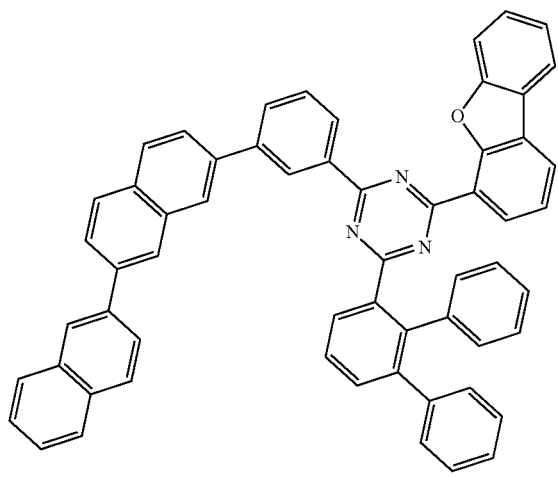
N 1-32
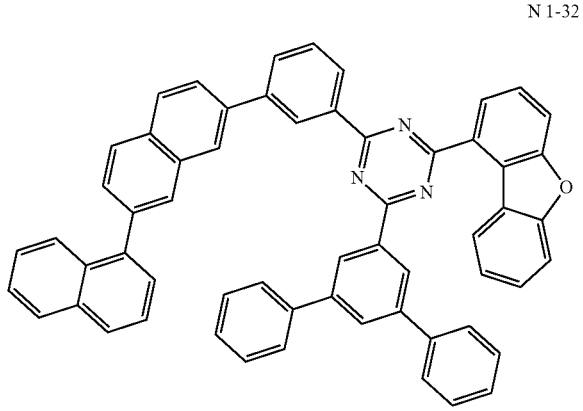
N 1-33
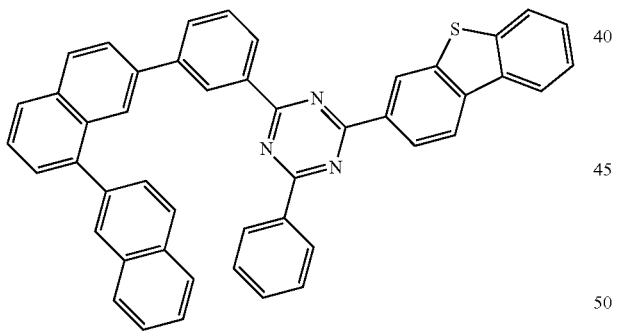
N 1-34
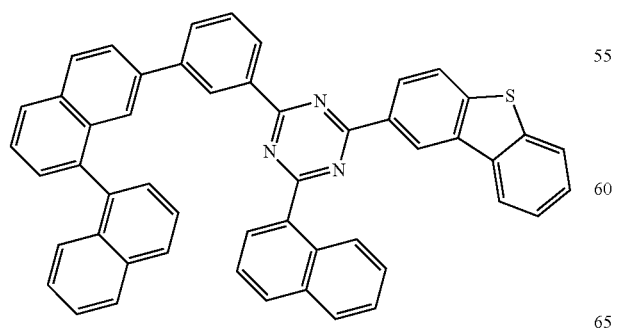
N 1-35
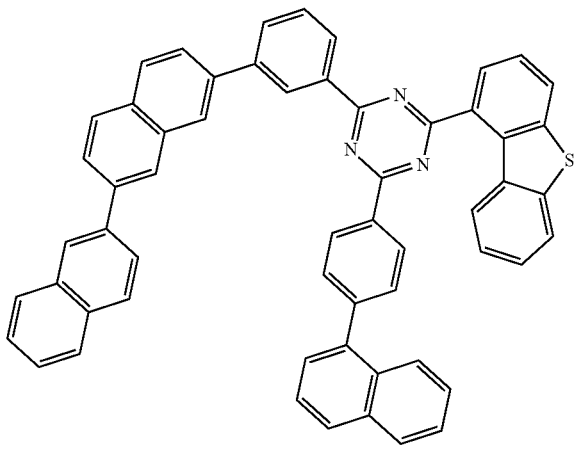
N 1-36
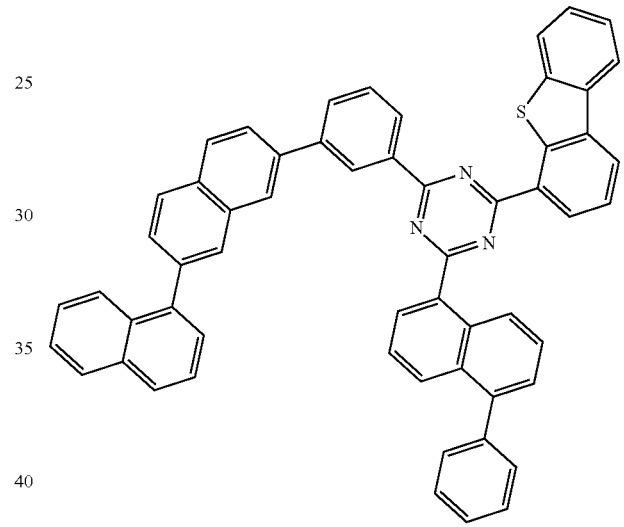
N 1-37
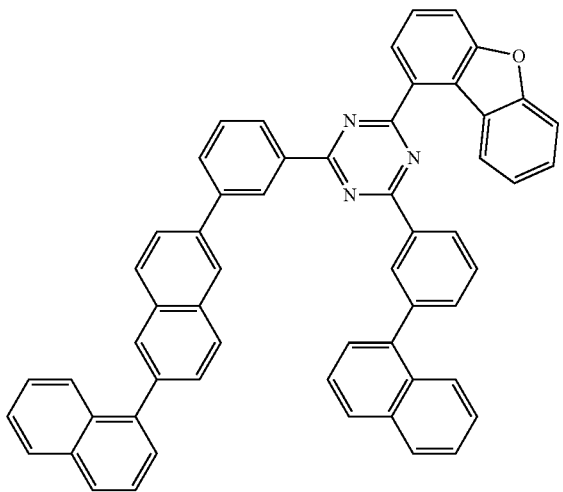

N1-38
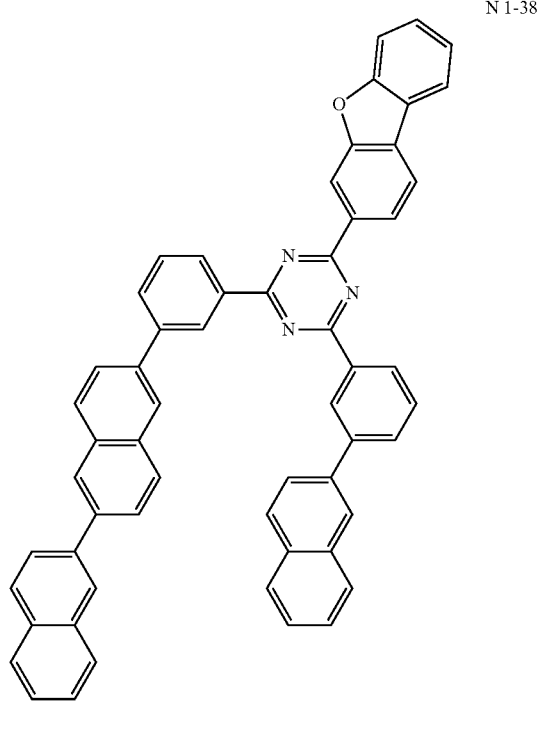
N1-39
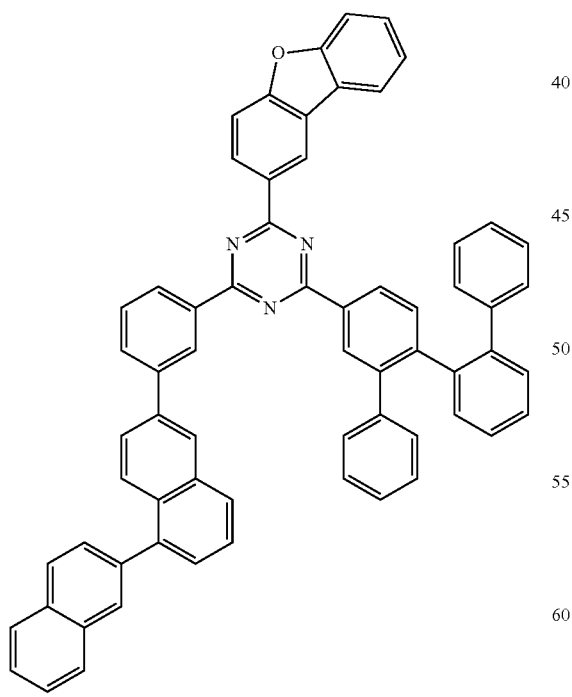
N1-40
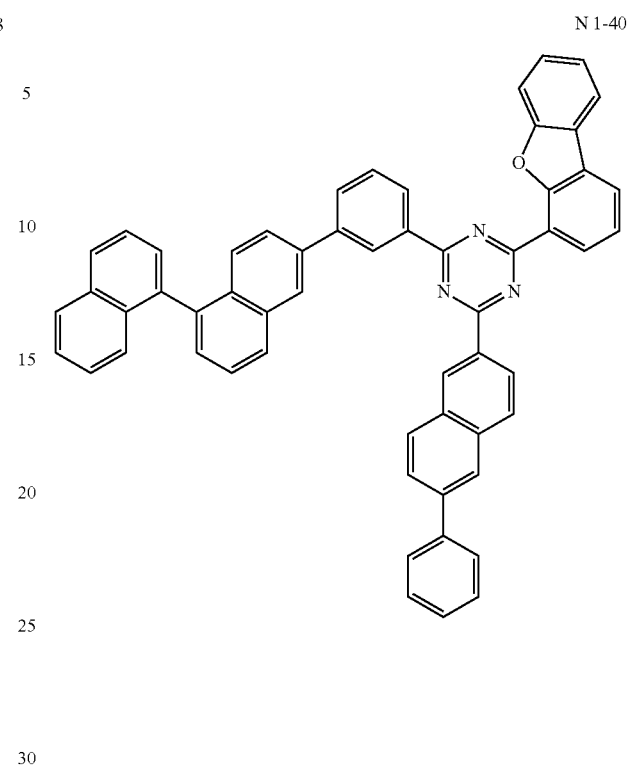
N1-41
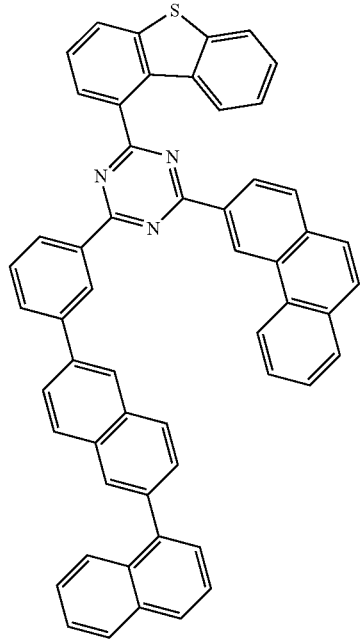

N 1-42
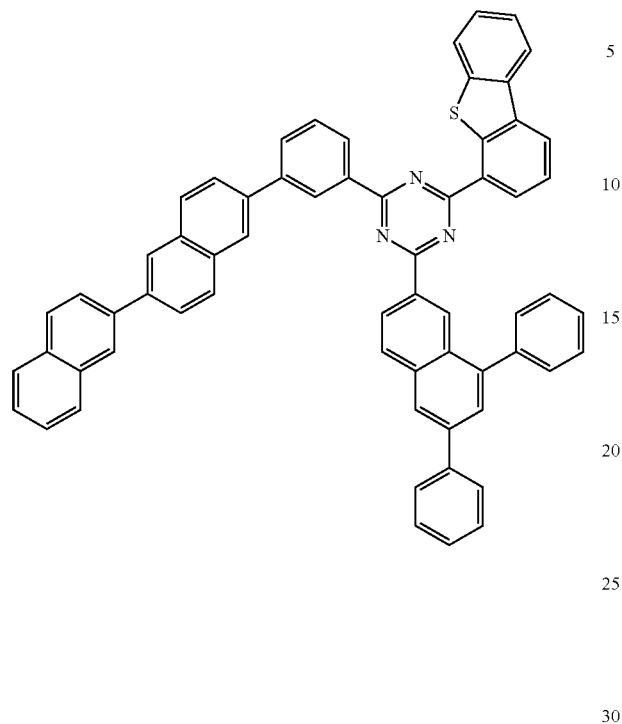
N 1-44
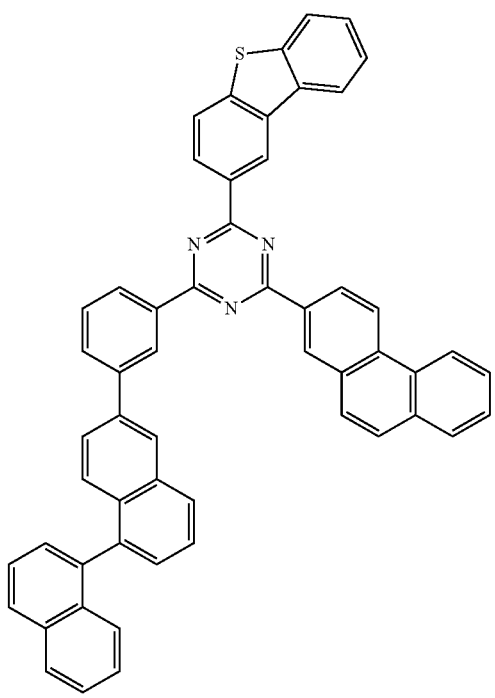
N 1-43
N 1-45
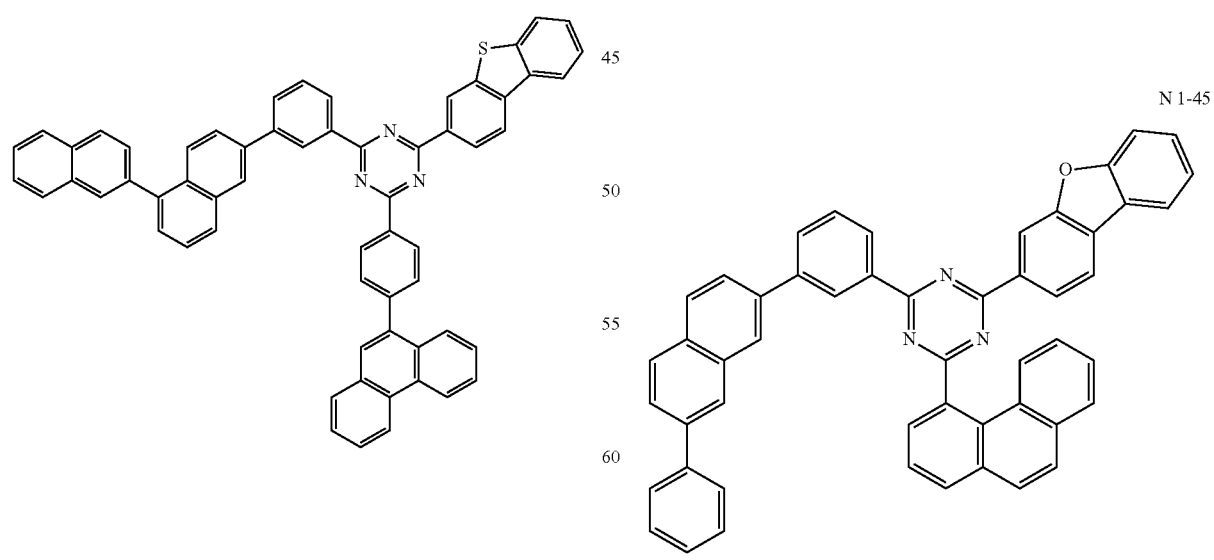

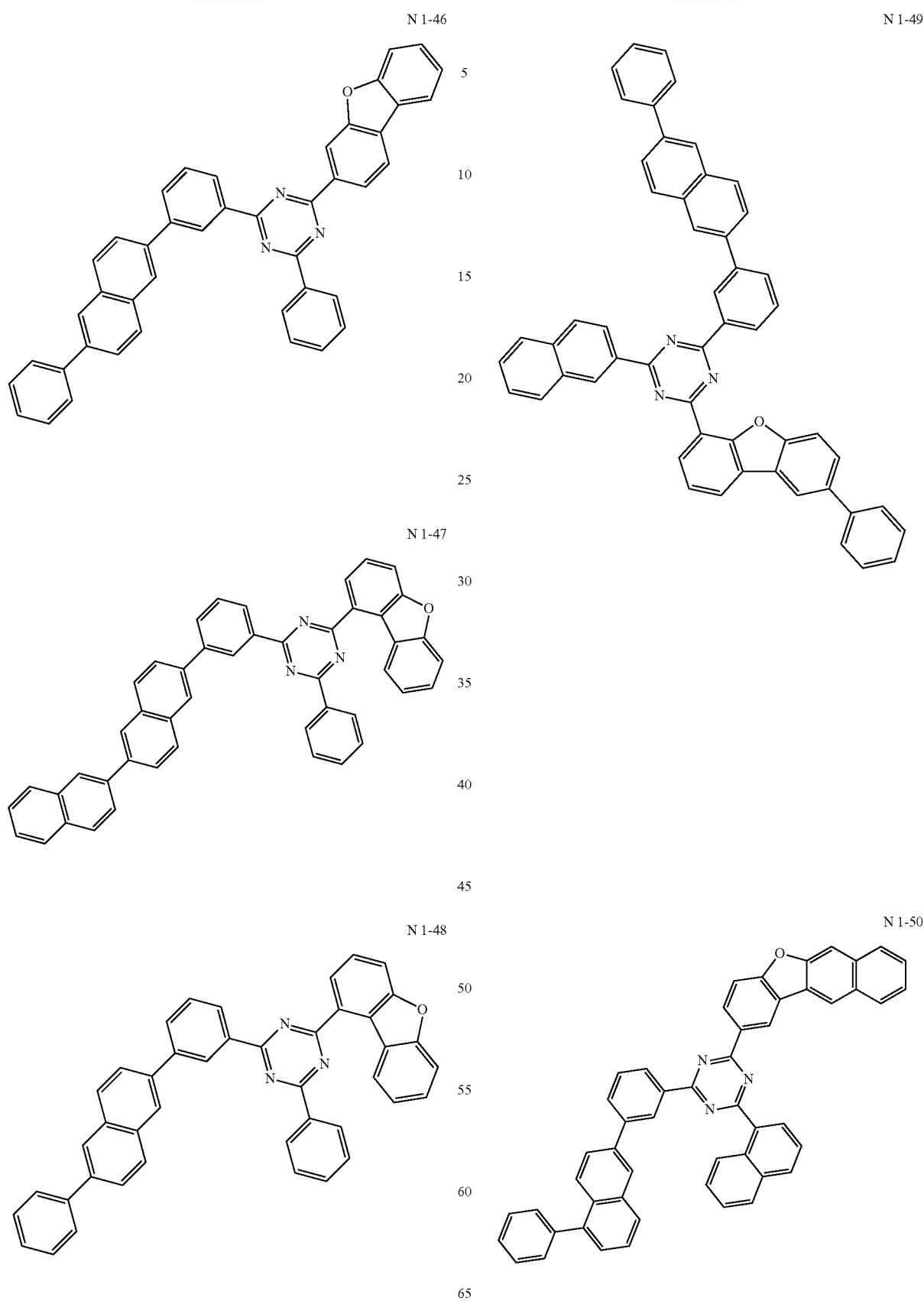

N 1-51
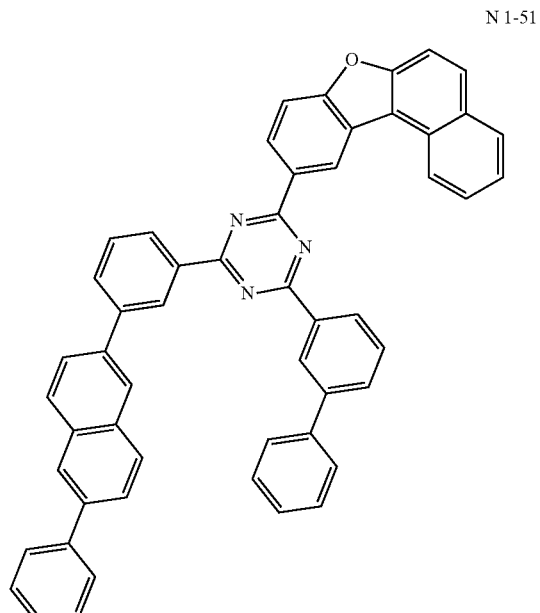
N 1-52
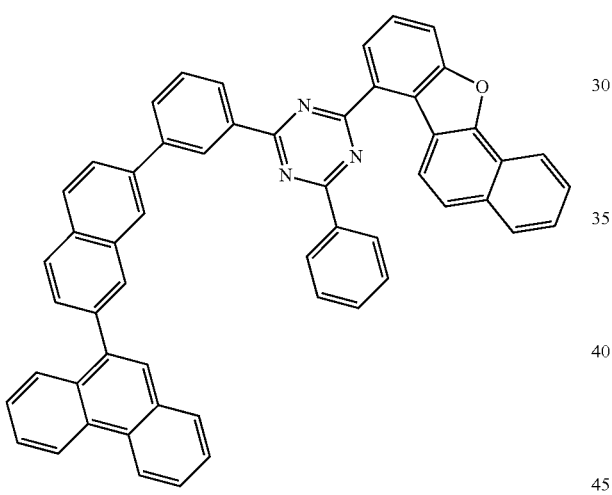
N 1-53
N 1-54
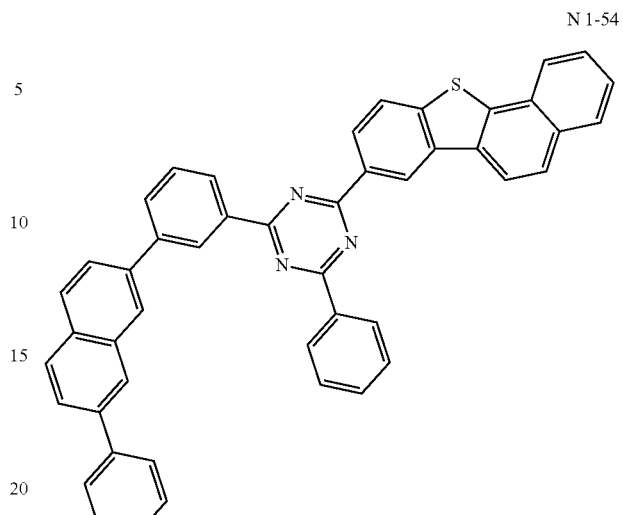
N 1-55
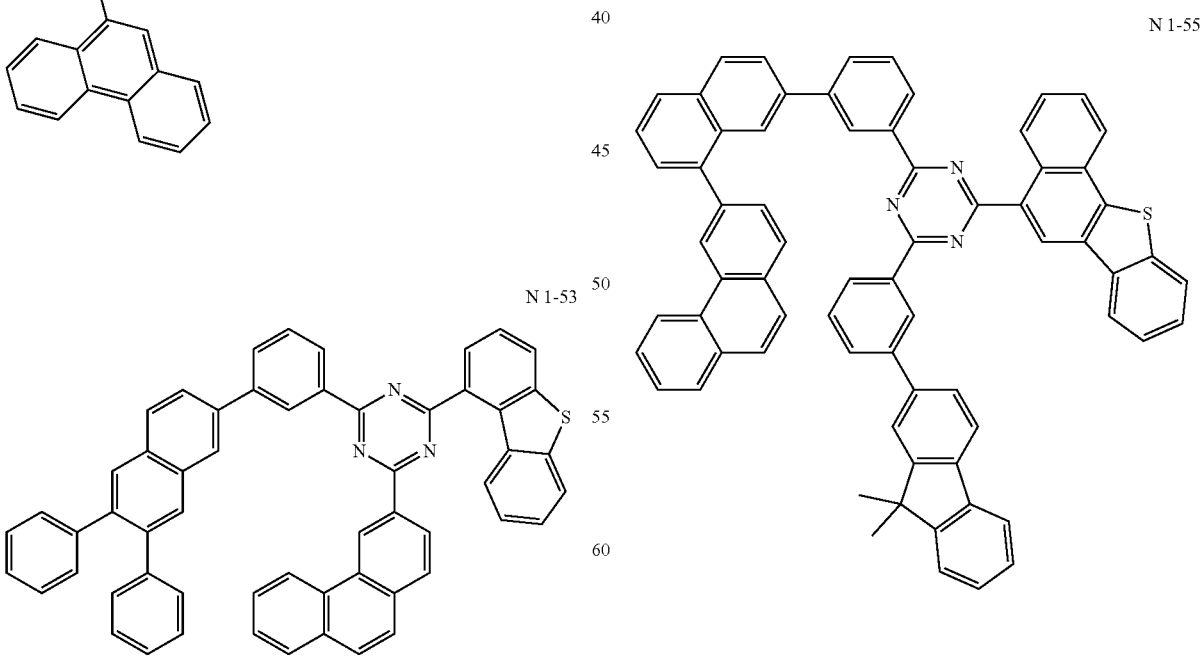

N1-56
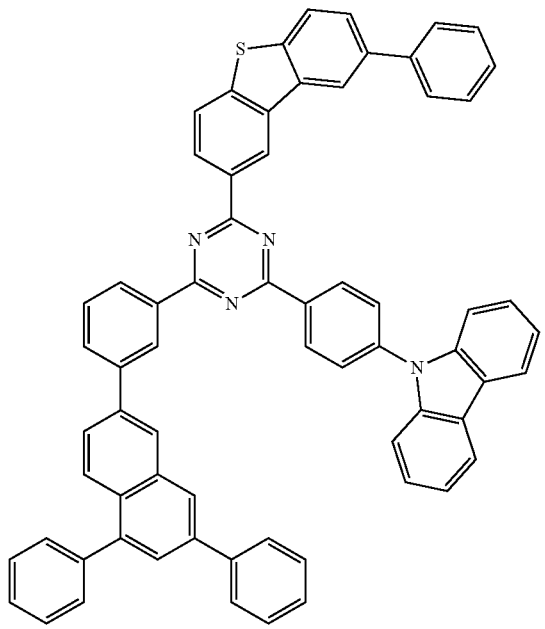
N1-57
N1-58
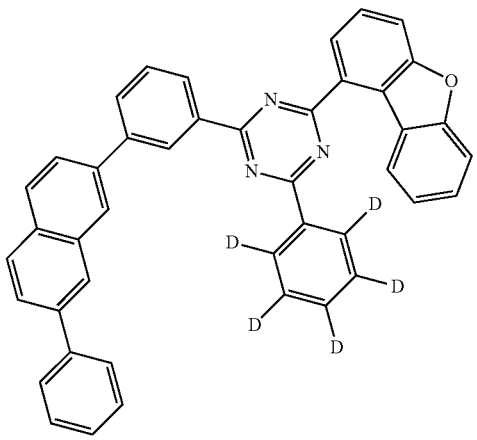
N1-59
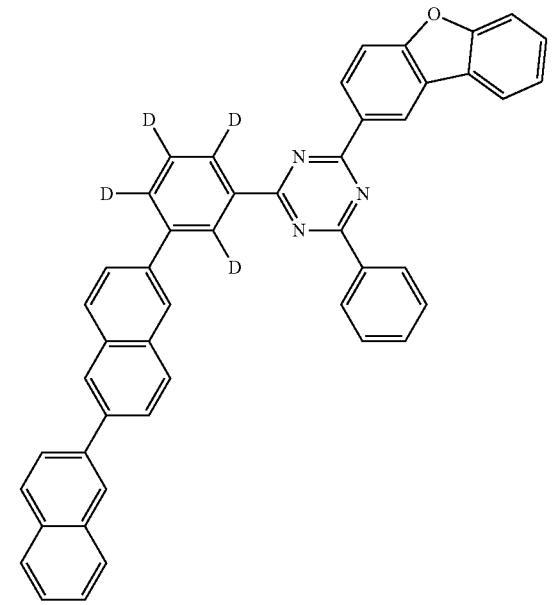
N1-60
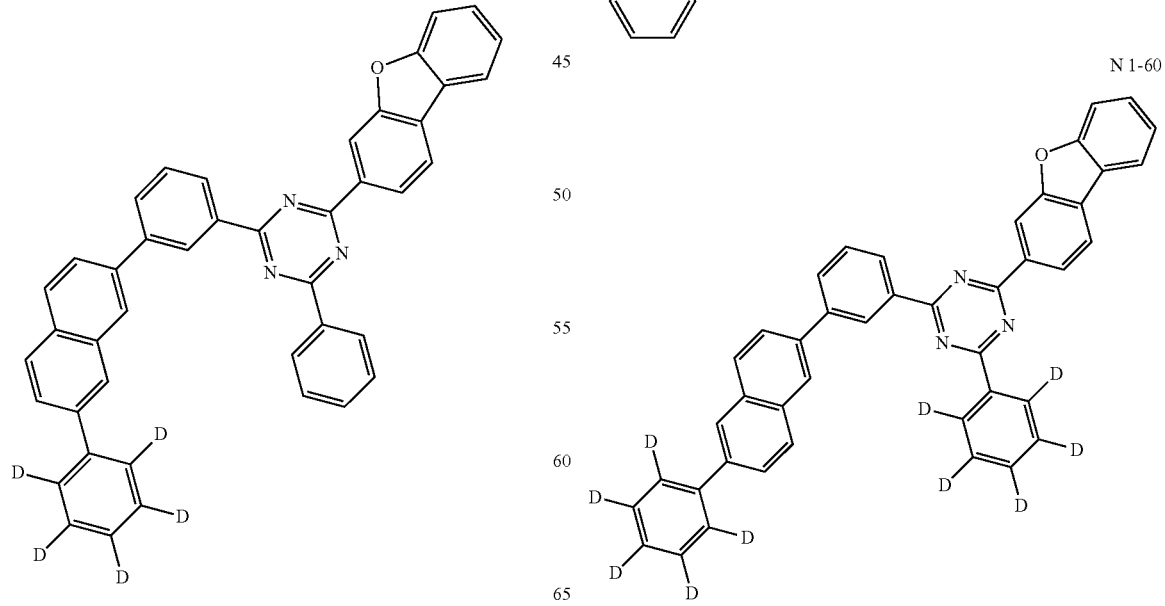

N 1-61
N 1-62
N 1-63
N 1-64
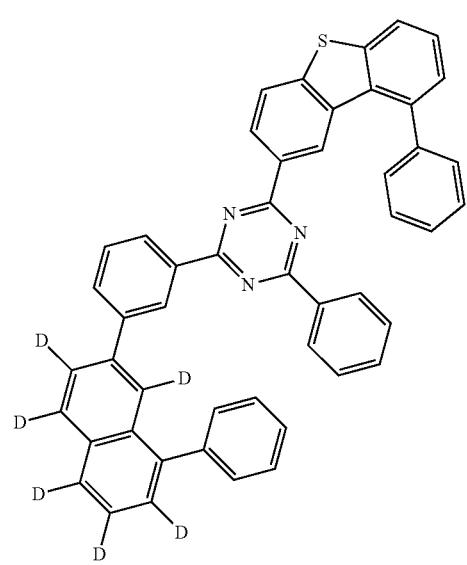
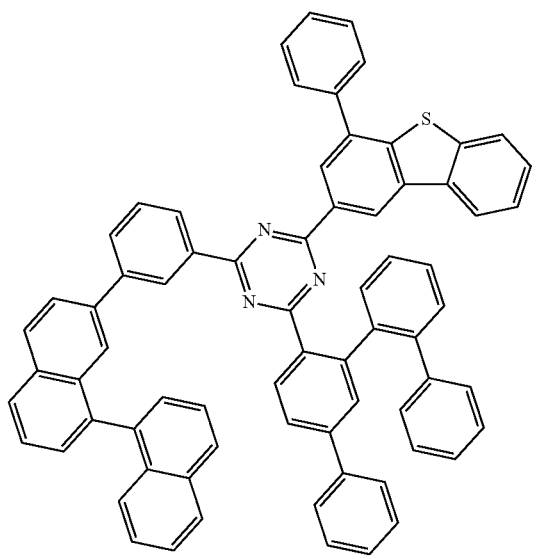
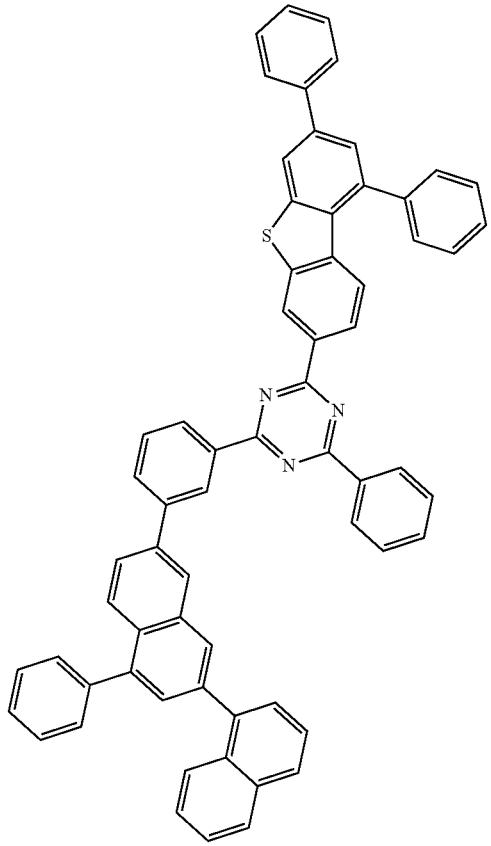

N 1-65
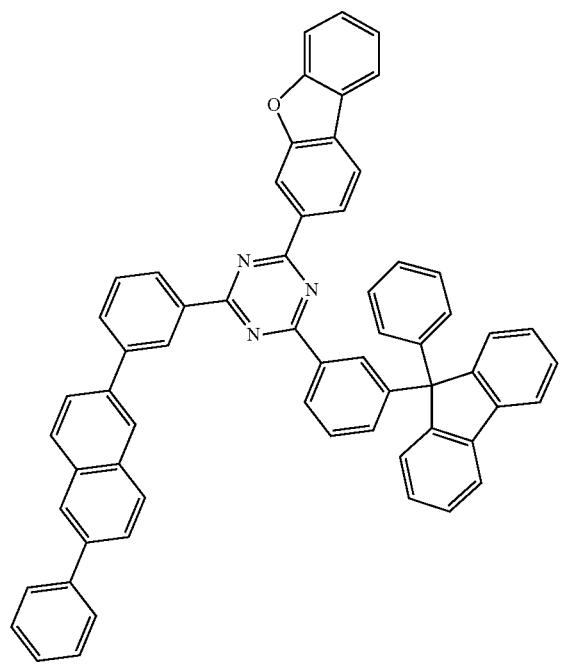
N 1-66
N 1-67
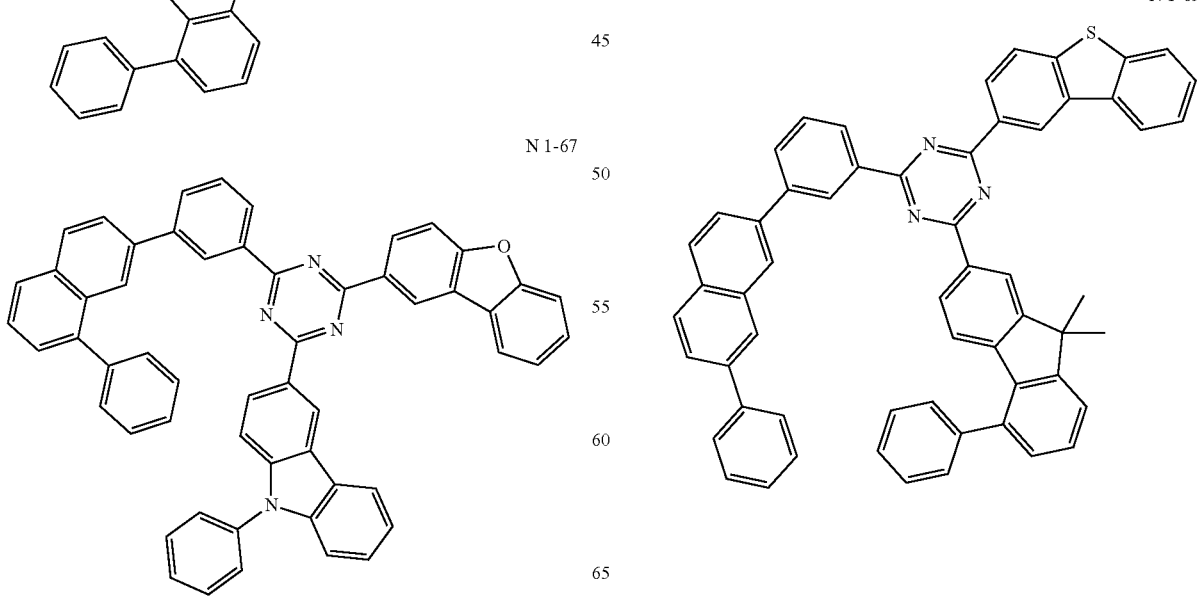
N 1-68
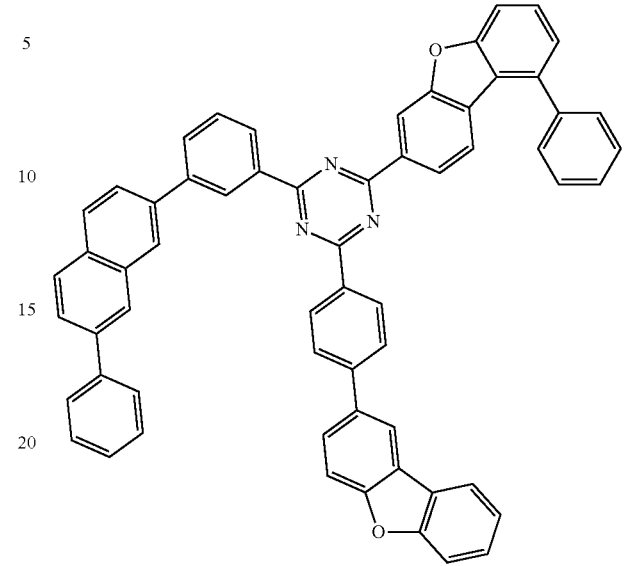
N 1-69

-continued
N1-70
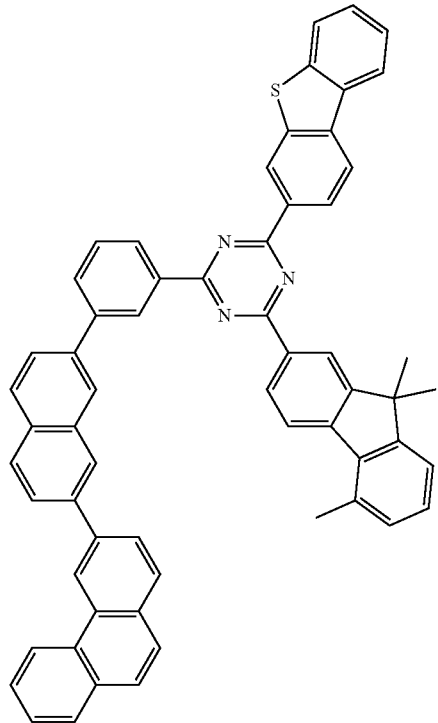
N1-72
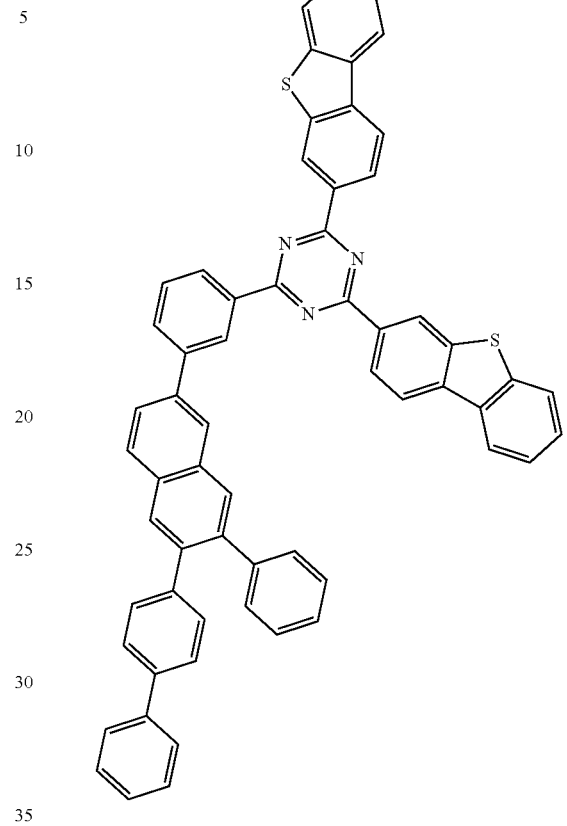
N1-71
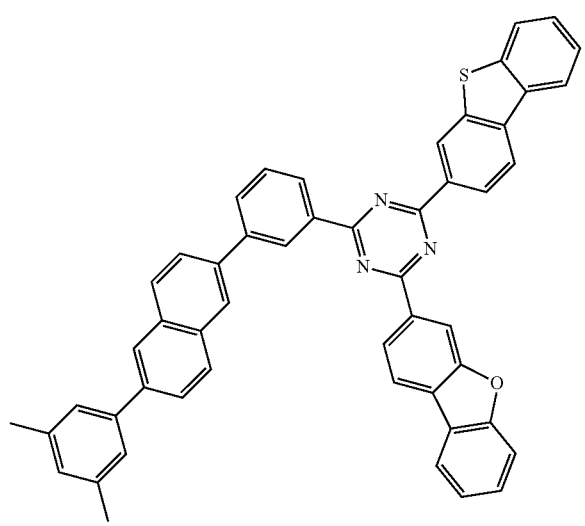
N1-73
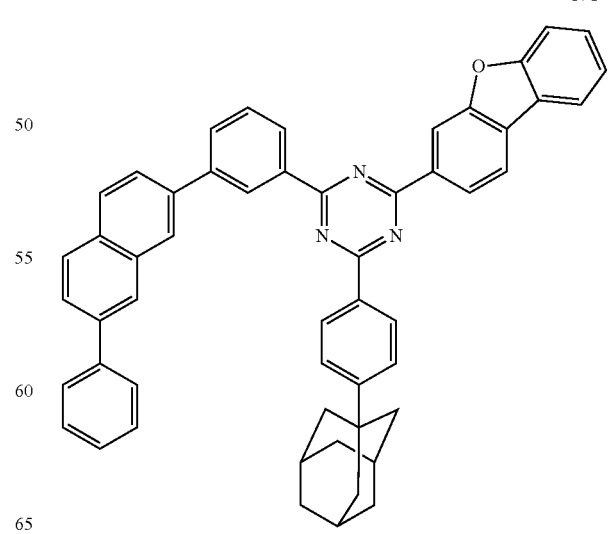

N 1-74
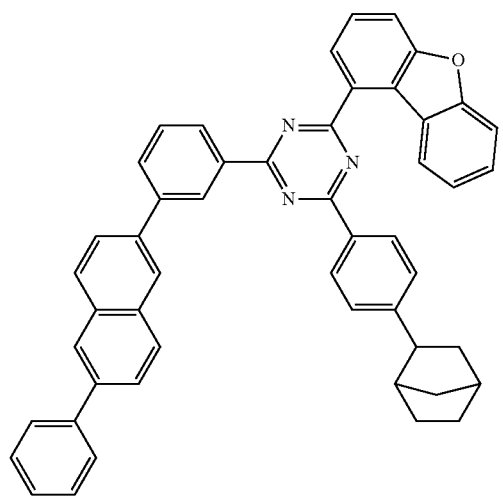
N 1-76
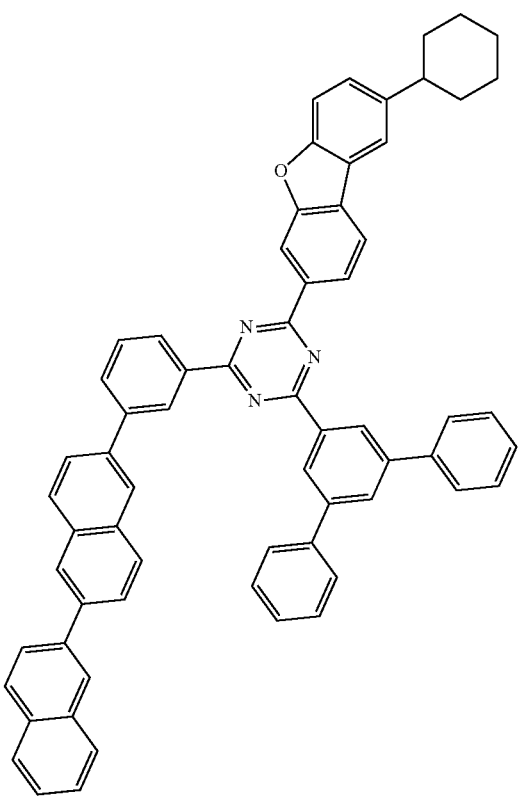
N 1-75
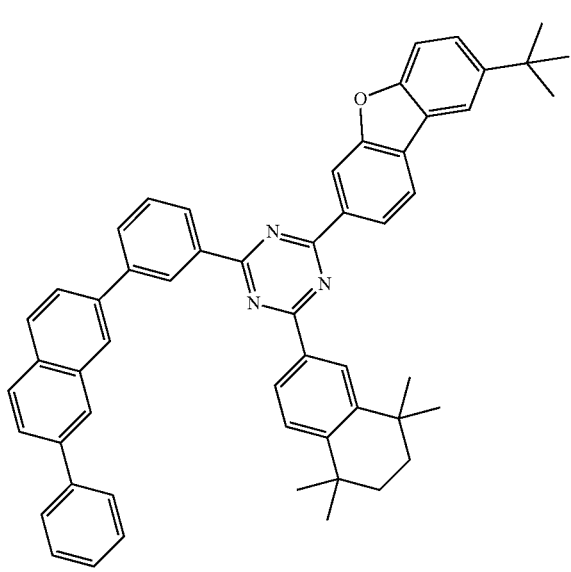
N 1-77
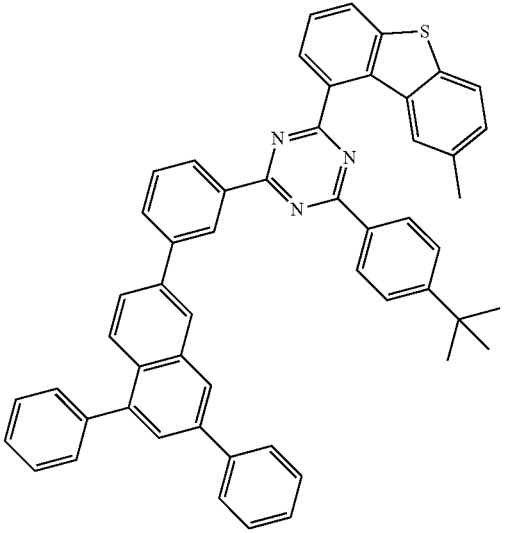

N 1-78
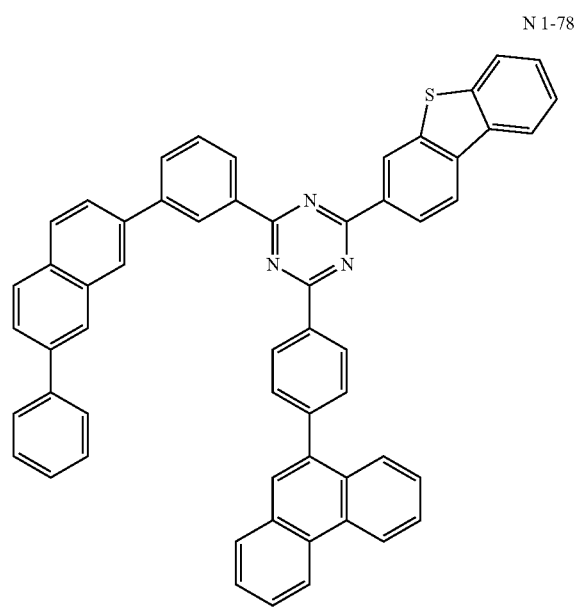
N 1-79
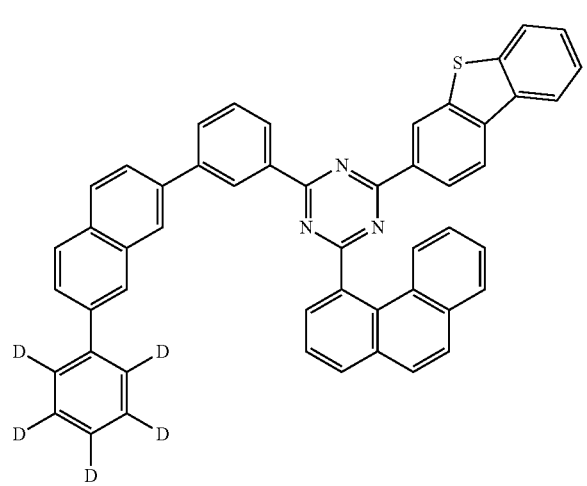
N 1-80
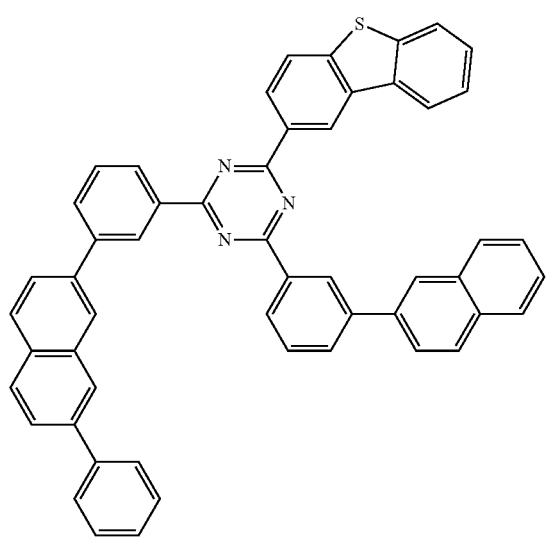
N 1-81
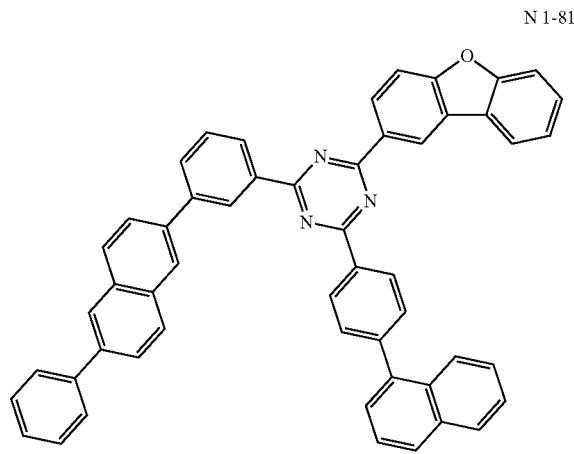
N 1-82
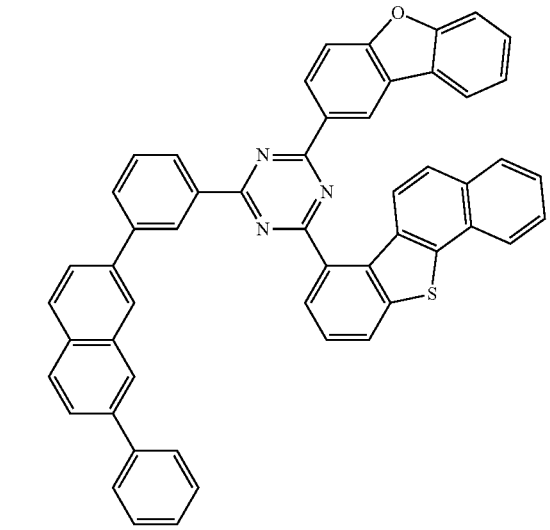
N 1-83
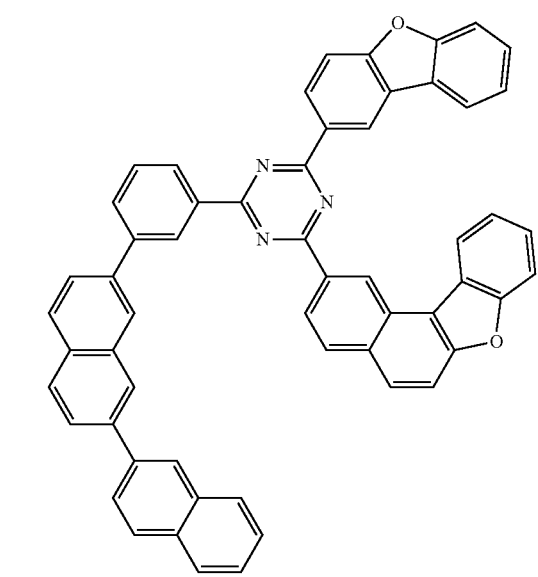

N 1-84
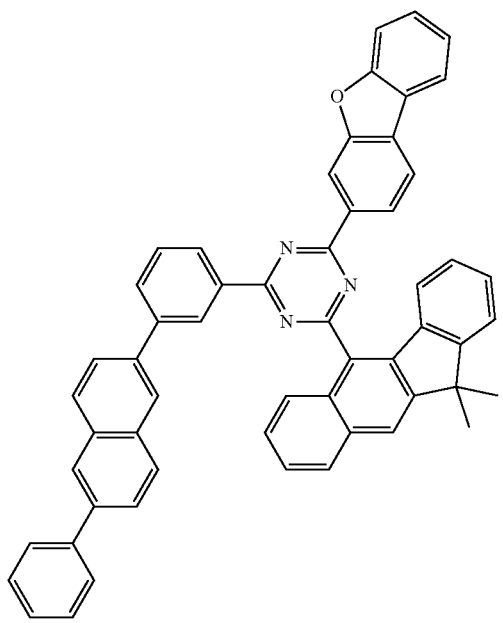
N 1-85
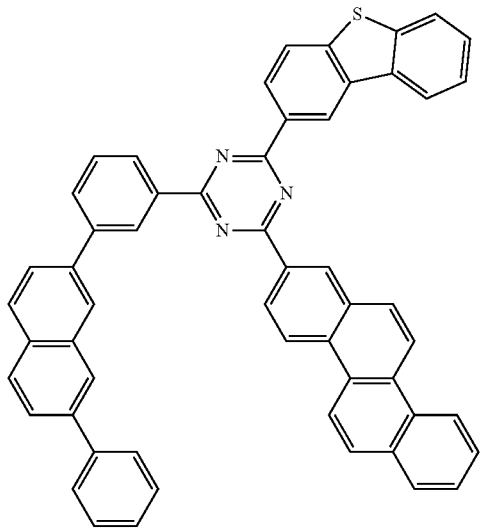
N 1-86
N 1-87
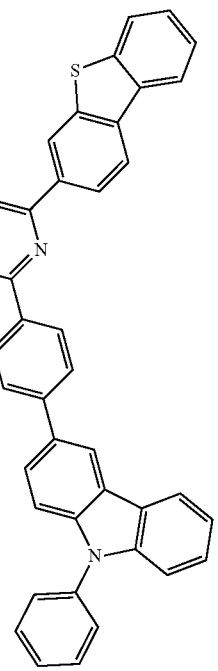

N 1-88
N 1-89
N 1-90
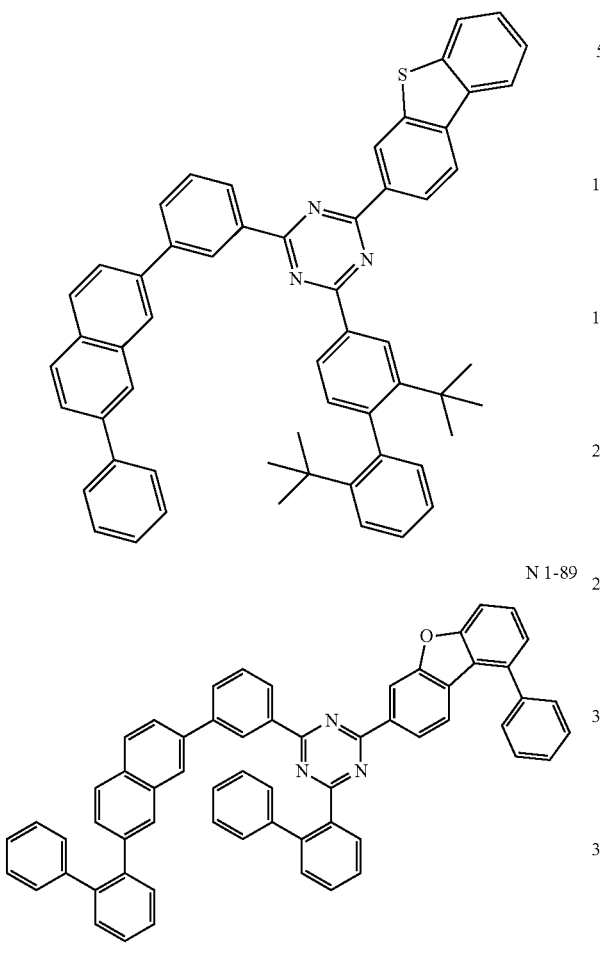
N 1-91
N 1-92
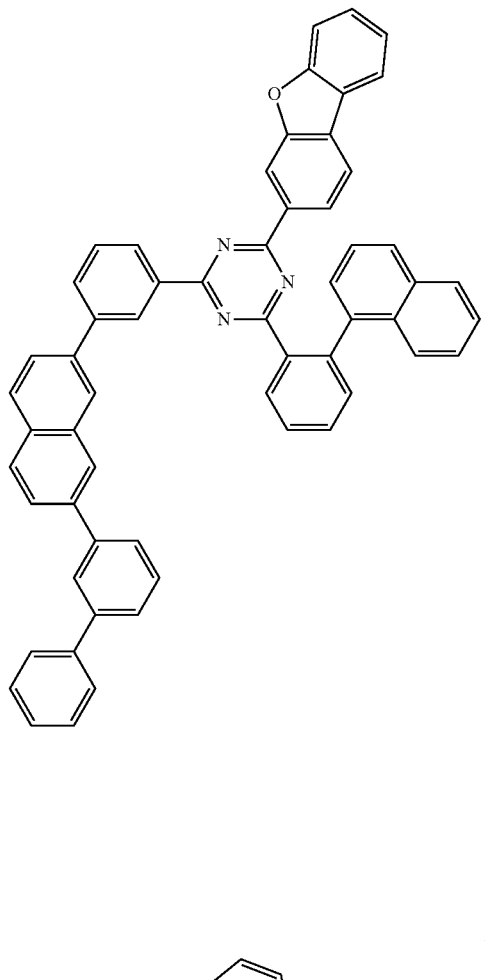

N 1-93
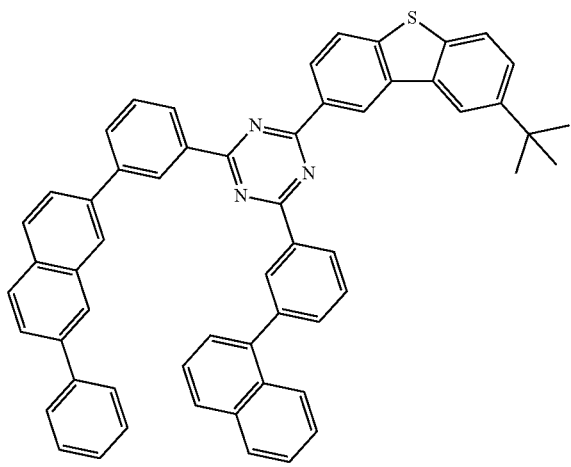
N 1-94
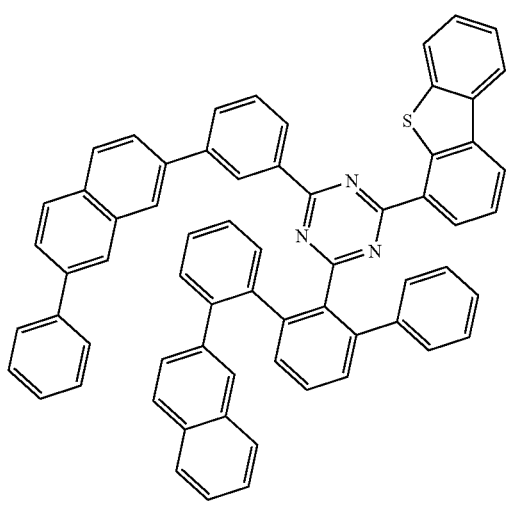
N 1-95
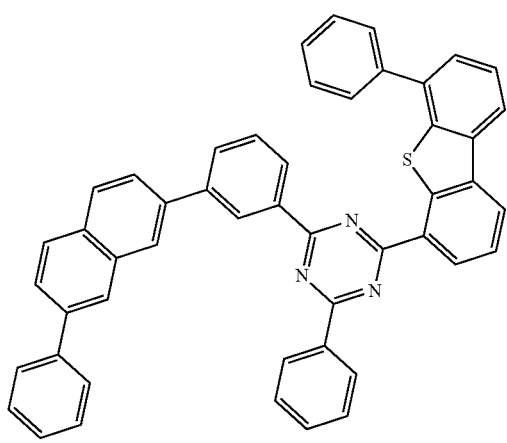
N 1-96
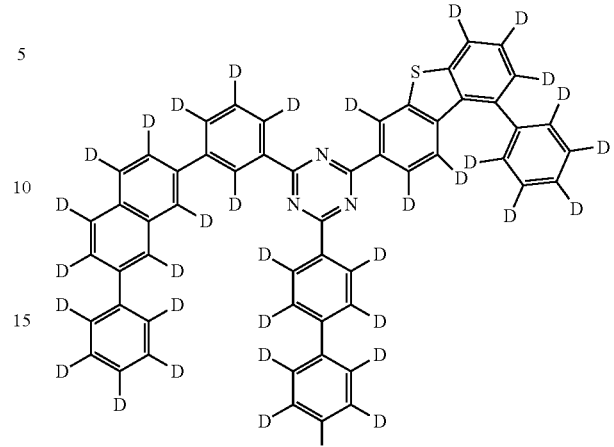
N 1-97
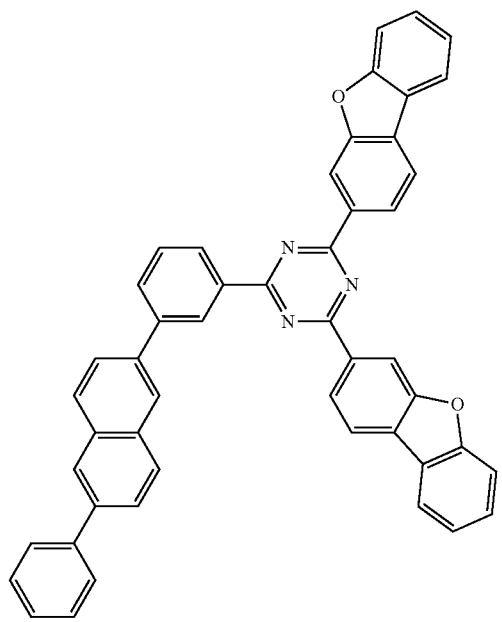
N 1-98
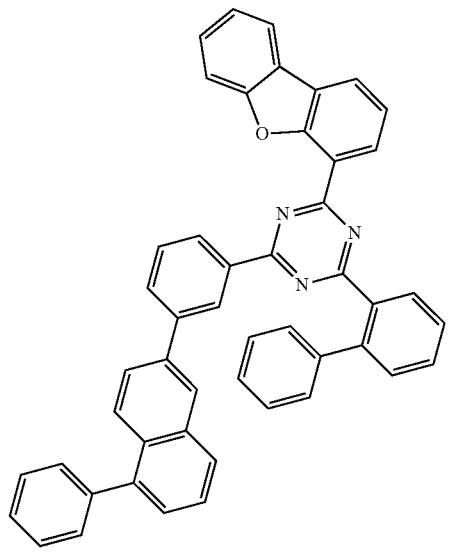

-continued

N 1-99

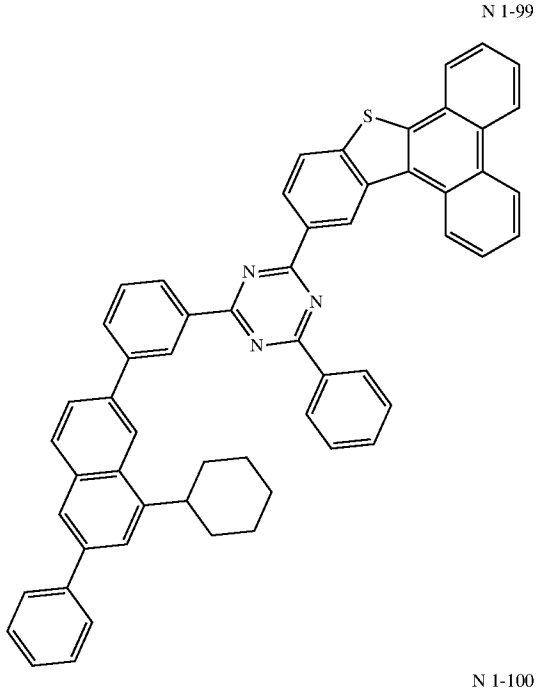

N 1-100

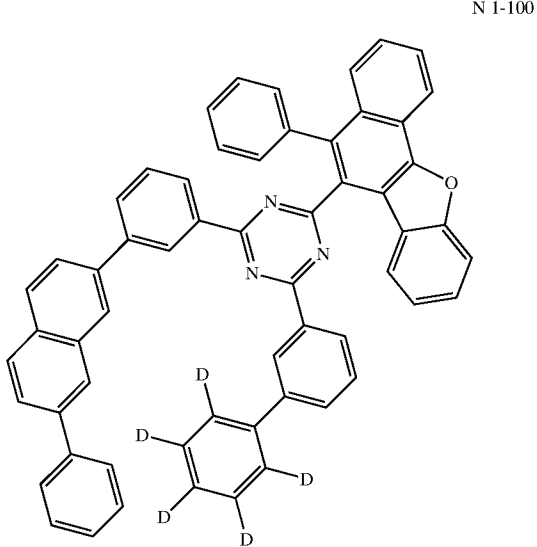

Reorganization energy refers to the energy lost due to changes in molecular structure arrangement during the movement of charges (electrons, holes). It depends on the molecular geometry, and has a characteristic that the value becomes smaller as the difference between the PES (Potential Energy Surface) of the neutral state and the PES of the charged state is small. RE value can be obtained by the following formula.

$$RE_{hole}: \lambda^+ = (E_{NOCE} - E_{COCE}) + (E_{CONE} - E_{NONE})$$

$$RE_{elec}: \lambda^- = (E_{NOAE} - E_{AOAE}) + (E_{AONE} - E_{NONE})$$

Each factor is described as NONE: Neutral geometry of Neutral molecules (=NO opt.), NOAE: Anion geometry of Neutral molecules, NOCE: Cation geometry of Neutral molecules, AONE: Neutral geometry of Anion molecules, AOAE: Anion geometry of Anion molecules (=AO opt.), CONE: Neutral geometry of Cation molecules, COCE: Cation geometry of Cation molecules (=CO opt.)

The value of Reorganization Energy is inversely proportional to mobility, and under the condition that they have the same r and T values, RE value of each material directly affects the mobility. The relation between RE value and mobility is expressed as follows.

$$\mu = k \frac{r^2}{2k_B T/e}$$

$$k = \left(\frac{4\pi^2}{h}\right) \frac{t^2}{\sqrt{4\pi \lambda k_B T}} \exp\left[-\frac{\lambda}{4k_B T}\right]$$

Each factor is described as $\lambda$: Reorganization energy/$\mu$: mobility/r: dimer displacement/t: intermolecular charge transfer matrix element. From the above equation, it can be seen that the lower RE value, the faster the mobility.

Reorganization energy value requires a simulation tool that can calculate the potential energy according to the molecular structure, we used Gaussian09 (hereinafter G09) and Jaguar module of Schrodinger Materials Science (hereinafter JG). Both G09 and JG are tools to analyze the properties of molecules through quantum mechanical (QM) calculations, and have the function of optimizing the molecular structure or calculating the energy for a given molecular structure (single-point energy).

The process of performing QM calculations in molecular structures requires large computational resources, and our company uses 2 cluster servers for these calculations. Each cluster server consists of 4 node workstations and 1 master workstation, each node performed molecular QM calculations by Parallel computing through symmetric multi-processing (SMP) using a CPU with more than 36 cores.

Using G09, the optimized molecular structure and its potential energy (NONE/COCE) in the neutral/charged state required for rearrangement energy were calculated. The charge state potential energy (NOCE) of the structure optimized for the neutral state and the neutral state potential energy (CONE) of the structure optimized for the charge state were calculated by changing only the charges to the 2 optimized structures. After that, the rearrangement energy was calculated according to the following relation.

$$RE_{charge}: \lambda = (E_{NOCE} - E_{COCE}) + (E_{CONE} - E_{NONE})$$

Because Schrodinger provides a function to automatically perform such a calculation process, the potential energy according to each state was sequentially calculated through the JG module by providing the molecular structure (NO) of the basic state, and the RE value was calculated.

According to an embodiment of the present invention, more electrons are attracted to an element having a greater electronegativity among two atoms in one covalent bond. Here, the relatively high electronegative atom has a $\delta-$ charge, the low electronegativity atoms have a $\delta+$ charge. As described above, the difference in polarity of two atoms is called a dipole. At this time, Dipole moment can be calculated as a vector quantity multiplied by the intensity of the two poles and the distance between the two atomic nuclei. In other words, Dipole moment can be calculated by the following equation.

$$\mu = \delta * d$$

Each factor is described by $\mu$: dipole moment/$\delta$: magnitude of the partial charges $\delta^+$ and $\delta^-$/d: distance between $\delta^+$ and $\delta^-$.

Our company used G09 to optimize the molecular structure with B3LYP/6-31G(d). Based on the result, Mulliken Charge value of each atom was obtained, and Dipole moment was calculated by multiplying the vector in the axial direction. Dipole moment is the vector sum of each bond dipole moment. Dipole moment value means the magnitude of the vector dipole moment, and it can be expressed as the value of the vector length as follows.

$$|\mu| = \sqrt{x^2 + y^2 + z^2}$$

The RE value of Formula 3 calculated in this way may be preferably 0.100 to 0.290, more preferably 0.150 to 0.260.

Also, the present invention relates to an organic electronic element comprising a first electrode; a second electrode; and an organic material layer formed between the first electrode and the second electrode, wherein the organic material layer includes an emitting layer, wherein the emitting layer is a phosphorescent emitting layer, and comprises a first host compound represented by Formula 3 and a second host compound represented by Formula 4 or Formula 5.

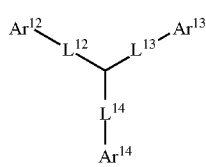

Formula 4

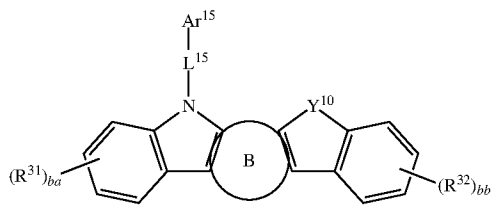

Formula 5

In Formula 4 and Formula 5, each symbol may be defined as follows.

$Ar^{12}$, $Ar^{13}$ and $Ar^{14}$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

When $Ar^{12}$, $Ar^{13}$ and $Ar^{14}$ are an aryl group, it may be preferably a $C_6$-$C_{30}$ aryl group, and more preferably a $C_6$-$C_{25}$ aryl group, for example, it may be phenylene, biphenyl, naphthalene, terphenyl, phenanthrene, etc, When $Ar^{12}$, $Ar^{13}$ and $Ar^{14}$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $Ar^{12}$, $Ar^{13}$ and $Ar^{14}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

$Ar^{15}$ is each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L"-$NR^fR^g$, When $Ar^{15}$ is an aryl group, it may be preferably a $C_6$-$C_{30}$ aryl group, and more preferably a $C_6$-$C_{25}$ aryl group, for example, it may be phenylene, biphenyl, naphthalene, terphenyl, phenanthrene, etc, When $Ar^{15}$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $Ar^{15}$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

$L^{12}$, $L^{13}$, $L^{14}$, $L^{15}$ and L" are each independently selected from the group consisting of a single bond; a $C_6$-$C_{60}$ arylene group; fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; When $L^{12}$, $L^{13}$, $L^{14}$, $L^{15}$ and L" are an arylene group, it may be preferably a $C_6$-$C_{30}$ arylene group, more preferably a $C_6$-$C_{24}$ arylene group, for example, phenylene, biphenyl, naphthalene, terphenyl, etc., When $L^{12}$, $L^{13}$, $L^{14}$, $L^{15}$ and L" are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, When $L^{12}$, $L^{13}$, $L^{14}$, $L^{15}$ and L" are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., $R^f$ and $R^g$ are each independently selected from the group consisting of a $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring;

When $R^f$ and $R^g$ are an aryl group, it may be preferably a $C_6$-$C_{30}$ aryl group, and more preferably a $C_6$-$C_{25}$ aryl group, for example, it may be phenylene, biphenyl, naphthalene, terphenyl, etc, When $R^f$ and $R^g$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $R^f$ and $R^g$ are aliphatic groups, they may be preferably $C_3$-$C_{30}$ aliphatic groups, more preferably $C_3$-$C_{24}$ aliphatic groups.

$Y^{10}$ is O, S, $CR^{51}R^{52}$ or $NR^{53}$,

B ring is a $C_6$-$C_{20}$ aryl group, $R^{31}$ and $R^{32}$ are the same or different, and each independently selected from the group consisting of a hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^{31}$s or a plurality of $R^{32}$s may be bonded to each other to form a ring, When $R^{31}$ and $R^{32}$ are an aryl group, it may be preferably a $C_6$-$C_{30}$ aryl group, and more preferably a $C_6$-$C_{25}$ aryl group, for example, it may be phenyl, biphenyl, naphthalene, terphenyl, phenanthrene, etc, When $R^{31}$ and $R^{32}$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine etc., When $R^{31}$ and $R^{32}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^{31}$ and $R^{32}$ are an alkyl group, it may be preferably a $C_1$-$C_{30}$ alkyl group, and more preferably a $C_1$-$C_{24}$ alkyl group.

When $R^{31}$ and $R^{32}$ are an alkenyl group, it may be preferably an $C_2$-$C_{30}$ alkenyl group, and more preferably a $C_2$-$C_{24}$ alkenyl group.

When $R^{31}$ and $R^{32}$ are an alkynyl group, it may be preferably an $C_2$-$C_{30}$ alkynyl group, and more preferably a $C_2$-$C_{24}$ alkynyl group.

When $R^{31}$ and $R^{32}$ are alkoxyl groups, they may be preferably $C_1$~$C_{30}$ alkoxyl groups, and more preferably $C_1$-$C_{24}$ alkoxyl groups, When $R^{31}$ and $R^{32}$ are an aryloxy group, it may be preferably a $C_6$~$C_{30}$ aryloxy group, and more preferably a $C_6$-$C_{24}$ aryloxy, $R^{51}$, $R^{52}$ and $R^{53}$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_6$-$C_{60}$ aryloxy group; or $R^{51}$ and $R^{52}$ may be bonded to each other to form a spiro, When $R^{51}$, $R^{52}$ and $R^{53}$ are an aryl group, it may be preferably a $C_6$-$C_{30}$ aryl group, and more preferably a $C_6$-$C_{25}$ aryl group, for example, it may be phenylene, biphenyl, naphthalene, terphenyl, phenanthrene, etc, When $R^{51}$, $R^{52}$ and $R^{53}$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, benzothienopyrimidine, benzofuropyrimidine, phenothiazine, phenylphenothiazine, etc., When $R^{51}$, $R^{52}$ and $R^{53}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^{51}$, $R^{52}$ and $R^{53}$ are an alkyl group, it may be preferably a $C_1$-$C_{30}$ alkyl group, and more preferably a $C_1$-$C_{24}$ alkyl group.

When $R^{51}$, $R^{52}$ and $R^{53}$ are an alkenyl group, it may be preferably an $C_2$-$C_{30}$ alkenyl group, and more preferably a $C_2$-$C_{24}$ alkenyl group.

When $R^{51}$, $R^{52}$ and $R^{53}$ are an alkynyl group, it may be preferably an $C_2$-$C_{30}$ alkynyl group, and more preferably a $C_2$-$C_{24}$ alkynyl group.

When $R^{51}$, $R^{52}$ and $R^{53}$ are alkoxyl groups, they may be preferably $C_1$~$C_{30}$ alkoxyl groups, and more preferably $C_1$~$C_{24}$ alkoxyl groups, When $R^{51}$, $R^{52}$ and $R^{53}$ are an aryloxy group, it may be preferably a $C_6$~$C_{30}$ aryloxy group, and more preferably a $C_6$~$C_{24}$ aryloxy, ba and bb are independently integers from 0 to 4;

wherein the aryl group, arylene group, heterocyclic group, fluorenyl group, fluorenylene group, aliphatic ring group, fused ring group, alkyl group, alkenyl group, alkynyl group, alkoxyl group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula 4 may be represented by any one of Formulas 4-1 to 4-3.

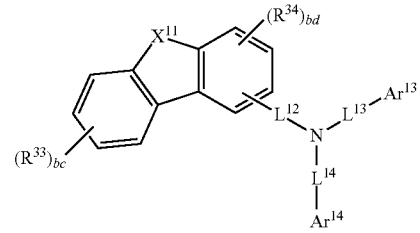

<Formula 4-1>

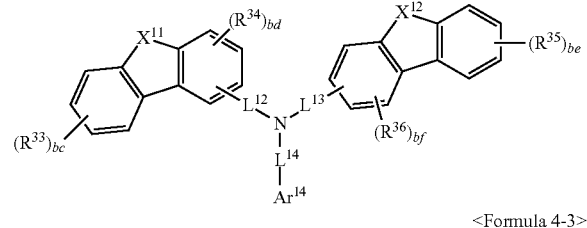

<Formula 4-2>

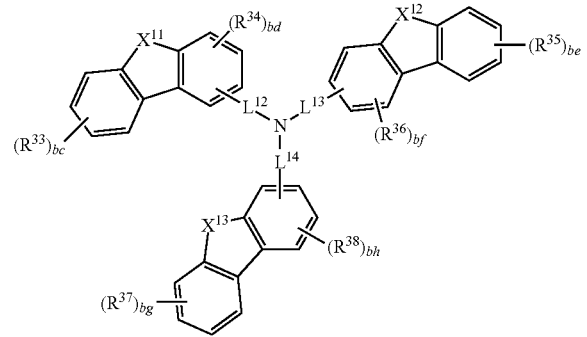

<Formula 4-3>

Wherein,

Ar$^{13}$, Ar$^{14}$, L$^{12}$, L$^{13}$ and L$^{14}$ are the same as defined in Formula 4, X$^{11}$, X$^{12}$ and X$^{13}$ are the same as the definition of Y$^{10}$, R$^{33}$, R$^{34}$, R$^{35}$, R$^{36}$, R$^{37}$ and R$^{38}$ are the same as the definition of R$^{31}$, or an adjacent plurality of R$^{33}$s, a plurality of R$^{34}$s, a plurality of R$^{35}$s, a plurality of R$^{36}$s, a plurality of R$^{37}$s, or a plurality of R$^{38}$s may bond to each other to form a ring, bc, be and bg are each independently integers from 0 to 4, and bd, bf and bh are each independently integers from 0 to 3, Formula 5 may be represented by any one of Formulas 5-1 to 5-6.

<Formula 5-1>

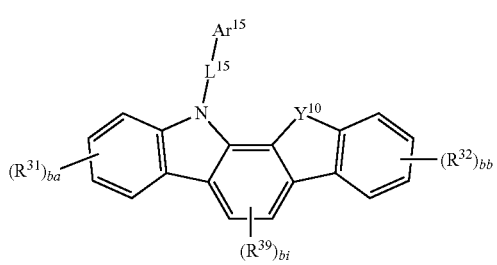

<Formula 5-2>

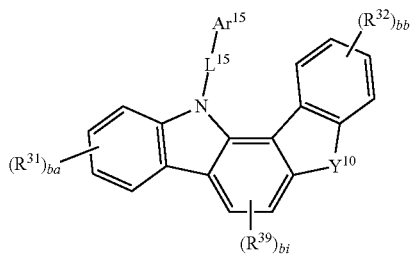

<Formula 5-3>

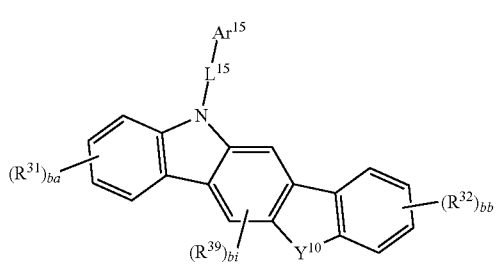

<Formula 5-4>

<Formula 5-5>

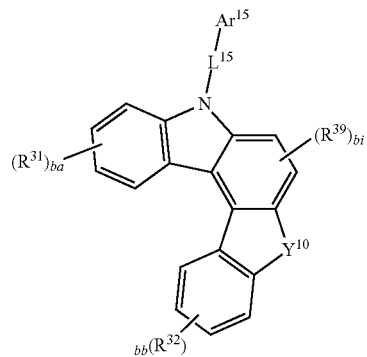

<Formula 5-6>

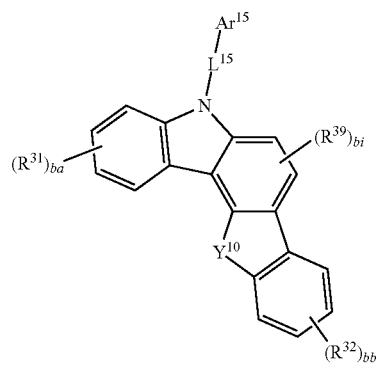

Wherein,

Y$^{10}$, R$^{31}$, R$^{32}$, Ar 15, L$^{15}$, ba and bb are the same as defined in Formula 5, R$^{39}$ is the e same as defined in Formula 5, same as the definition of R$^{31}$, bi is an integer of 0 to 2.

Formula 5 may be represented by any one of Formulas 5-7 to 5-9.

<Formula 5-7>

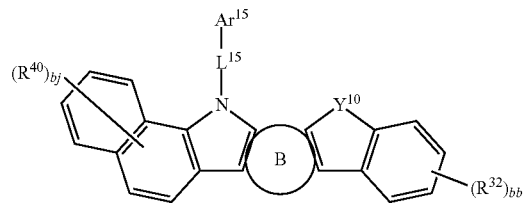

<Formula 5-8>

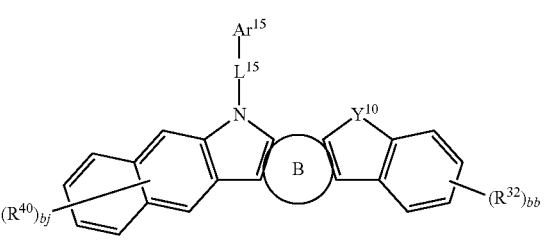

<Formula 5-9>

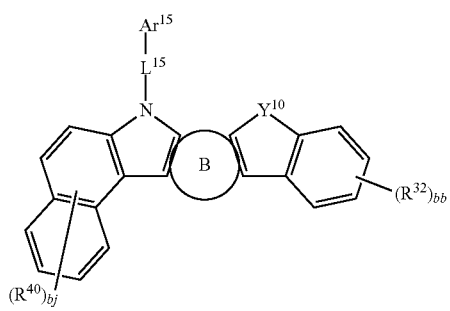

Wherein,
Y$^{10}$, B ring, R$^{32}$, bb, L$^{15}$ and Ar$^{15}$ are the same as defined in Formula 5,
R$^{40}$ is the e same as defined in Formula 5, same as the definition of R$^{31}$,
bj is an integer of 0 to 6.
Formula 5 may be represented by any one of Formulas 5-10 to 5-12.

<Formula 5-10>

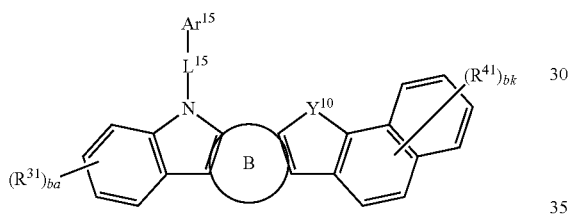

<Formula 5-11>

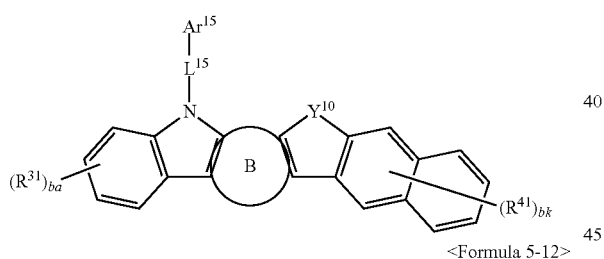

<Formula 5-12>

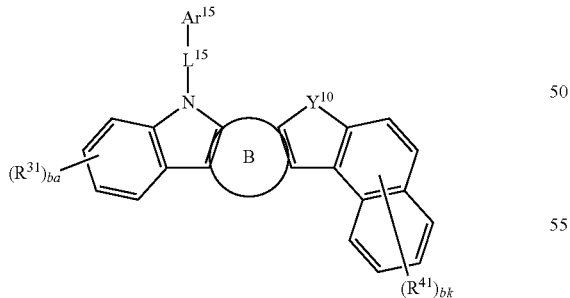

Wherein,
Y$^{10}$, B ring, R$^{31}$, ba, L$^{15}$ and Ar$^{15}$ are the same as defined in Formula 5,
R$^{41}$ is the e same as defined in Formula 5, same as the definition of R$^{31}$,
bk is an integer of 0 to 6.
Formula 5 may be represented by any one of Formulas 5-13 to 5-18.

<Formula 5-13>

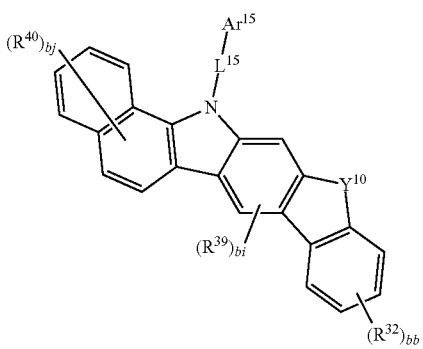

<Formula 5-14>

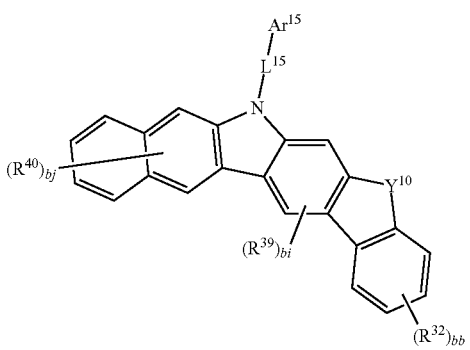

<Formula 5-15>

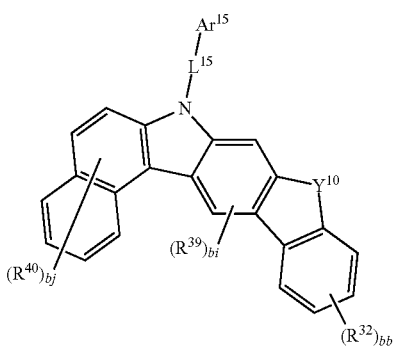

<Formula 5-16>

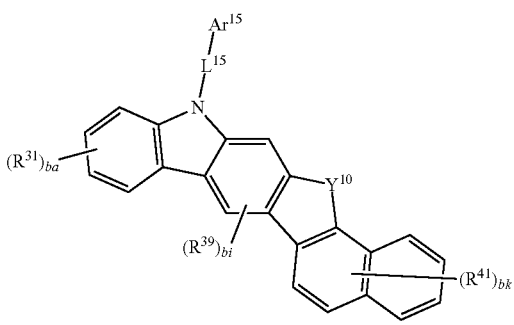

-continued

<Formula 5-17>

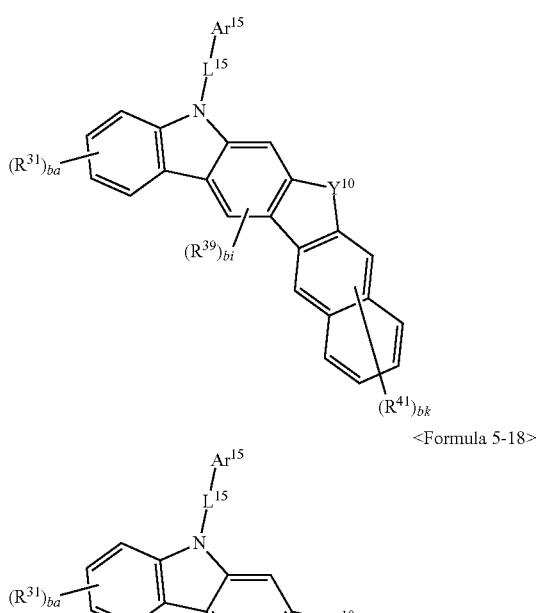

<Formula 5-18>

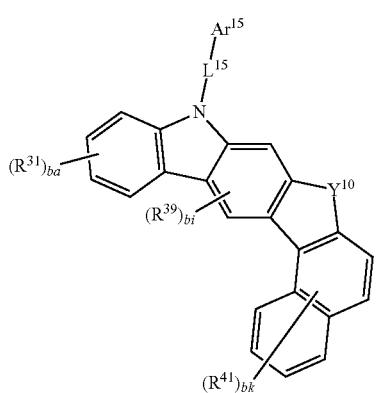

Wherein,
$Y^{10}$, $R^{31}$, $R^{32}$,
ba, bb, $L^{15}$ and $Ar^{15}$ are the same as defined in Formula 5,
$R^{39}$, $R^{40}$ and $R^{41}$ are the e same as defined in Formula 5, same as the definition of $R^{31}$,
bi is an integer of 0 to 2, bj and bk are each independently integers from 0 to 6.

Formula 5 may be represented by Formula 5-19.

<Formula 5-19>

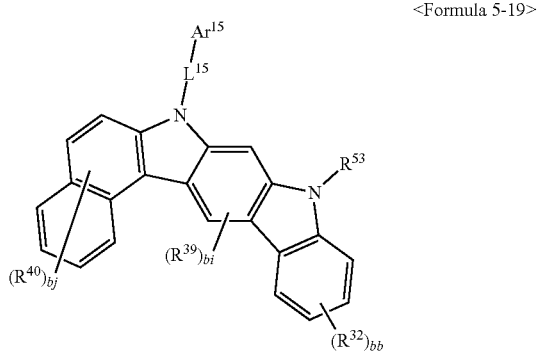

Wherein,
$R^{32}$, $R^{53}$, bb, $L^{15}$ and $Ar^{15}$ are the same as defined in Formula 5,
$R^{39}$ and $R^{40}$ are the e same as defined in Formula 5, same as the definition of $R^{31}$,
bi is an integer of 0 to 2, bj is an integer from 0 to 6.

Specifically, the compound represented by Formula 4 may be any one of the following compounds H-1 to H-100, but is not limited thereto.

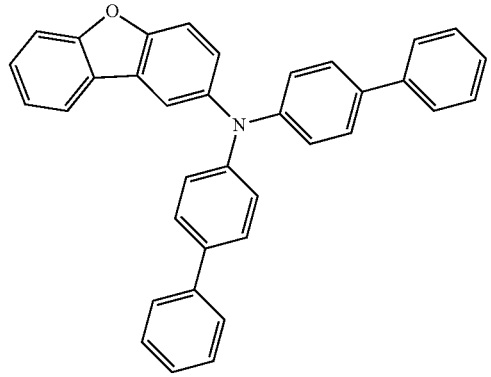

H-1

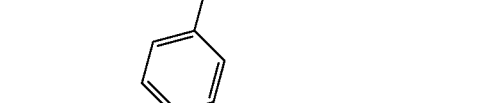

H-2

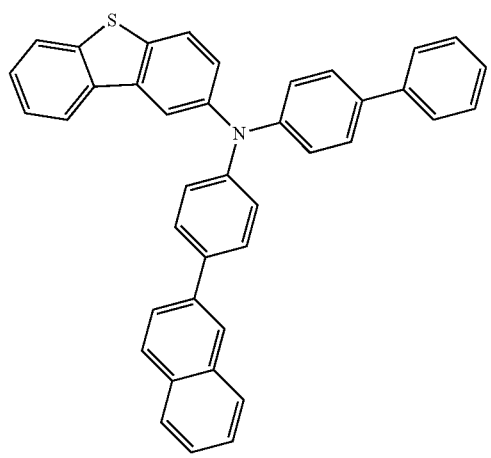

H-3

H-4
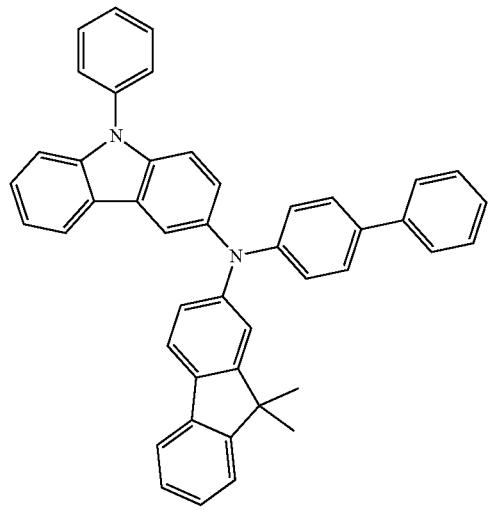
H-7
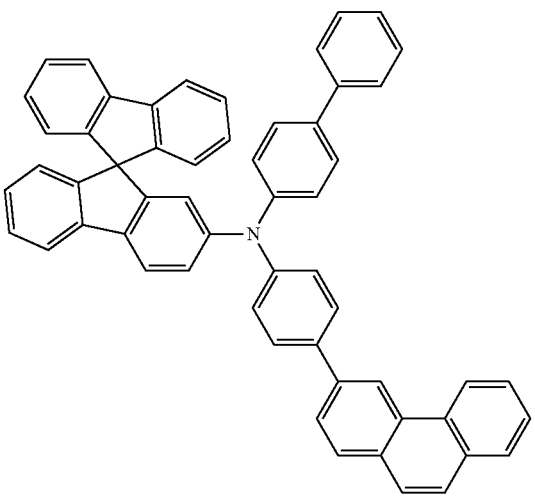
H-5
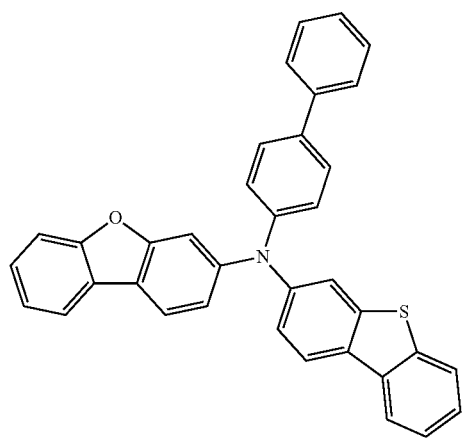
H-8
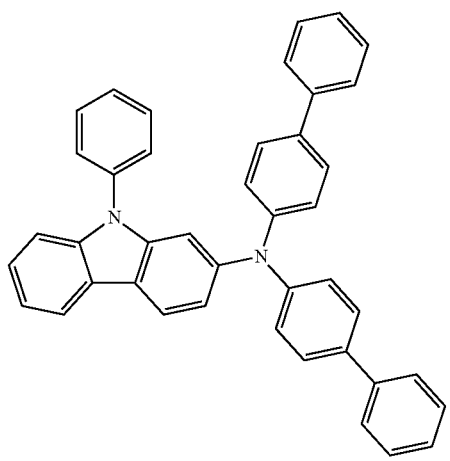
H-6
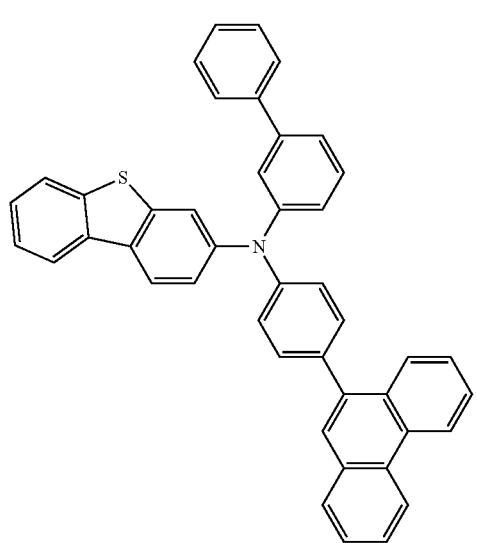
H-9
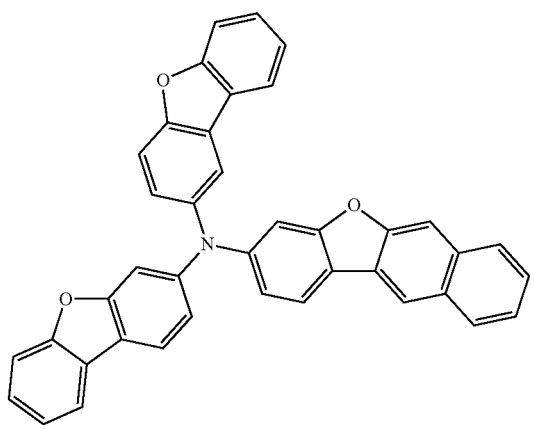

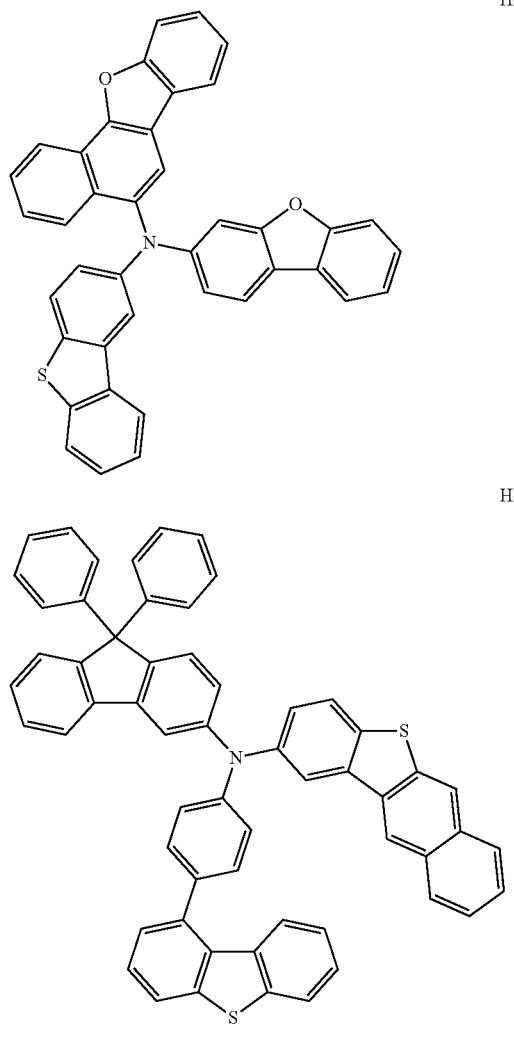
H-10
H-11
H-12
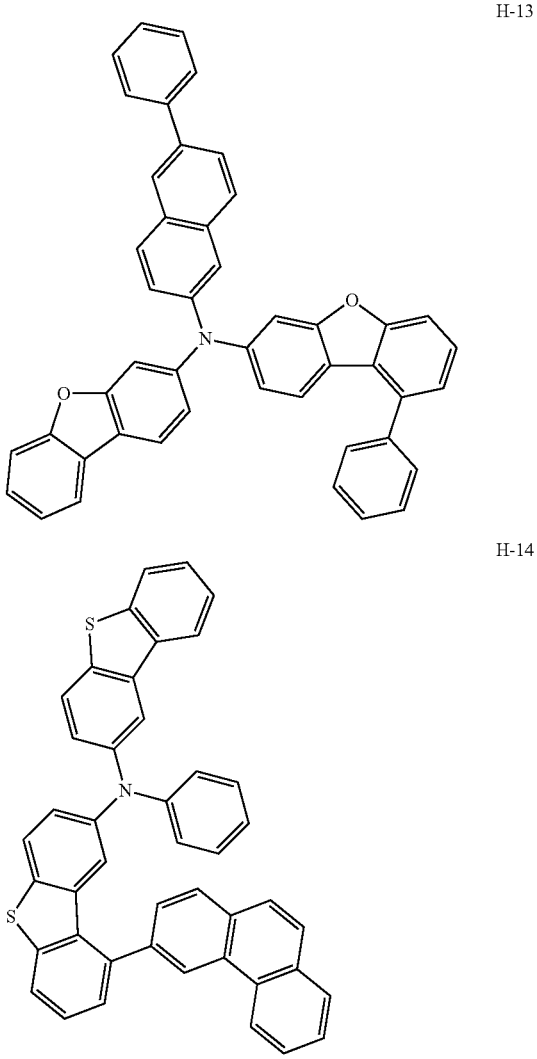
H-13
H-14
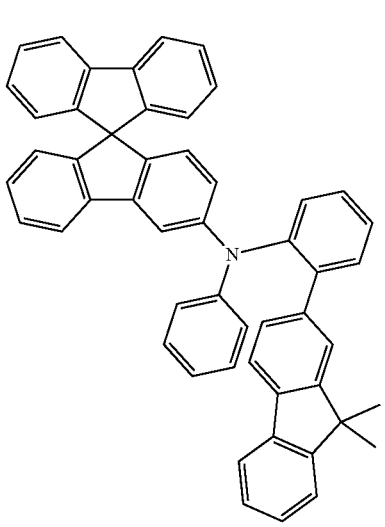
H-15

US 11,917,914 B1
137
-continued
H-16
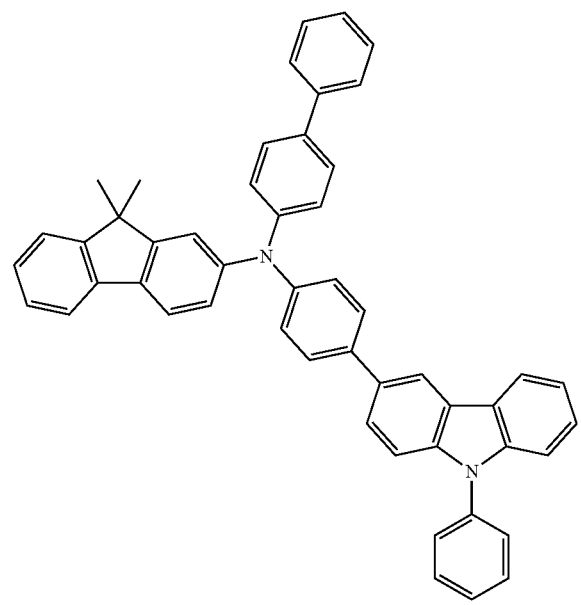
H-17
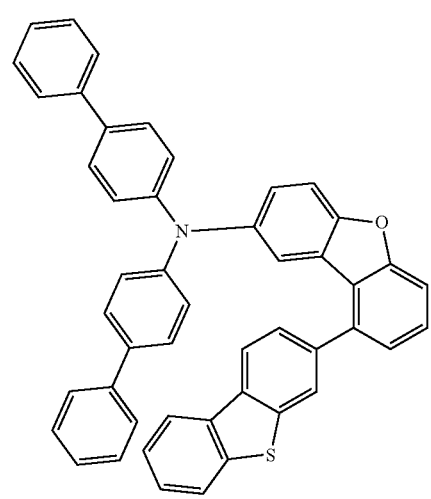
H-18
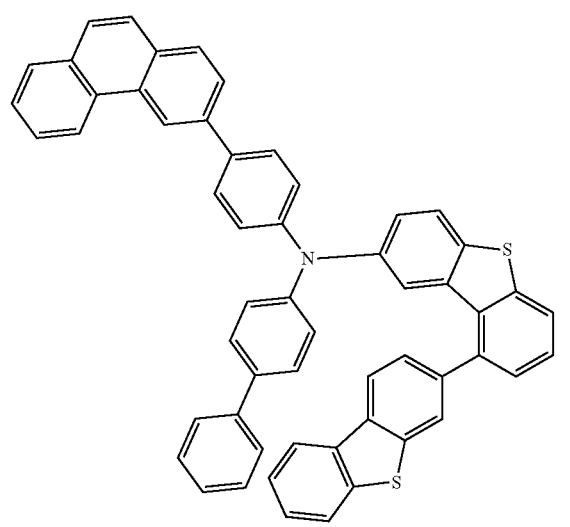
138
-continued
H-19
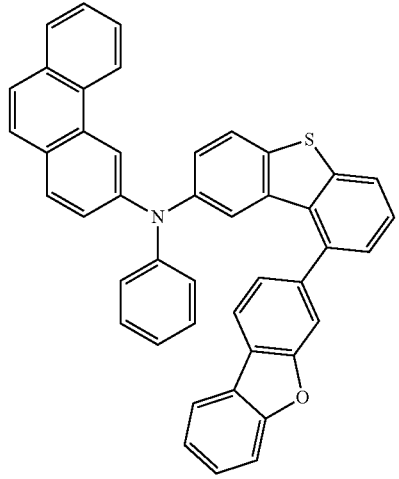
H-20
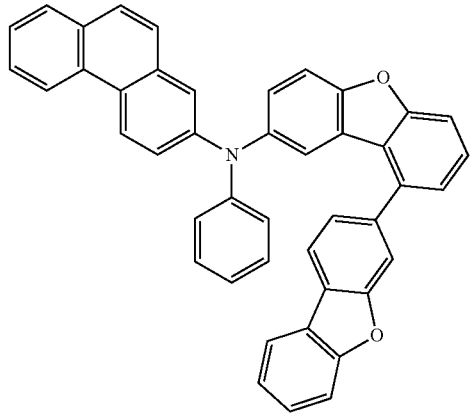
H-21
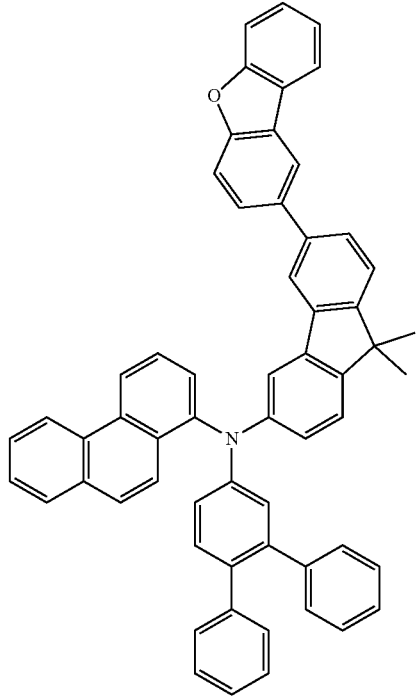

H-22
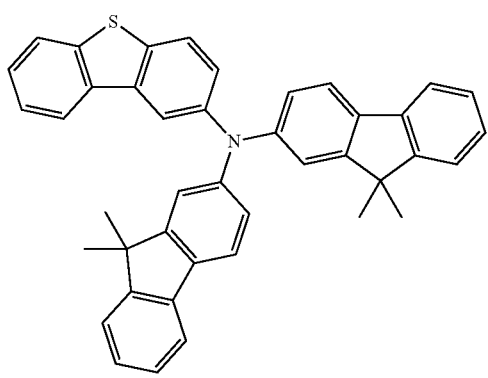
H-23
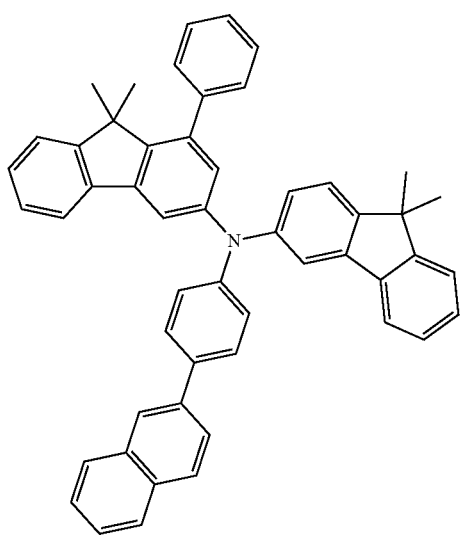
H-24
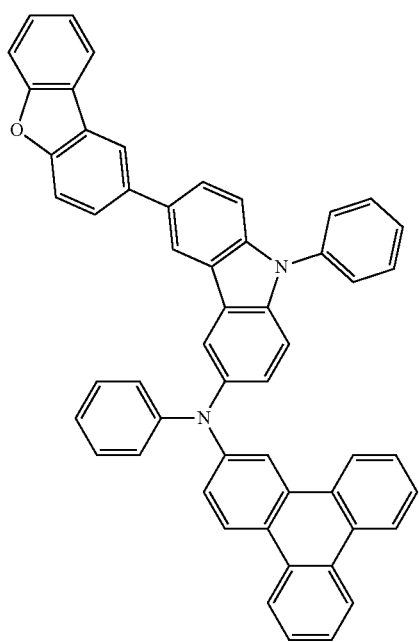
H-25
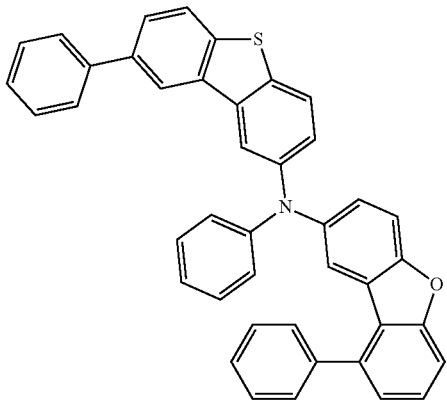
H-26
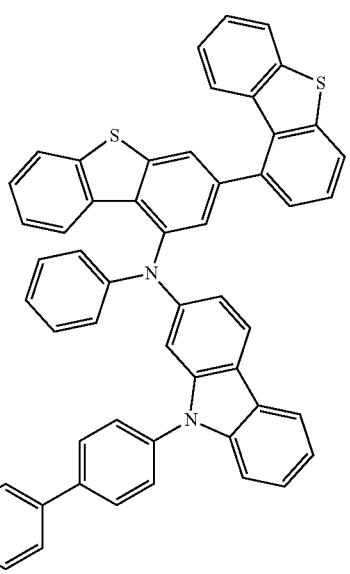
H-27
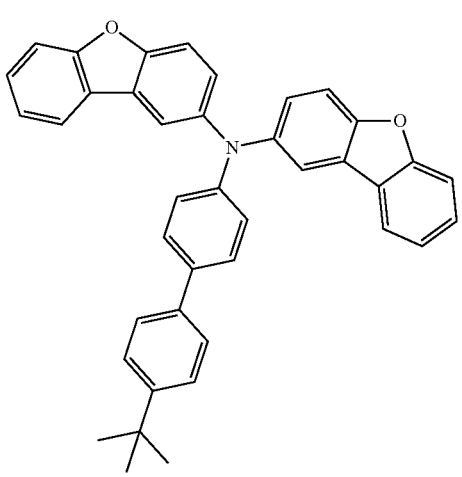

-continued
H-28
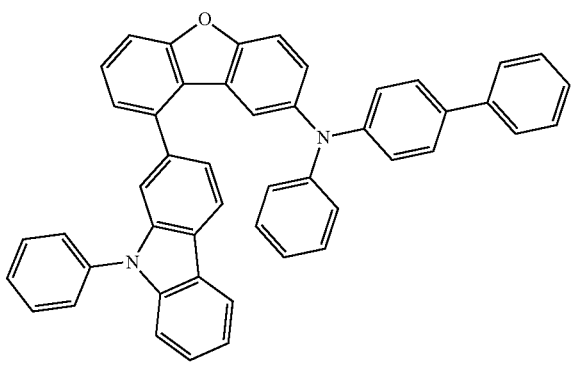
H-29
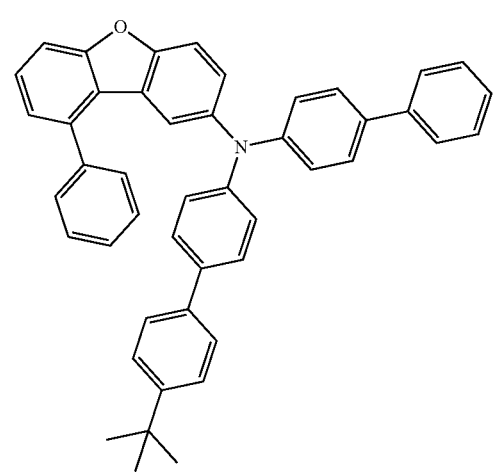
H-30
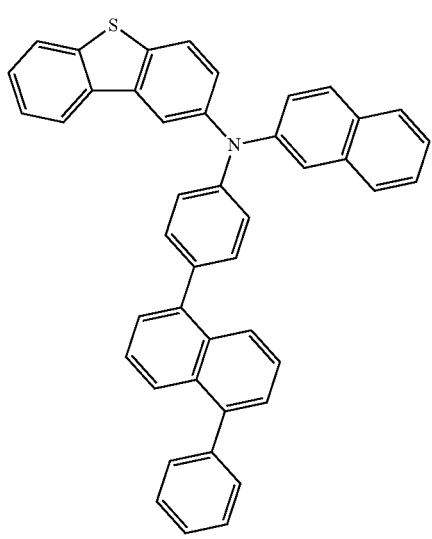
H-31
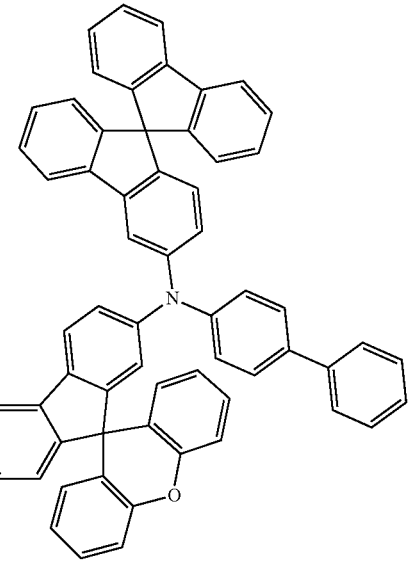
H-32
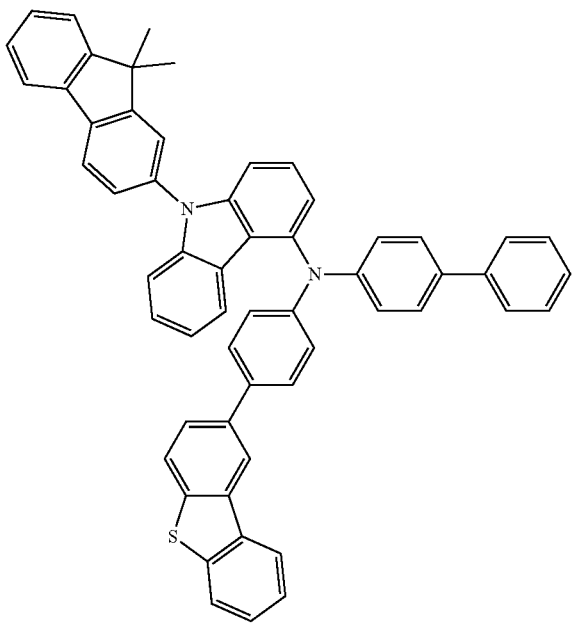
H-33
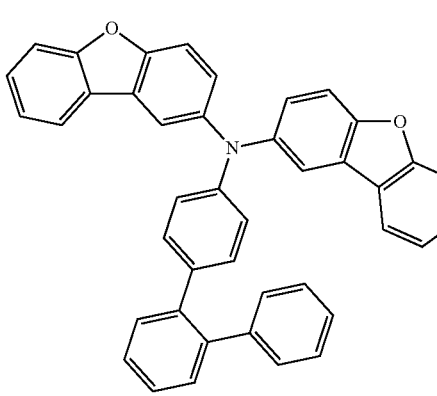

H-34
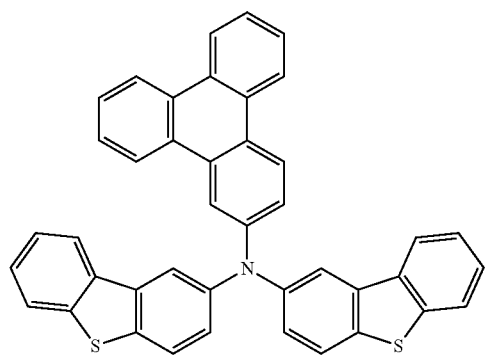
H-37
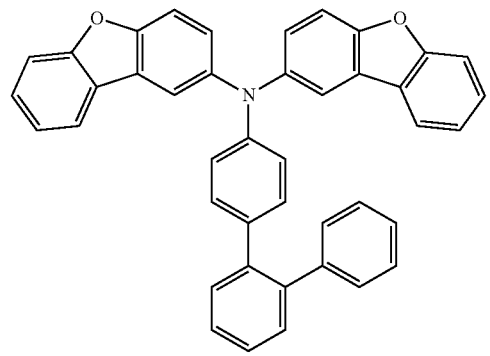
H-35
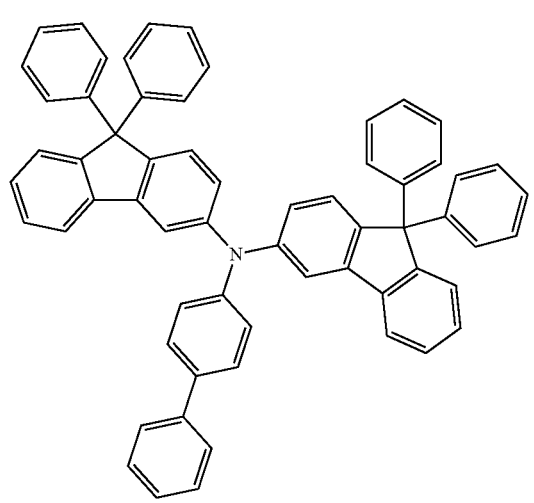
H-38
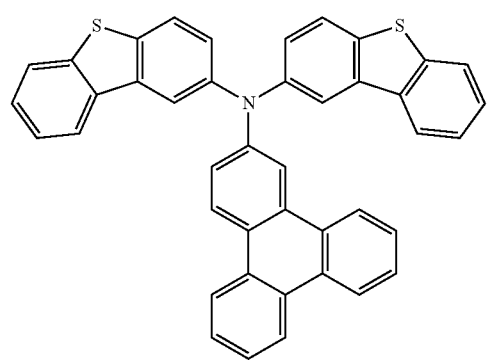
H-36
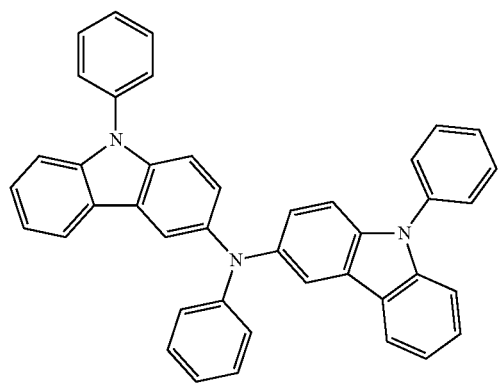
H-39
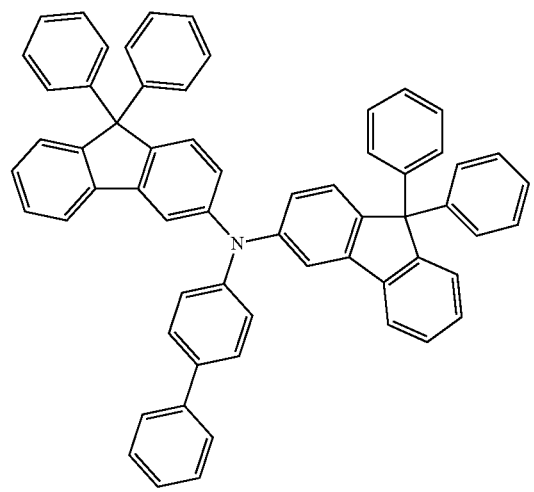

H-40
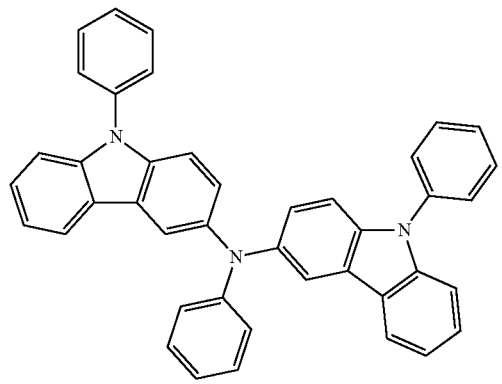
H-43
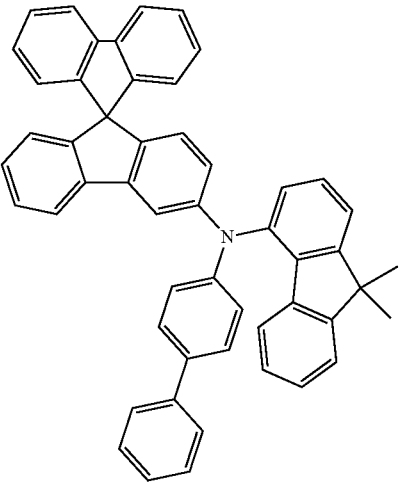
H-41
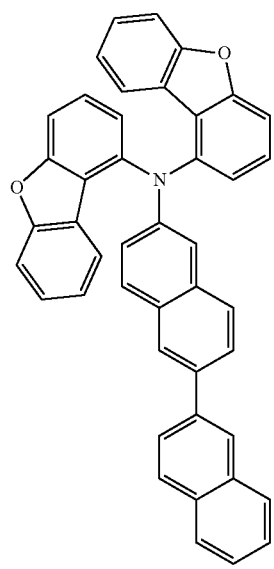
H-44
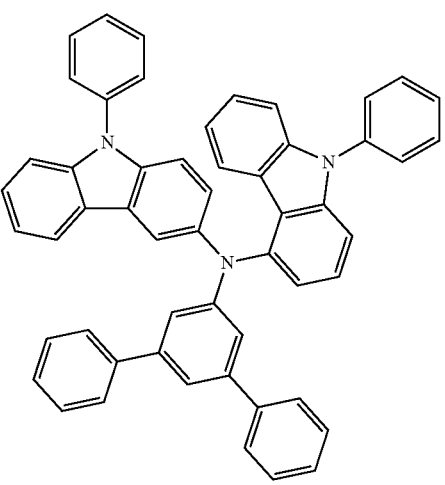
H-42
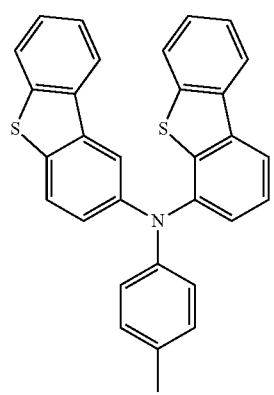
H-45
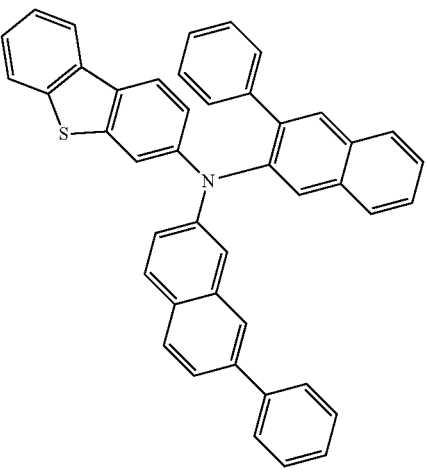

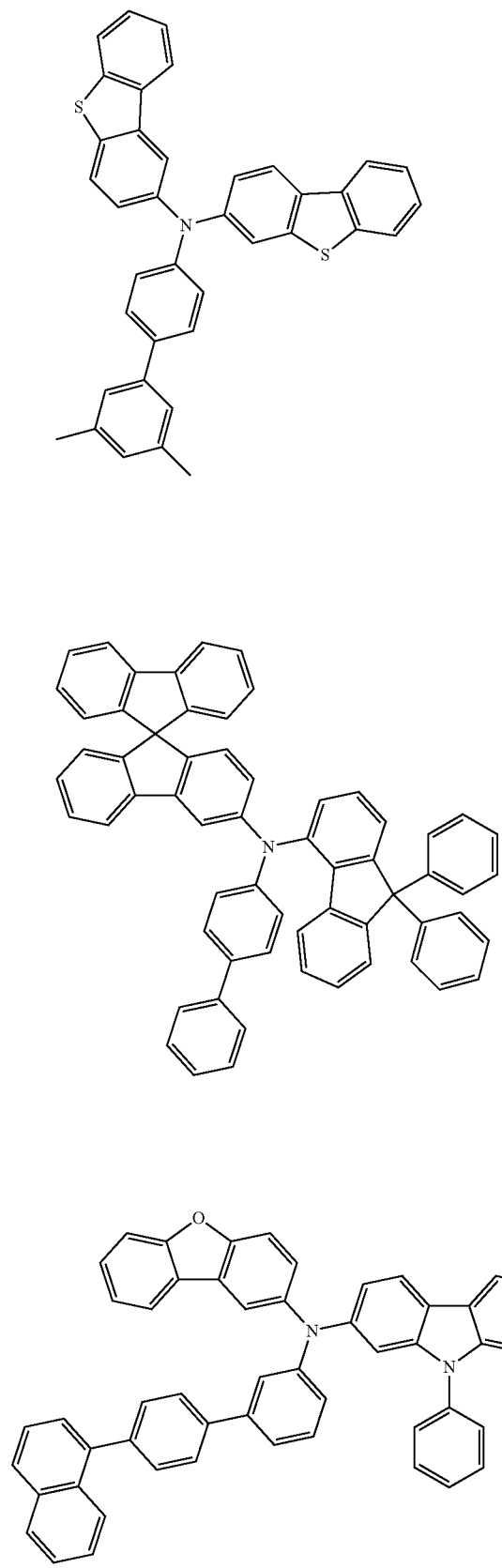
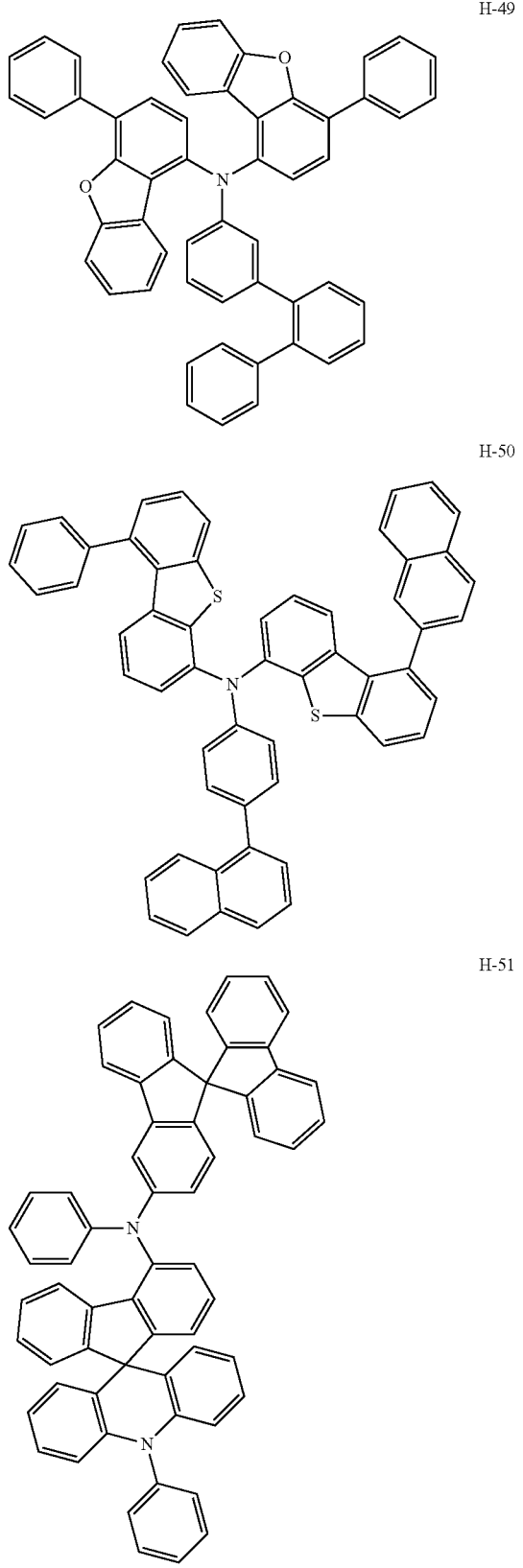

H-52
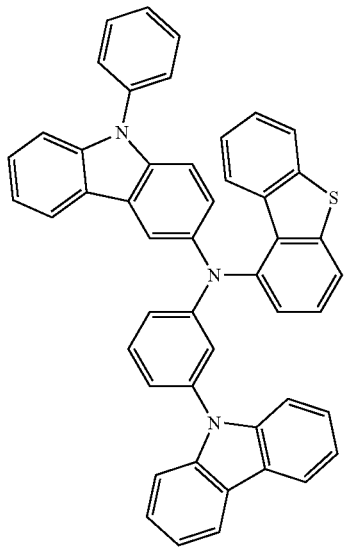
H-55
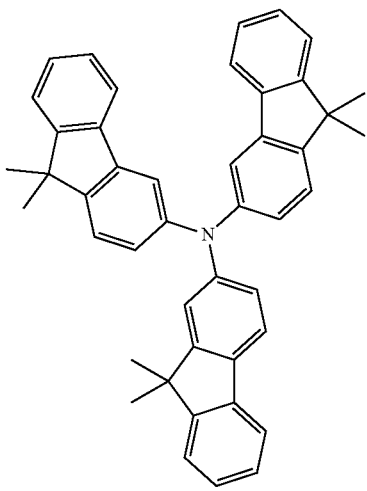
H-53
H-56
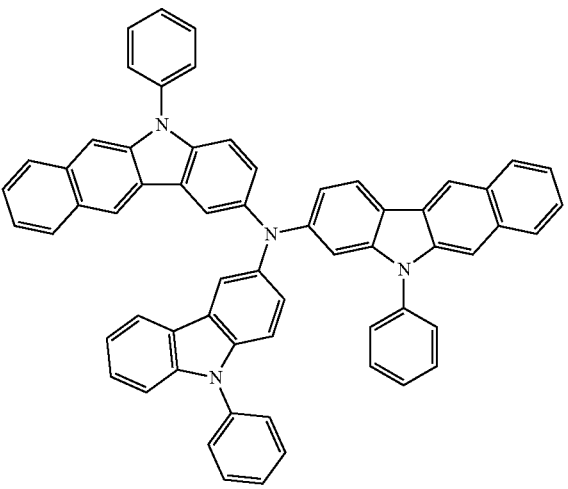
H-54
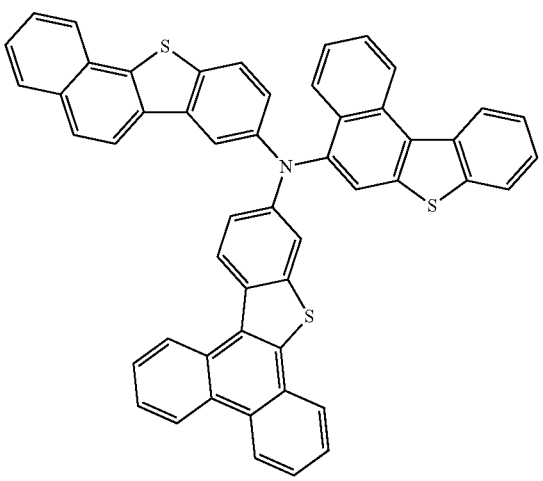
H-57

H-58
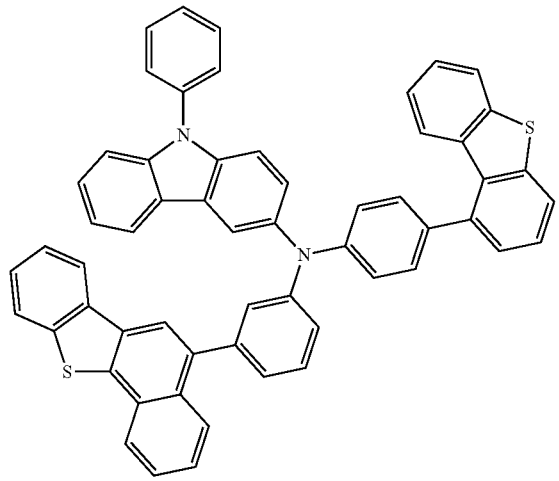
H-61
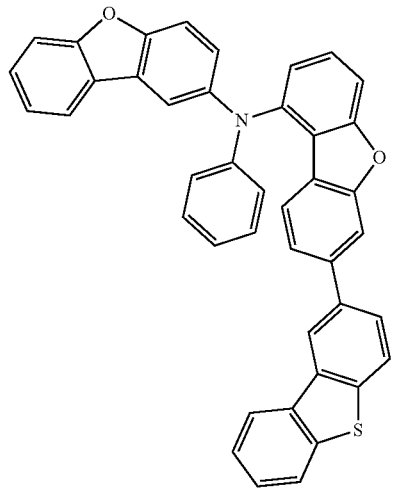
H-59
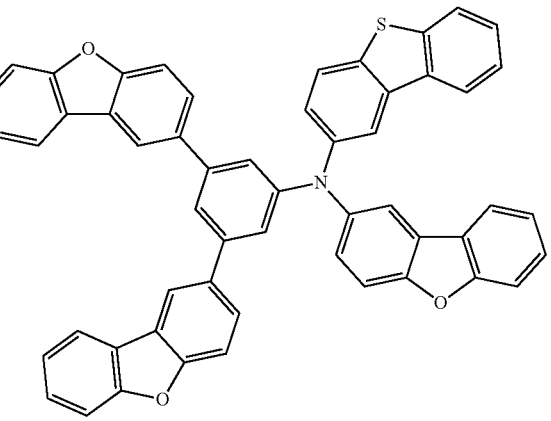
H-62
H-60
H-63
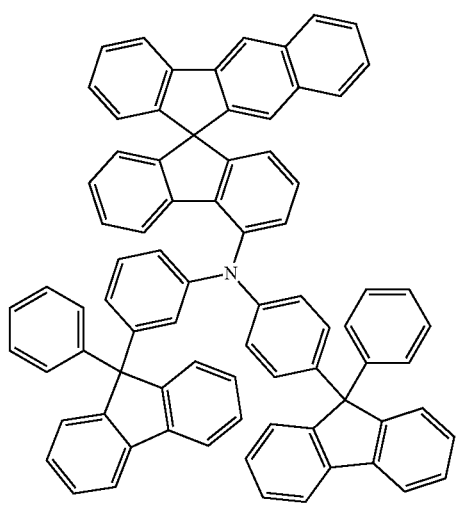

-continued
H-64
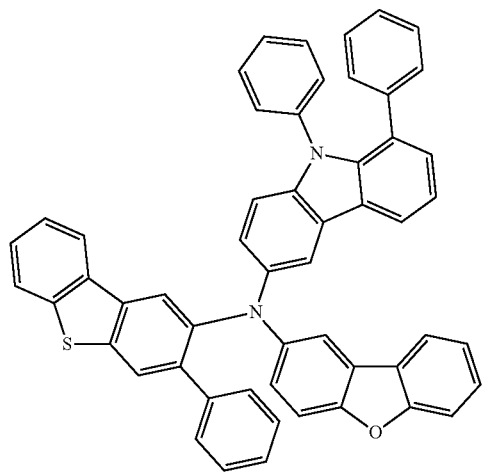
H-65
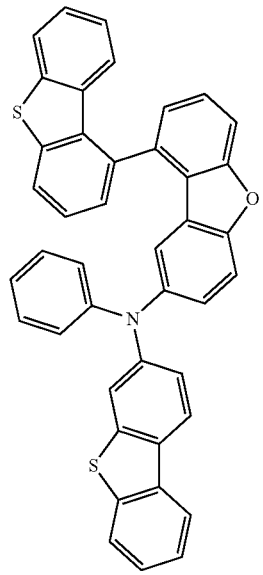
H-66
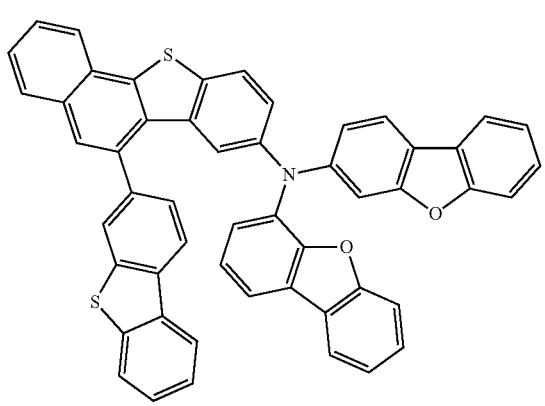
-continued
H-67
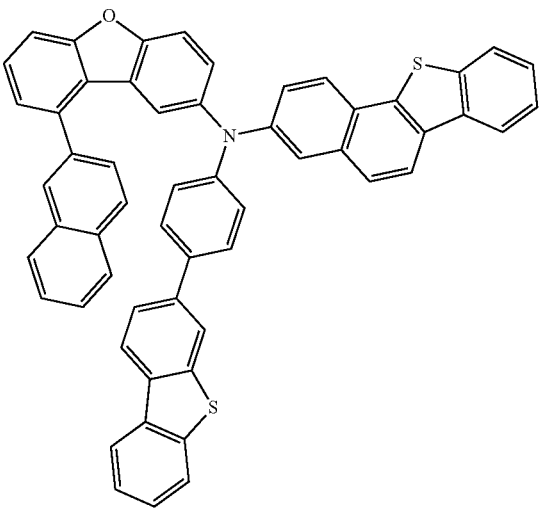
H-68
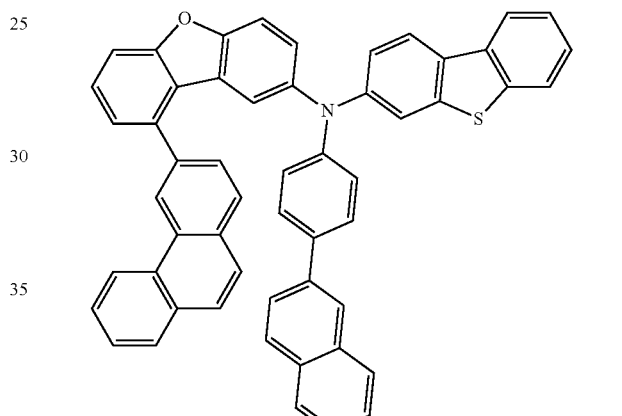
H-69
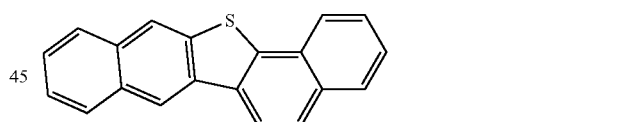
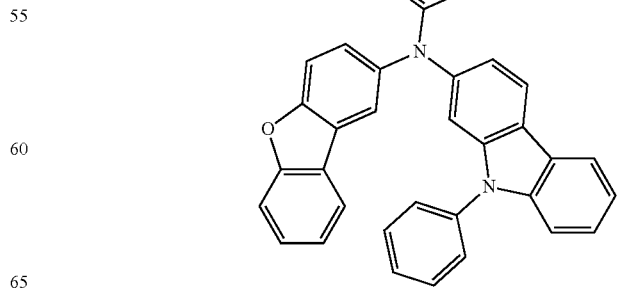

H-70
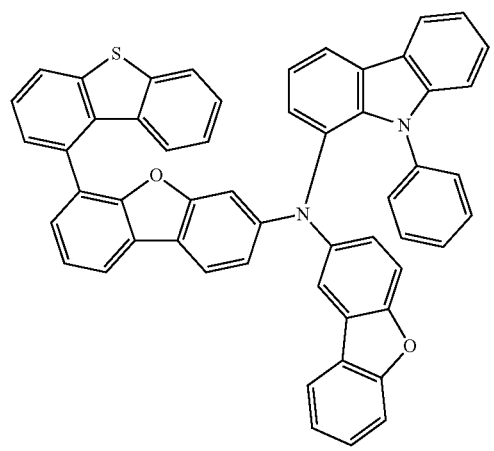
H-71
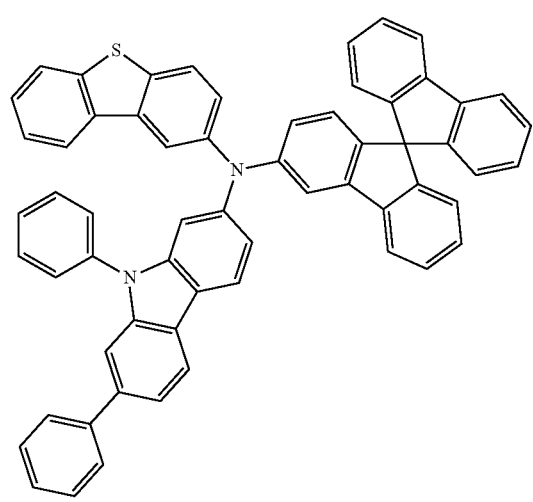
H-72
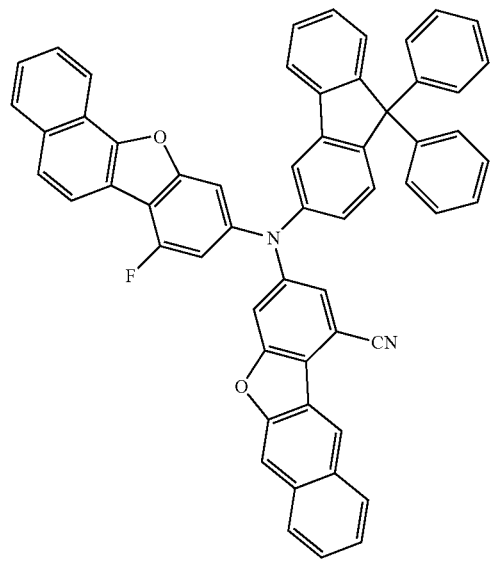
H-73
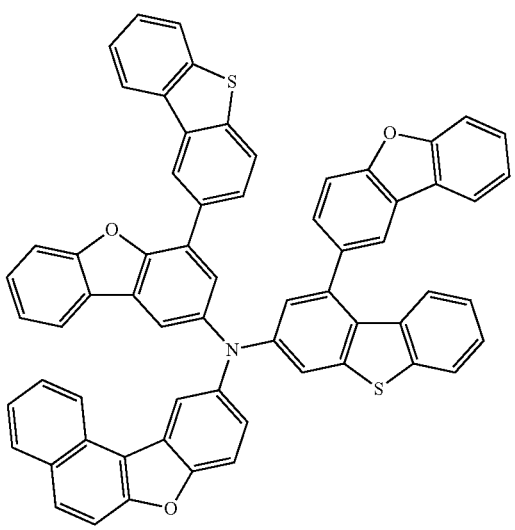
H-74
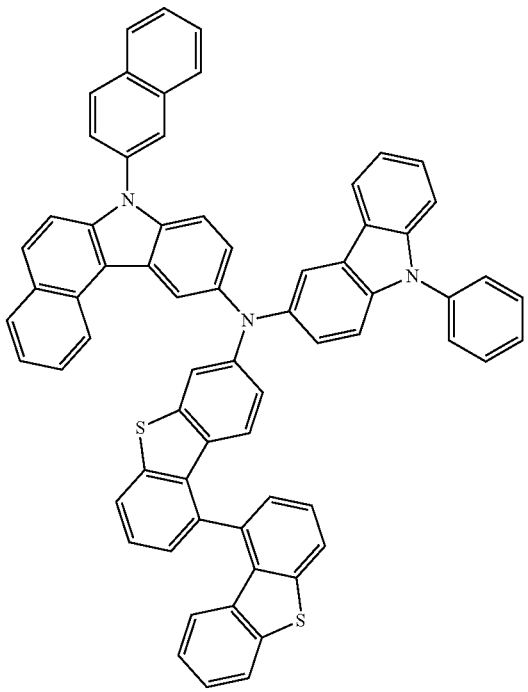

-continued
H-75
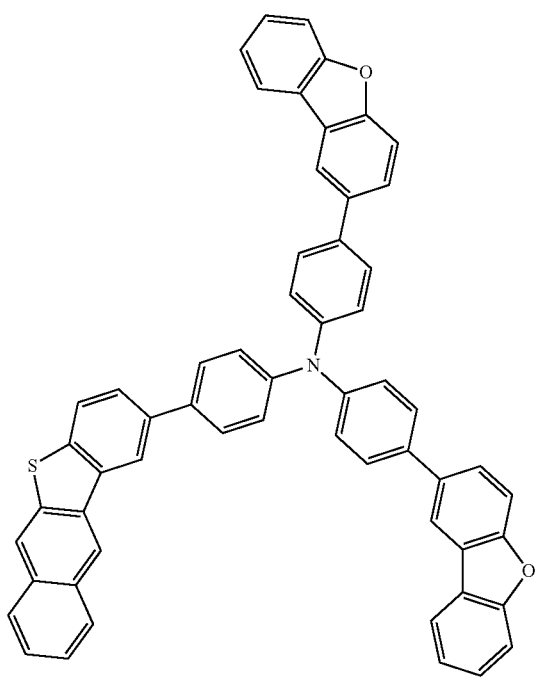
H-76
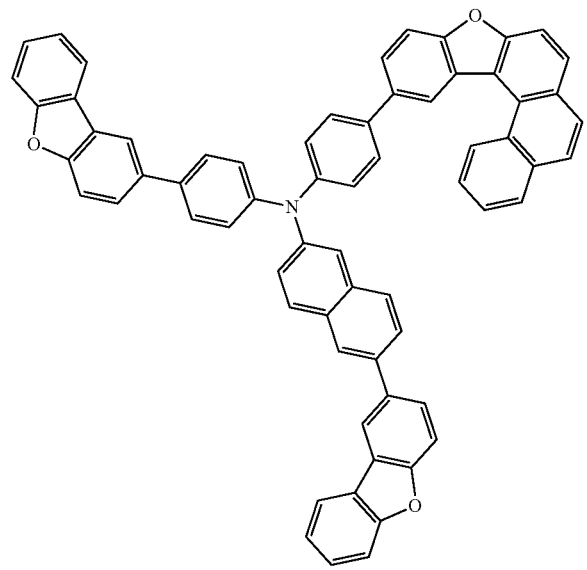
H-77
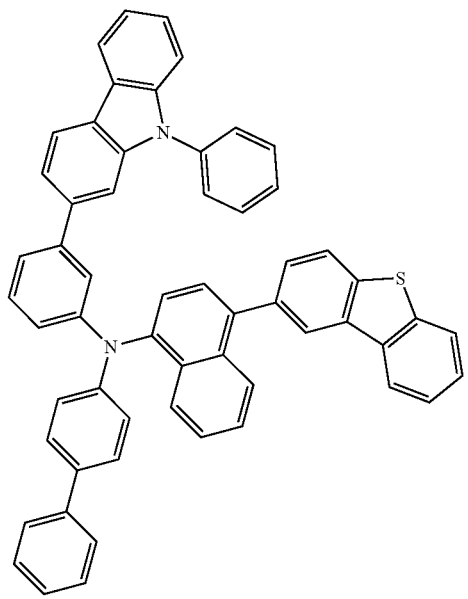
H-78
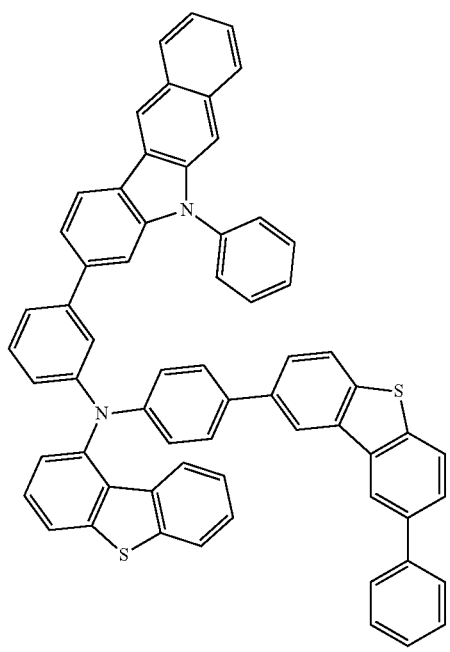

H-79
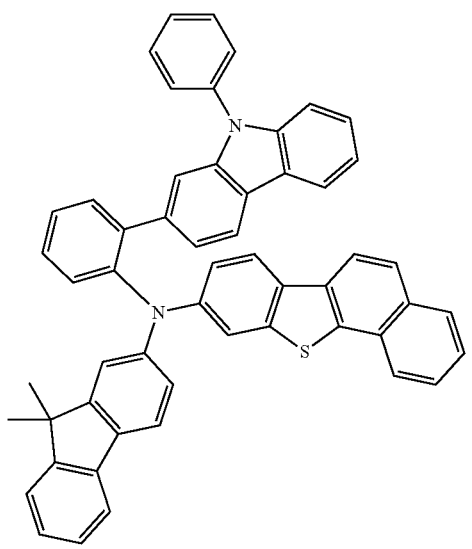
H-81
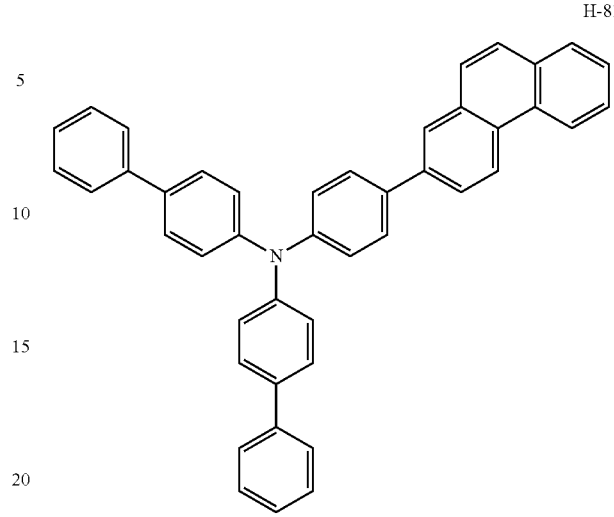
H-80
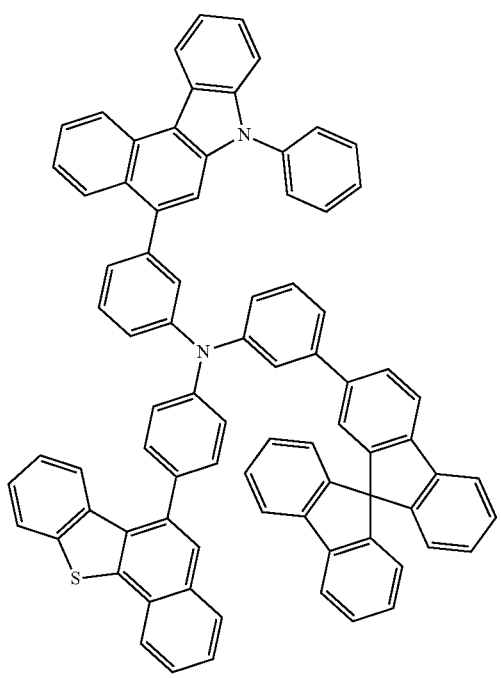
H-82
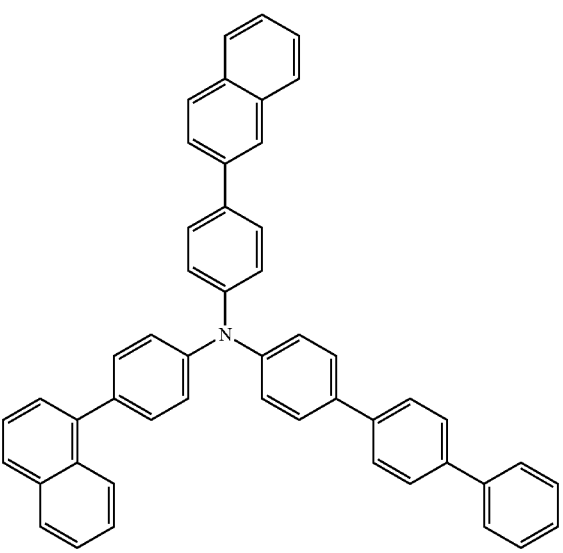

H-83
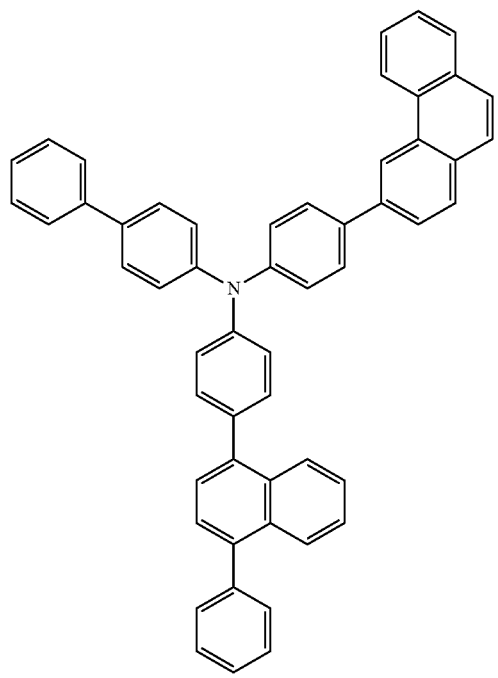
H-84
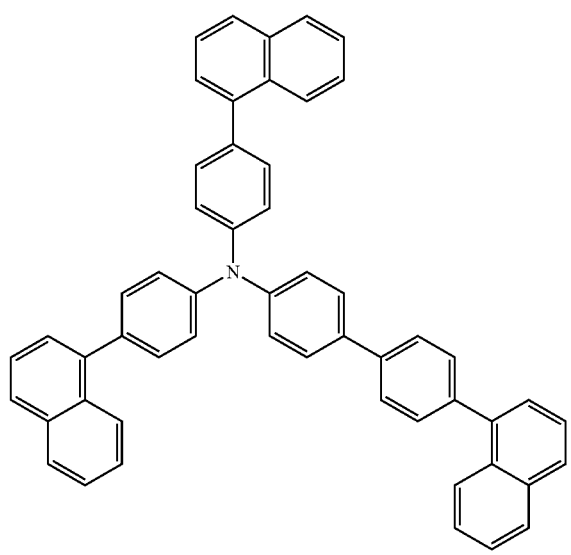
H-85
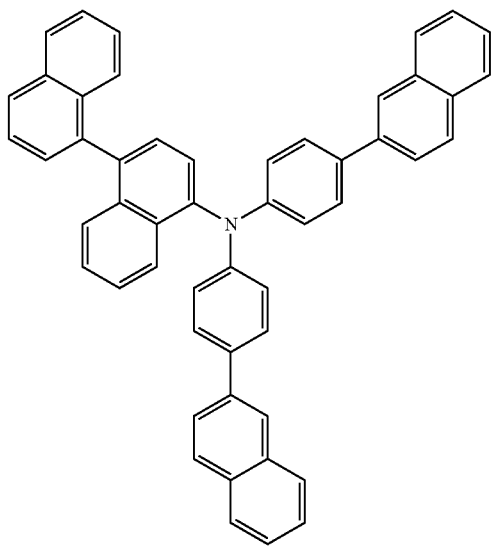
H-86
H-87
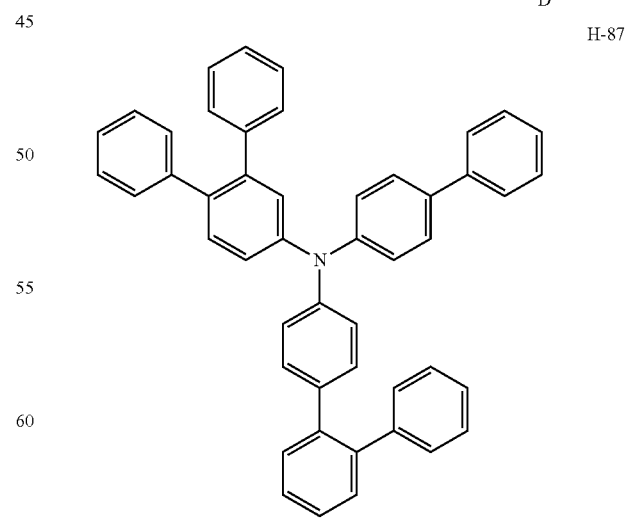

H-88
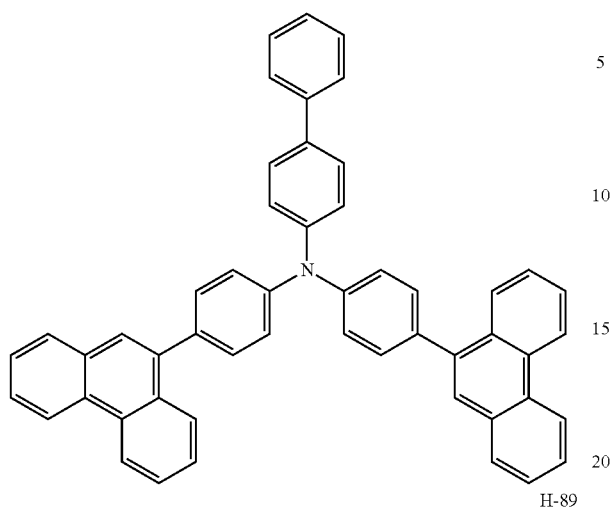
H-91
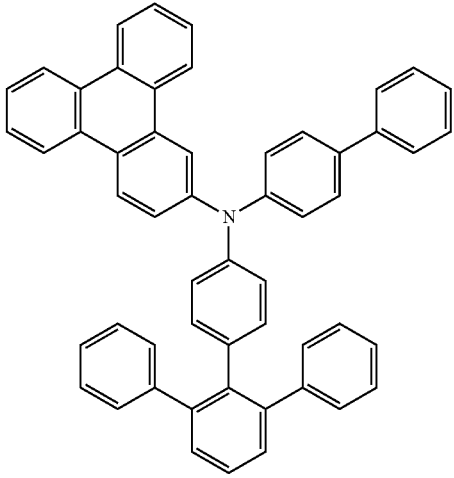
H-89
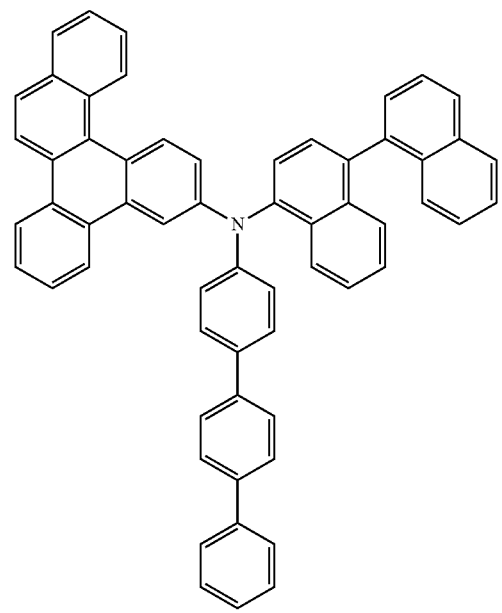
H-92
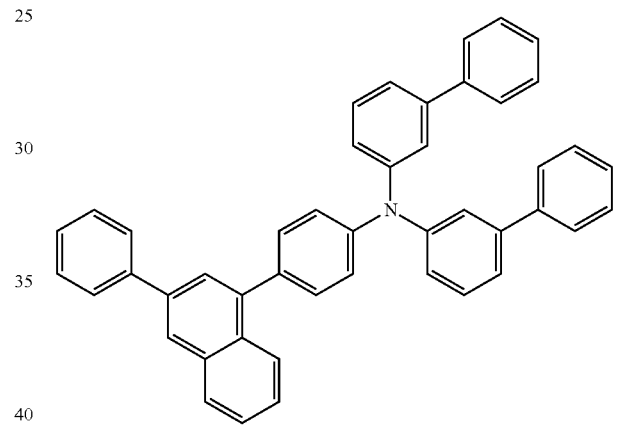
H-90
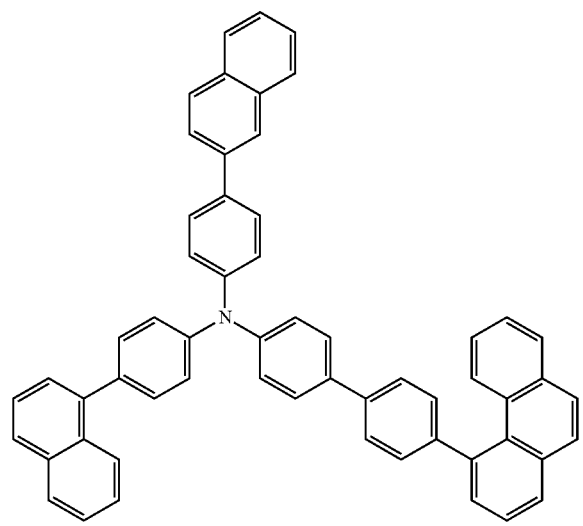
H-93
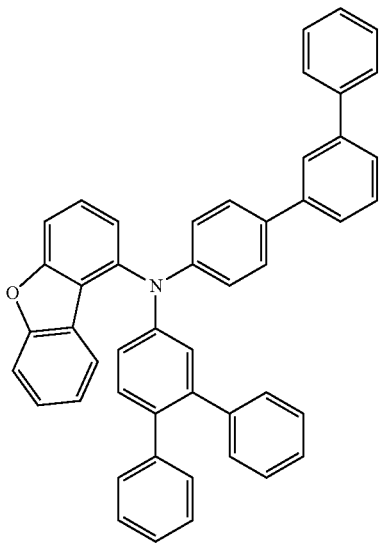

-continued
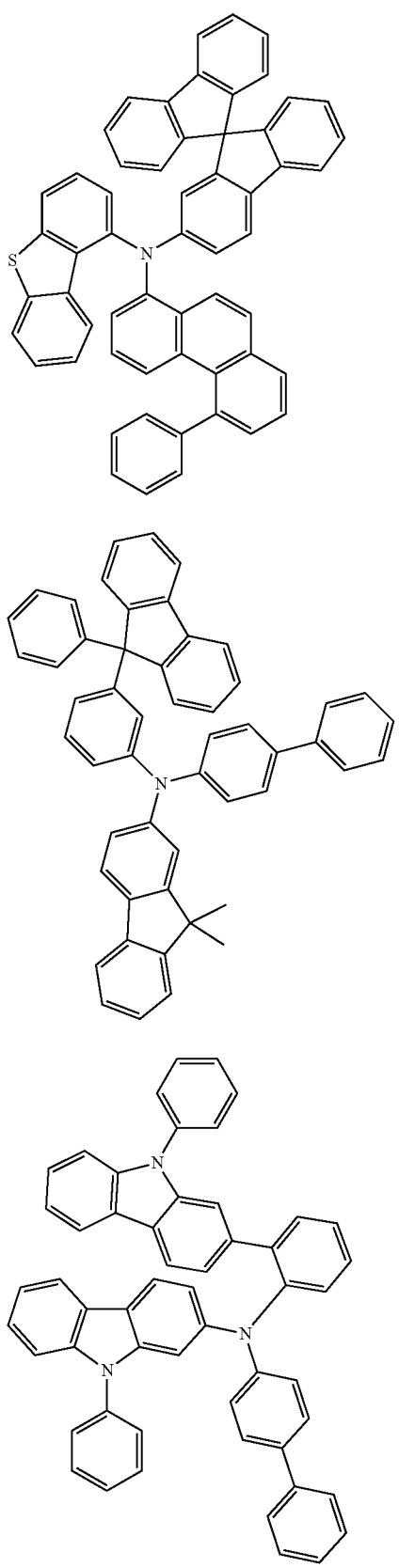
H-94
H-95
H-96
-continued
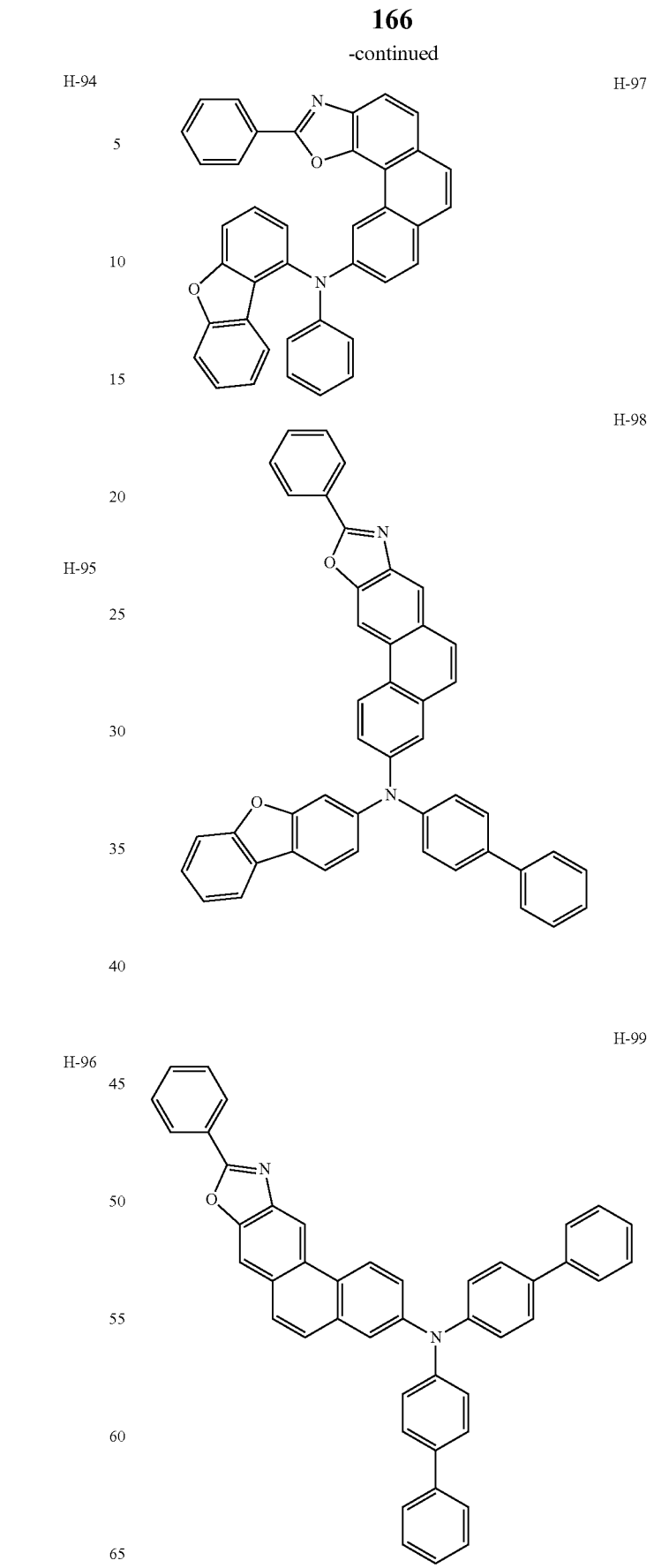
H-97
H-98
H-99

167
-continued
H-100
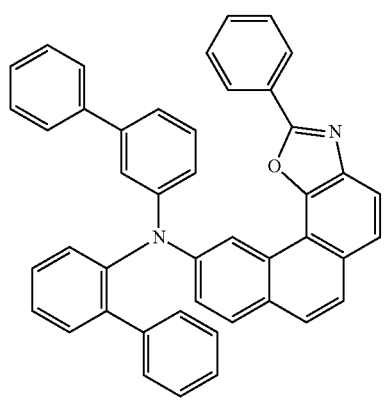
Specifically, the compound represented by Formula 5 may be any one of the following compounds S-1 to S-108, but is not limited thereto.
S-1
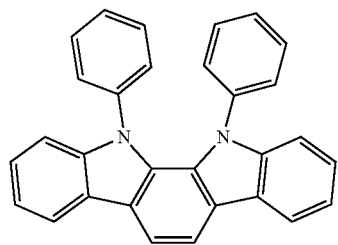
S-2
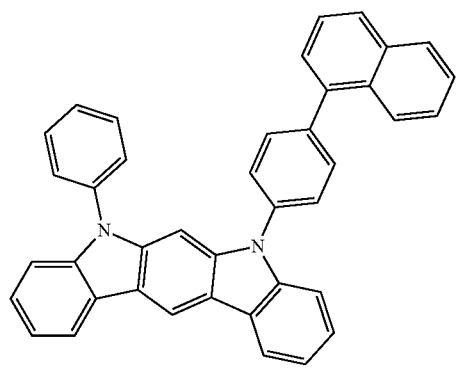
168
-continued
S-3
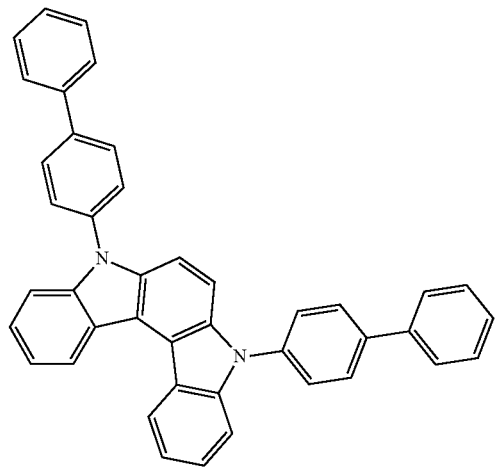
S-4
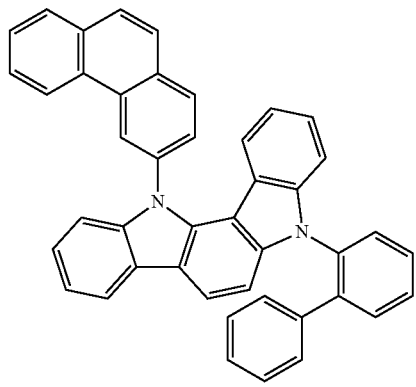
S-5
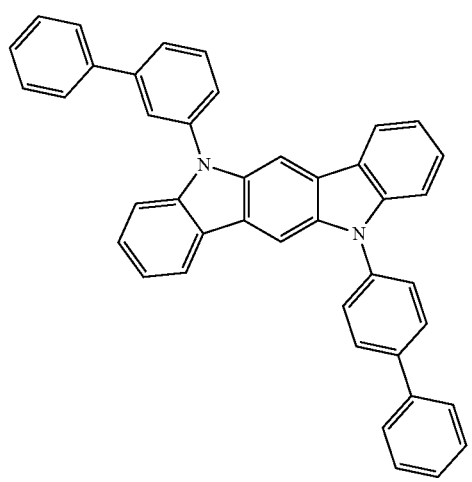

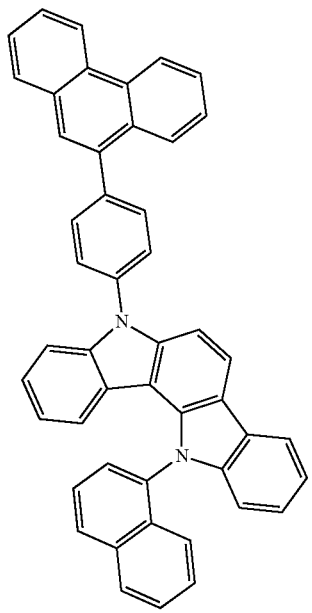
S-6
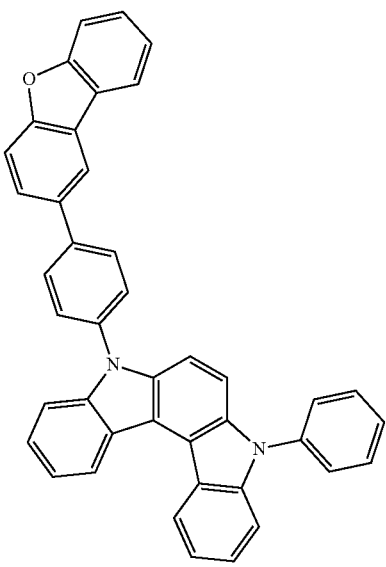
S-9
S-7
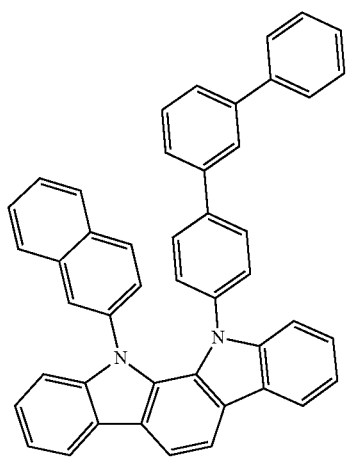
S-10
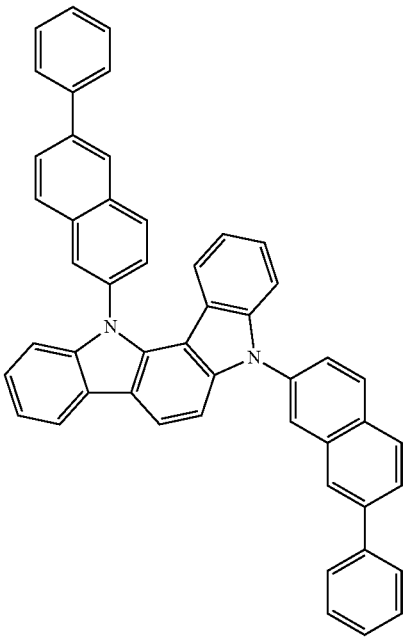
S-8
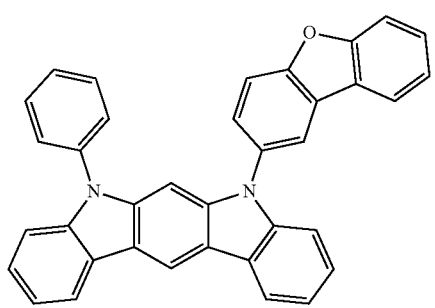

S-11
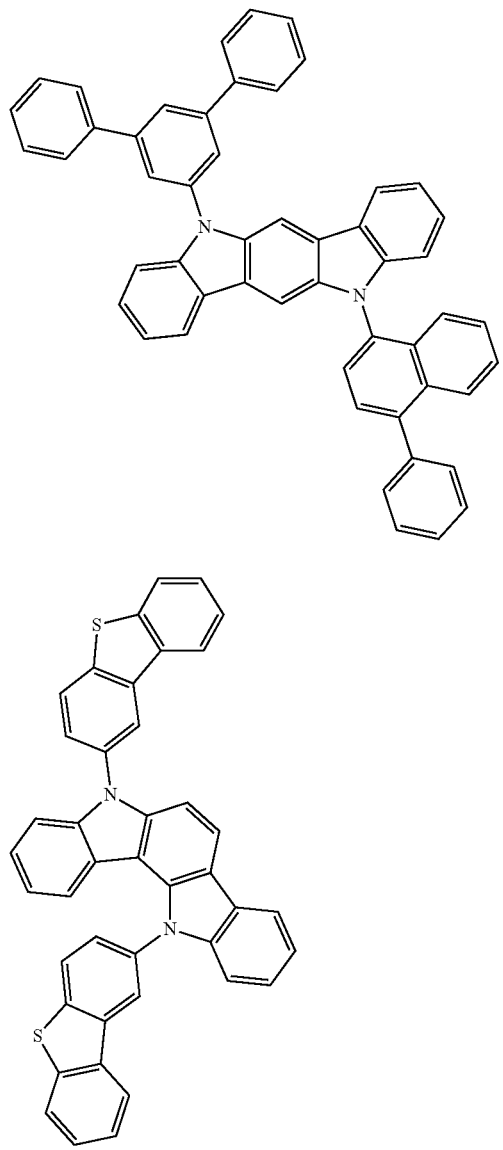
S-12
S-13
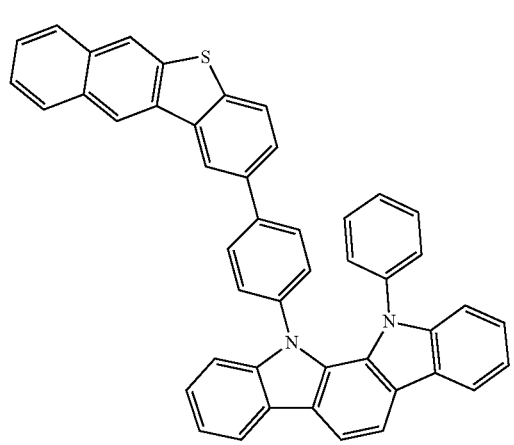
S-14
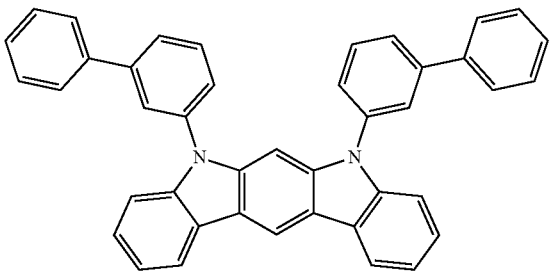
S-15
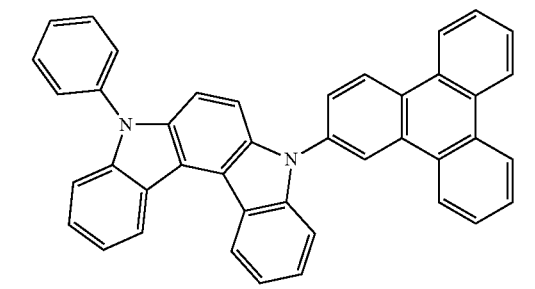
S-16
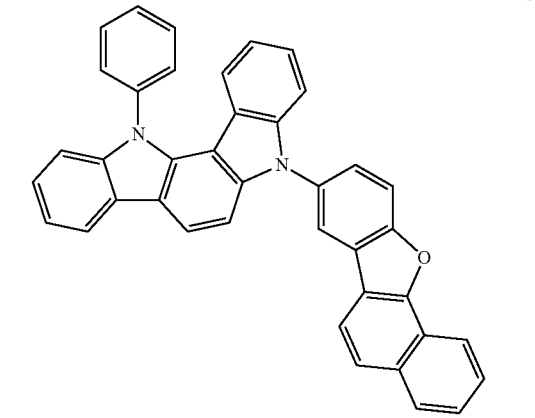
S-17
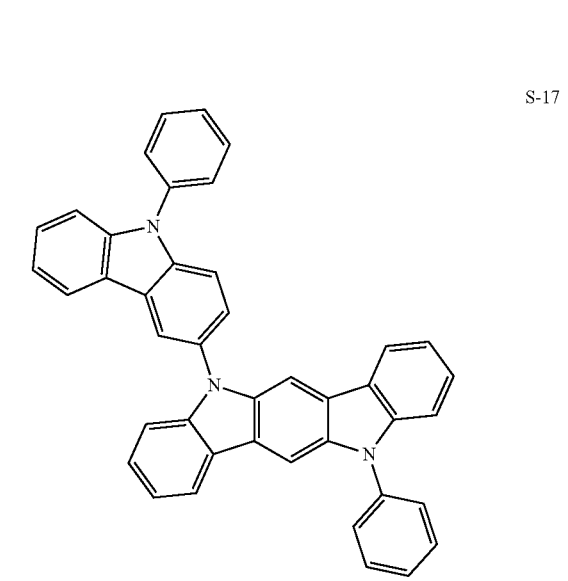

S-18
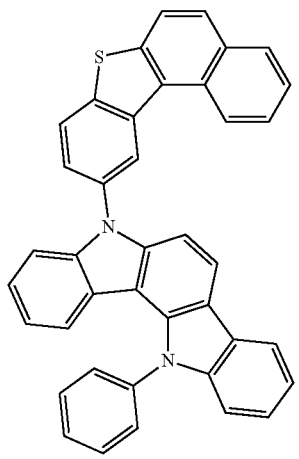
S-19
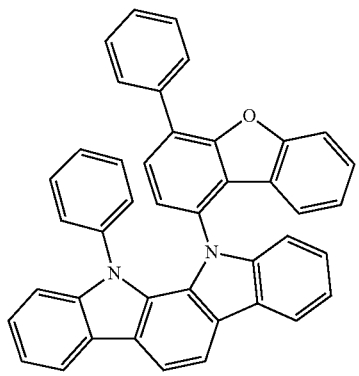
S-20
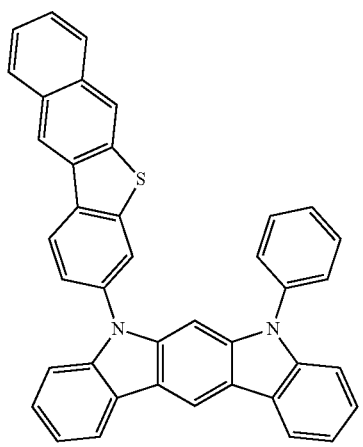
S-21
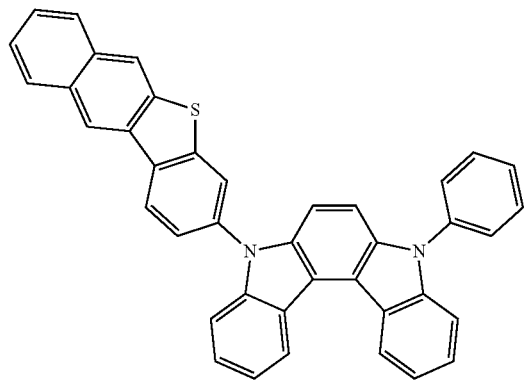
S-22
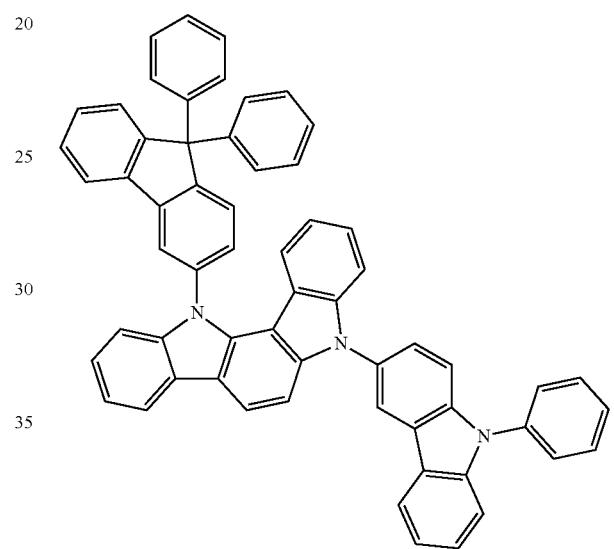
S-23
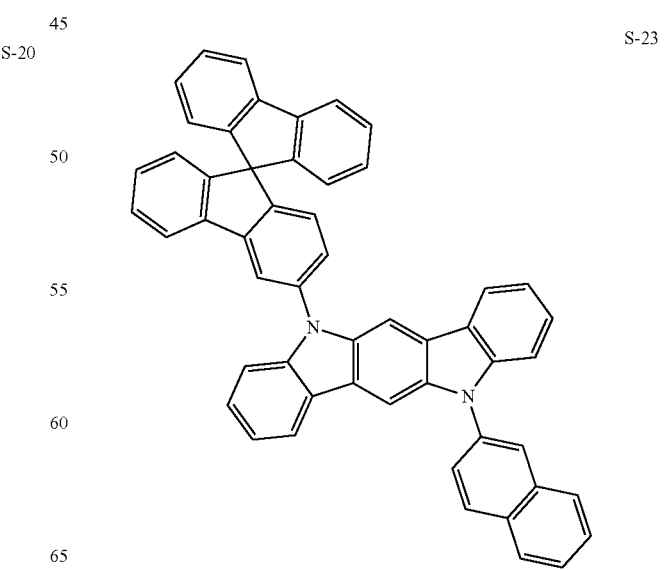

S-24
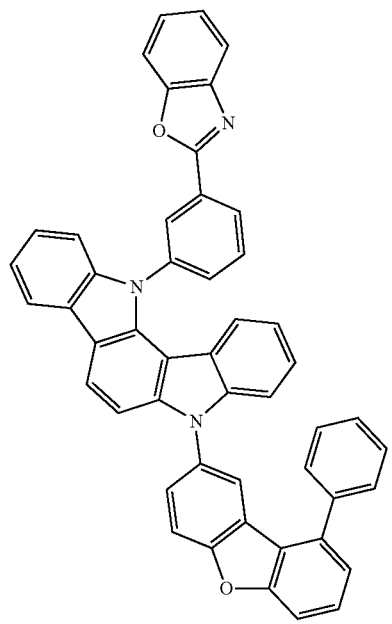
S-27
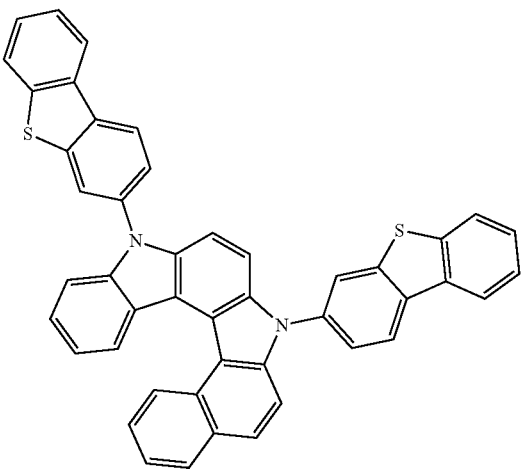
S-25
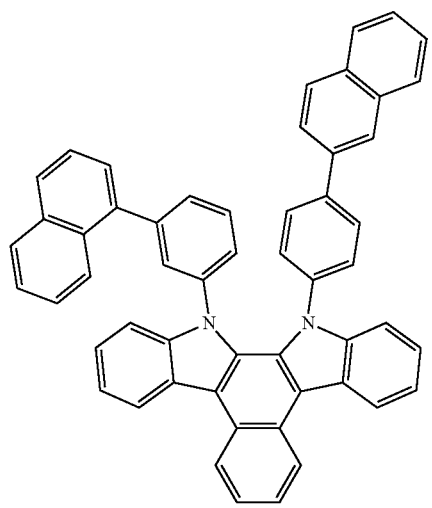
S-28
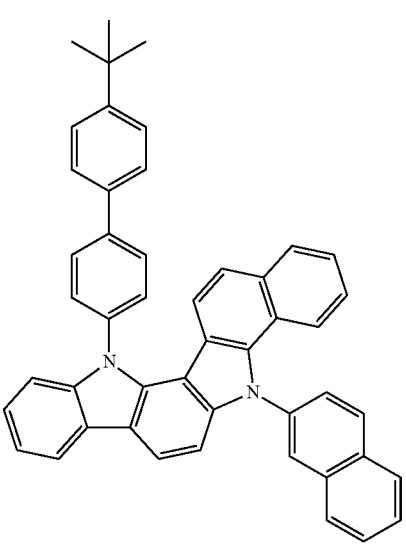
S-26
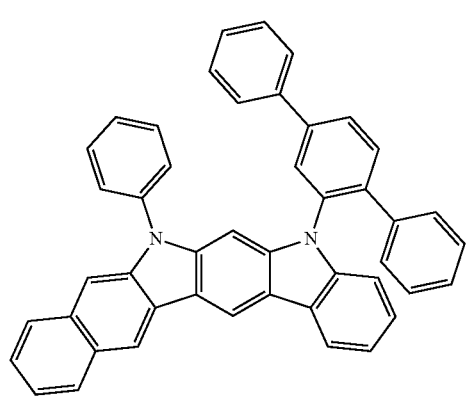
S-29
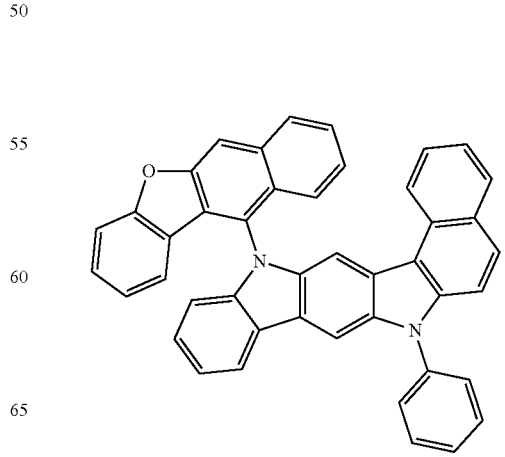

-continued
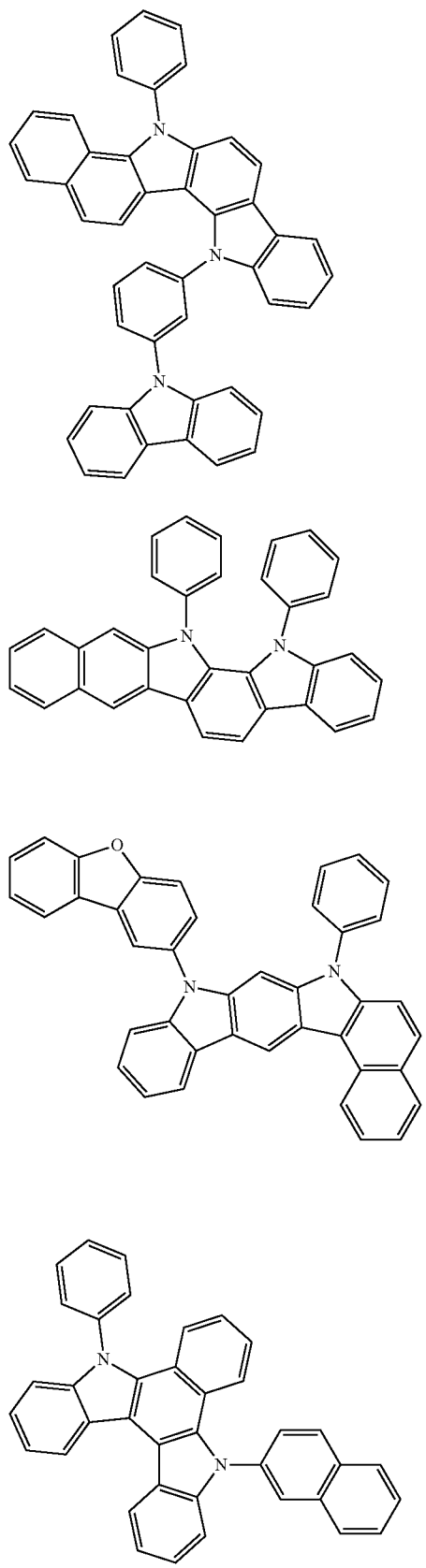
S-30
S-31
S-32
S-33
-continued
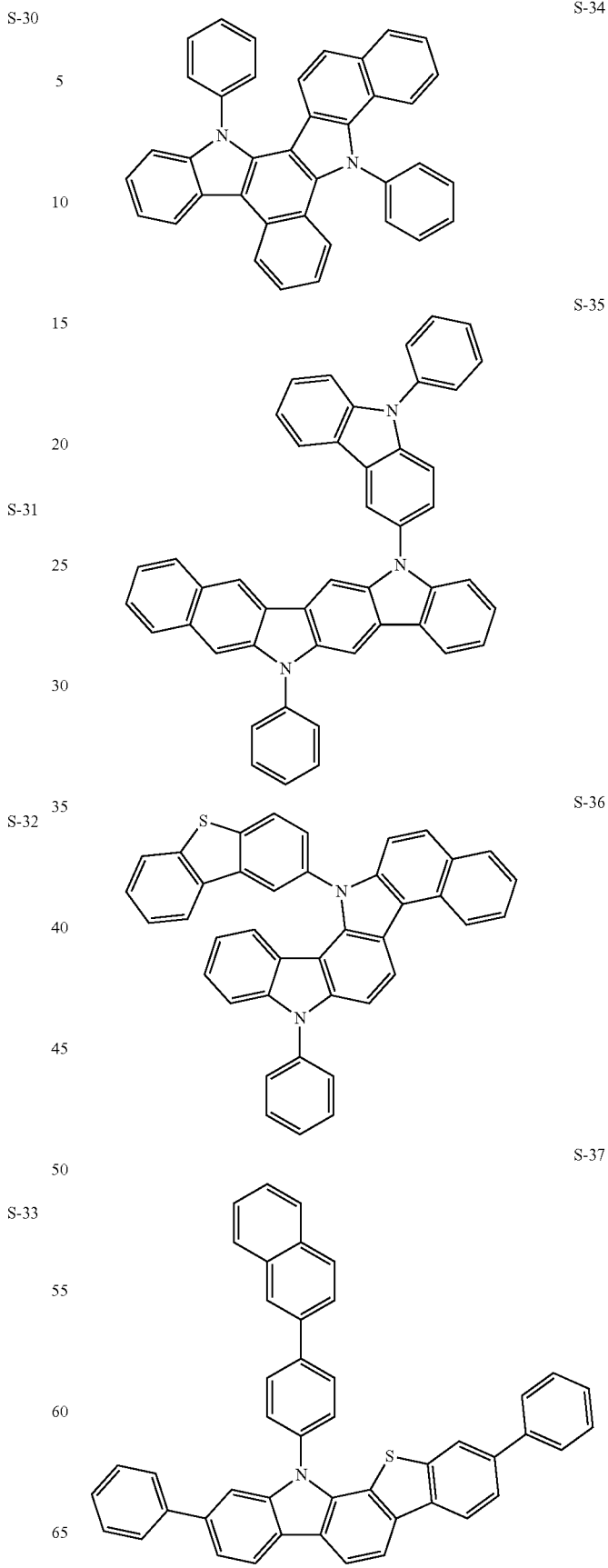
S-34
S-35
S-36
S-37

-continued
S-38
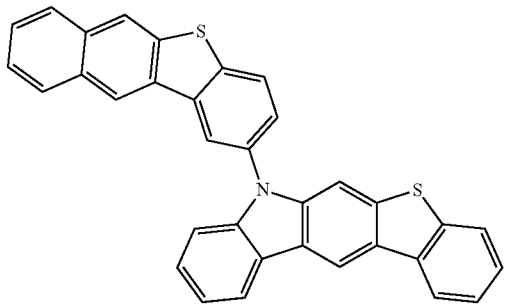
S-39
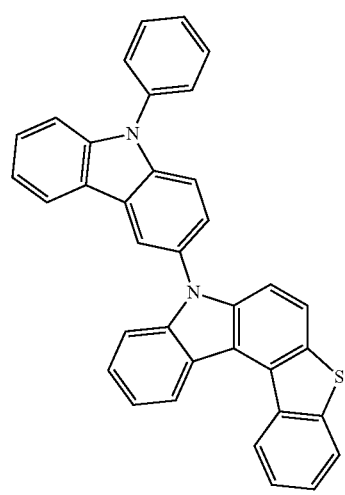
S-40
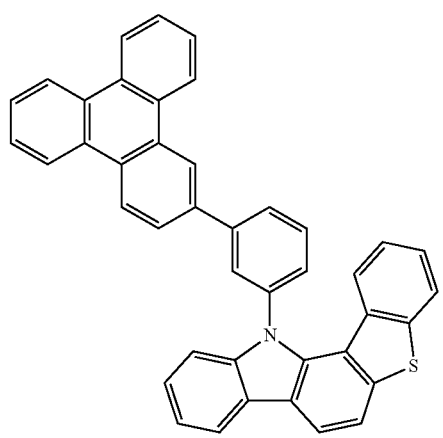
-continued
S-41
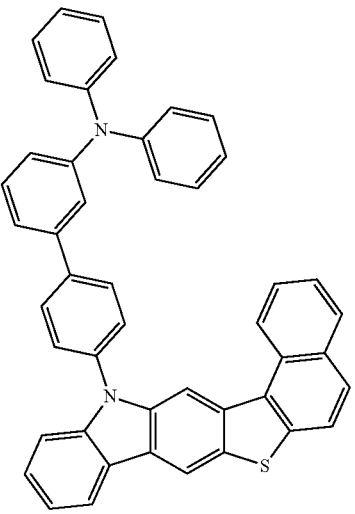
S-42
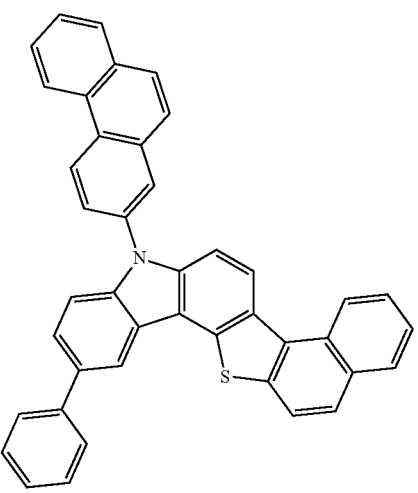
S-43
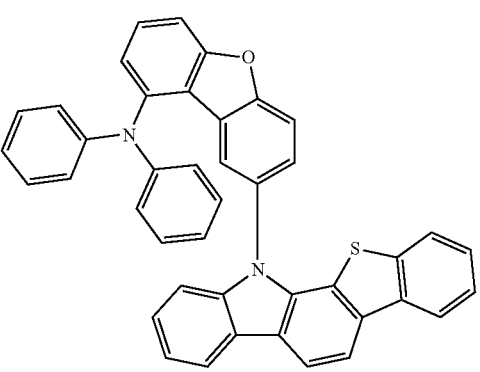

-continued
S-44
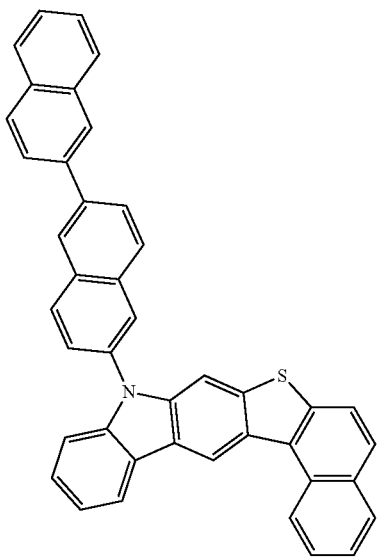
S-45
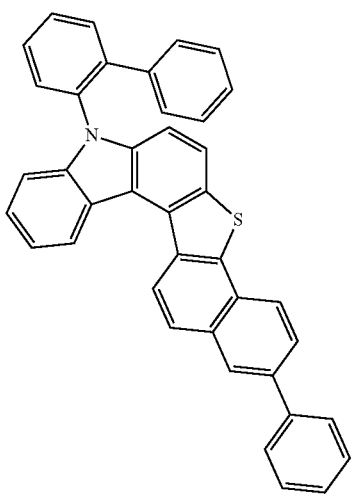
S-46
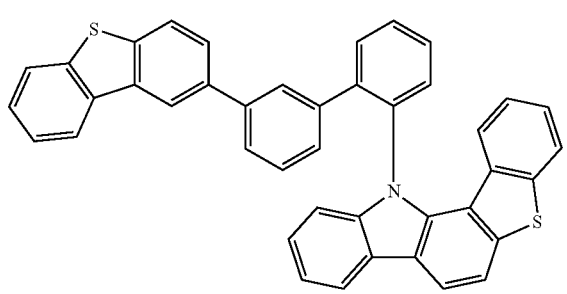
-continued
S-47
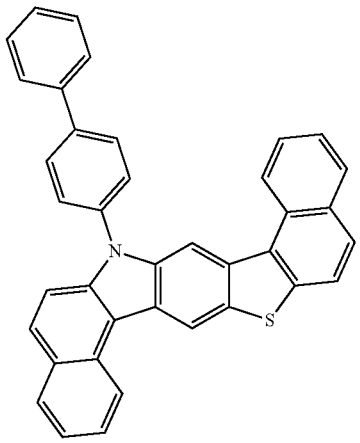
S-48
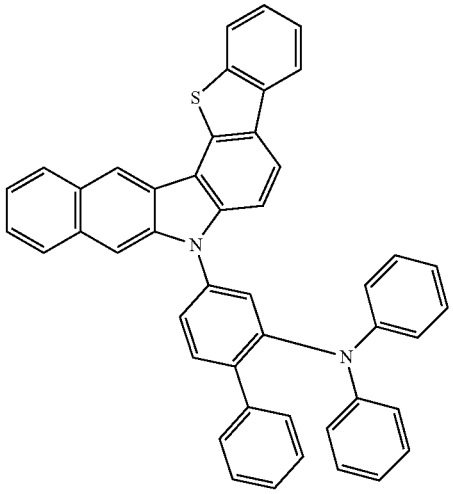
S-49
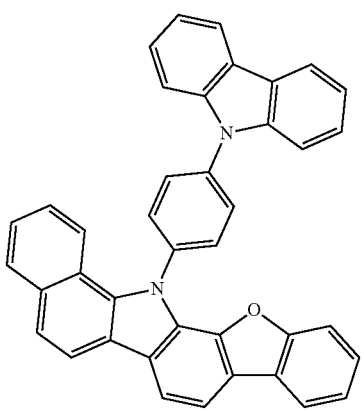

S-50
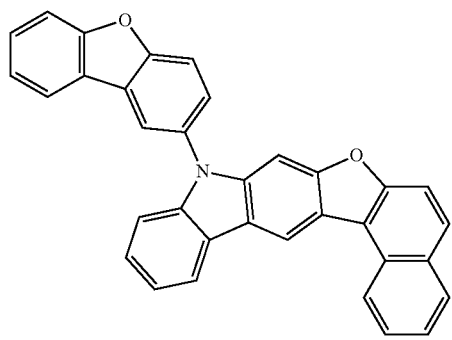
S-51
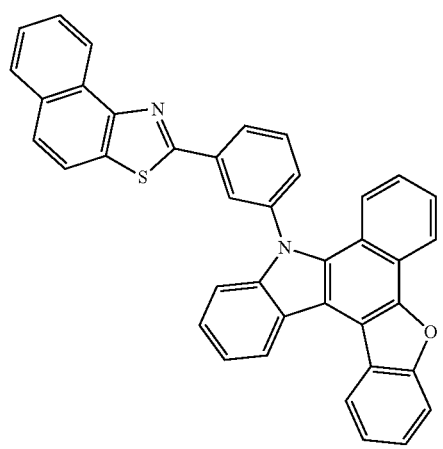
S-52
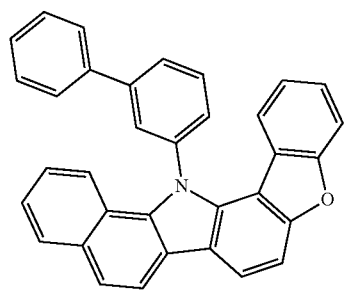
S-53
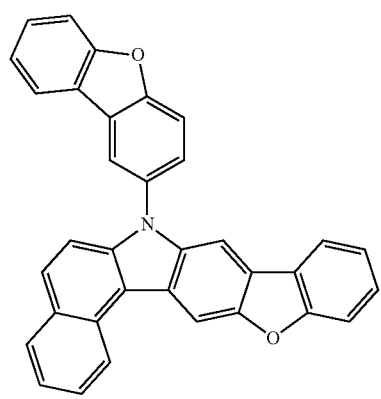
S-54
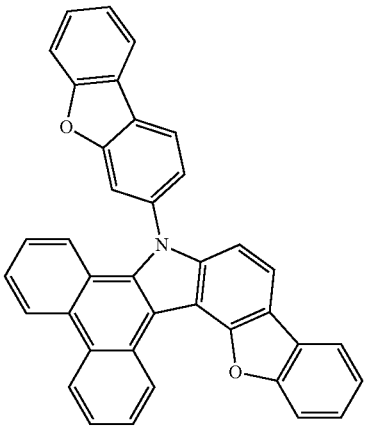
S-55
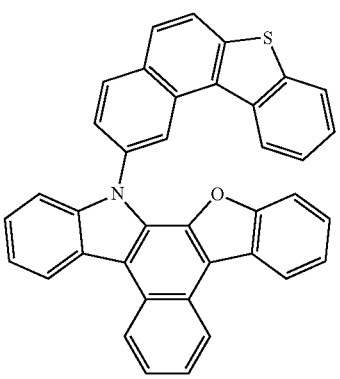
S-56
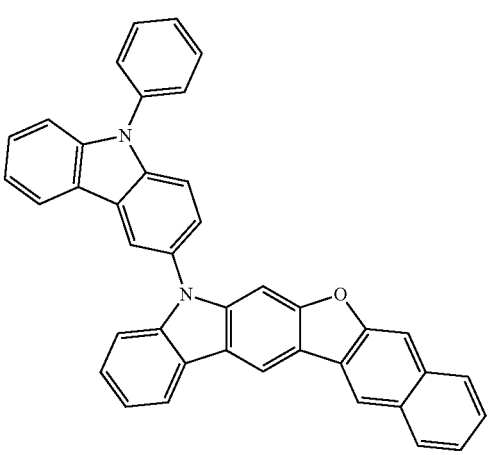
S-57
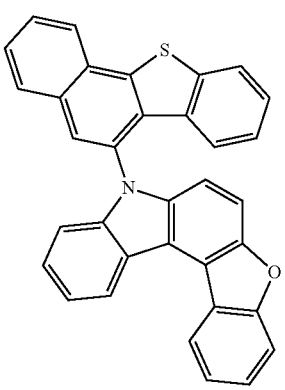

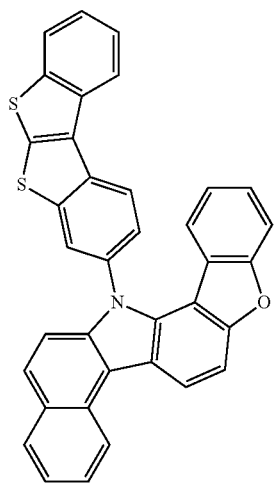
S-58
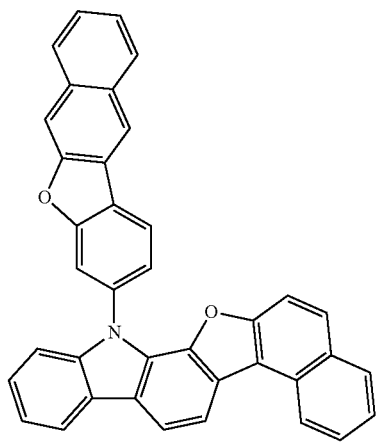
S-61
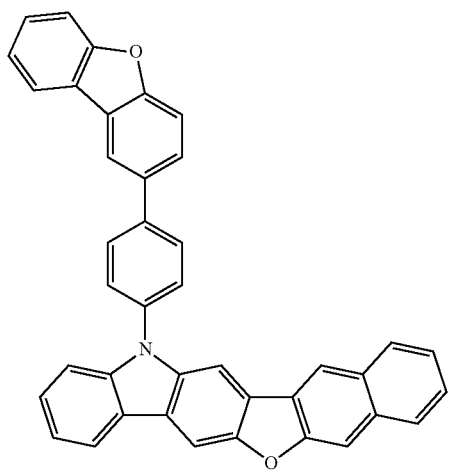
S-59
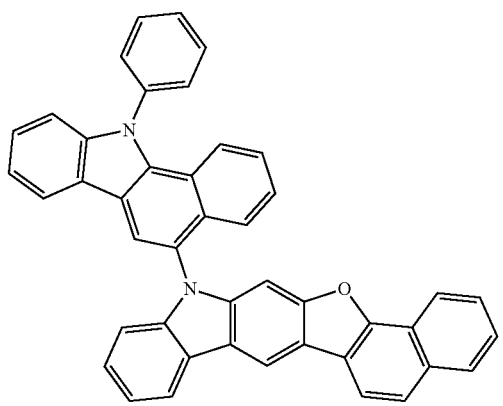
S-62
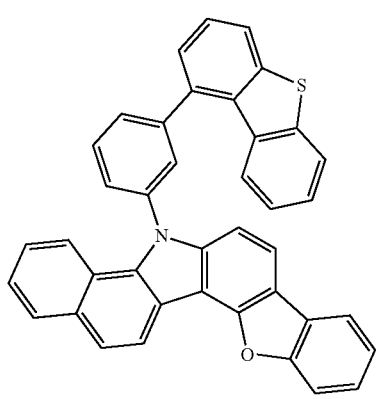
S-60
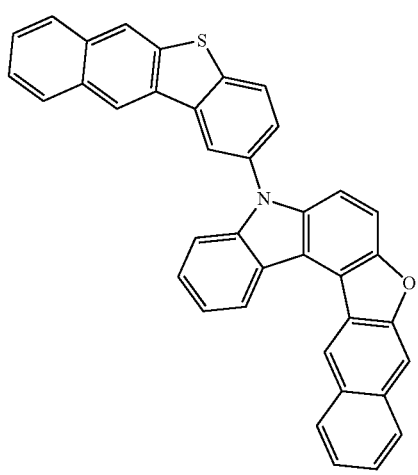
S-63

S-64
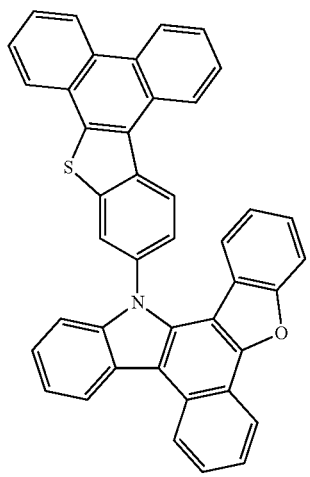
S-65
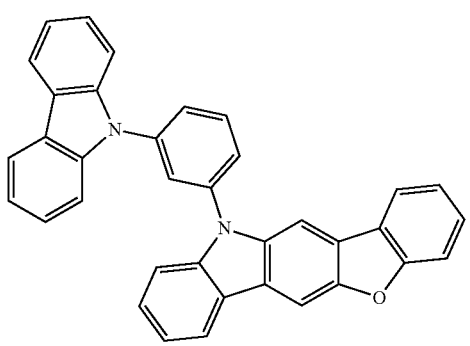
S-66
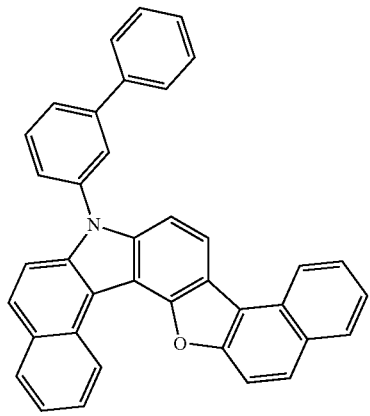
S-67
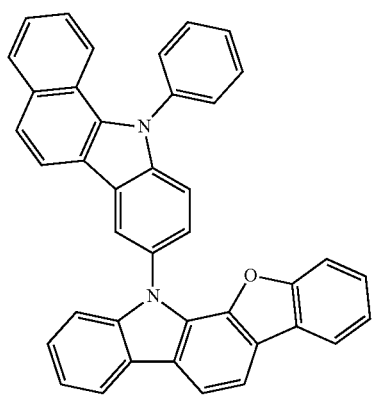
S-68
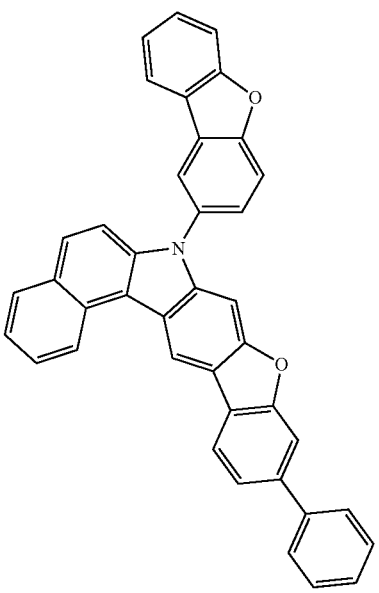
S-69
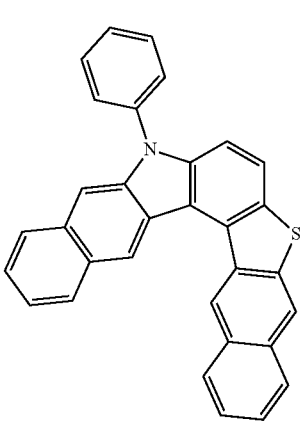
S-70
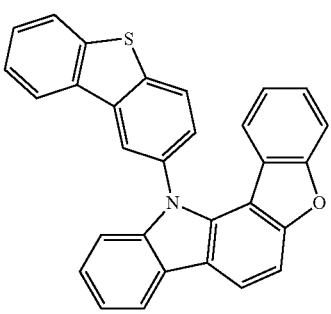

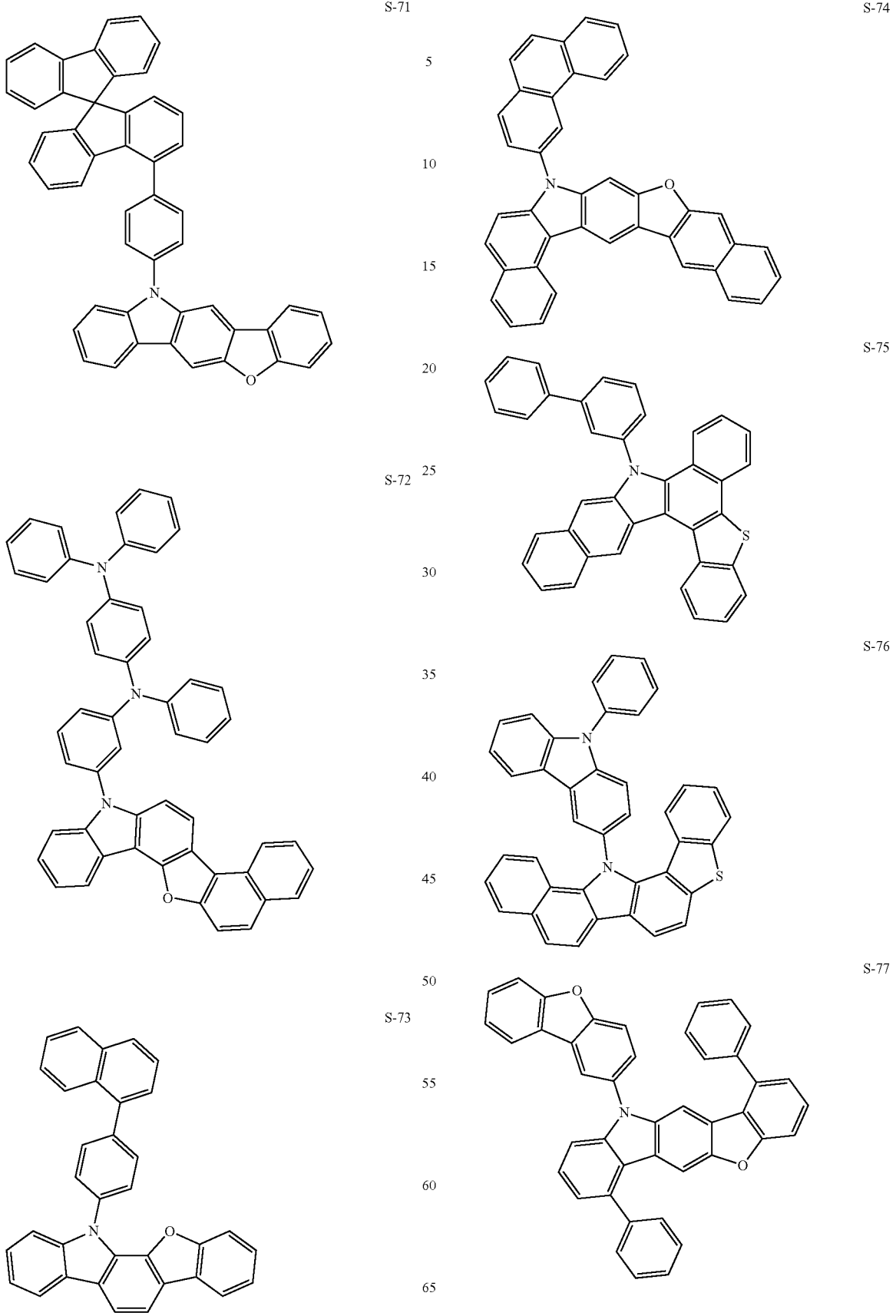

-continued
S-78
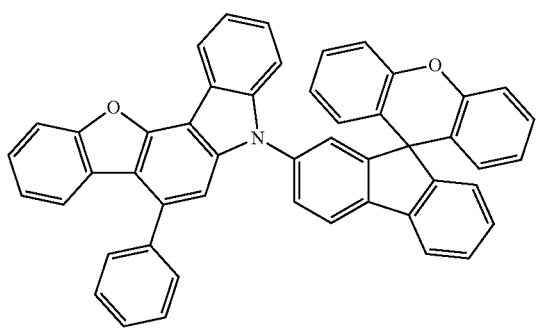
S-79
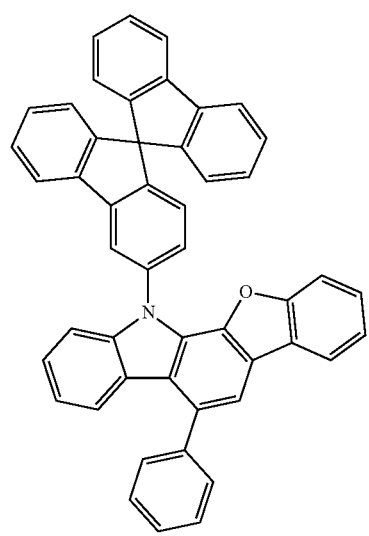
S-80
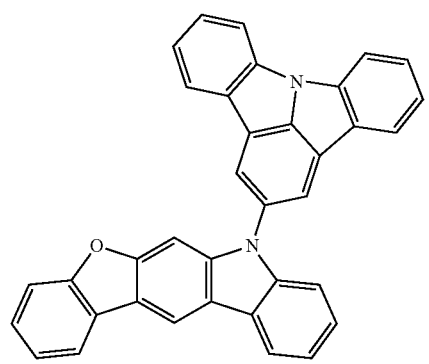
S-81
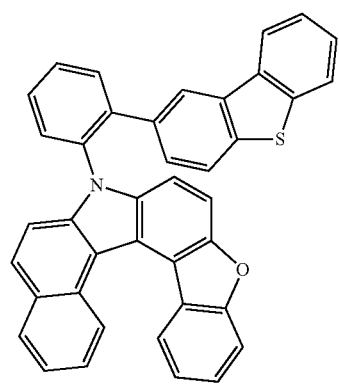
-continued
S-82
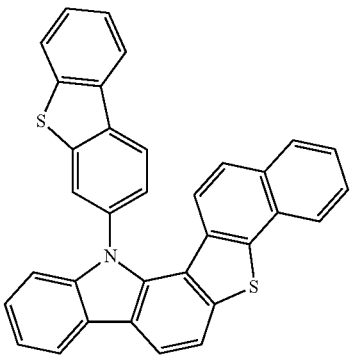
S-83
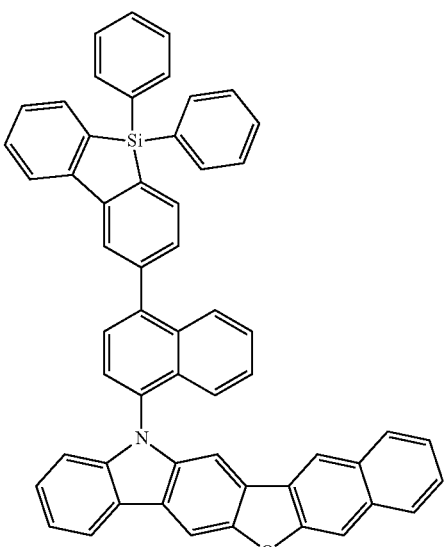
S-84
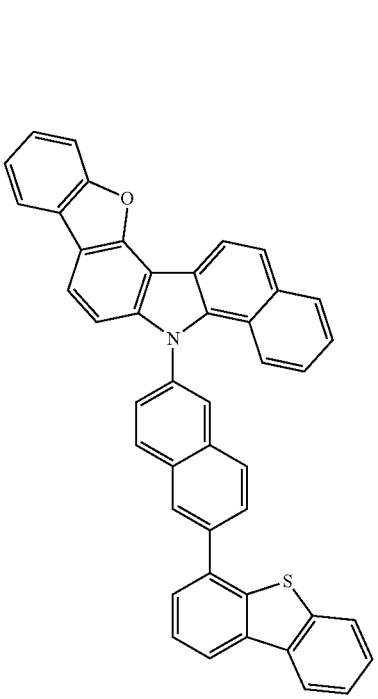

S-85
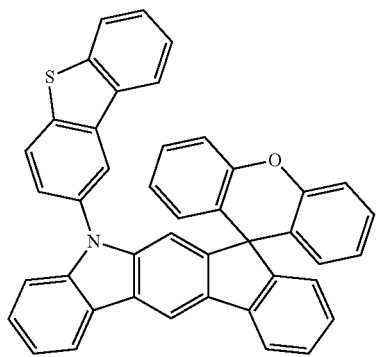
S-88
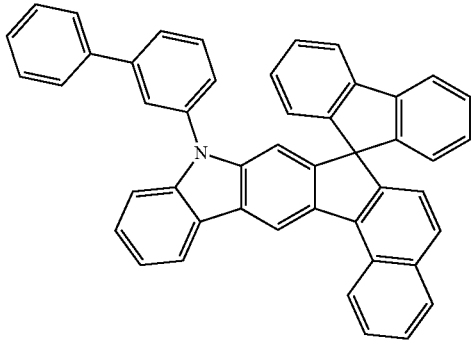
S-86
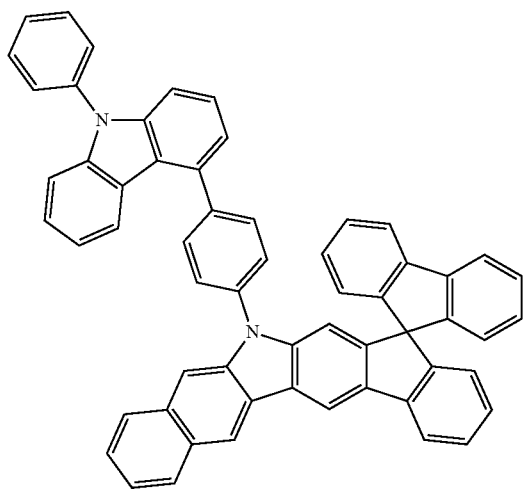
S-89
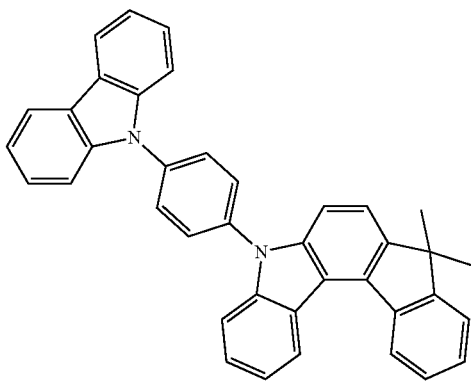
S-90
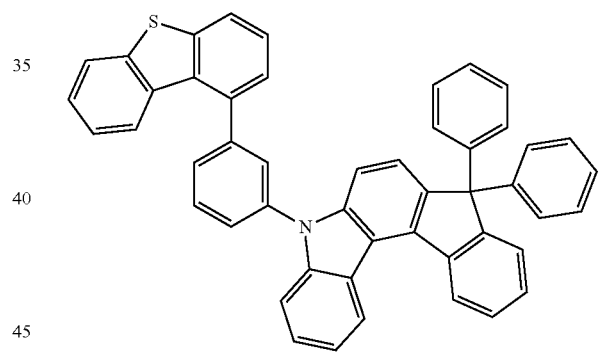
S-87
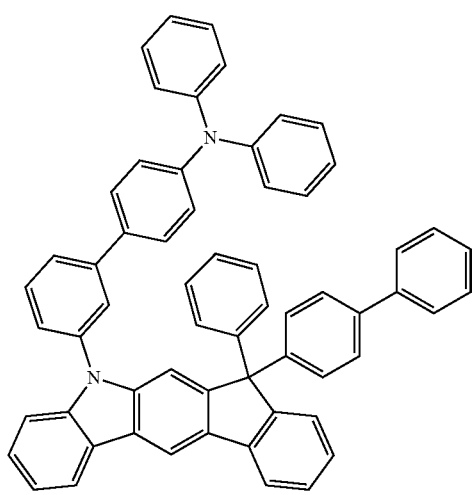
S-91
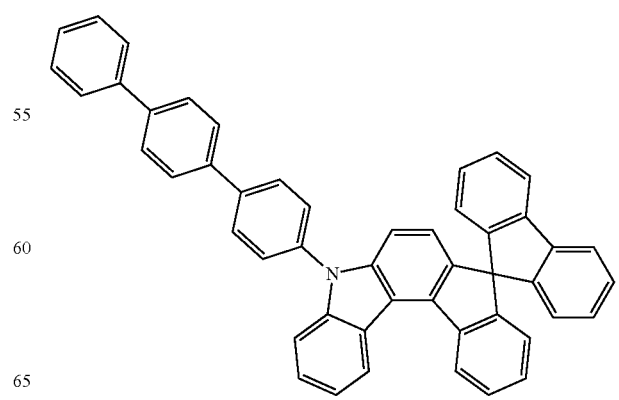

S-92
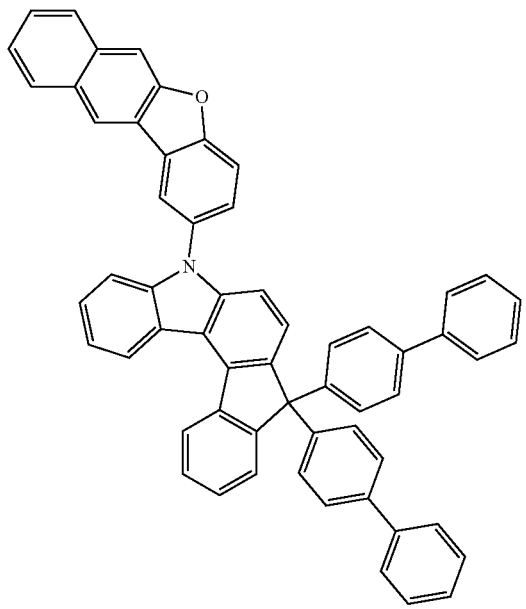
S-93
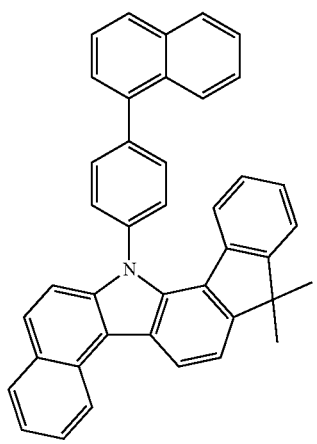
S-94
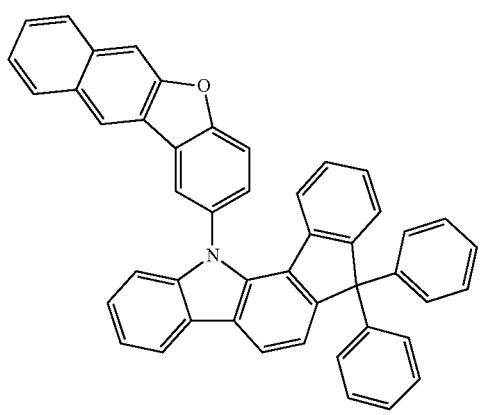
S-95
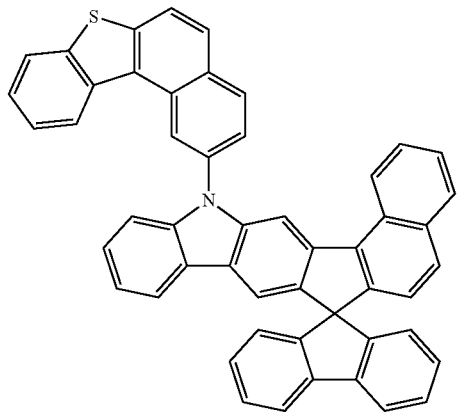
S-96
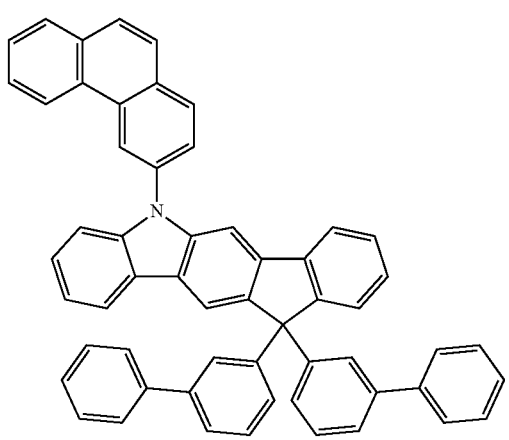
S-97
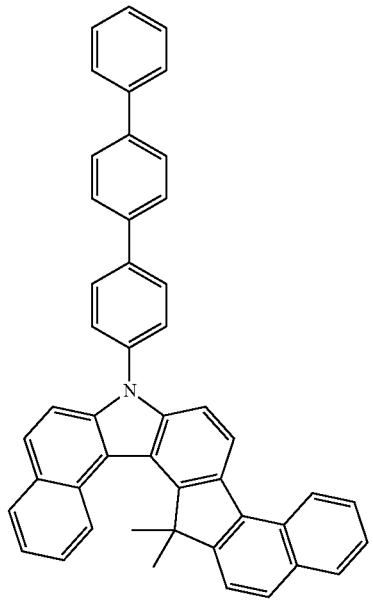

S-98
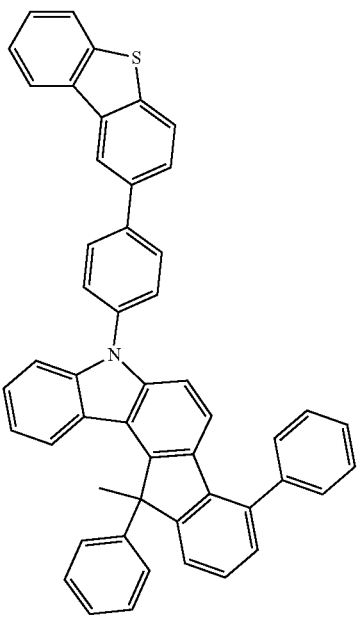
S-99
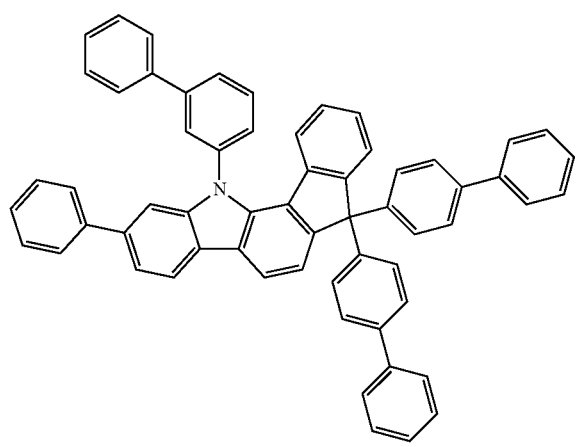
S-100
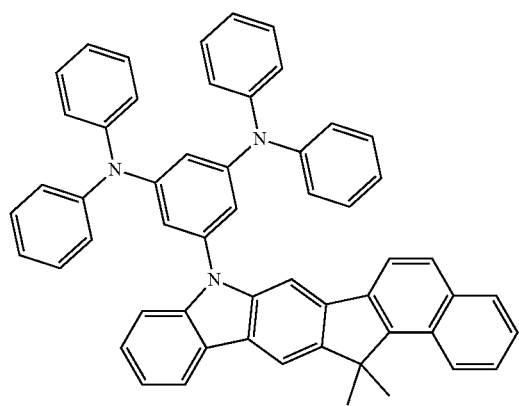
S-101
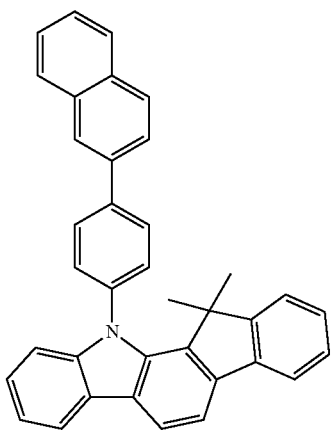
S-102
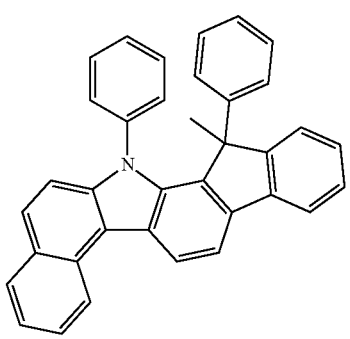
S-103
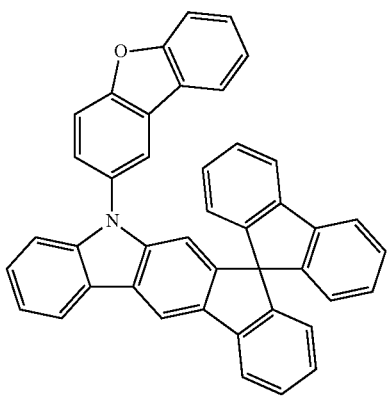
S-104
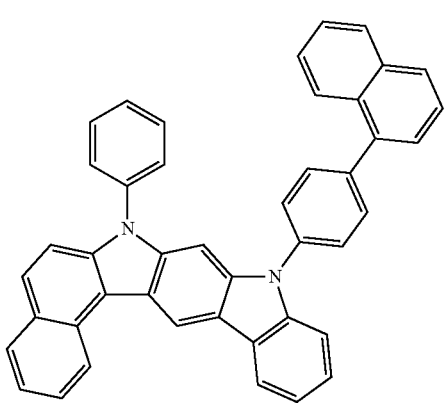

-continued

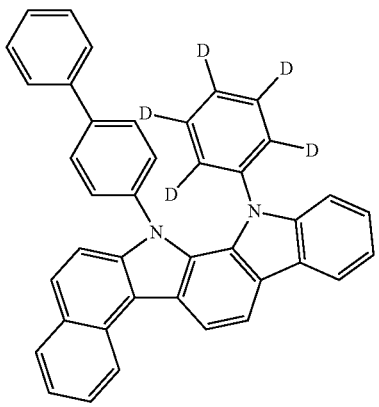
S-105

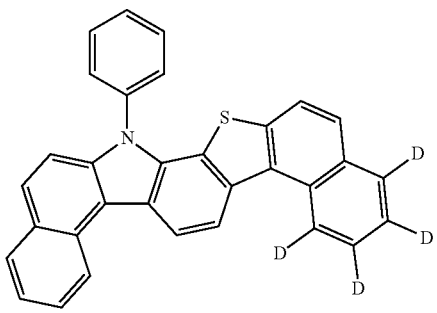
S-106

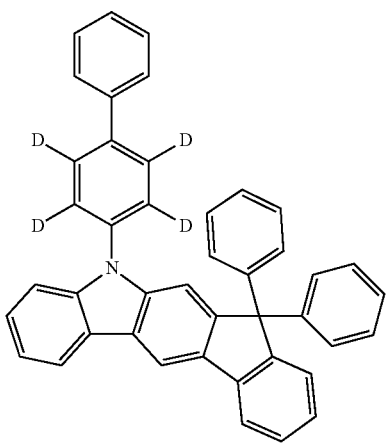
S-107

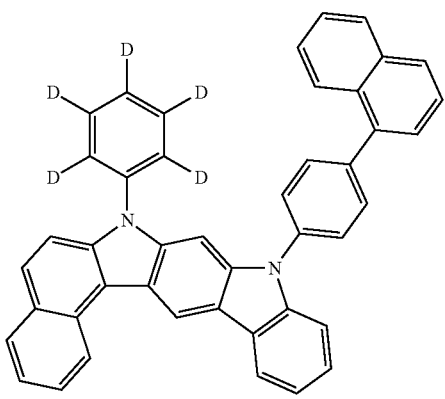
S-108

In another aspect, the present invention provides a method for reusing the compound represented by Formula 3 comprising:

a step of depositing an organic emitting material including the compound represented by Formula 3 in a manufacturing process of an organic light emitting device;
a step of removing impurities from the crude organic light emitting material recovered from the deposition apparatus;
a step of recovering the removed impurities; and
a step of purifying the recovered impurities to a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N, N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention includes a first electrode (110), a second electrode (170), an organic material layer comprising single compound represented by Formula 3 or 2 or more compounds between the first electrode (110) and the second electrode (170), Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
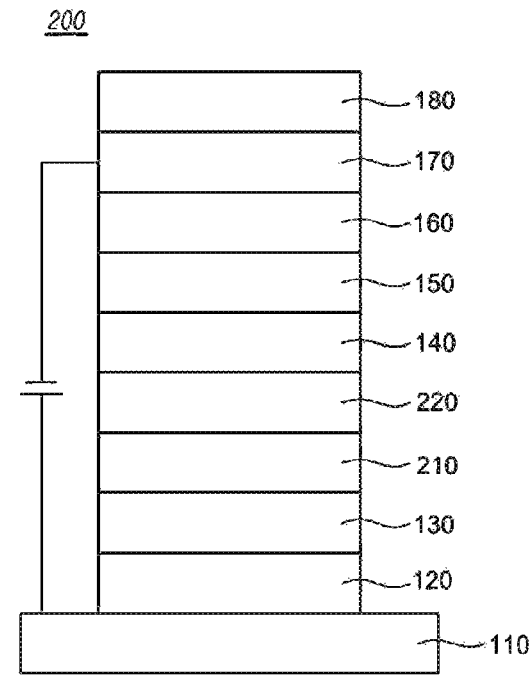

The organic material layer may sequentially comprise a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the compound according to Formula 3 of the present invention may be used as a host material for the emitting layer.

Figure 3:
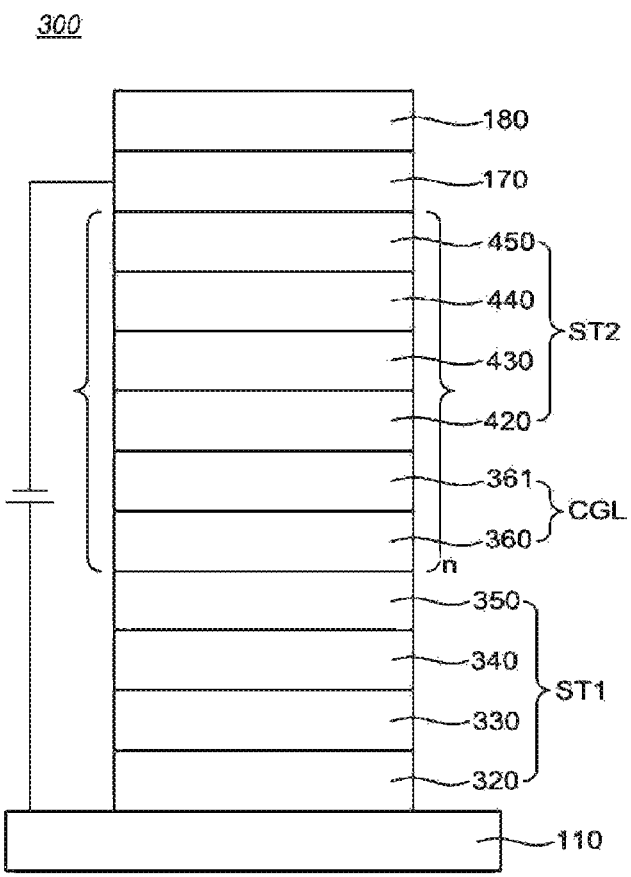
Figure 4:
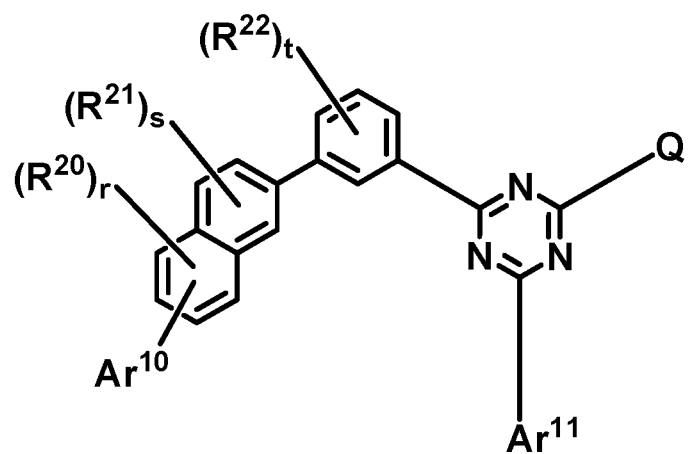
FIG. 4 shows a Formula according to one aspect of the present invention.

The organic material layer may include 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials(mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula 3 to the organic material layer.

Also, the present invention provides an emitting layer composition comprising a compound represented by Formula 3, and provides an organic electronic element comprising the emitting layer.

Also, the present invention also provides an electronic device comprising a display device including the organic electronic element; and a control unit for driving the display device.

According to another aspect, the present invention provides an display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, Synthesis examples of the compound represented by Formulas 2 to 5 and preparation examples of the organic electronic element of the present invention will be described in detail by way of example, but are not limited to the following examples.

[Synthesis Example 1] Compound Represented by Formula 2

The compound (final product 2) represented by Formula 2 according to the present invention may be prepared by reacting as in Reaction Scheme 4, but is not limited thereto.

<Reaction Scheme 4>(Hal$^4$=I, Br or Cl)

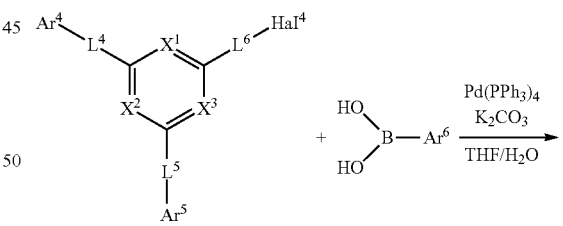

Final product 2

I. Synthesis of Final Product 2

1. Synthesis Example of N-1

2. Synthesis Example of N-19

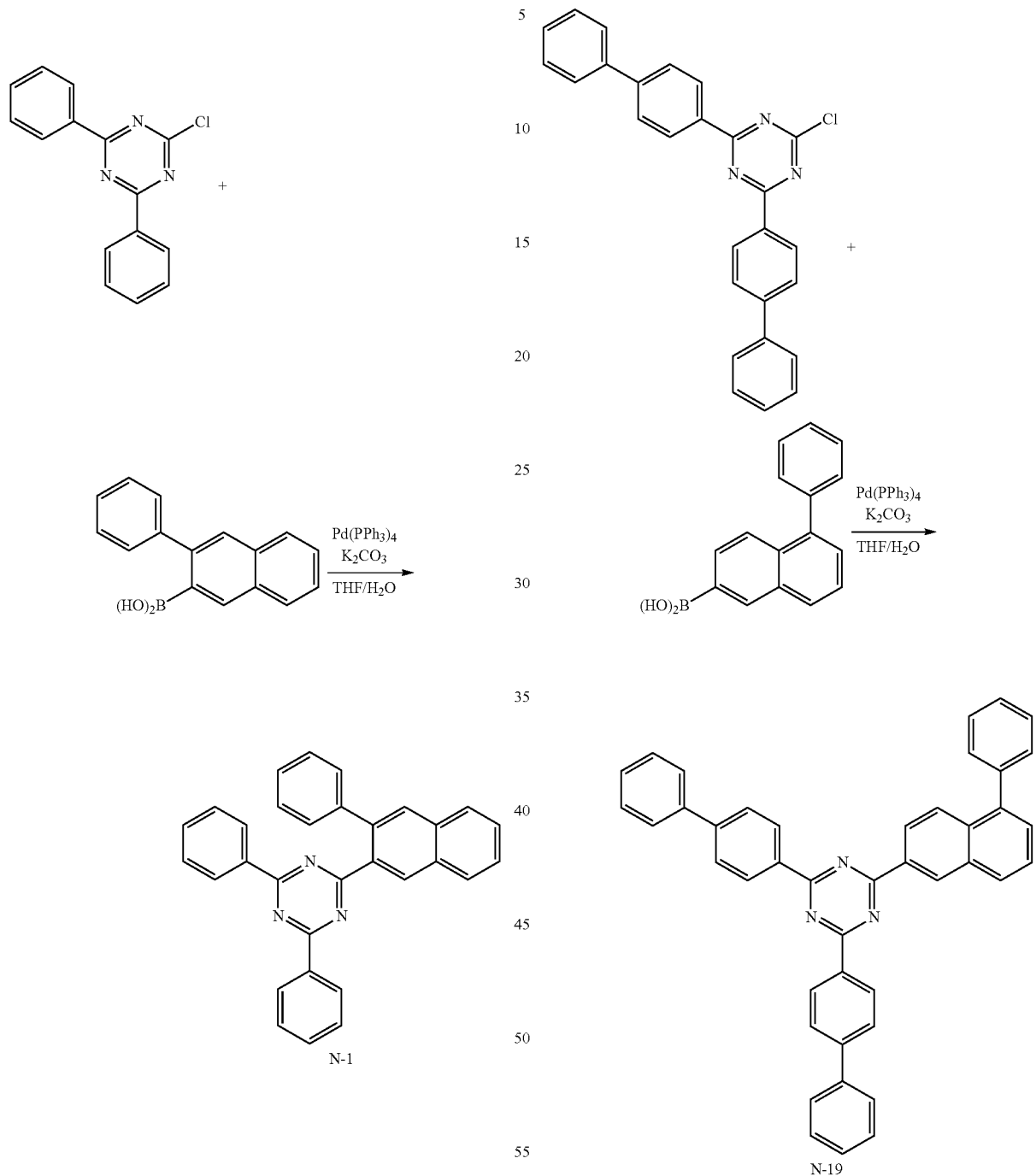

2-chloro-4,6-diphenyl-1,3,5-triazine (8 g, 30 mmol) and (3-phenylnaphthalen-2-yl)boronic acid (8.2 g, 33 mmol), K₂CO₃ (12.4 g, 90 mmol), Pd(PPh₃)₄ (1.7 g, 1.5 mmol) were placed in a round flask, after dissolving in THF and water, the mixture was refluxed at 80° C. for 12 hours. When the reaction was completed, the reactant was cooled to room temperature, extracted with CH₂Cl₂, and washed with water. After drying the organic layer with MgSO₄ and concentrating, the resulting organic material was separated using a silica gel column to obtain the desired product (9.54 g, 73%).

2,4-di([1,1'-biphenyl]-4-yl)-6-chloro-1,3,5-triazine (12.6 g, 30 mmol) and (5-phenylnaphthalen-2-yl)boronic acid (8.2 g, 33 mmol) were used for the synthesis method of N-1 to obtain 15.5 g (yield: 88%) of a product.

3. Synthesis Example of N-33

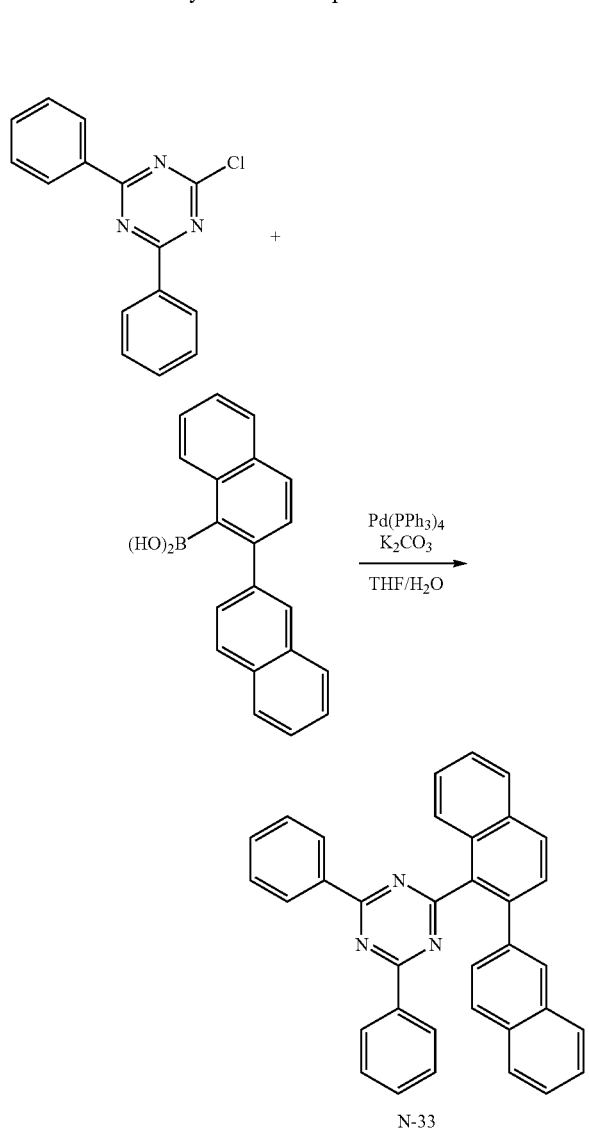

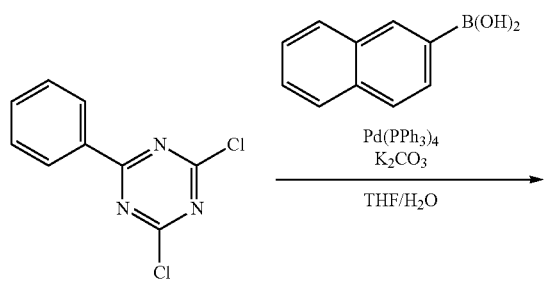

2-chloro-4,6-diphenyl-1,3,5-triazine (8 g, 30 mmol) and [2,2'-binaphthalen]-1-ylboronic acid (9.8 g, 33 mmol) were used for the synthesis method of N-1 to obtain 9.8 g (yield: 67%) of a product.

4. Synthesis Example of N-53

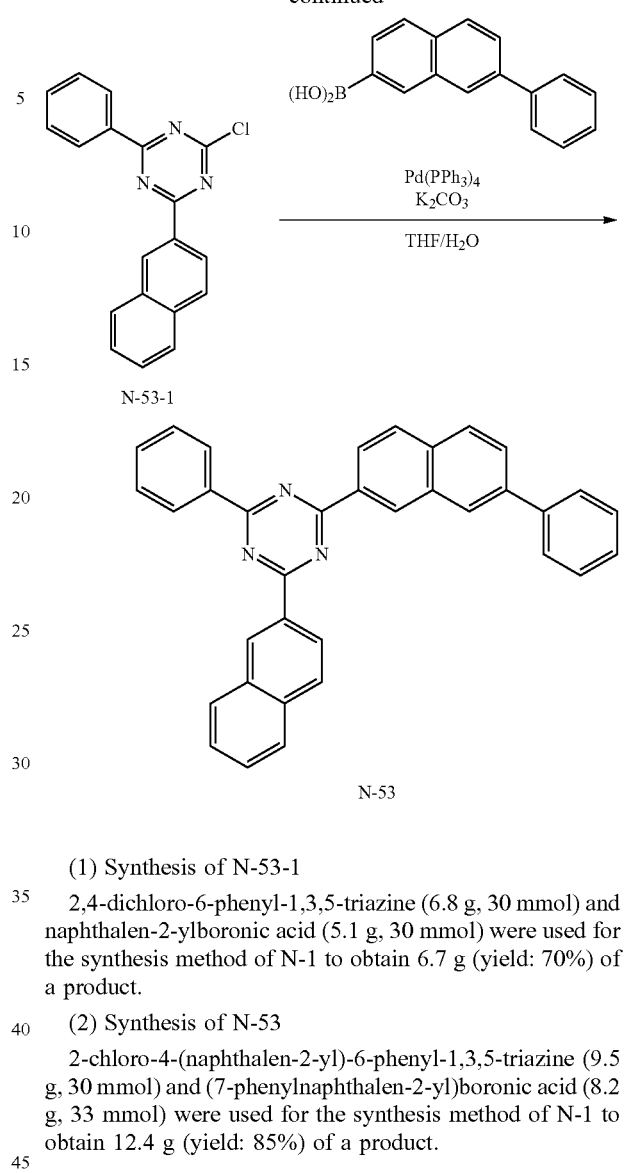

(1) Synthesis of N-53-1

2,4-dichloro-6-phenyl-1,3,5-triazine (6.8 g, 30 mmol) and naphthalen-2-ylboronic acid (5.1 g, 30 mmol) were used for the synthesis method of N-1 to obtain 6.7 g (yield: 70%) of a product.

(2) Synthesis of N-53

2-chloro-4-(naphthalen-2-yl)-6-phenyl-1,3,5-triazine (9.5 g, 30 mmol) and (7-phenylnaphthalen-2-yl)boronic acid (8.2 g, 33 mmol) were used for the synthesis method of N-1 to obtain 12.4 g (yield: 85%) of a product.

5. Synthesis Example of N-87

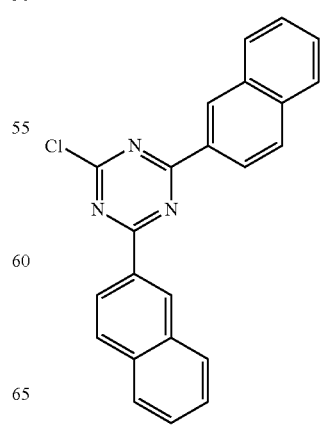

-continued

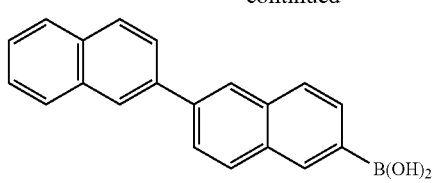

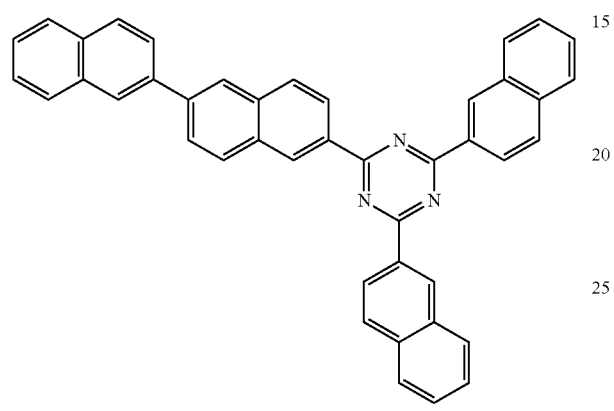
N-87

2-chloro-4,6-di(naphthalen-2-yl)-1,3,5-triazine (11 g, 30 mmol) and [2,2'-binaphthalen]-6-ylboronic acid (9.8 g, 33 mmol) were used for the synthesis method of N-1 to obtain 14.8 g (yield: 84%) of a product.

6. Synthesis Example of N-113

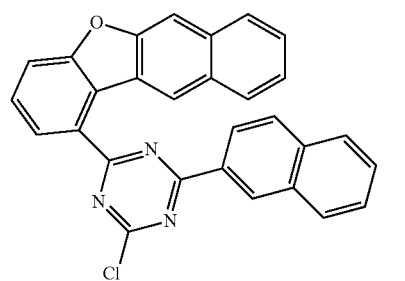

+

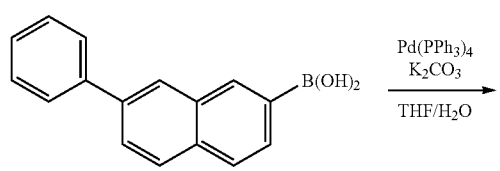

-continued

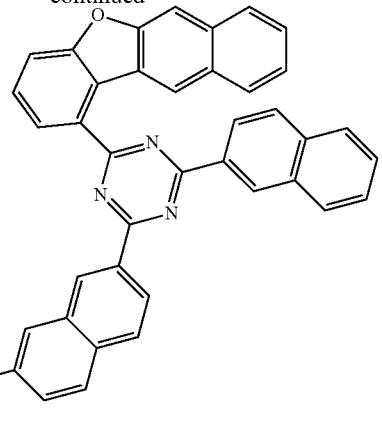
N-113

2-chloro-4-(naphthalen-2-yl)-6-(naphtho[2,3-b]benzo-furan-1-yl)-1,3,5-triazine (13.7 g, 30 mmol) and (7-phenylnaphthalen-2-yl)boronic acid (8.2 g, 33 mmol) were used for the synthesis method of N-1 to obtain 14.5 g (yield: 77%) of a product.

7. Synthesis Example of N-115

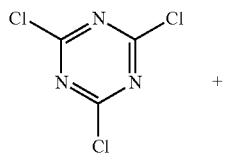

+

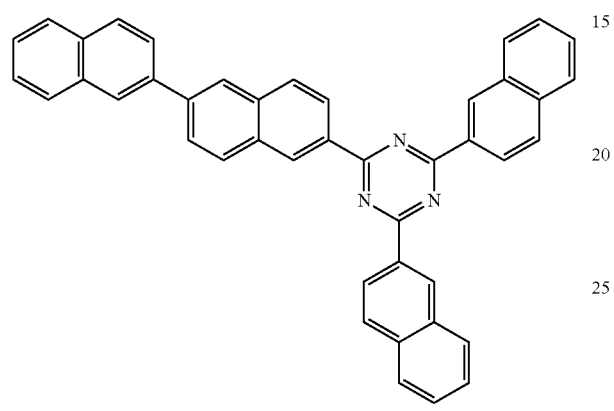
N-115

2,4,6-trichloro-1,3,5-triazine (5.5 g, 30 mmol) and (6-phenylnaphthalen-2-yl)boronic acid (23 g, 93 mmol) were used for the synthesis method of N-1 to obtain 15 g (yield: 73%) of a product.

8. Synthesis Example of N-165

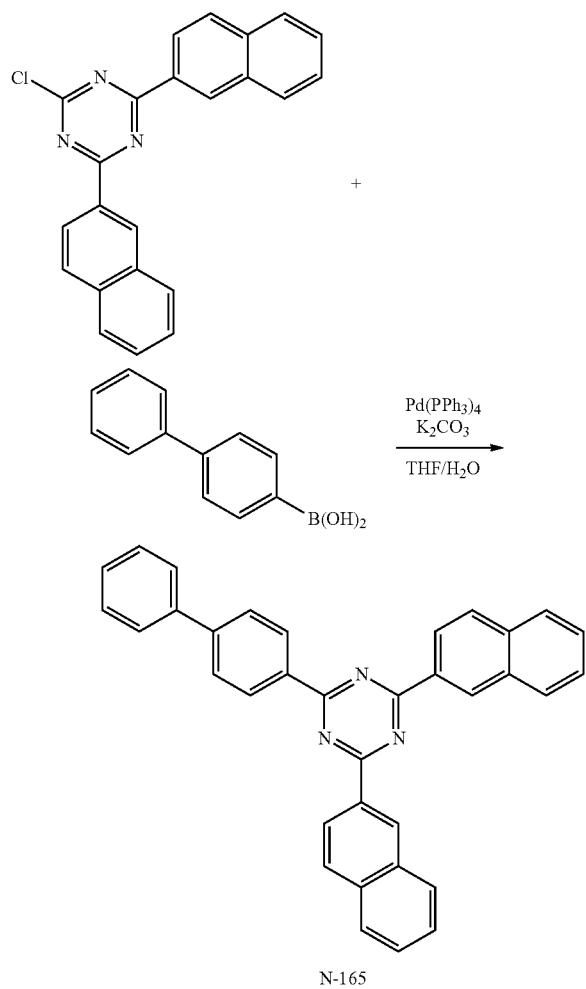

N-165

2-chloro-4,6-di(naphthalen-2-yl)-1,3,5-triazine (11 g, 30 mmol) and [1,1'-biphenyl]-4-ylboronic acid (5.9 g, 30 mmol) were used for the synthesis method of N-1 to obtain 11.9 g (yield: 82%) of a product.

9. Synthesis Example of N-117

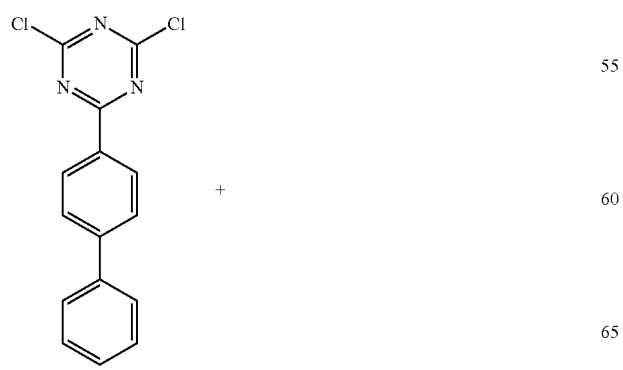

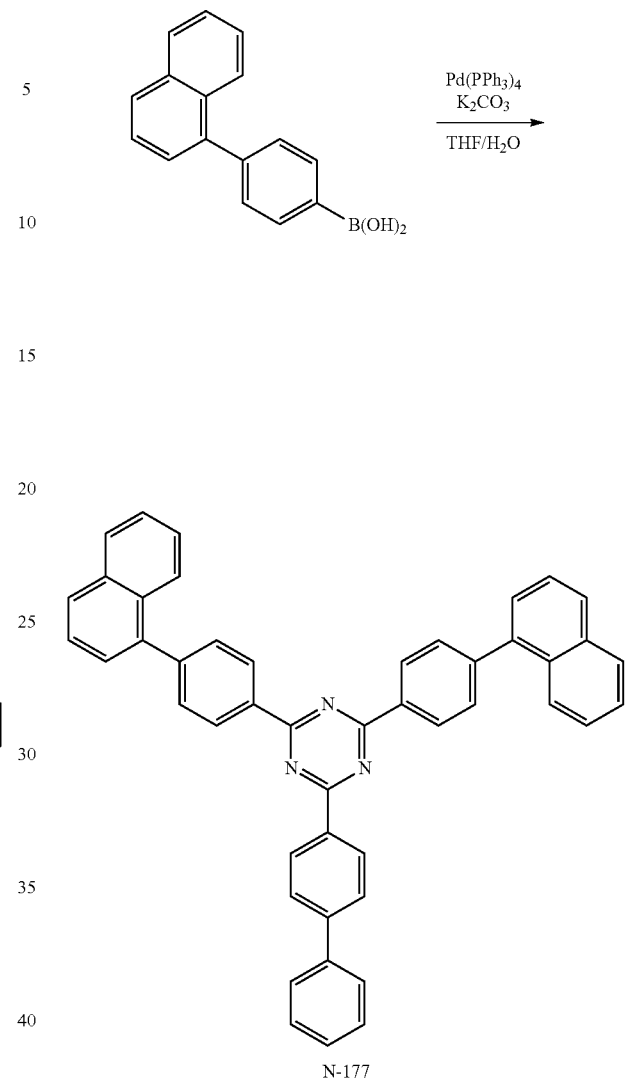

N-177

2-([1,1'-biphenyl]-4-yl)-4,6-dichloro-1,3,5-triazine (9 g, 30 mmol) and (4-(naphthalen-1-yl)phenyl)boronic acid (15.4 g, 62 mmol) were used for the synthesis method of N-1 to obtain 12.8 g (yield: 67%) of a product.

Further, the FD-MS values of the compounds N-1 to N-184 of the present invention prepared according to the Synthesis Example as described above are shown in Table 4.

TABLE 4

| compound | FD-MS | compound | FD-MS |
| --- | --- | --- | --- |
| N-1 | m/z = 435.17($C_{31}H_{21}N_3$ = 435.53) | N-2 | m/z = 435.17($C_{31}H_{21}N_3$ = 435.53) |
| N-3 | m/z = 435.17($C_{31}H_{21}N_3$ = 435.53) | N-4 | m/z = 435.17($C_{31}H_{21}N_3$ = 435.53) |
| N-5 | m/z = 435.17($C_{31}H_{21}N_3$ = 435.53) | N-6 | m/z = 435.17($C_{31}H_{21}N_3$ = 435.53) |
| N-7 | m/z = 435.17($C_{31}H_{21}N_3$ = 435.53) | N-8 | m/z = 434.18($C_{32}H_{22}N_2$ = 434.54) |
| N-9 | m/z = 511.2($C_{37}H_{25}N_3$ = 511.63) | N-10 | m/z = 611.24($C_{45}H_{29}N_3$ = 611.75) |
| N-11 | m/z = 485.19($C_{35}H_{23}N_3$ = 485.59) | N-12 | m/z = 511.2($C_{37}H_{25}N_3$ = 511.63) |
| N-13 | m/z = 511.2($C_{37}H_{25}N_3$ = 511.63) | N-14 | m/z = 485.19($C_{35}H_{23}N_3$ = 485.59) |
| N-15 | m/z = 434.18($C_{32}H_{22}N_2$ = 434.54) | N-16 | m/z = 434.18($C_{32}H_{22}N_2$ = 434.54) |
| N-17 | m/z = 511.2($C_{37}H_{25}N_3$ = 511.63) | N-18 | m/z = 561.22($C_{41}H_{27}N_3$ = 561.69) |
| N-19 | m/z = 587.24($C_{43}H_{29}N_3$ = 587.73) | N-20 | m/z = 511.2($C_{37}H_{25}N_3$ = 511.63) |
| N-21 | m/z = 511.2($C_{37}H_{25}N_3$ = 511.63) | N-22 | m/z = 511.2($C_{37}H_{25}N_3$ = 511.63) |
| N-23 | m/z = 511.2($C_{37}H_{25}N_3$ = 511.63) | N-24 | m/z = 587.24($C_{43}H_{29}N_3$ = 587.73) |
| N-25 | m/z = 435.17($C_{31}H_{21}N_3$ = 435.53) | N-26 | m/z = 435.17($C_{31}H_{21}N_3$ = 435.53) |
| N-27 | m/z = 435.17($C_{31}H_{21}N_3$ = 435.53) | N-28 | m/z = 435.17($C_{31}H_{21}N_3$ = 435.53) |
| N-29 | m/z = 435.17($C_{31}H_{21}N_3$ = 435.53) | N-30 | m/z = 435.17($C_{31}H_{21}N_3$ = 435.53) |
| N-31 | m/z = 435.17($C_{31}H_{21}N_3$ = 435.53) | N-32 | m/z = 434.18($C_{32}H_{22}N_2$ = 434.54) |
| N-33 | m/z = 485.19($C_{35}H_{23}N_3$ = 485.59) | N-34 | m/z = 511.2($C_{37}H_{25}N_3$ = 511.63) |
| N-35 | m/z = 511.2($C_{37}H_{25}N_3$ = 511.63) | N-36 | m/z = 511.2($C_{37}H_{25}N_3$ = 511.63) |
| N-37 | m/z = 485.19($C_{35}H_{23}N_3$ = 485.59) | N-38 | m/z = 511.2($C_{37}H_{25}N_3$ = 511.63) |
| N-39 | m/z = 485.19($C_{35}H_{23}N_3$ = 485.59) | N-40 | m/z = 611.24($C_{45}H_{29}N_3$ = 611.75) |
| N-41 | m/z = 511.2($C_{37}H_{25}N_3$ = 511.63) | N-42 | m/z = 511.2($C_{37}H_{25}N_3$ = 511.63) |
| N-43 | m/z = 587.24($C_{43}H_{29}N_3$ = 587.73) | N-44 | m/z = 587.24($C_{43}H_{29}N_3$ = 587.73) |
| N-45 | m/z = 587.24($C_{43}H_{29}N_3$ = 587.73) | N-46 | m/z = 561.22($C_{41}H_{27}N_3$ = 561.69) |
| N-47 | m/z = 511.2($C_{37}H_{25}N_3$ = 511.63) | N-48 | m/z = 587.24($C_{43}H_{29}N_3$ = 587.73) |
| N-49 | m/z = 485.19($C_{35}H_{23}N_3$ = 485.59) | N-50 | m/z = 485.19($C_{35}H_{23}N_3$ = 485.59) |
| N-51 | m/z = 485.19($C_{35}H_{23}N_3$ = 485.59) | N-52 | m/z = 485.19($C_{35}H_{23}N_3$ = 485.59) |
| N-53 | m/z = 485.19($C_{35}H_{23}N_3$ = 485.59) | N-54 | m/z = 535.2($C_{39}H_{25}N_3$ = 535.65) |
| N-55 | m/z = 485.19($C_{35}H_{23}N_3$ = 485.59) | N-56 | m/z = 485.19($C_{35}H_{23}N_3$ = 485.59) |
| N-57 | m/z = 561.22($C_{41}H_{27}N_3$ = 561.69) | N-58 | m/z = 561.22($C_{41}H_{27}N_3$ = 561.69) |
| N-59 | m/z = 561.22($C_{41}H_{27}N_3$ = 561.69) | N-60 | m/z = 637.25($C_{47}H_{31}N_3$ = 637.79) |
| N-61 | m/z = 561.22($C_{41}H_{27}N_3$ = 561.69) | N-62 | m/z = 561.22($C_{41}H_{27}N_3$ = 561.69) |
| N-63 | m/z = 637.25($C_{47}H_{31}N_3$ = 637.79) | N-64 | m/z = 637.25($C_{47}H_{31}N_3$ = 637.79) |
| N-65 | m/z = 637.25($C_{47}H_{31}N_3$ = 637.79) | N-66 | m/z = 485.19($C_{35}H_{23}N_3$ = 485.59) |
| N-67 | m/z = 485.19($C_{35}H_{23}N_3$ = 485.59) | N-68 | m/z = 611.24($C_{45}H_{29}N_3$ = 611.75) |
| N-69 | m/z = 485.19($C_{35}H_{23}N_3$ = 485.59) | N-70 | m/z = 485.19($C_{35}H_{23}N_3$ = 485.59) |
| N-71 | m/z = 611.24($C_{45}H_{29}N_3$ = 611.75) | N-72 | m/z = 485.19($C_{35}H_{23}N_3$ = 485.59) |
| N-73 | m/z = 485.19($C_{35}H_{23}N_3$ = 485.59) | N-74 | m/z = 561.22($C_{41}H_{27}N_3$ = 561.69) |
| N-75 | m/z = 485.19($C_{35}H_{23}N_3$ = 485.59) | N-76 | m/z = 485.19($C_{35}H_{23}N_3$ = 485.59) |
| N-77 | m/z = 611.24($C_{45}H_{29}N_3$ = 611.75) | N-78 | m/z = 611.24($C_{45}H_{29}N_3$ = 611.75) |
| N-79 | m/z = 485.19($C_{35}H_{23}N_3$ = 485.59) | N-80 | m/z = 485.19($C_{35}H_{23}N_3$ = 485.59) |
| N-81 | m/z = 485.19($C_{35}H_{23}N_3$ = 485.59) | N-82 | m/z = 485.19($C_{35}H_{23}N_3$ = 485.59) |
| N-83 | m/z = 535.2($C_{39}H_{25}N_3$ = 535.65) | N-84 | m/z = 535.2($C_{39}H_{25}N_3$ = 535.65) |
| N-85 | m/z = 585.22($C_{43}H_{27}N_3$ = 585.71) | N-86 | m/z = 535.2($C_{39}H_{25}N_3$ = 535.65) |
| N-87 | m/z = 585.22($C_{43}H_{27}N_3$ = 585.71) | N-88 | m/z = 585.22($C_{43}H_{27}N_3$ = 585.71) |
| N-89 | m/z = 611.24($C_{45}H_{29}N_3$ = 611.75) | N-90 | m/z = 611.24($C_{45}H_{29}N_3$ = 611.75) |
| N-91 | m/z = 585.22($C_{43}H_{27}N_3$ = 585.71) | N-92 | m/z = 611.24($C_{45}H_{29}N_3$ = 611.75) |
| N-93 | m/z = 687.27($C_{51}H_{33}N_3$ = 687.85) | N-94 | m/z = 611.24($C_{45}H_{29}N_3$ = 611.75) |
| N-95 | m/z = 511.2($C_{37}H_{25}N_3$ = 511.63) | N-96 | m/z = 611.24($C_{45}H_{29}N_3$ = 611.75) |
| N-97 | m/z = 561.22($C_{41}H_{27}N_3$ = 561.69) | N-98 | m/z = 587.24($C_{43}H_{29}N_3$ = 587.73) |
| N-99 | m/z = 663.27($C_{49}H_{33}N_3$ = 663.82) | N-100 | m/z = 713.28($C_{53}H_{35}N_3$ = 713.88) |
| N-101 | m/z = 575.2($C_{41}H_{25}N_3O$ = 575.67) | N-102 | m/z = 601.22($C_{43}H_{27}N_3O$ = 601.71) |
| N-103 | m/z = 700.26($C_{51}H_{32}N_4$ = 700.85) | N-104 | m/z = 701.25($C_{51}H_{31}N_3O$ = 701.83) |
| N-105 | m/z = 667.21($C_{47}H_{29}N_3S$ = 667.83) | N-106 | m/z = 541.16($C_{37}H_{23}N_3S$ = 541.67) |
| N-107 | m/z = 612.23($C_{44}H_{28}N_4$ = 612.74) | N-108 | m/z = 562.22($C_{40}H_{26}N_4$ = 562.68) |
| N-109 | m/z = 689.26($C_{49}H_{31}N_5$ = 689.82) | N-110 | m/z = 639.24($C_{45}H_{29}N_5$ = 639.76) |
| N-111 | m/z = 701.25($C_{51}H_{31}N_3O$ = 701.83) | N-112 | m/z = 631.17($C_{43}H_{25}N_3OS$ = 631.75) |
| N-113 | m/z = 625.22($C_{45}H_{27}N_3O$ = 625.73) | N-114 | m/z = 591.18($C_{41}H_{25}N_3S$ = 591.73) |
| N-115 | m/z = 687.27($C_{51}H_{33}N_3$ = 687.85) | N-116 | m/z = 701.25($C_{51}H_{31}N_3O$ = 701.83) |
| N-117 | m/z = 619.3($C_{45}H_{37}N_3$ = 619.81) | N-118 | m/z = 601.25($C_{44}H_{31}N_3$ = 601.75) |
| N-119 | m/z = 667.23($C_{47}H_{29}N_3O_2$ = 667.77) | N-120 | m/z = 540.24($C_{39}H_{20}D_5N_3$ = 540.68) |
| N-121 | m/z = 521.17($C_{35}H_{21}F_2N_3$ = 521.57) | N-122 | m/z = 510.18($C_{36}H_{22}N_3$ = 510.6) |
| N-123 | m/z = 652.23($C_{46}H_{28}N_4O$ = 652.76) | N-124 | m/z = 527.24($C_{38}H_{29}N_3$ = 527.67) |
| N-125 | m/z = 535.2($C_{39}H_{25}N_3$ = 535.65) | N-126 | m/z = 535.2($C_{39}H_{25}N_3$ = 535.65) |
| N-127 | m/z = 535.2($C_{39}H_{25}N_3$ = 535.65) | N-128 | m/z = 535.2($C_{39}H_{25}N_3$ = 535.65) |
| N-129 | m/z = 587.24($C_{43}H_{29}N_3$ = 587.73) | N-130 | m/z = 612.23($C_{44}H_{28}N_4$ = 612.74) |
| N-131 | m/z = 561.22($C_{41}H_{27}N_3$ = 561.69) | N-132 | m/z = 687.27($C_{51}H_{33}N_3$ = 687.85) |
| N-133 | m/z = 663.27($C_{49}H_{33}N_3$ = 663.82) | N-134 | m/z = 601.22($C_{43}H_{27}N_3O$ = 601.71) |
| N-135 | m/z = 617.19($C_{43}H_{27}N_3S$ = 617.77) | N-136 | m/z = 752.29($C_{55}H_{36}N_4$ = 752.92) |
| N-137 | m/z = 651.23($C_{47}H_{29}N_3O$ = 651.77) | N-138 | m/z = 677.25($C_{49}H_{31}N_3O$ = 677.81) |
| N-139 | m/z = 541.16($C_{37}H_{23}N_3S$ = 541.67) | N-140 | m/z = 750.28($C_{55}H_{34}N_4$ = 750.91) |
| N-141 | m/z = 707.24($C_{59}H_{33}N_3S$ = 707.9) | N-142 | m/z = 651.23($C_{47}H_{29}N_3O$ = 651.77) |
| N-143 | m/z = 617.19($C_{43}H_{27}N_3S$ = 617.77) | N-144 | m/z = 667.21($C_{47}H_{29}N_3S$ = 667.83) |
| N-145 | m/z = 631.17($C_{43}H_{25}N_3OS$ = 631.75) | N-146 | m/z = 767.26($C_{55}H_{33}N_3O_2$ = 767.89) |
| N-147 | m/z = 647.15($C_{43}H_{25}N_3S_2$ = 647.81) | N-148 | m/z = 690.24($C_{49}H_{30}N_4O$ = 690.81) |
| N-149 | m/z = 511.2($C_{37}H_{25}N_3$ = 511.63) | N-150 | m/z = 587.24($C_{43}H_{29}N_3$ = 587.73) |
| N-151 | m/z = 511.2($C_{37}H_{25}N_3$ = 511.63) | N-152 | m/z = 511.2($C_{37}H_{25}N_3$ = 511.63) |
| N-153 | m/z = 511.2($C_{37}H_{25}N_3$ = 511.63) | N-154 | m/z = 511.2($C_{37}H_{25}N_3$ = 511.63) |
| N-155 | m/z = 511.2($C_{37}H_{25}N_3$ = 511.63) | N-156 | m/z = 561.22($C_{41}H_{27}N_3$ = 561.69) |

TABLE 4-continued

| compound | FD-MS | compound | FD-MS |
|---|---|---|---|
| N-157 | m/z = 485.19($C_{35}H_{23}N_3$ = 485.59) | N-158 | m/z = 561.22($C_{41}H_{27}N_3$ = 561.69) |
| N-159 | m/z = 611.24($C_{45}H_{29}N_3$ = 611.75) | N-160 | m/z = 561.22($C_{41}H_{27}N_3$ = 561.69) |
| N-161 | m/z = 535.2($C_{39}H_{25}N_3$ = 535.65) | N-162 | m/z = 561.22($C_{41}H_{27}N_3$ = 561.69) |
| N-163 | m/z = 611.24($C_{45}H_{29}N_3$ = 611.75) | N-164 | m/z = 561.22($C_{41}H_{27}N_3$ = 561.69) |
| N-165 | m/z = 485.19($C_{35}H_{23}N_3$ = 485.59) | N-166 | m/z = 561.22($C_{41}H_{27}N_3$ = 561.69) |
| N-167 | m/z = 611.24($C_{45}H_{29}N_3$ = 611.75) | N-168 | m/z = 561.22($C_{41}H_{27}N_3$ = 561.69) |
| N-169 | m/z = 485.19($C_{35}H_{23}N_3$ = 485.59) | N-170 | m/z = 561.22($C_{41}H_{27}N_3$ = 561.69) |
| N-171 | m/z = 535.2($C_{39}H_{25}N_3$ = 535.65) | N-172 | m/z = 535.2($C_{39}H_{25}N_3$ = 535.65) |
| N-173 | m/z = 561.22($C_{41}H_{27}N_3$ = 561.69) | N-174 | m/z = 637.25($C_{47}H_{31}N_3$ = 637.79) |
| N-175 | m/z = 587.24($C_{43}H_{29}N_3$ = 587.73) | N-176 | m/z = 687.27($C_{51}H_{33}N_3$ = 687.85) |
| N-177 | m/z = 637.25($C_{47}H_{31}N_3$ = 637.79) | N-178 | m/z = 561.22($C_{41}H_{27}N_3$ = 561.69) |
| N-179 | m/z = 499.17($C_{35}H_{21}N_3O$ = 499.57) | N-180 | m/z = 541.16($C_{37}H_{23}N_3S$ = 541.67) |
| N-181 | m/z = 611.24($C_{45}H_{29}N_3$ = 611.75) | N-182 | m/z = 687.27($C_{51}H_{33}N_3$ = 687.85) |
| N-183 | m/z = 676.26($C_{49}H_{32}N_4$ = 676.82) | N-184 | m/z = 525.22($C_{38}H_{27}N_3$ = 525.66) |

[Synthesis Example 2] Compound Represented by Formula 3

The compound (Final Product) represented by Formula 3 according to the present invention is synthesized as shown in Reaction Scheme 5, but is not limited thereto.

I. Synthesis of Sub 3

1. Synthesis Example of Sub 3-1

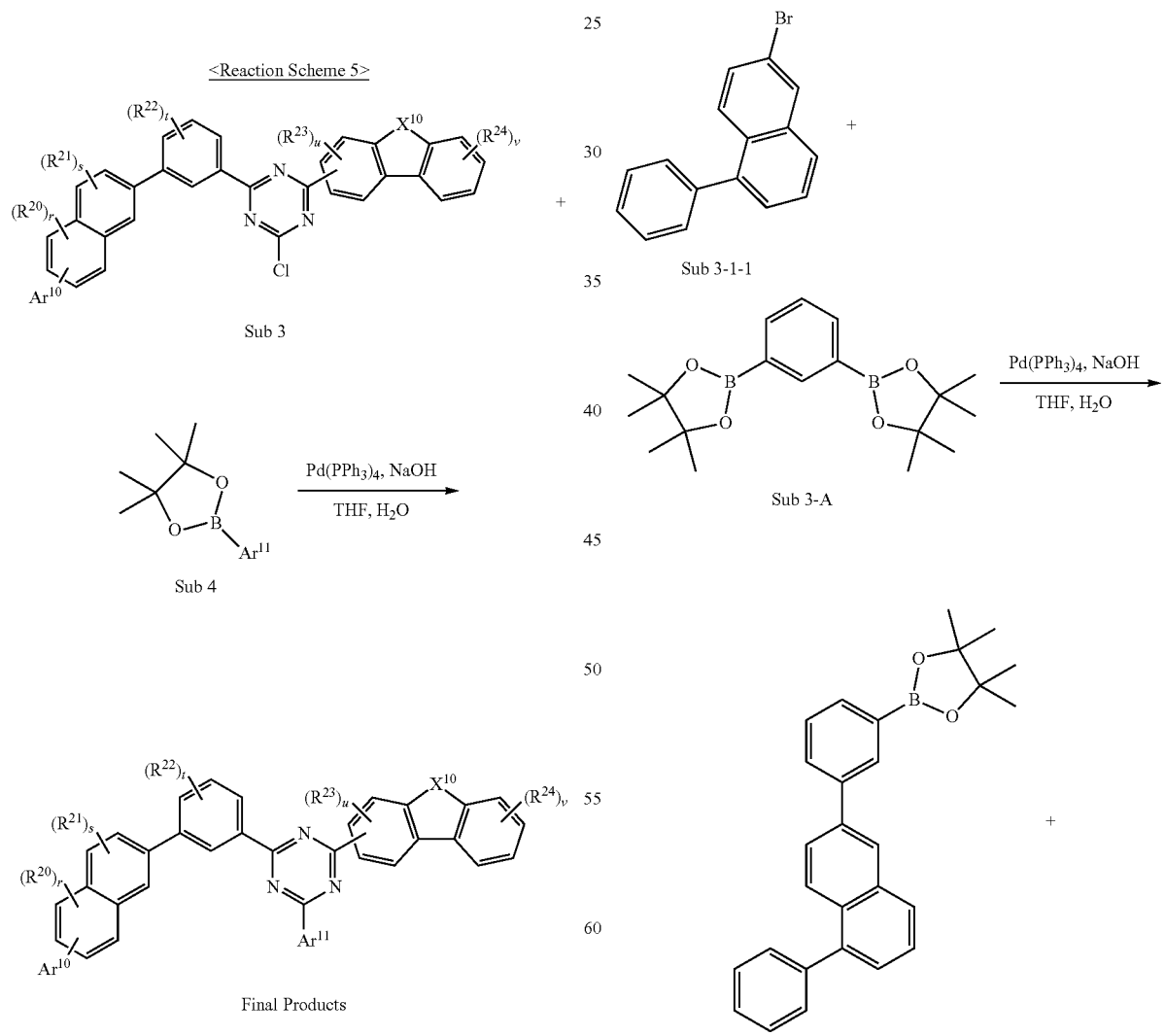

Wherein, $R^{20}$, $R^{21}$, $R^{22}$, $R^{23}$, $R^{24}$, $Ar^{10}$, $Ar^{11}$, $X^{10}$, r, s, t, u and v are the same as defined in Formula 3.

215

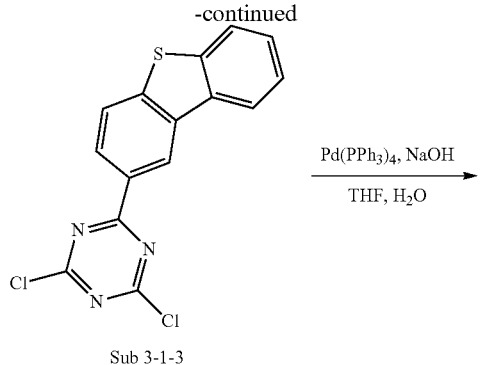

Sub 3-1-3

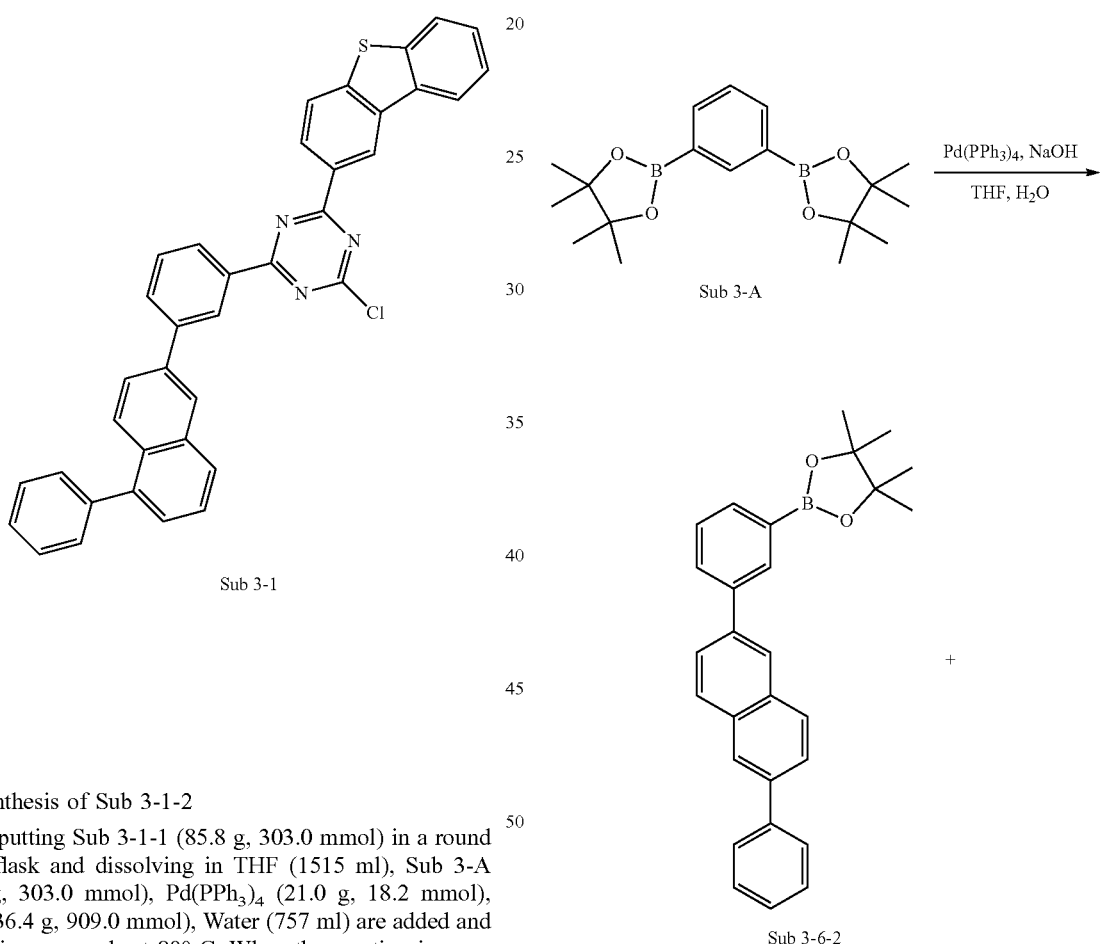

Sub 3-1

1) Synthesis of Sub 3-1-2

After putting Sub 3-1-1 (85.8 g, 303.0 mmol) in a round bottom flask and dissolving in THF (1515 ml), Sub 3-A (100.0 g, 303.0 mmol), Pd(PPh$_3$)$_4$ (21.0 g, 18.2 mmol), NaOH (36.4 g, 909.0 mmol), Water (757 ml) are added and the reaction proceeds at 80° C. When the reaction is complete, the mixture was extracted with CH$_2$Cl$_2$ and water, the organic layer was dried over MgSO$_4$, concentrated, and the resulting compound was recrystallized by silicagel column to obtain 102.7 g (yield: 83.4%) of the product.

2) Synthesis of Sub 3-1

After putting Sub 3-1-2 (102.7 g, 252.7 mmol) in a round bottom flask and dissolving in THF (1263 ml), Sub 3-1-3 (83.9 g, 252.7 mmol), Pd(PPh$_3$)$_4$ (17.5 g, 15.2 mmol), NaOH (30.3 g, 758.1 mmol), Water (632 ml) were added and tested in the same manner as in Sub 3-1-2 to obtain 118.8 g of product. (Yield: 81.6%)

216

2. Synthesis Example of Sub 3-6

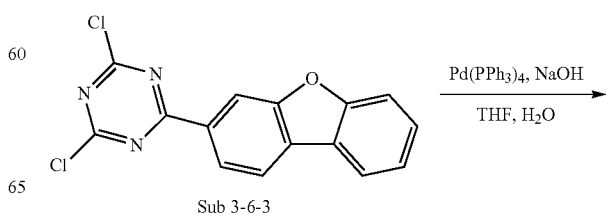

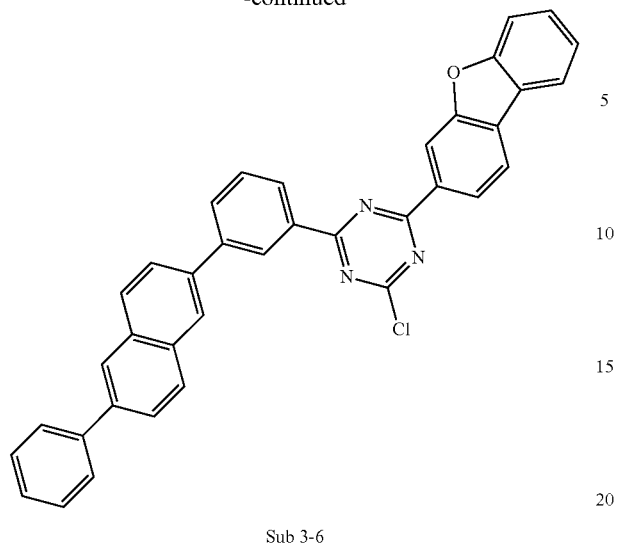

Sub 3-6

1) Synthesis of Sub 3-6-2

After putting Sub 3-6-1 (85.8 g, 303.0 mmol) in a round bottom flask and dissolving in THF (1515 ml), Sub 3-A (100.0 g, 303.0 mmol), Pd(PPh$_3$)$_4$ (21.0 g, 18.2 mmol), NaOH (36.4 g, 909.0 mmol), Water (757 ml) were added and tested in the same manner as in Sub 3-1-2 to obtain 103.5 g of product. (Yield: 81.4%)

2) Synthesis of Sub 3-6

After putting Sub 3-6-2 (103.5 g, 254.8 mmol) in a round bottom flask and dissolving in THF (1274 ml), Sub 3-6-3 (80.6 g, 254.8 mmol), Pd(PPh$_3$)$_4$ (17.7 g, 15.3 mmol), NaOH (30.6 g, 764.5 mmol), Water (637 ml) were added and tested in the same manner as in Sub 3-1-2 to obtain 117.3 g of product. (Yield: 82.2%)

3. Synthesis of Sub 3-13

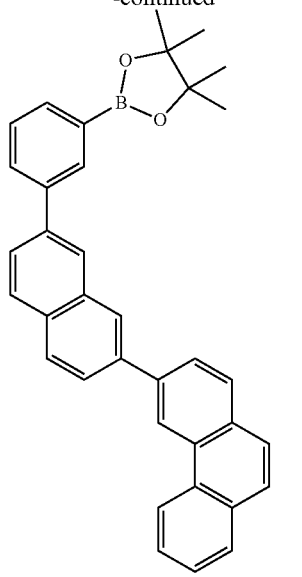

Sub 3-13-2

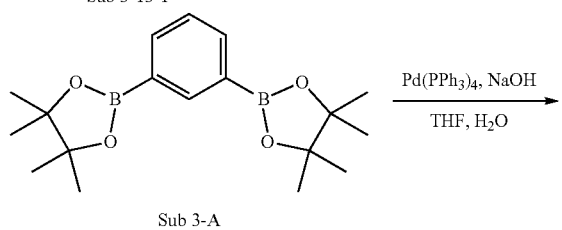

Sub 3-13-1

+

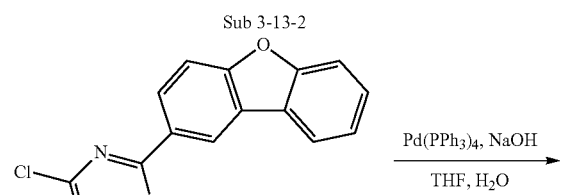

Sub 3-A

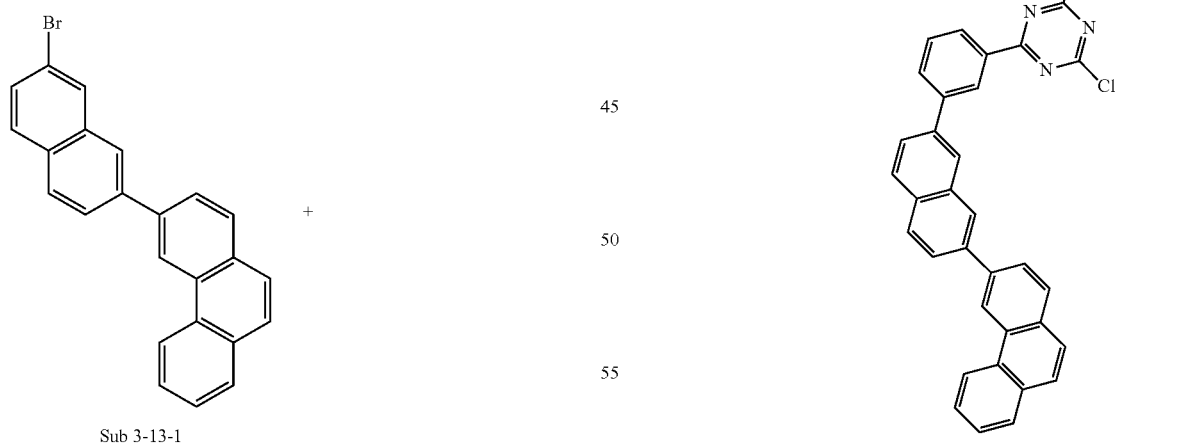

Sub 3-13

1) Synthesis of Sub 3-13-2

After putting Sub 3-13-1 (116.1 g, 303.0 mmol) in a round bottom flask and dissolving in THF (1515 ml), Sub 3-A (100.0 g, 303.0 mmol), Pd(PPh$_3$)$_4$ (21.0 g, 18.2 mmol), NaOH (36.4 g, 909.0 mmol), Water (757 ml) were added and tested in the same manner as in Sub 3-1-2 to obtain 125.4 g of product. (Yield: 81.7%)

2) Synthesis of Sub 3-13

After putting Sub 3-13-2 (125.4 g, 247.5 mmol) in a round bottom flask and dissolving in THF (1238 ml), Sub 3-13-3 (78.3 g, 247.5 mmol), Pd(PPh₃)₄ (17.2 g, 14.9 mmol), NaOH (29.7 g, 742.6 mmol), Water (619 ml) were added and tested in the same manner as in Sub 3-1-2 to obtain 131.6 g of product. (Yield: 80.5%)

4. Synthesis of Sub 3-41

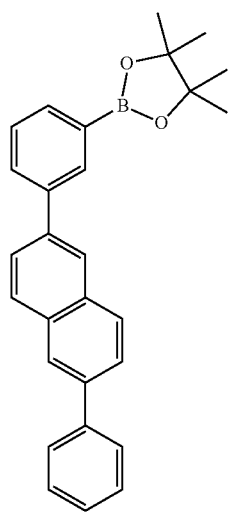

Sub 3-6-2

+

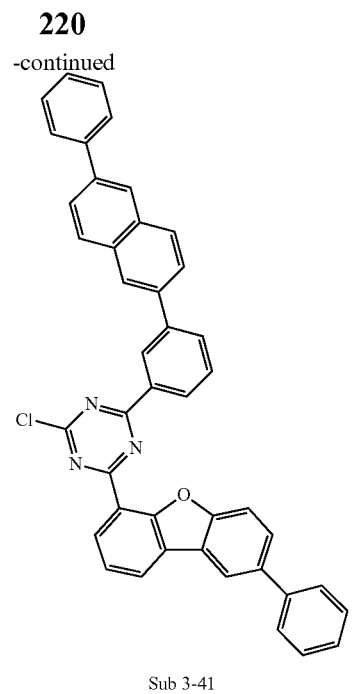

Sub 3-41

After putting Sub 3-6-2 (100.0 g, 246.1 mmol) in a round bottom flask and dissolving in THF (1231 ml), Sub 3-41-3 (96.5 g, 246.1 mmol), Pd(PPh₃)₄ (17.1 g, 14.8 mmol), NaOH (29.5 g, 738.3 mmol), Water (615 ml) were added and tested in the same manner as in Sub 3-1-2 to obtain 128.7 g of product. (Yield: 82.2%)

5. Synthesis of Sub 3-42

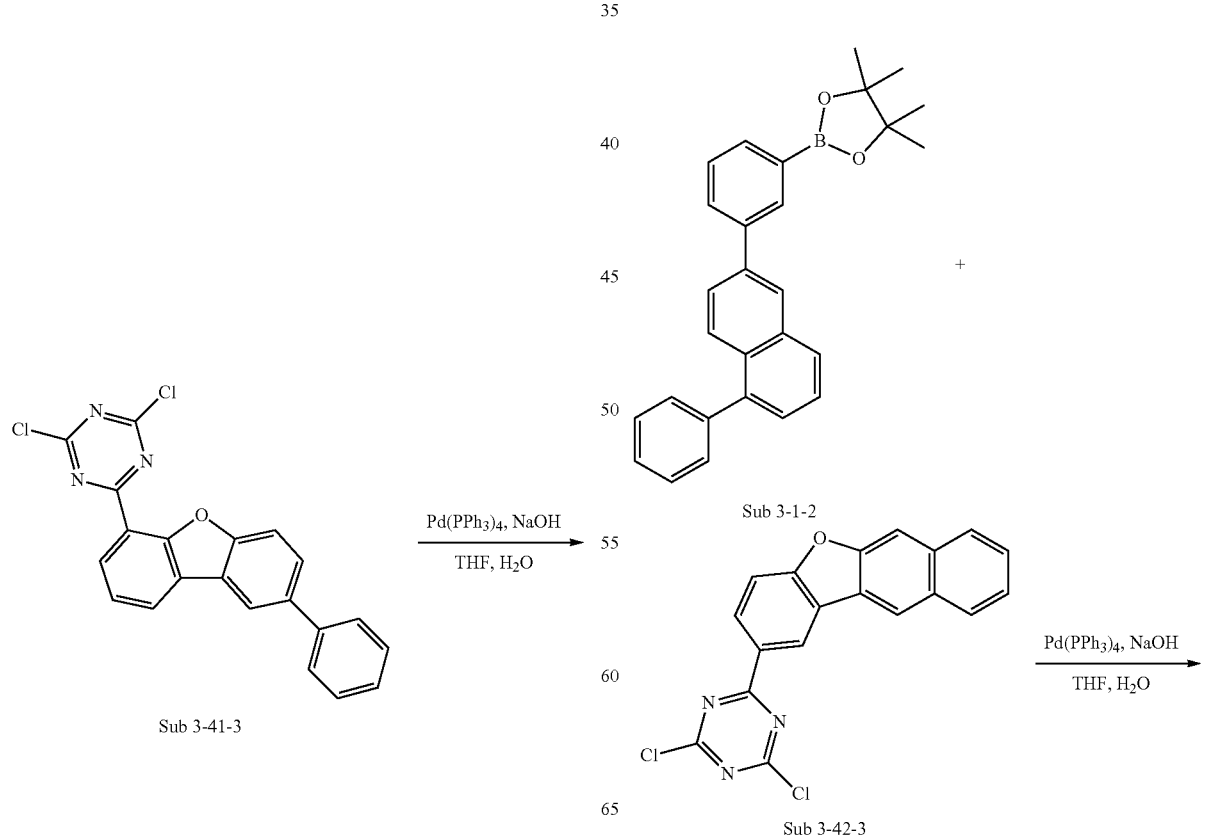

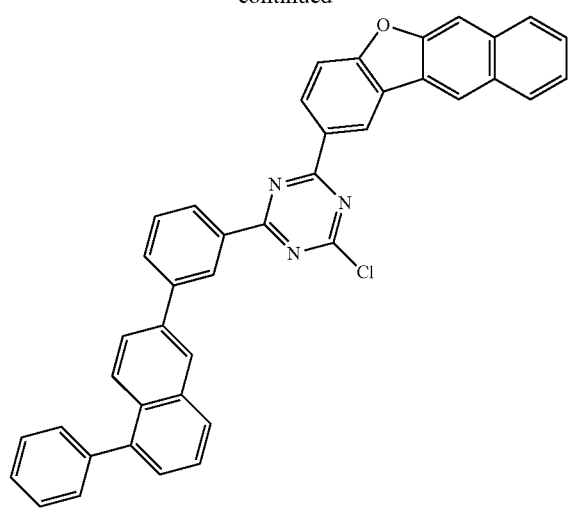

Sub 3-42

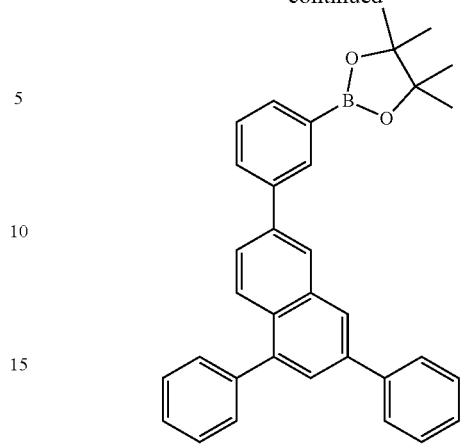

Sub 3-48-2

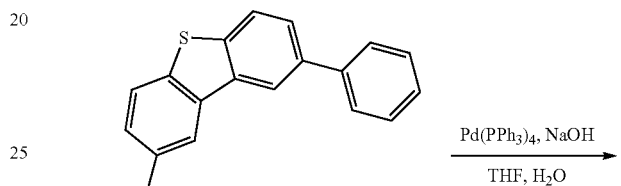

Sub 3-48-3

Sub 3-48

After putting Sub 3-1-2 (100.0 g, 246.1 mmol) in a round bottom flask and dissolving in THF (1231 ml), Sub 3-42-3 (90.1 g, 246.1 mmol), Pd(PPh$_3$)$_4$ (17.1 g, 14.8 mmol), NaOH (29.5 g, 738.3 mmol), Water (615 ml) were added and tested in the same manner as in Sub 3-1-2 to obtain 122.1 g of product. (Yield: 81.3%)

6. Synthesis of Sub 3-48

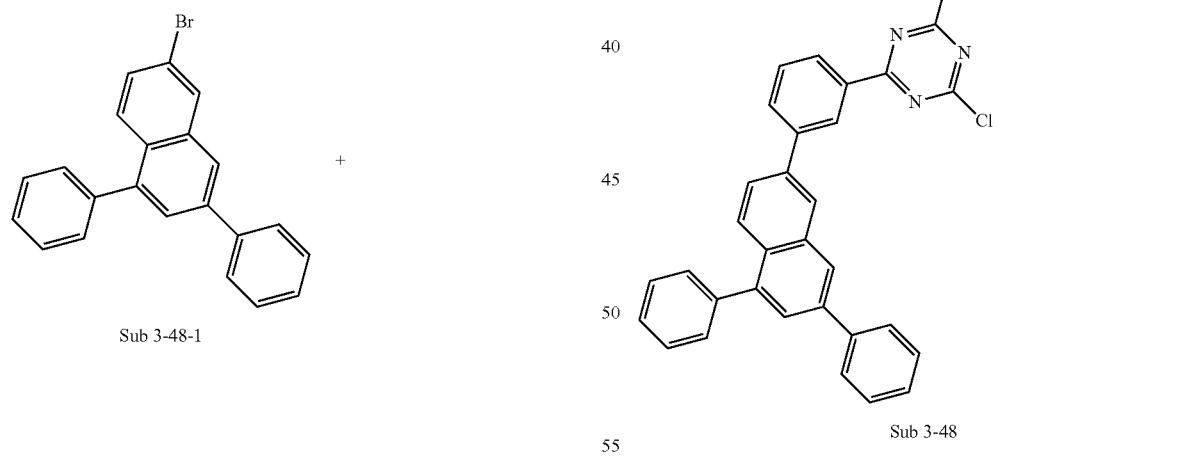

Sub 3-48-1

Sub 3-A

1) Synthesis of Sub 3-48-2

After putting Sub 3-48-1 (108.9 g, 303.0 mmol) in a round bottom flask and dissolving in THF (1515 ml), Sub 3-A (100.0 g, 303.0 mmol), Pd(PPh$_3$)$_4$ (21.0 g, 18.2 mmol), NaOH (36.4 g, 909.0 mmol), Water (757 ml) were added and tested in the same manner as in Sub 3-1-2 to obtain 118.3 g of product. (Yield: 80.9%)

2) Synthesis of Sub 3-48

After putting Sub 3-48-2 (118.3 g, 245.1 mmol) in a round bottom flask and dissolving in THF (1226 ml), Sub 3-48-3 (100.1 g, 245.1 mmol), Pd(PPh$_3$)$_4$ (17.0 g, 14.7 mmol), NaOH (29.4 g, 735.4 mmol), Water (613 ml) were added and tested in the same manner as in Sub 3-1-2 to obtain 143.0 g of product. (Yield:
7. Synthesis of Sub 3-64
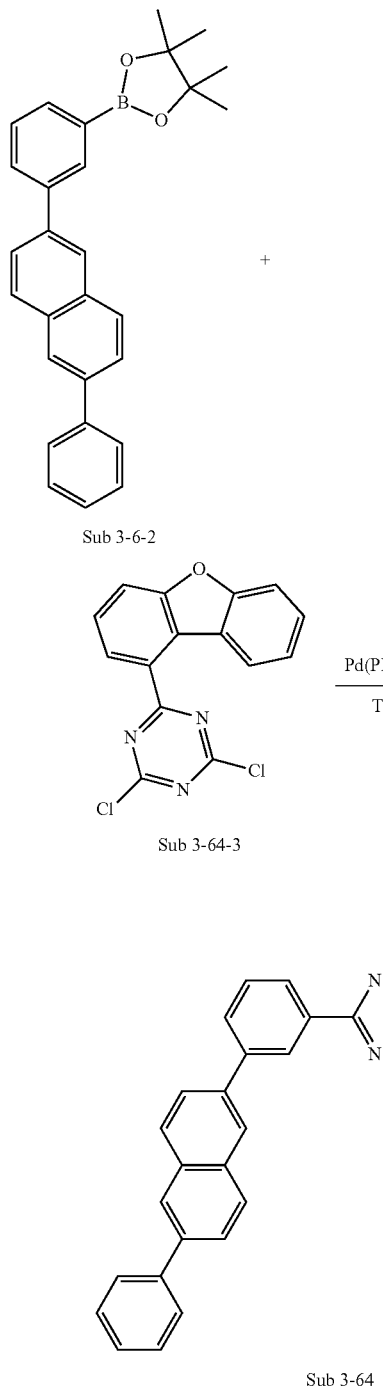
8. Synthesis of Sub 3-9
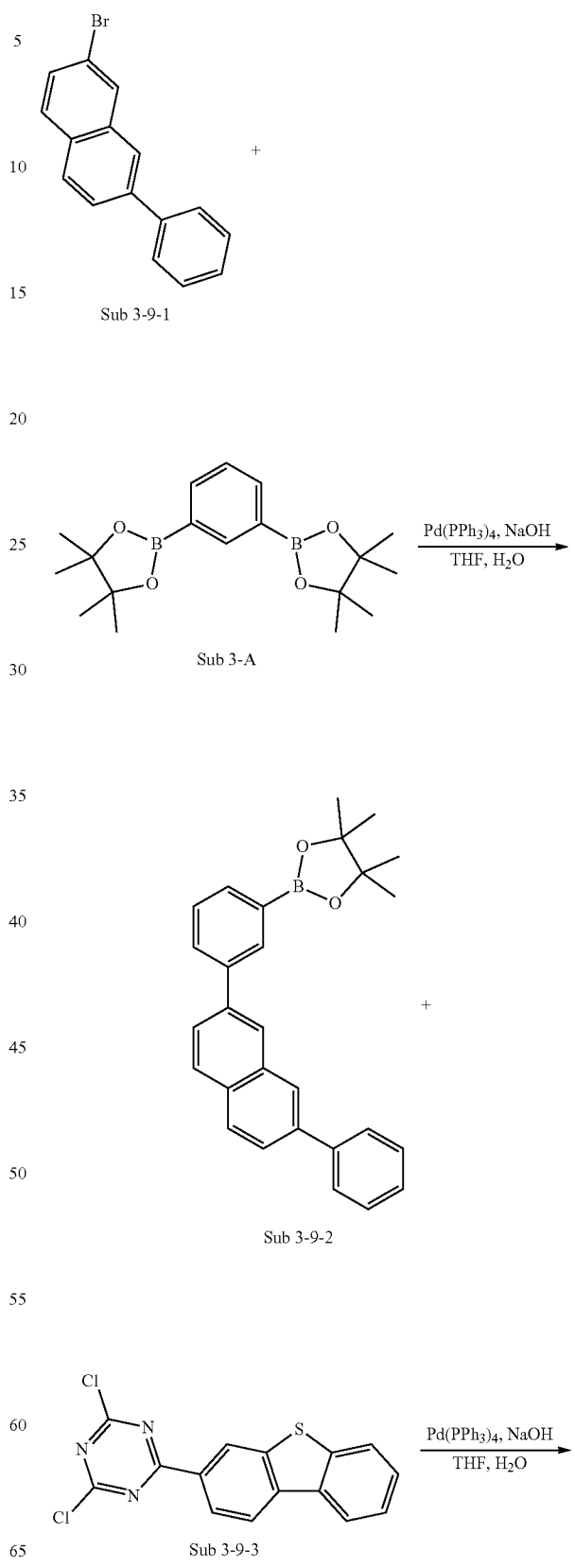
After putting Sub 3-6-2 (100.0 g, 246.1 mmol) in a round bottom flask and dissolving in THF (1231 ml), Sub 3-64-3 (77.8 g, 246.1 mmol), Pd(PPh$_3$)$_4$ (17.1 g, 14.8 mmol), NaOH (29.5 g, 738.3 mmol), Water (615 ml) were added and tested in the same manner as in Sub 3-1-2 to obtain 114.4 g of product. (Yield: 83.0%)

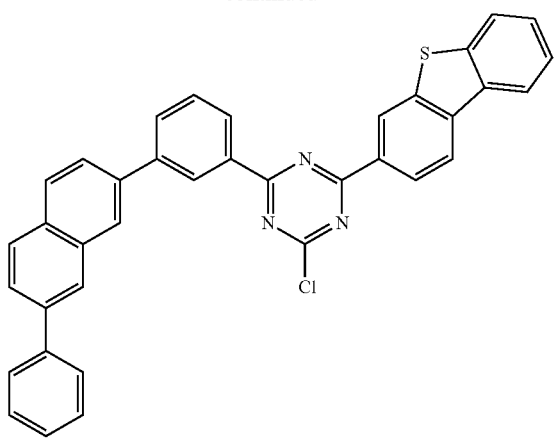

Sub 3-9

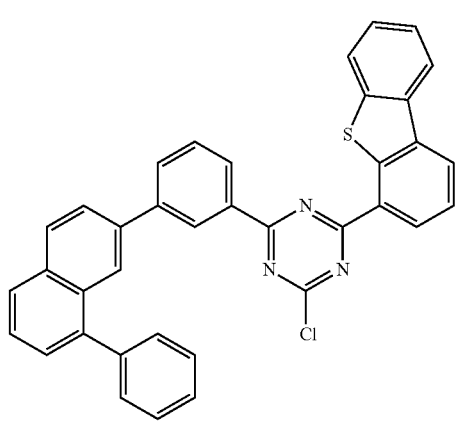

Sub 3-2

1) Synthesis of Sub 3-9-2

After putting Sub 3-9-1 (85.8 g, 303.0 mmol) in a round bottom flask and dissolving in THF (1515 ml), Sub 3-A (100.0 g, 303.0 mmol), Pd(PPh$_3$)$_4$ (21.0 g, 18.2 mmol), NaOH (36.4 g, 909.0 mmol), Water (757 ml) were added and tested in the same manner as in Sub 3-1-2 to obtain 100.8 g of product. (Yield: 81.9%)

2) Synthesis of Sub 3-9

After putting Sub 3-9-2 (100.8 g, 248.2 mmol) in a round bottom flask and dissolving in THF (1223 ml), Sub 3-9-3 (82.4 g, 248.2 mmol), Pd(PPh$_3$)$_4$ (17.2 g, 14.9 mmol), NaOH (29.8 g, 744.5 mmol), Water (620 ml) were added and tested in the same manner as in Sub 3-1-2 to obtain 117.4 g of product. (Yield: 82.1%)

The compound belonging to Sub 3 may be the following compounds, but is not limited thereto, and Table 5 shows the FD-MS (Field Desorption-Mass Spectrometry) values of the compounds belonging to Sub 3.

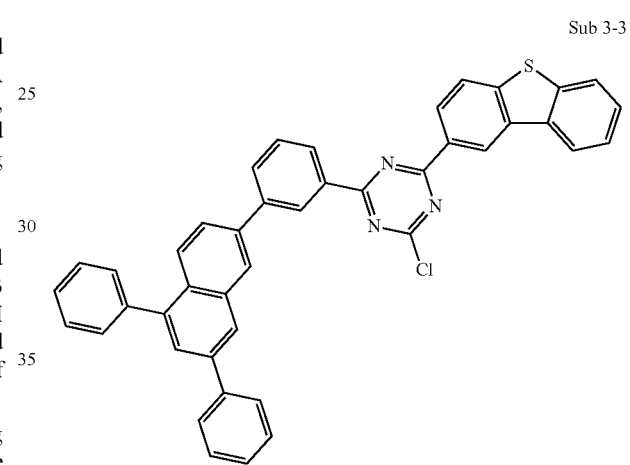

Sub 3-3

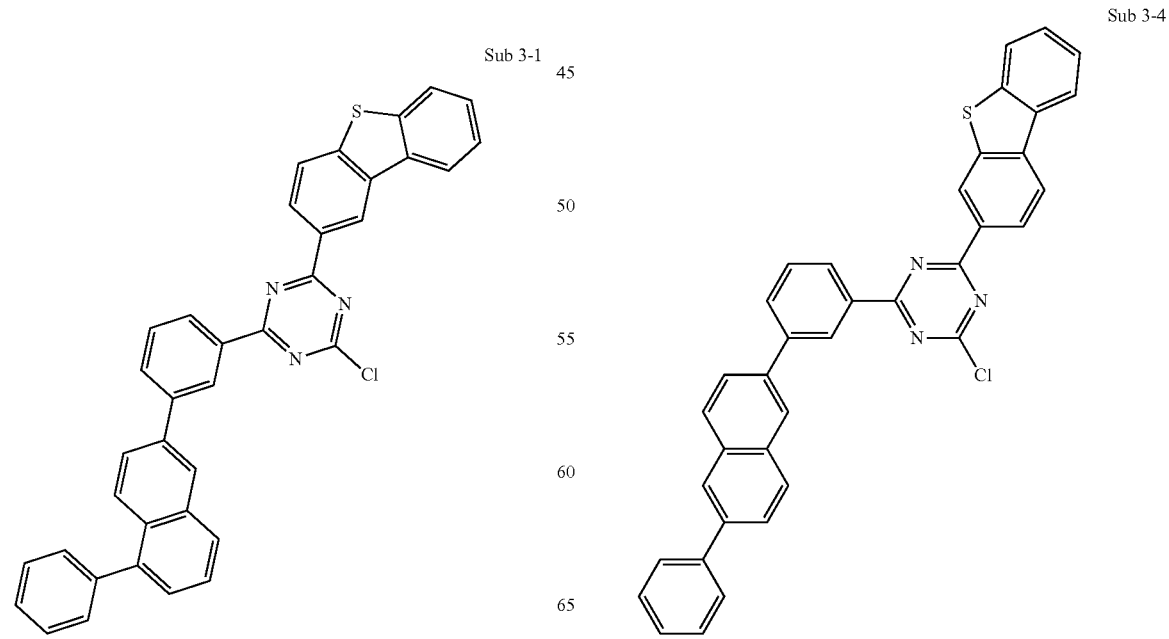

Sub 3-1

Sub 3-4

Sub 3-5
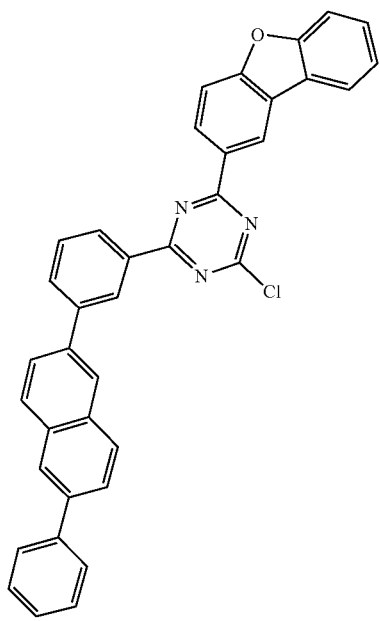
Sub 3-7
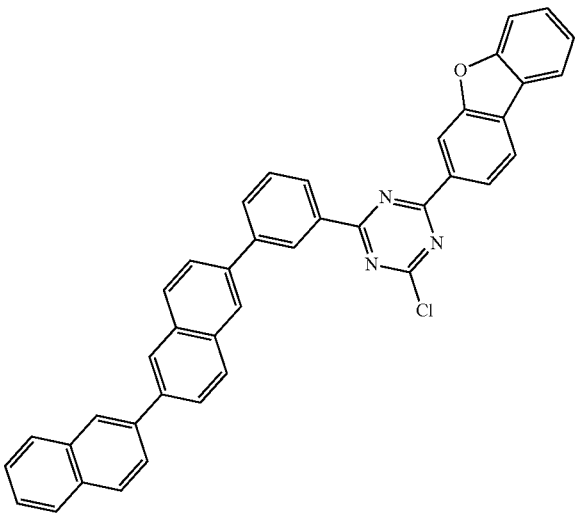
Sub 3-6
Sub 3-8
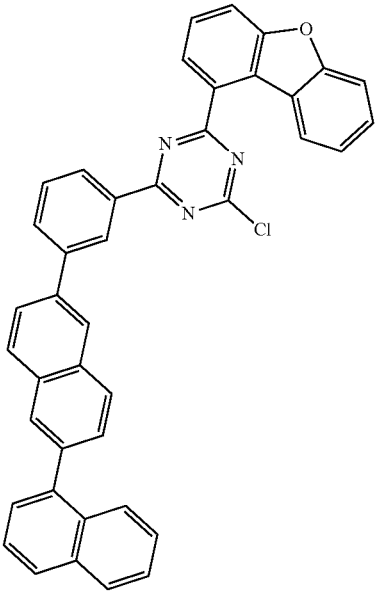

-continued
Sub 3-9
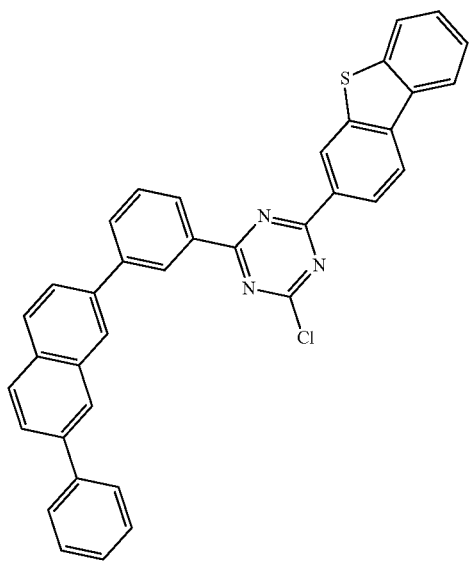
Sub 3-10
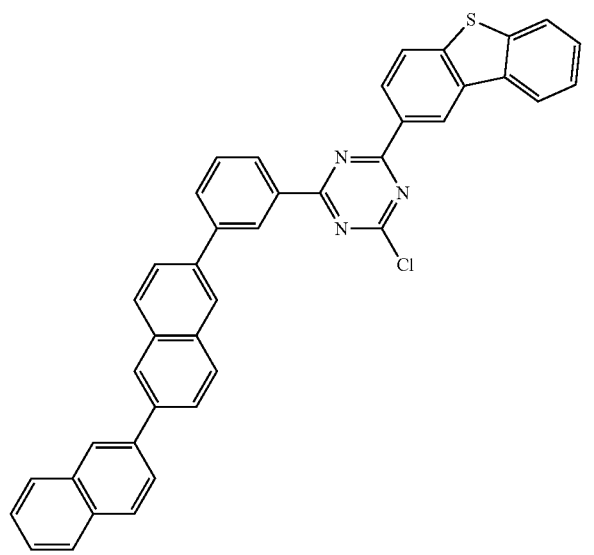
Sub 3-11
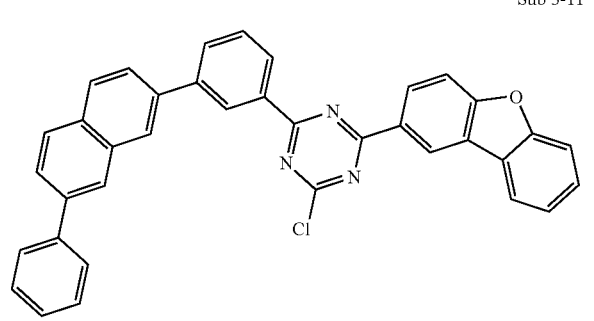
-continued
Sub 3-12
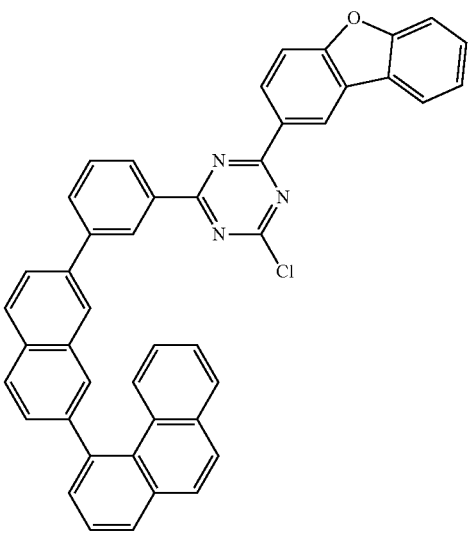
Sub 3-13
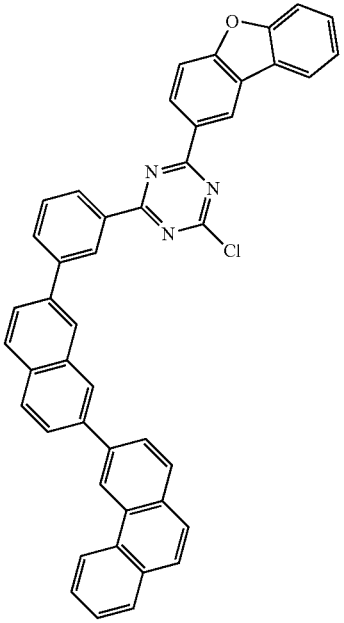
Sub 3-14
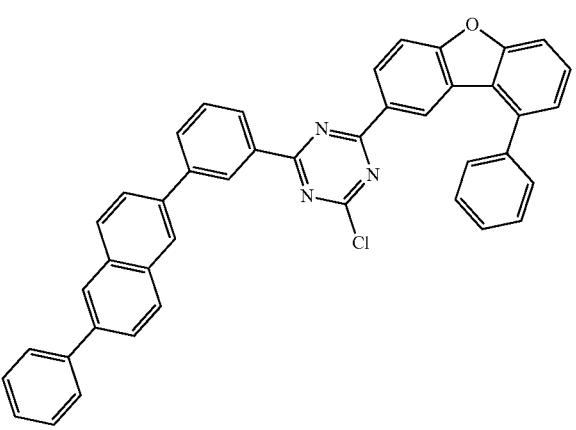

Sub 3-15
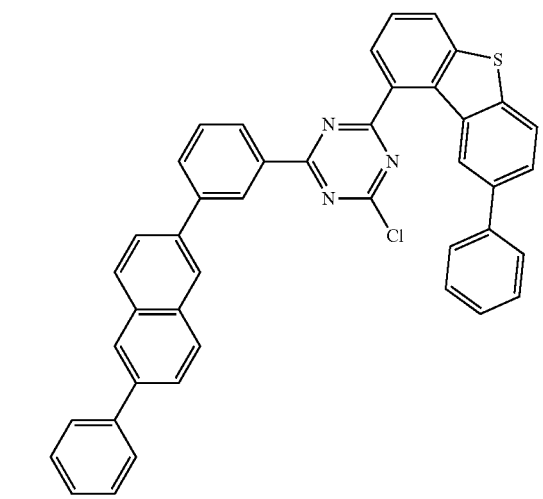
Sub 3-16
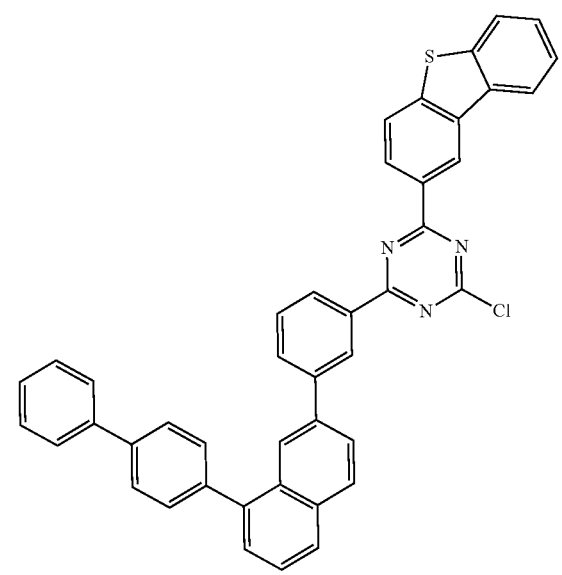
Sub 3-17
Sub 3-18
Sub 3-19
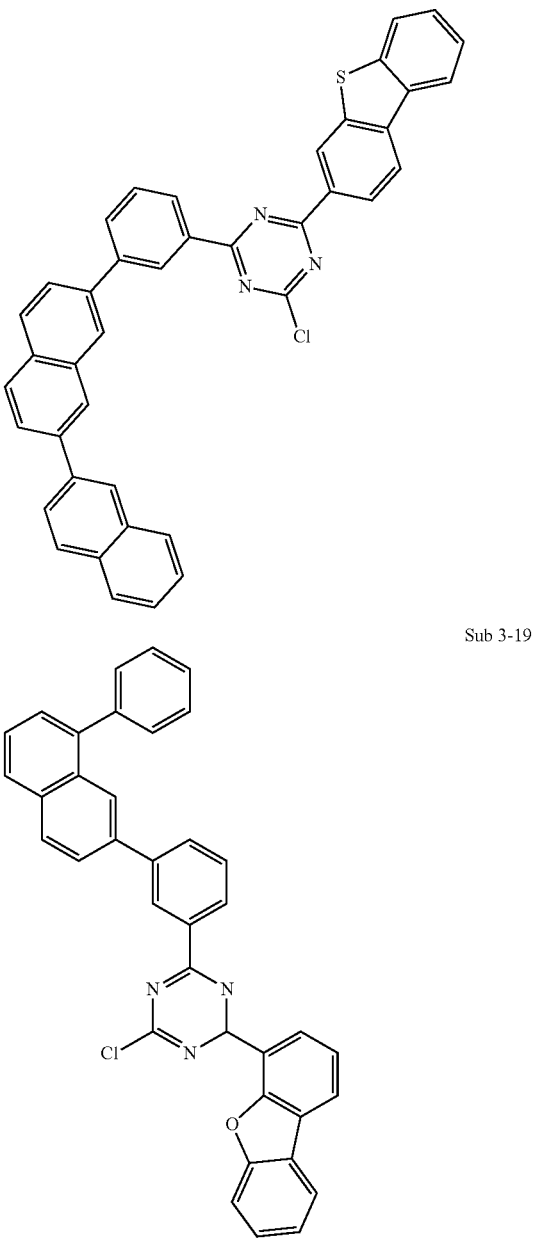
Sub 3-20
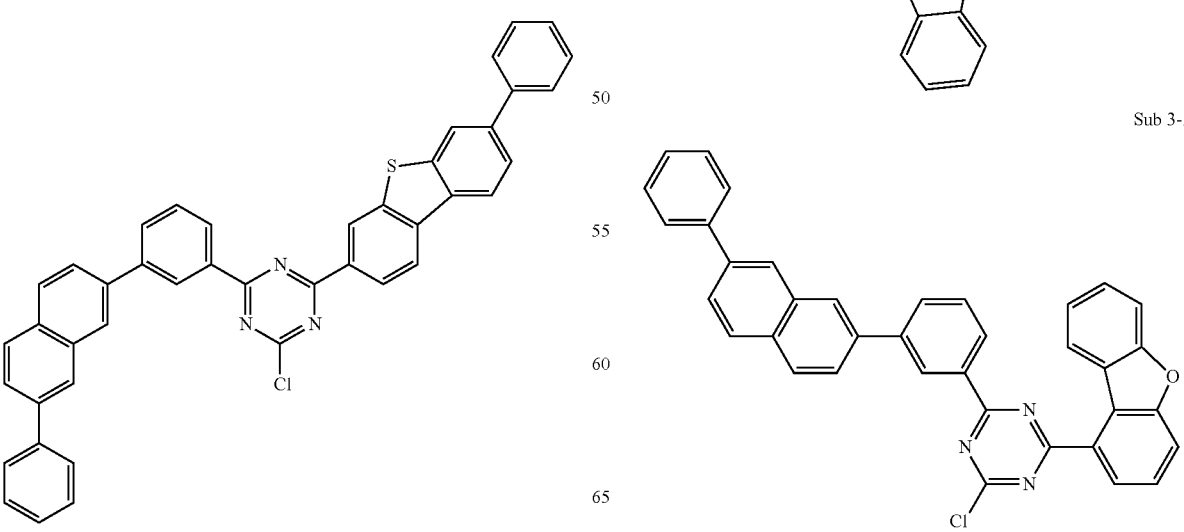

-continued
Sub 3-21
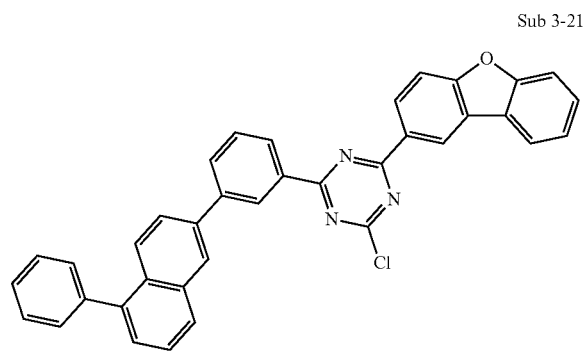
Sub 3-22
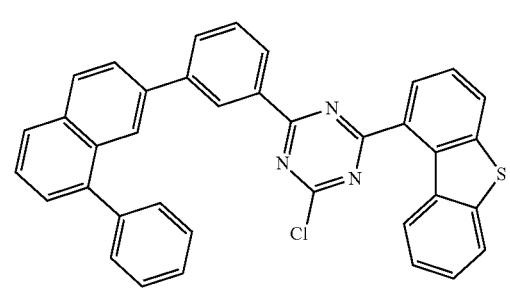
Sub 3-23
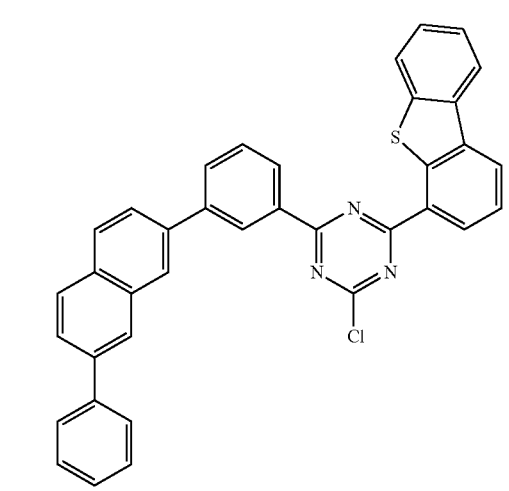
Sub 3-24
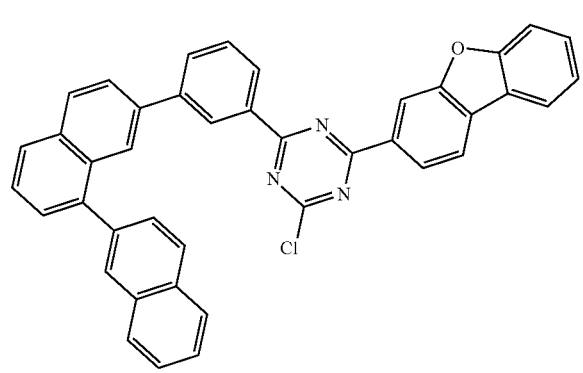
Sub 3-25
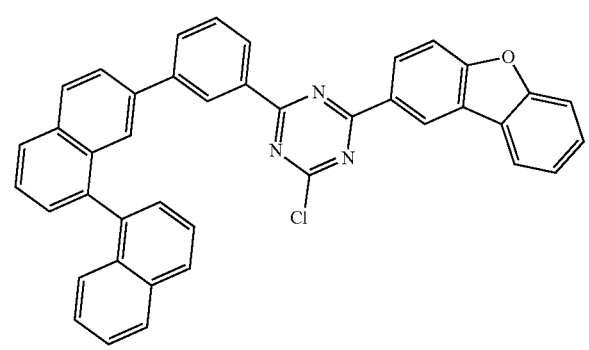
Sub 3-26
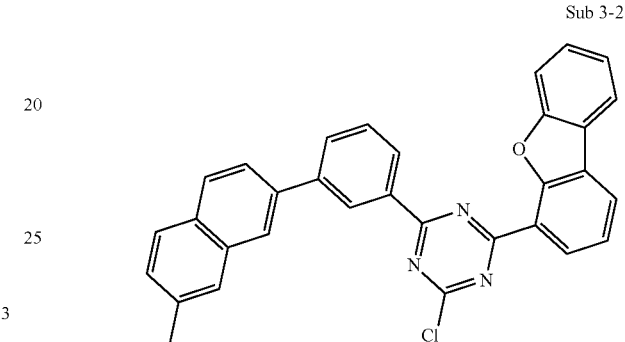
Sub 3-27
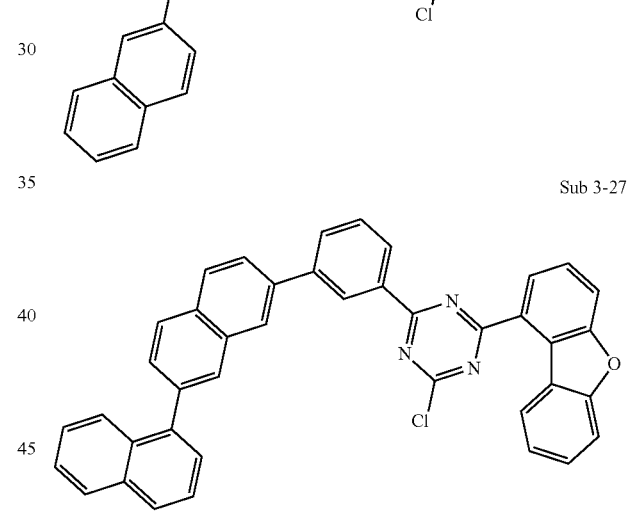
Sub 3-28
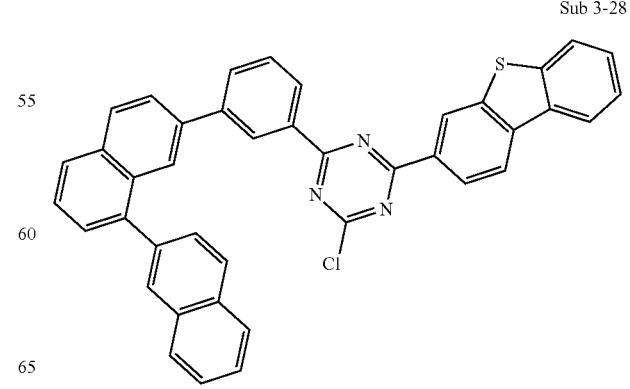

Sub 3-29
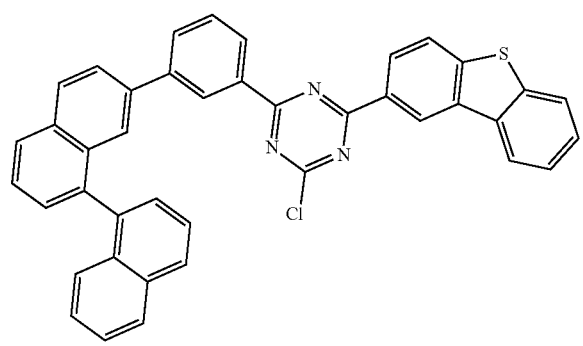
Sub 3-30
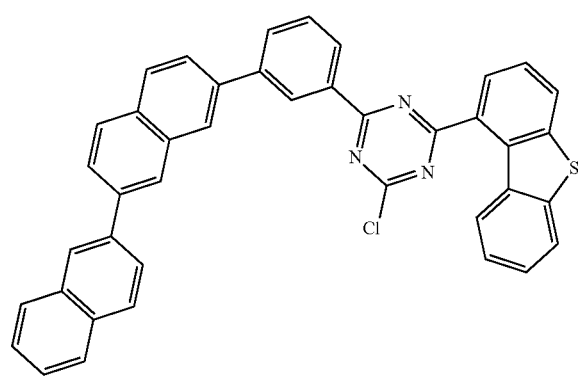
Sub 3-31
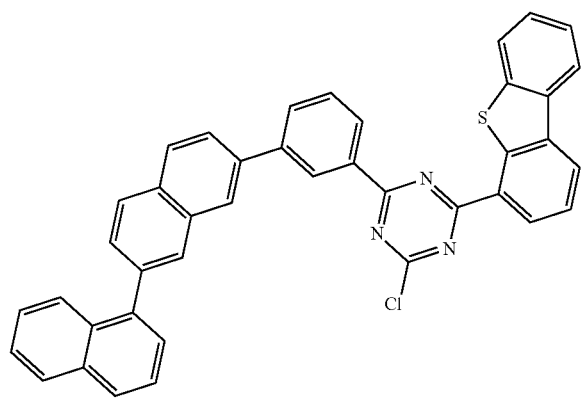
Sub 3-32
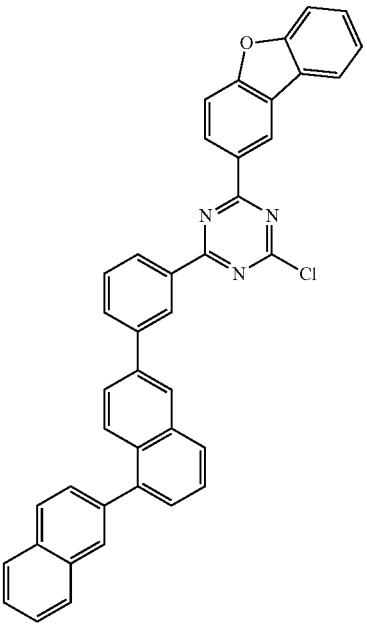
Sub 3-33
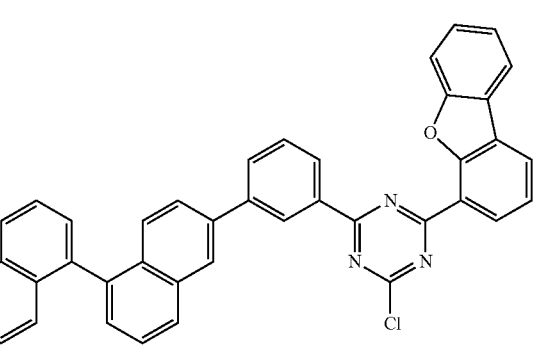
Sub 3-34
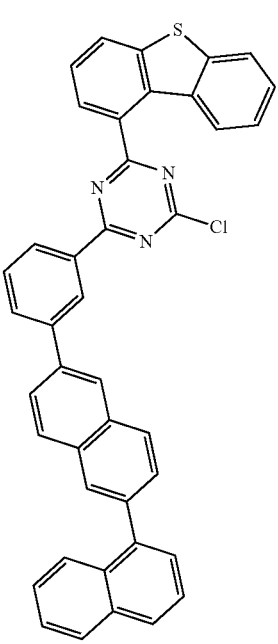

Sub 3-35
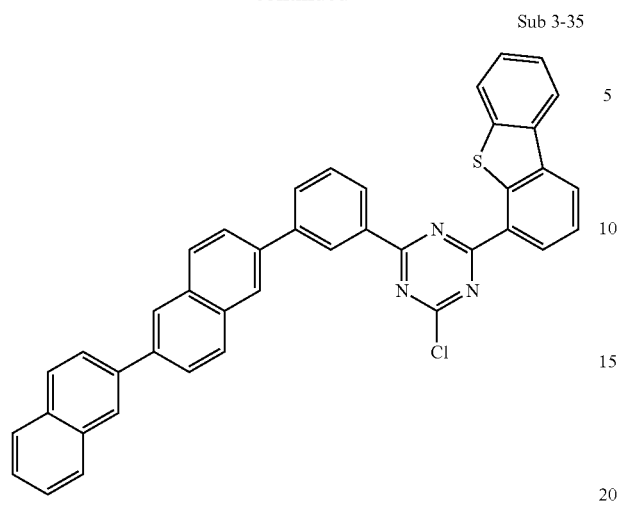
Sub 3-36
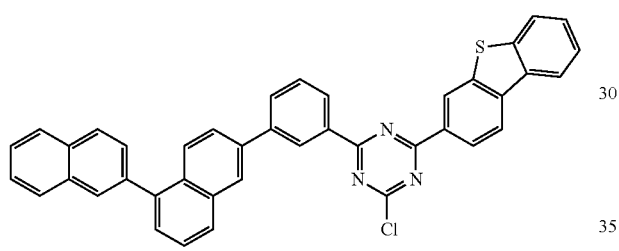
Sub 3-37
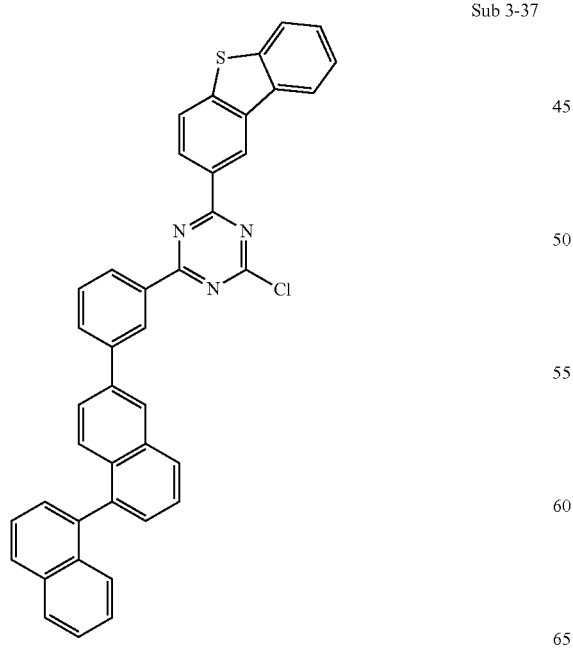
Sub 3-38
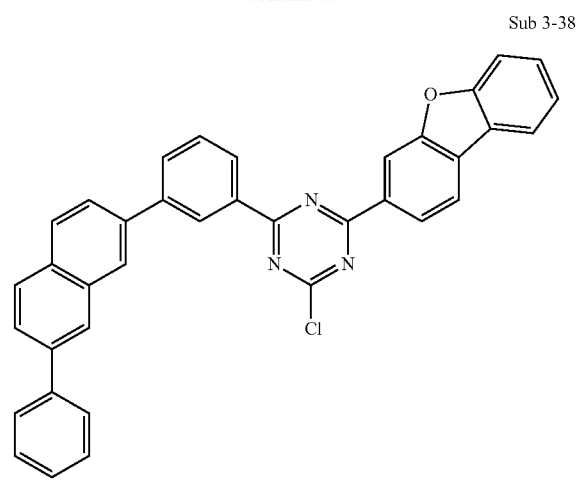
Sub 3-39
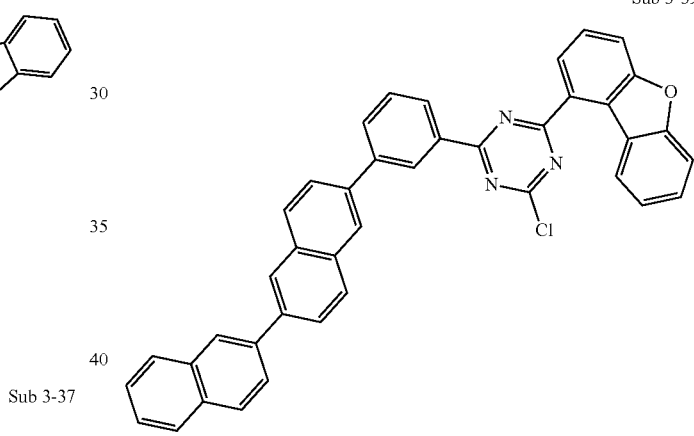
Sub 3-40
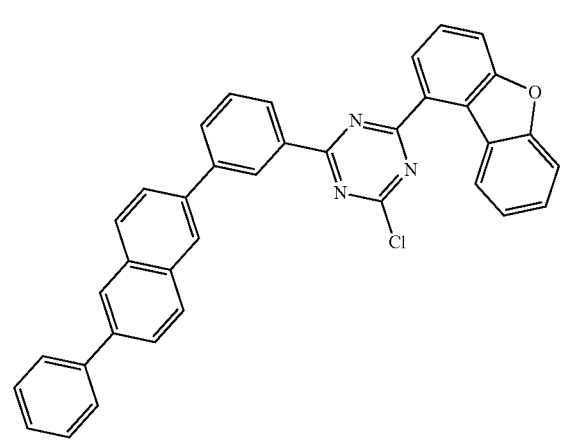

Sub 3-41
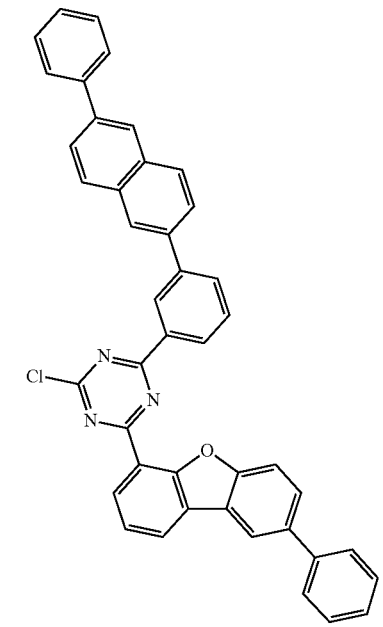
Sub 3-42
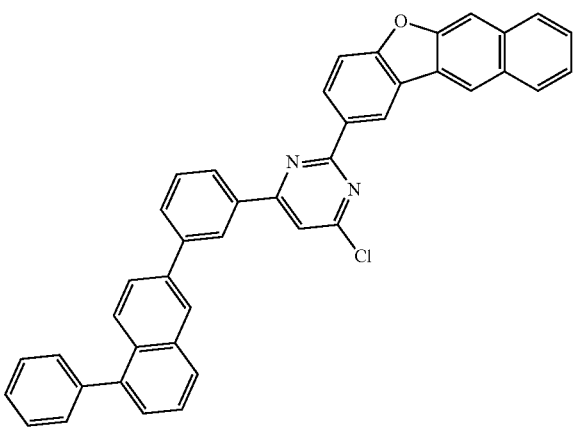
Sub 3-43
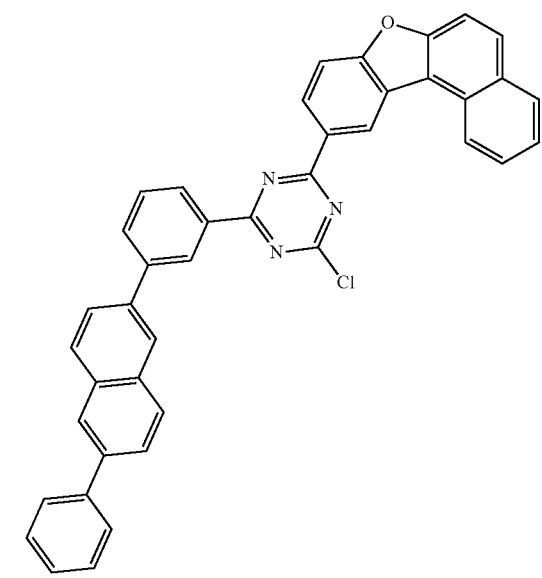
Sub 3-44
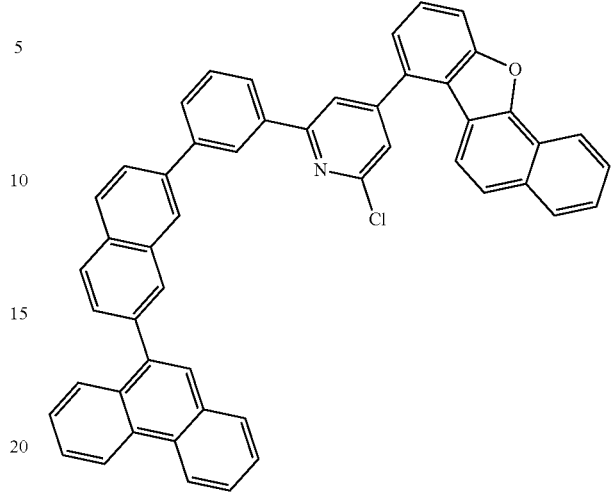
Sub 3-45
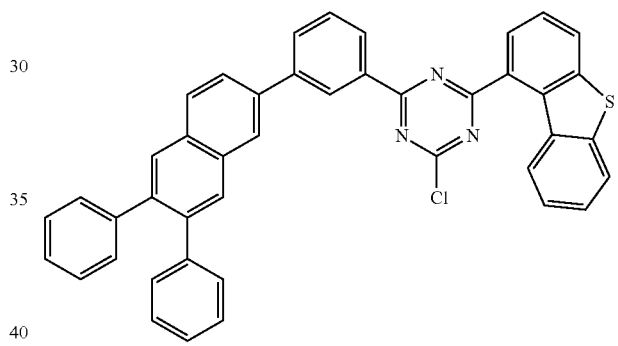
Sub 3-46
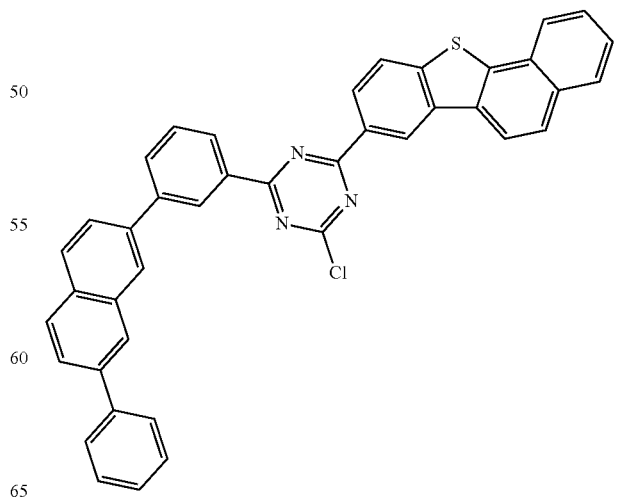

Sub 3-47
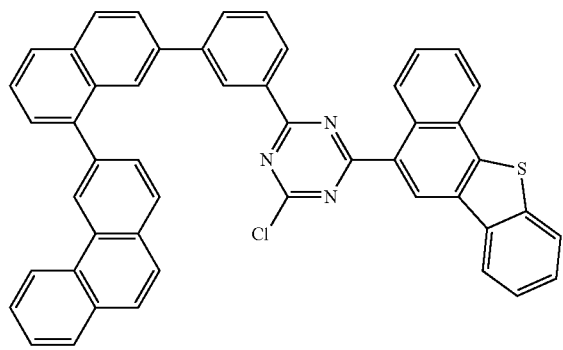
Sub 3-48
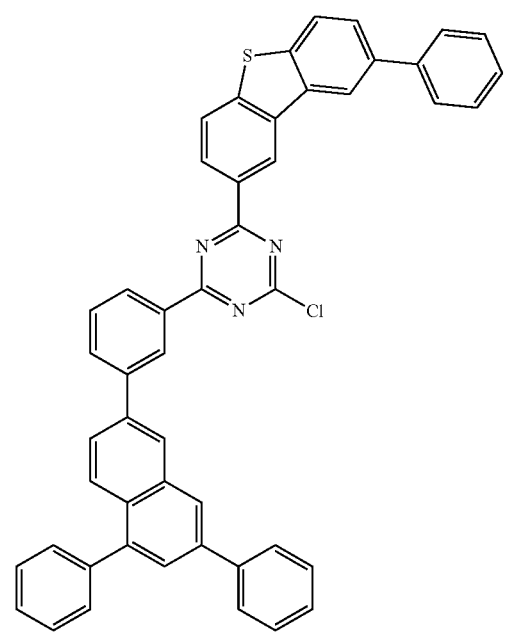
Sub 3-49
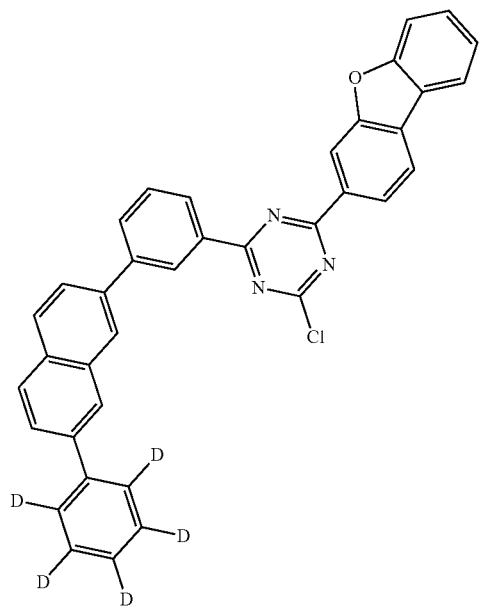
Sub 3-50
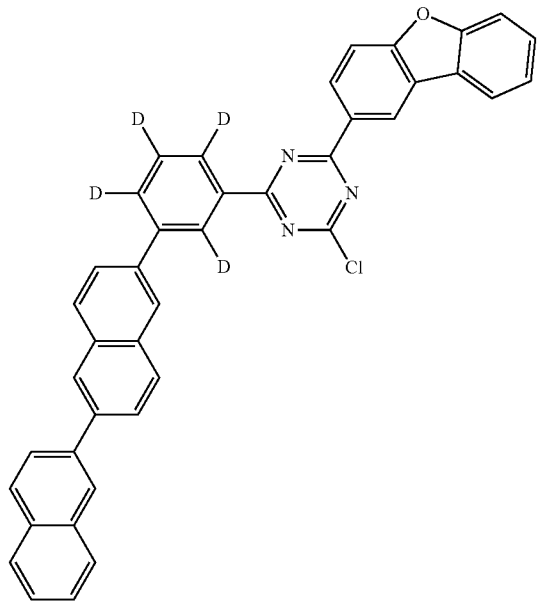
Sub 3-51
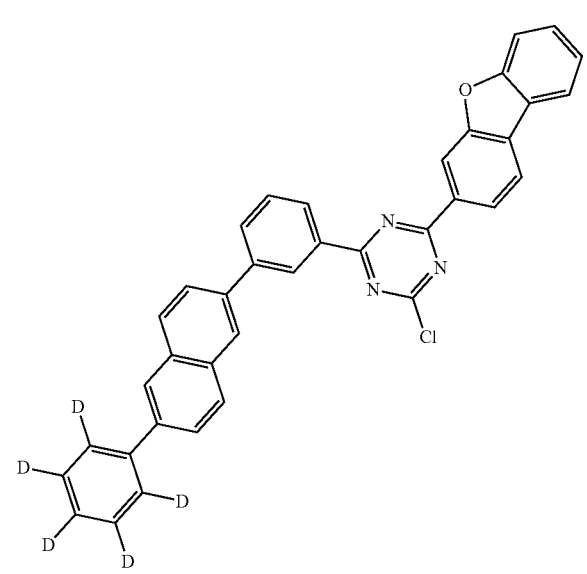

Sub 3-52
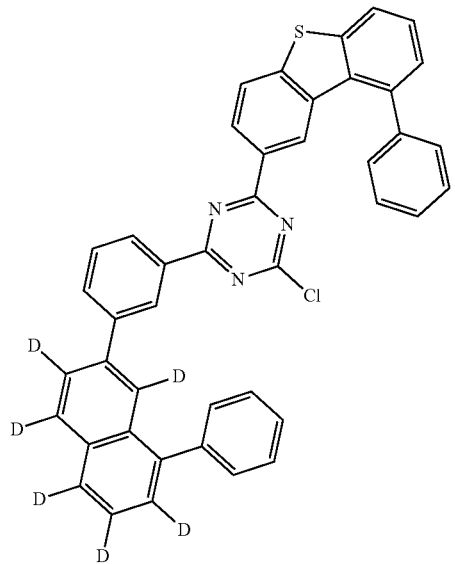
Sub 3-54
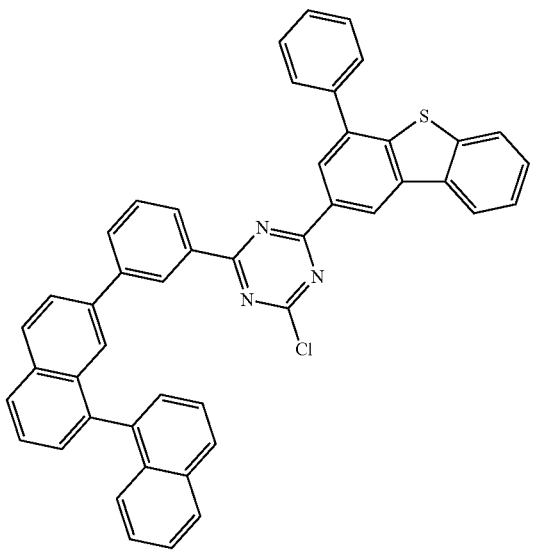
Sub 3-53
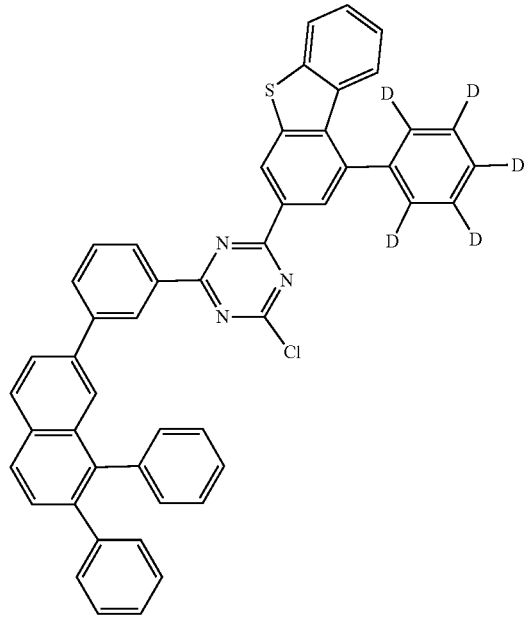
Sub 3-55
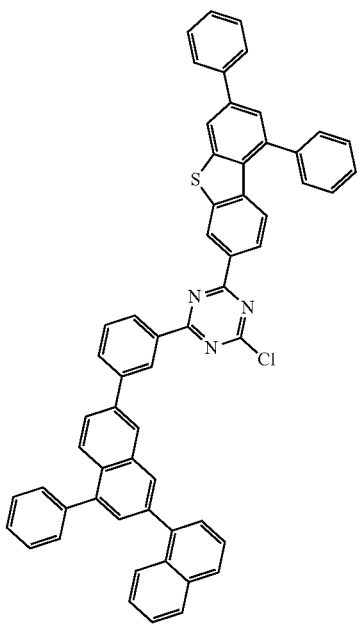

Sub 3-56
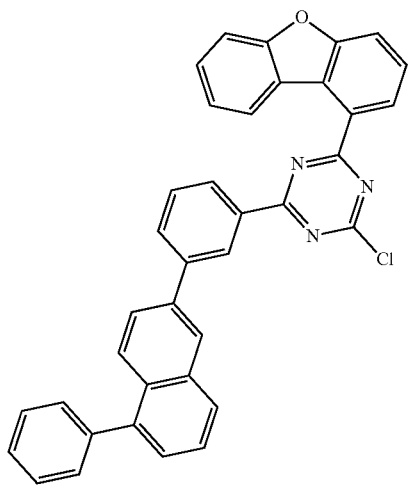
Sub 3-59
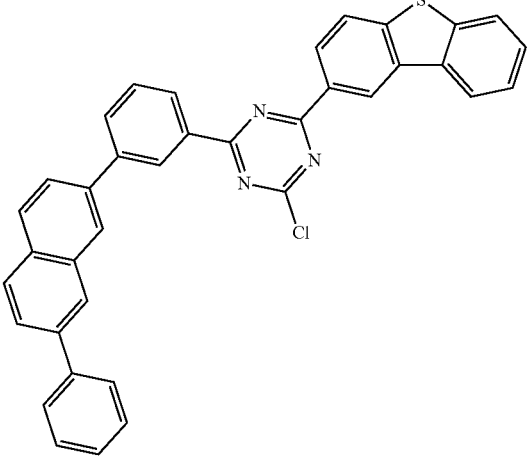
Sub 3-57
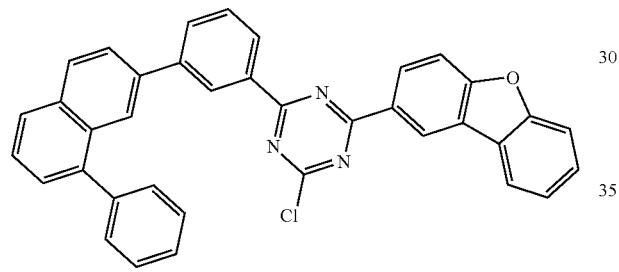
Sub 3-58
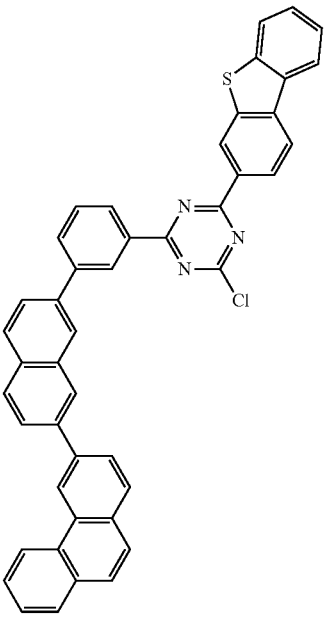
Sub 3-60

247
-continued
Sub 3-61
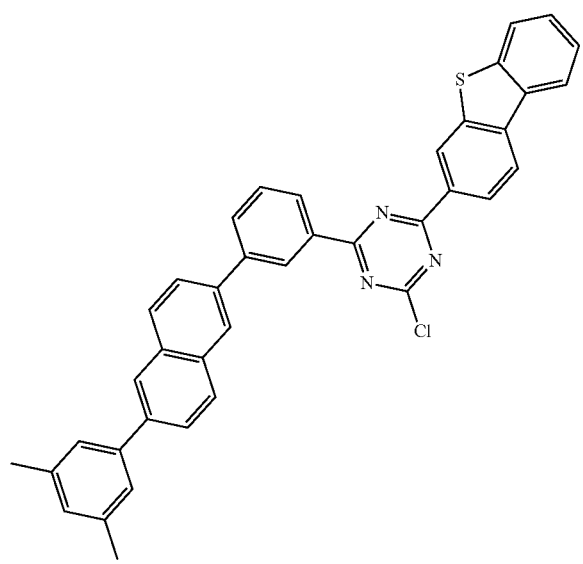
Sub 3-62
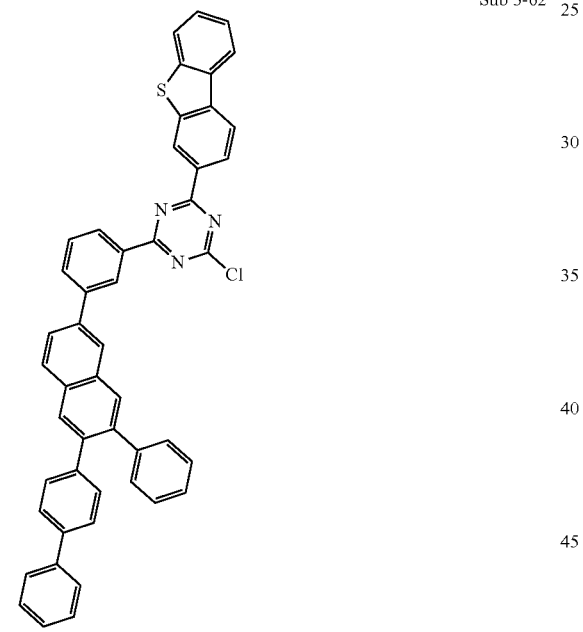
248
-continued
Sub 3-64
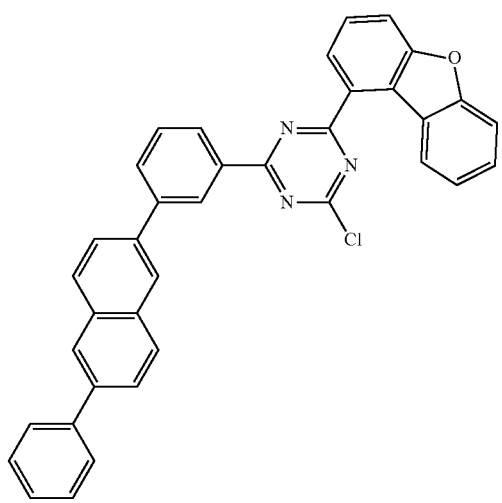
Sub 3-65
Sub 3-63
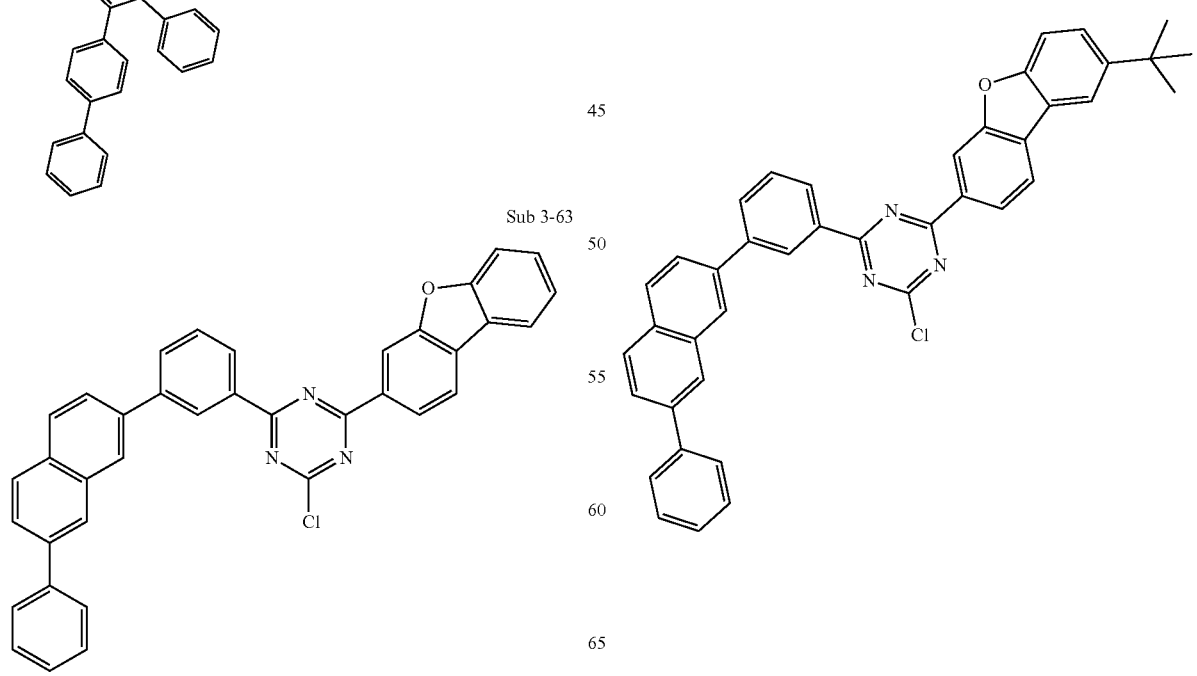

Sub 3-66
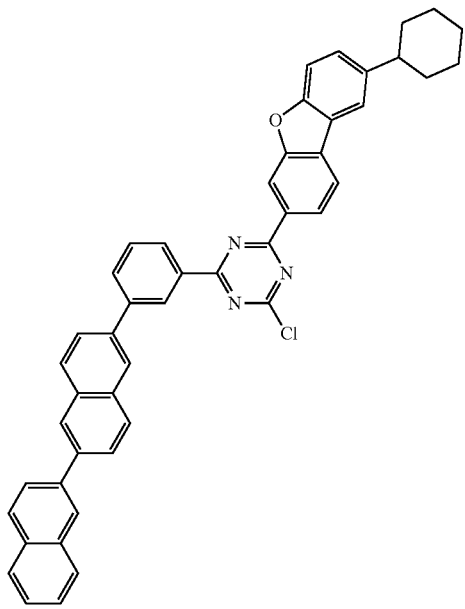
Sub 3-67
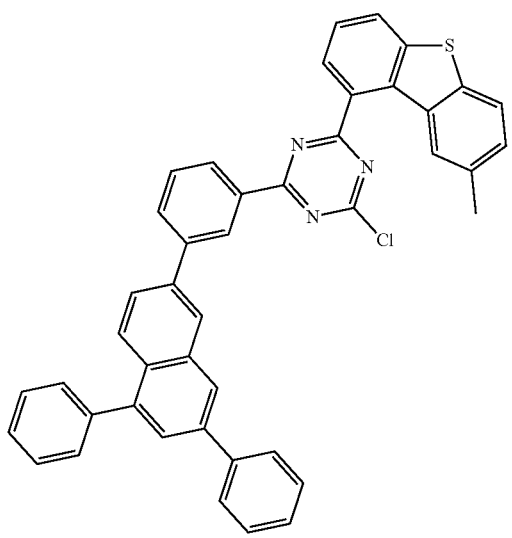
Sub 3-68
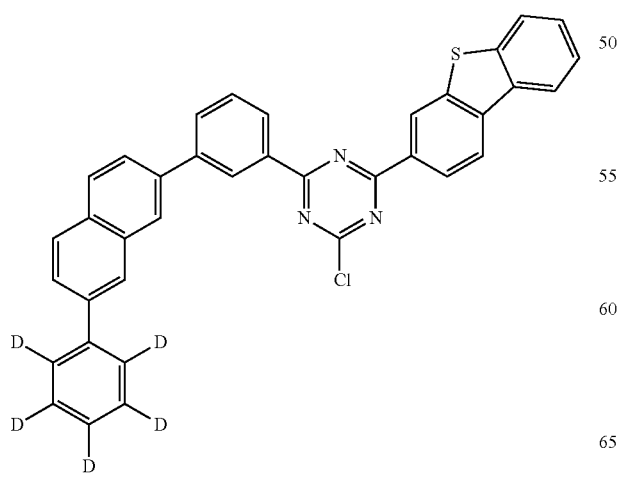
Sub 3-69
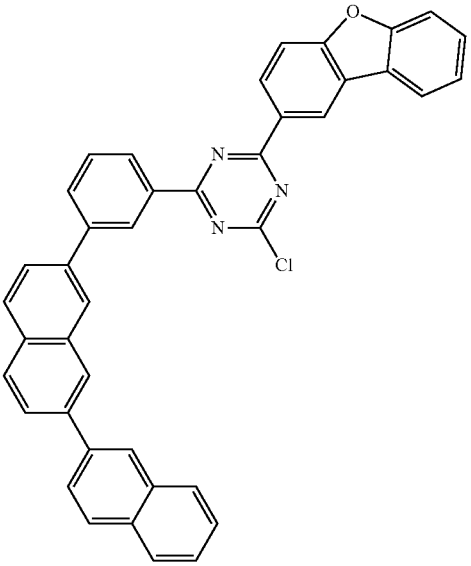
Sub 3-70
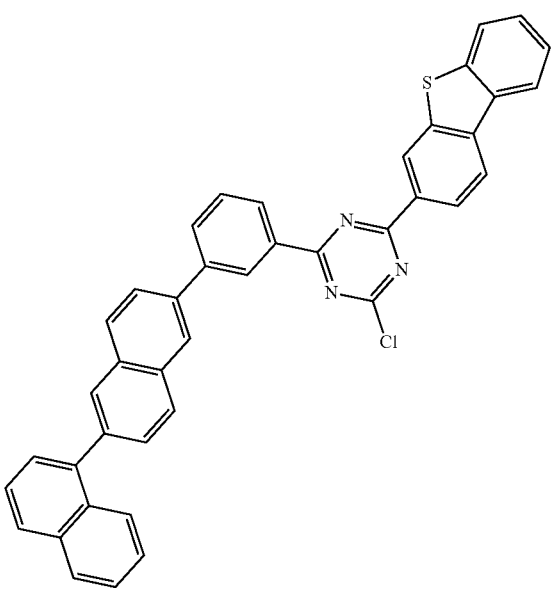
Sub 3-71
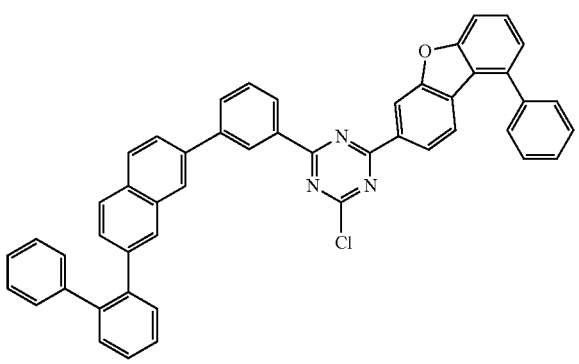

-continued
Sub 3-72
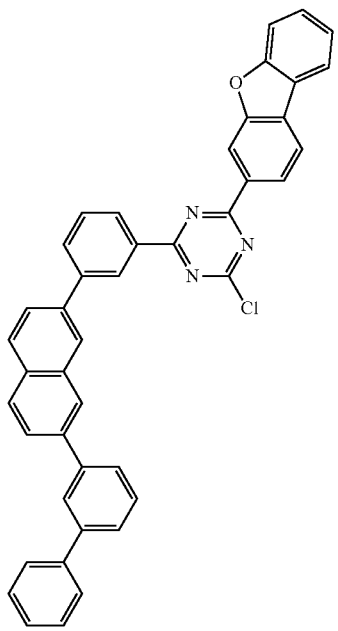
Sub 3-74
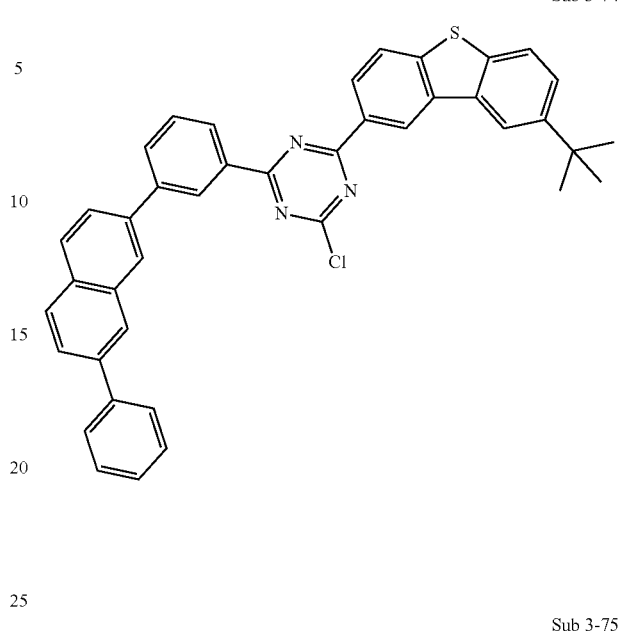
Sub 3-73
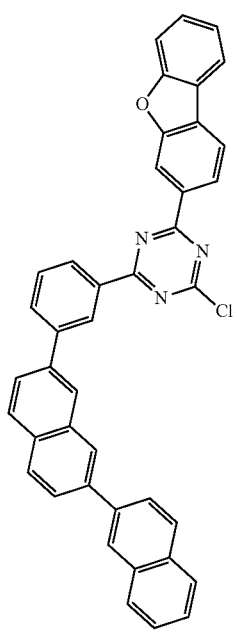
Sub 3-75
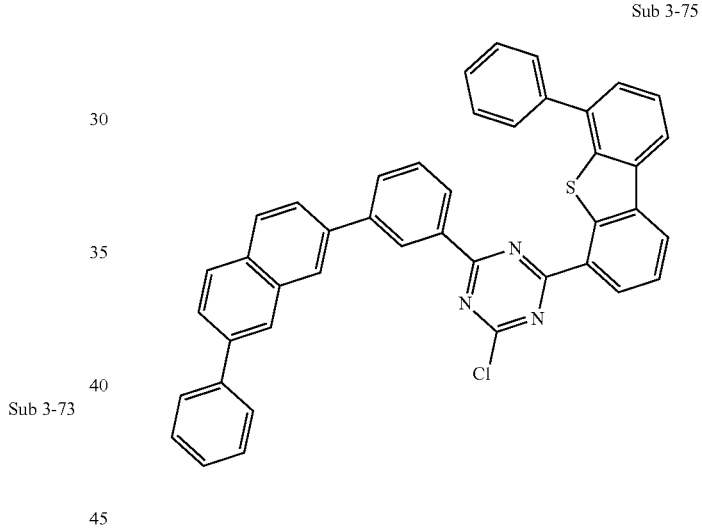
Sub 3-76
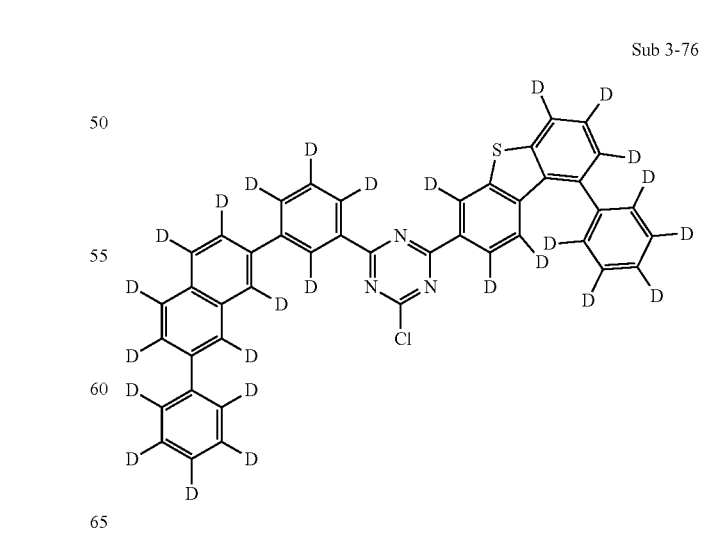

TABLE 5

| compound | FD-MS | compound | FD-MS |
|---|---|---|---|
| Sub 3-1 | m/z = 575.12($C_{37}H_{22}ClN_3S$ = 576.11) | Sub 3-2 | m/z = 575.12($C_{37}H_{22}ClN_3S$ = 576.11) |
| Sub 3-3 | m/z = 651.15($C_{43}H_{26}ClN_3S$ = 652.21) | Sub 3-4 | m/z = 575.12($C_{37}H_{22}ClN_3S$ = 576.11) |
| Sub 3-5 | m/z = 559.15($C_{37}H_{22}ClN_3O$ = 560.05) | Sub 3-6 | m/z = 559.15($C_{37}H_{22}ClN_3O$ = 560.05) |
| Sub 3-7 | m/z = 609.16($C_{41}H_{24}ClN_3O$ = 610.11) | Sub 3-8 | m/z = 609.16($C_{41}H_{24}ClN_3O$ = 610.11) |
| Sub 3-9 | m/z = 575.12($C_{37}H_{22}ClN_3S$ = 576.11) | Sub 3-10 | m/z = 625.14($C_{41}H_{24}ClN_3S$ = 626.17) |
| Sub 3-11 | m/z = 559.15($C_{37}H_{22}ClN_3O$ = 560.05) | Sub 3-12 | m/z = 659.18($C_{45}H_{26}ClN_3O$ = 660.17) |
| Sub 3-13 | m/z = 659.18($C_{45}H_{26}ClN_3O$ = 660.17) | Sub 3-14 | m/z = 635.18($C_{43}H_{26}ClN_3O$ = 636.15) |
| Sub 3-15 | m/z = 651.15($C_{43}H_{26}ClN_3S$ = 652.21) | Sub 3-16 | m/z = 651.15($C_{43}H_{26}ClN_3S$ = 652.21) |
| Sub 3-17 | m/z = 651.15($C_{43}H_{26}ClN_3S$ = 652.21) | Sub 3-18 | m/z = 625.14($C_{41}H_{24}ClN_3S$ = 626.17) |
| Sub 3-19 | m/z = 559.15($C_{37}H_{22}ClN_3O$ = 560.05) | Sub 3-20 | m/z = 559.15($C_{37}H_{22}ClN_3O$ = 560.05) |
| Sub 3-21 | m/z = 559.15($C_{37}H_{22}ClN_3O$ = 560.05) | Sub 3-22 | m/z = 575.12($C_{37}H_{22}ClN_3S$ = 576.11) |
| Sub 3-23 | m/z = 575.12($C_{37}H_{22}ClN_3S$ = 576.11) | Sub 3-24 | m/z = 609.16($C_{41}H_{24}ClN_3O$ = 610.11) |
| Sub 3-25 | m/z = 609.16($C_{41}H_{24}ClN_3O$ = 610.11) | Sub 3-26 | m/z = 609.16($C_{41}H_{24}ClN_3O$ = 610.11) |
| Sub 3-27 | m/z = 609.16($C_{41}H_{24}ClN_3O$ = 610.11) | Sub 3-28 | m/z = 625.14($C_{41}H_{24}ClN_3S$ = 626.17) |
| Sub 3-29 | m/z = 625.14($C_{41}H_{24}ClN_3S$ = 626.17) | Sub 3-30 | m/z = 625.14($C_{41}H_{24}ClN_3S$ = 626.17) |
| Sub 3-31 | m/z = 625.14($C_{41}H_{24}ClN_3S$ = 626.17) | Sub 3-32 | m/z = 609.16($C_{41}H_{24}ClN_3O$ = 610.11) |
| Sub 3-33 | m/z = 609.16($C_{41}H_{24}ClN_3O$ = 610.11) | Sub 3-34 | m/z = 625.14($C_{41}H_{24}ClN_3S$ = 626.17) |
| Sub 3-35 | m/z = 625.14($C_{41}H_{24}ClN_3S$ = 626.17) | Sub 3-36 | m/z = 625.14($C_{41}H_{24}ClN_3S$ = 626.17) |
| Sub 3-37 | m/z = 625.14($C_{41}H_{24}ClN_3S$ = 626.17) | Sub 3-38 | m/z = 559.15($C_{37}H_{22}ClN_3O$ = 560.05) |
| Sub 3-39 | m/z = 609.16($C_{41}H_{24}ClN_3O$ = 610.11) | Sub 3-40 | m/z = 559.15($C_{37}H_{22}ClN_3O$ = 560.05) |
| Sub 3-41 | m/z = 635.18($C_{43}H_{26}ClN_3O$ = 636.15) | Sub 3-42 | m/z = 609.16($C_{41}H_{24}ClN_3O$ = 610.11) |
| Sub 3-43 | m/z = 609.16($C_{41}H_{24}ClN_3O$ = 610.11) | Sub 3-44 | m/z = 709.19($C_{49}H_{28}ClN_3O$ = 710.23) |
| Sub 3-45 | m/z = 651.15($C_{43}H_{26}ClN_3S$ = 652.21) | Sub 3-46 | m/z = 625.14($C_{41}H_{24}ClN_3S$ = 626.17) |
| Sub 3-47 | m/z = 725.17($C_{49}H_{28}ClN_3S$ = 726.29) | Sub 3-48 | m/z = 727.18($C_{49}H_{30}ClN_3S$ = 728.31) |
| Sub 3-49 | m/z = 564.18($C_{37}H_{17}D_5ClN_3O$ = 565.08) | Sub 3-50 | m/z = 613.19($C_{41}H_{20}D_4ClN_3O$ = 614.14) |
| Sub 3-51 | m/z = 564.18($C_{37}H_{17}D_5ClN_3O$ = 565.08) | Sub 3-52 | m/z = 657.19($C_{43}H_{20}D_6ClN_3S$ = 658.25) |
| Sub 3-53 | m/z = 732.22($C_{49}H_{25}D_5ClN_3S$ = 733.34) | Sub 3-54 | m/z = 701.17($C_{47}H_{28}ClN_3S$ = 702.27) |
| Sub 3-55 | m/z = 853.23($C_{59}H_{36}ClN_3S$ = 854.47) | Sub 3-56 | m/z = 559.15($C_{37}H_{22}ClN_3O$ = 560.05) |
| Sub 3-57 | m/z = 559.15($C_{37}H_{22}ClN_3O$ = 560.05) | Sub 3-58 | m/z = 635.18($C_{43}H_{26}ClN_3O$ = 636.15) |
| Sub 3-59 | m/z = 575.12($C_{37}H_{22}ClN_3S$ = 576.11) | Sub 3-60 | m/z = 675.15($C_{45}H_{26}ClN_3S$ = 676.23) |
| Sub 3-61 | m/z = 603.15($C_{39}H_{26}ClN_3O$ = 604.17) | Sub 3-62 | m/z = 727.18($C_{49}H_{30}ClN_3S$ = 728.31) |
| Sub 3-63 | m/z = 559.15($C_{37}H_{22}ClN_3O$ = 560.05) | Sub 3-64 | m/z = 559.15($C_{37}H_{22}ClN_3O$ = 560.05) |
| Sub 3-65 | m/z = 615.21($C_{41}H_{30}ClN_3O$ = 616.16) | Sub 3-66 | m/z = 691.24($C_{47}H_{34}ClN_3O$ = 692.26) |
| Sub 3-67 | m/z = 665.17($C_{44}H_{28}ClN_3S$ = 666.24) | Sub 3-68 | m/z = 580.15($C_{37}H_{17}D_5ClN_3S$ = 581.14) |
| Sub 3-69 | m/z = 609.16($C_{41}H_{24}ClN_3O$ = 610.11) | Sub 3-70 | m/z = 625.14($C_{41}H_{24}ClN_3S$ = 626.17) |
| Sub 3-71 | m/z = 711.21($C_{49}H_{30}ClN_3O$ = 712.25) | Sub 3-72 | m/z = 635.18($C_{43}H_{26}ClN_3O$ = 636.15) |
| Sub 3-73 | m/z = 609.16($C_{41}H_{24}ClN_3O$ = 610.11) | Sub 3-74 | m/z = 631.18($C_{41}H_{30}ClN_3S$ = 632.22) |
| Sub 3-75 | m/z = 651.15($C_{43}H_{26}ClN_3S$ = 652.21) | Sub 3-76 | m/z = 677.32($C_{43}D_{26}ClN_3S$ = 678.37) |

Compounds belonging to Sub 4 may be the following compounds, but are not limited thereto, and Table 6 shows FD-MS (Field Desorption-Mass Spectrometry) values of compounds belonging to Sub 6.

Sub 4-1
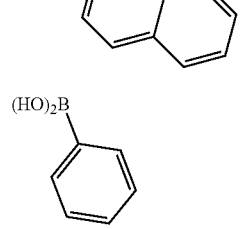

Sub 4-2

Sub 4-3
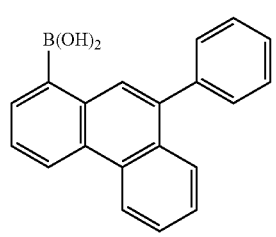

Sub 4-4
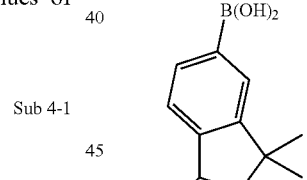

-continued

Sub 4-5
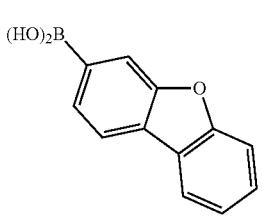

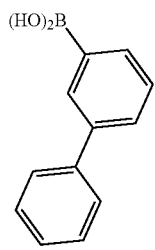
Sub 4-6
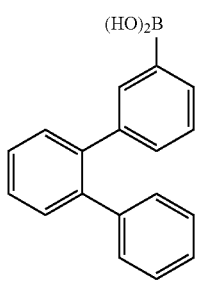
Sub 4-7
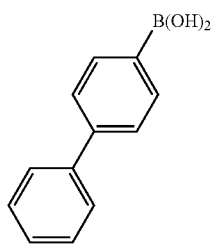
Sub 4-8
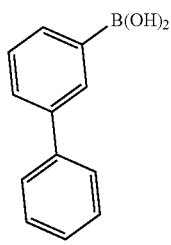
Sub 4-9
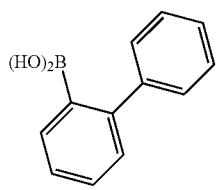
Sub 4-10
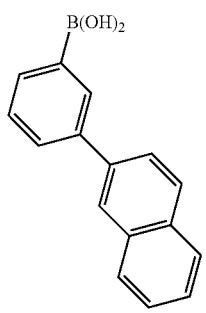
Sub 4-11
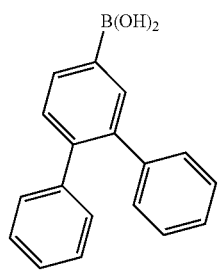
Sub 4-12
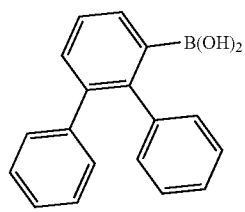
Sub 4-13
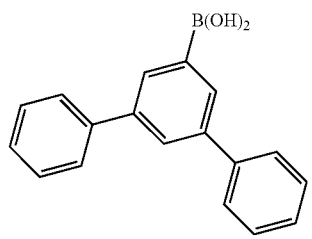
Sub 4-14
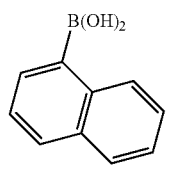
Sub 4-15
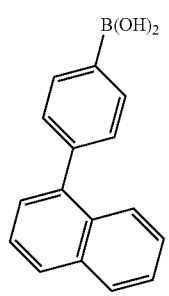
Sub 4-16
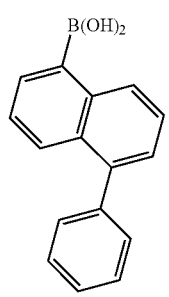
Sub 4-17

-continued
Sub 4-18
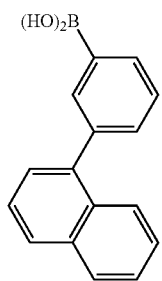
Sub 4-19
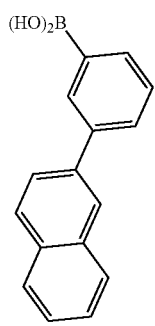
Sub 4-20
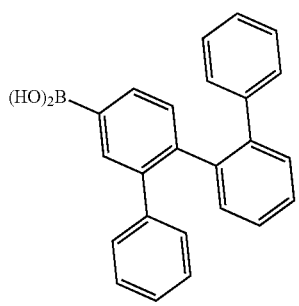
Sub 4-21
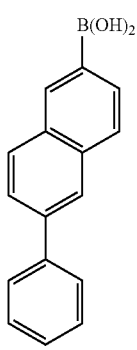
Sub 4-22
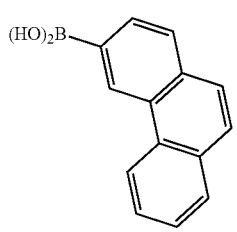
-continued
Sub 4-23
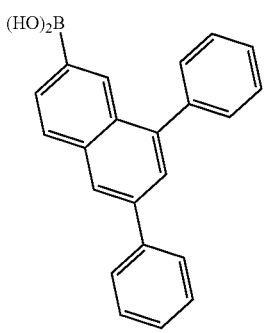
Sub 4-24
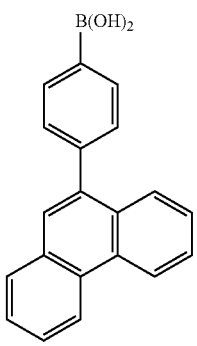
Sub 4-25
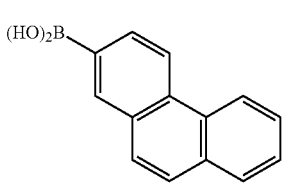
Sub 4-26
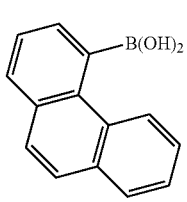
Sub 4-27
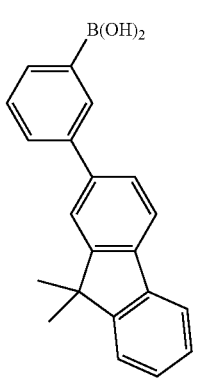
Sub 4-28
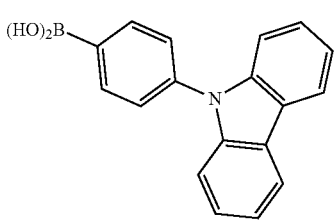

-continued
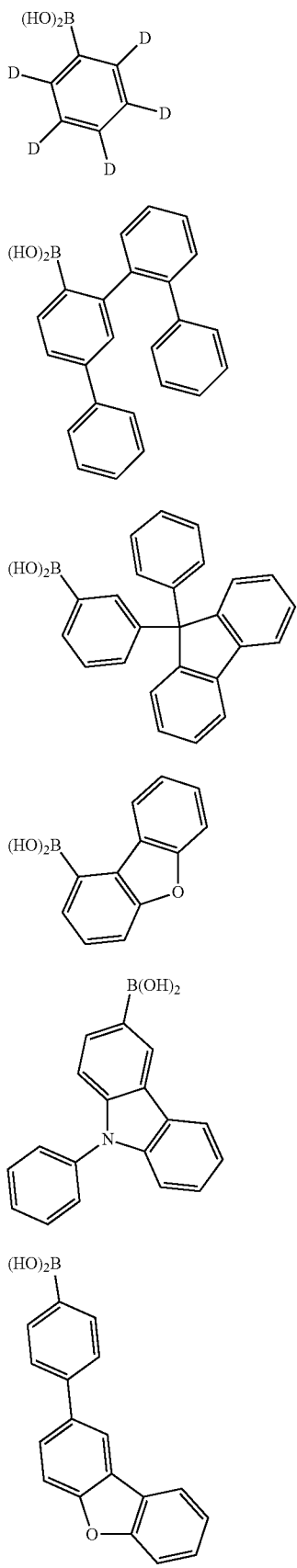
Sub 4-30
Sub 4-31
Sub 4-32
Sub 4-33
Sub 4-34
-continued
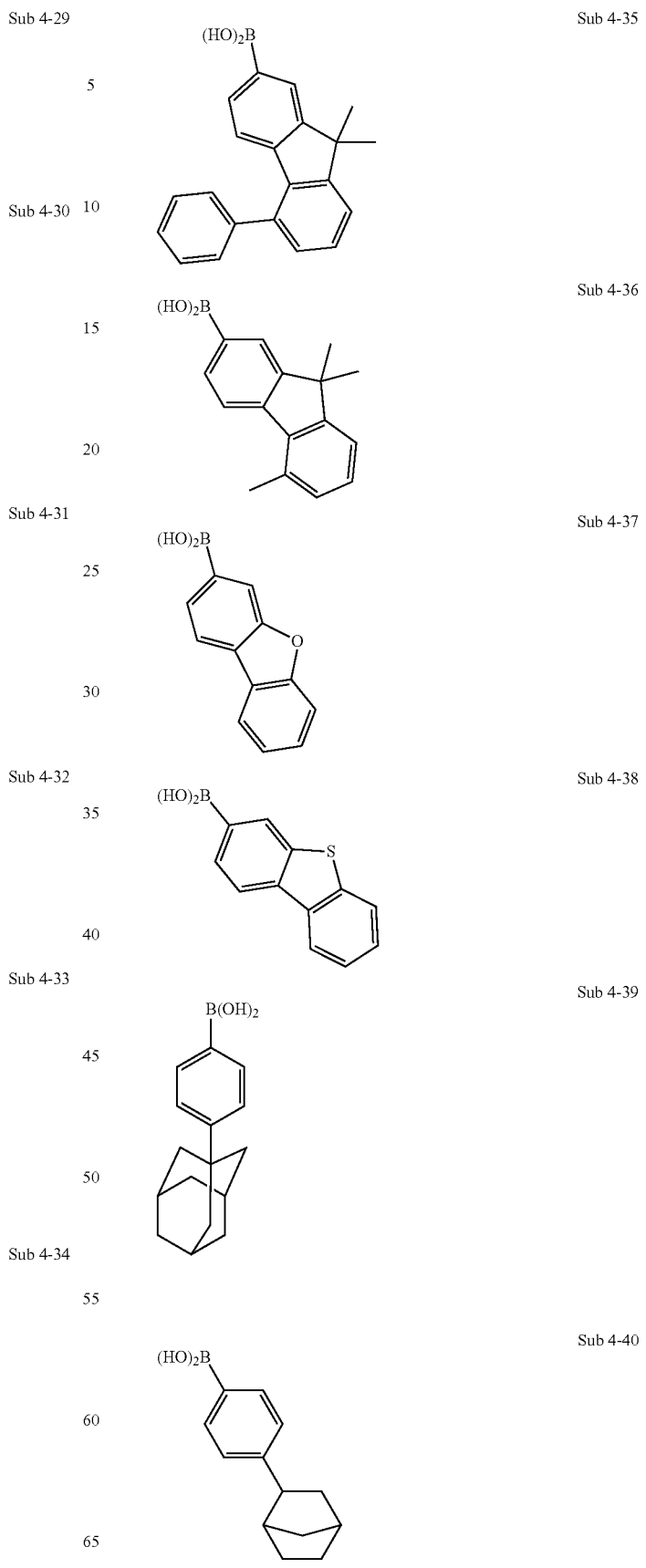
Sub 4-29
Sub 4-35
Sub 4-36
Sub 4-37
Sub 4-38
Sub 4-39
Sub 4-40

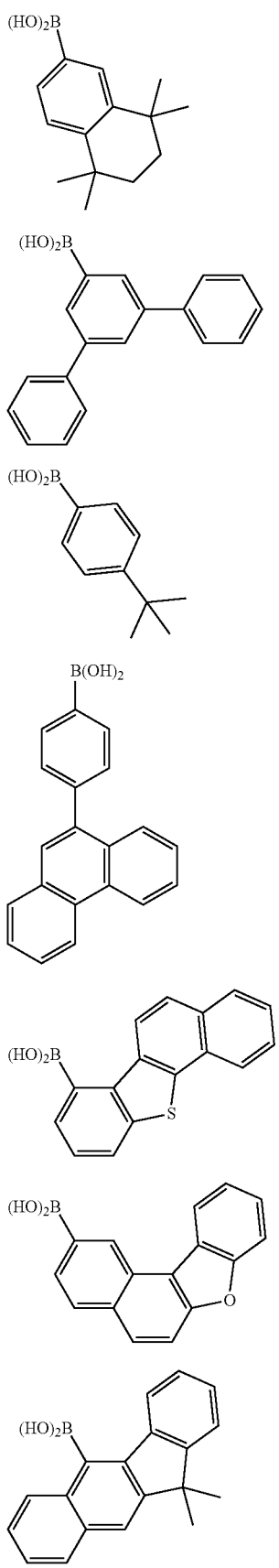
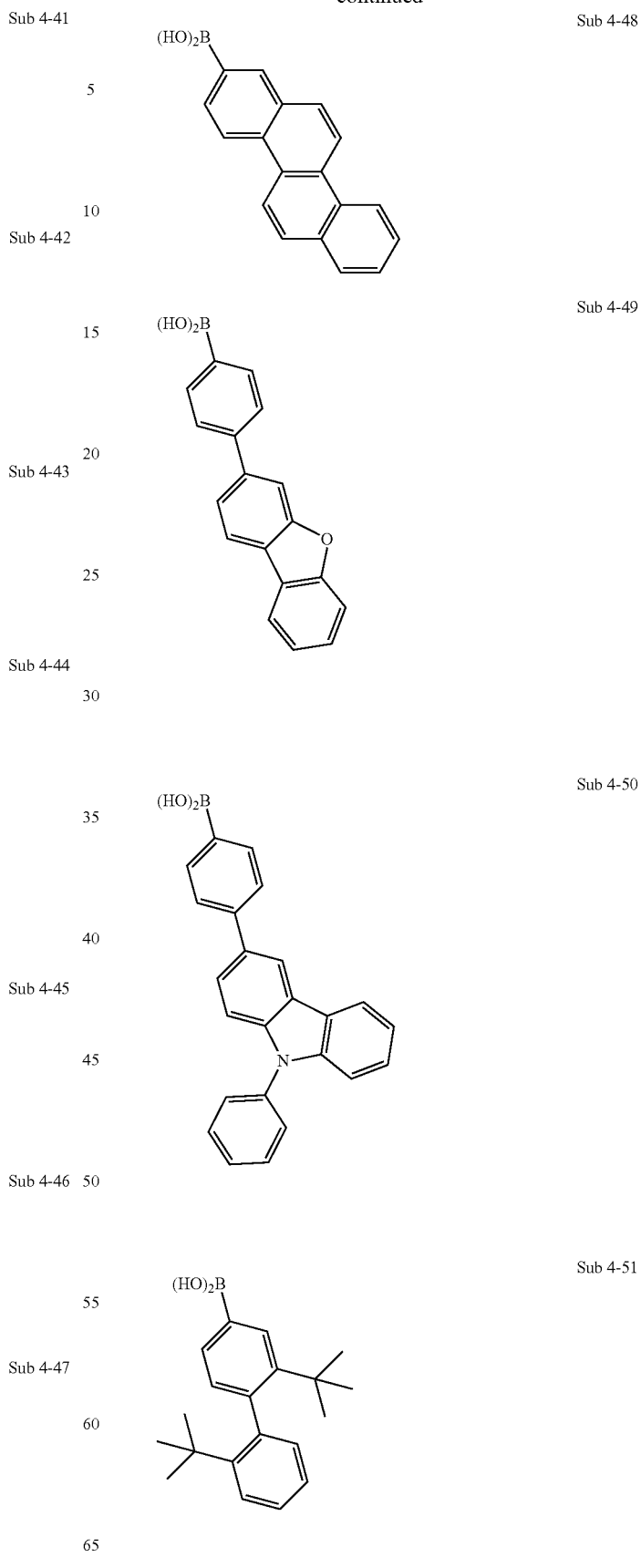

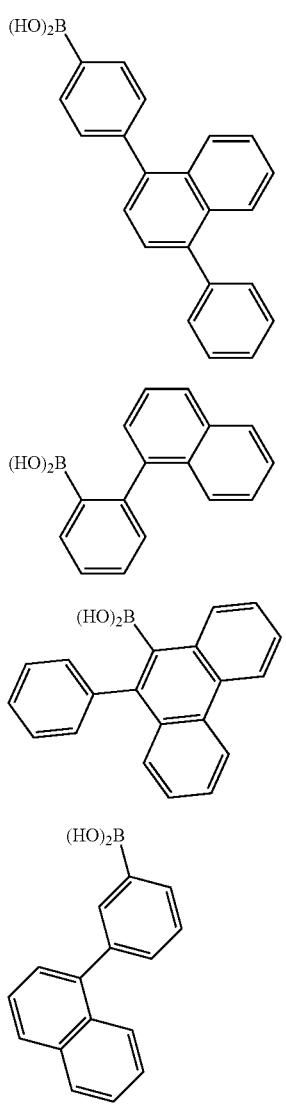

Sub 4-52

Sub 4-53

Sub 4-54

Sub 4-55

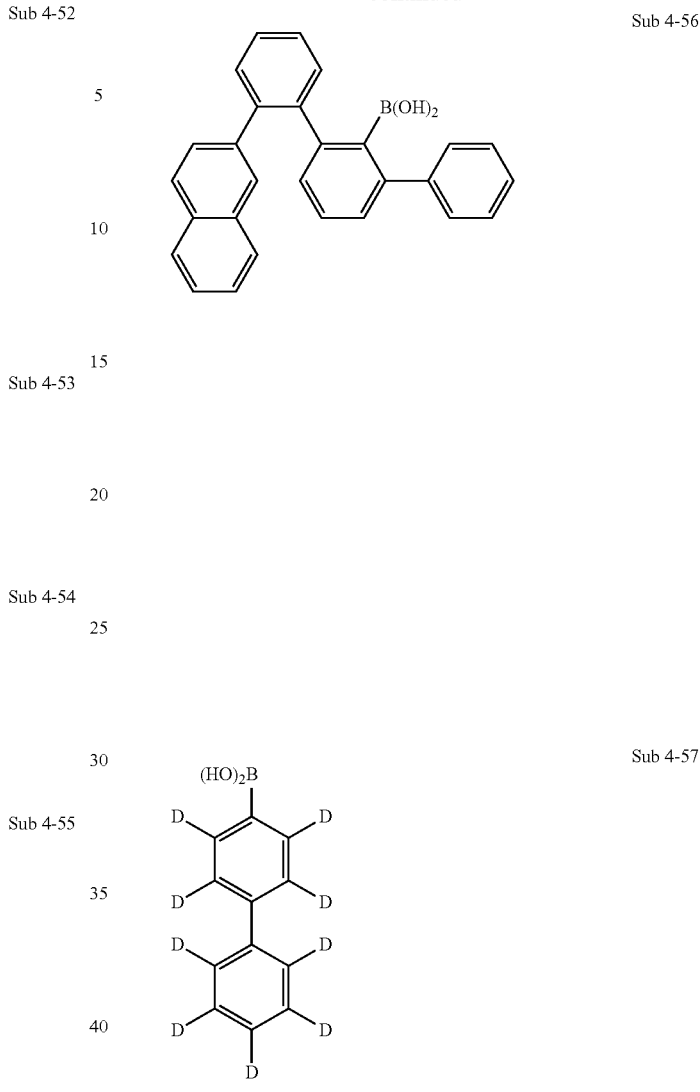

Sub 4-56

Sub 4-57

TABLE 6

| compound | FD-MS | compound | FD-MS |
| --- | --- | --- | --- |
| Sub 4-1 | m/z = 172.07($C_{10}H_9BO_2$ = 171.99) | Sub 4-2 | m/z = 122.05($C_6H_7BO_2$ = 121.93) |
| Sub 4-3 | m/z = 298.12($C_{20}H_{15}BO_2$ = 298.15) | Sub 4-4 | m/z = 238.12($C_{15}H_{15}BO_2$ = 238.09) |
| Sub 4-5 | m/z = 212.06($C_{12}H_9BO_3$ = 212.01) | Sub 4-6 | m/z = 198.09($C_{12}H_{11}BO_2$ = 198.03) |
| Sub 4-7 | m/z = 274.12($C_{18}H_{15}BO_2$ = 274.13) | Sub 4-8 | m/z = 198.09($C_{12}H_{11}BO_2$ = 198.03) |
| Sub 4-9 | m/z = 198.09($C_{12}H_{11}BO_2$ = 198.03) | Sub 4-10 | m/z = 198.09($C_{12}H_{11}BO_2$ = 198.03) |
| Sub 4-11 | m/z = 248.10($C_{16}H_{13}BO_2$ = 248.09) | Sub 4-12 | m/z = 274.12($C_{18}H_{15}BO_2$ = 274.13) |
| Sub 4-13 | m/z = 274.12($C_{18}H_{15}BO_2$ = 274.13) | Sub 4-14 | m/z = 274.12($C_{18}H_{15}BO_2$ = 274.13) |
| Sub 4-15 | m/z = 172.07($C_{10}H_9BO_2$ = 171.99) | Sub 4-16 | m/z = 248.10($C_{16}H_{13}BO_2$ = 248.09) |
| Sub 4-17 | m/z = 248.10($C_{16}H_{13}BO_2$ = 248.09) | Sub 4-18 | m/z = 248.10($C_{16}H_{13}BO_2$ = 248.09) |
| Sub 4-19 | m/z = 248.10($C_{16}H_{13}BO_2$ = 248.09) | Sub 4-20 | m/z = 350.15($C_{24}H_{19}BO_2$ = 350.22) |
| Sub 4-21 | m/z = 248.10($C_{16}H_{13}BO_2$ = 248.09) | Sub 4-22 | m/z = 222.09($C_{14}H_{11}BO_2$ = 222.05) |
| Sub 4-23 | m/z = 324.13($C_{22}H_{17}BO_2$ = 324.19) | Sub 4-24 | m/z = 298.12($C_{20}H_{15}BO_2$ = 298.15) |
| Sub 4-25 | m/z = 222.09($C_{14}H_{11}BO_2$ = 222.05) | Sub 4-26 | m/z = 222.09($C_{14}H_{11}BO_2$ = 222.05) |
| Sub 4-27 | m/z = 314.15($C_{21}H_{19}BO_2$ = 314.19) | Sub 4-28 | m/z = 287.11($C_{18}H_{14}BNO_2$ = 287.12) |
| Sub 4-29 | m/z = 127.09($C_6H_2D_5BO_2$ = 126.96) | Sub 4-30 | m/z = 350.15($C_{24}H_{19}BO_2$ = 350.22) |
| Sub 4-31 | m/z = 362.15($C_{25}H_{19}BO_2$ = 362.23) | Sub 4-32 | m/z = 212.06($C_{12}H_9BO_3$ = 212.01) |
| Sub 4-33 | m/z = 287.11($C_{18}H_{14}BNO_2$ = 287.12) | Sub 4-34 | m/z = 288.10($C_{18}H_{13}BO_3$ = 288.11) |
| Sub 4-35 | m/z = 314.15($C_{21}H_{19}BO_2$ = 314.19) | Sub 4-36 | m/z = 252.13($C_{16}H_{17}BO_2$ = 252.12) |
| Sub 4-37 | m/z = 212.06($C_{12}H_9BO_3$ = 212.01) | Sub 4-38 | m/z = 228.04($C_{12}H_9BO_2S$ = 228.07) |
| Sub 4-39 | m/z = 256.16($C_{16}H_{21}BO_2$ = 256.15) | Sub 4-40 | m/z = 216.13($C_{13}H_{17}BO_2$ = 216.09) |
| Sub 4-41 | m/z = 232.16($C_{14}H_{21}BO_2$ = 232.13) | Sub 4-42 | m/z = 274.12($C_{18}H_{15}BO_2$ = 274.13) |
| Sub 4-43 | m/z = 178.12($C_{10}H_{15}BO_2$ = 178.04) | Sub 4-44 | m/z = 298.12($C_{20}H_{15}BO_2$ = 298.15) |

TABLE 6-continued

| compound | FD-MS | compound | FD-MS |
|---|---|---|---|
| Sub 4-45 | m/z = 278.06(C$_{16}$H$_{11}$BO$_2$S = 278.13) | Sub 4-46 | m/z = 262.08(C$_{16}$HnBO$_3$ = 262.07) |
| Sub 4-47 | m/z = 288.13(C$_{19}$H$_{17}$BO$_2$ = 288.15) | Sub 4-48 | m/z = 272.10(C$_{18}$H$_{13}$BO$_2$ = 272.11) |
| Sub 4-49 | m/z = 288.10(C$_{18}$H$_{13}$BO$_3$ = 288.11) | Sub 4-50 | m/z = 363.14(C$_{24}$H$_{18}$BNO$_2$ = 363.22) |
| Sub 4-51 | m/z = 310.21(C$_{20}$H$_{27}$BO$_2$ = 310.24) | Sub 4-52 | m/z = 324.13(C$_{22}$H$_{17}$BO$_2$ = 324.19) |
| Sub 4-53 | m/z = 248.10(C$_{16}$H$_{13}$BO$_2$ = 248.09) | Sub 4-54 | m/z = 298.12(C$_{20}$H$_{15}$BO$_2$ = 298.15) |
| Sub 4-55 | m/z = 248.10(C$_{16}$H$_{13}$BO$_2$ = 248.09) | Sub 4-56 | m/z = 400.16(C$_{28}$H$_{21}$BO$_2$ = 400.28) |
| Sub 4-57 | m/z = 207.14(C$_{12}$H$_2$D$_9$BO$_2$ = 207.08) | | |

II. Synthesis of Final Product

1. Synthesis Example of N 1-1

After putting Sub 3-1 (50.0 g, 86.8 mmol) in a round bottom flask and dissolving in THF (434 ml), Sub 4-1 (14.9 g, 86.8 mmol), Pd(PPh$_3$)$_4$ (6.0 g, 5.2 mmol), NaOH (10.4 g, 260.4 mmol), Water (217 ml) were added and tested in the same manner as in Sub 3-1-2 to obtain 47.2 g of product. (Yield: 81.4%)

2. Synthesis Example of N 1-6

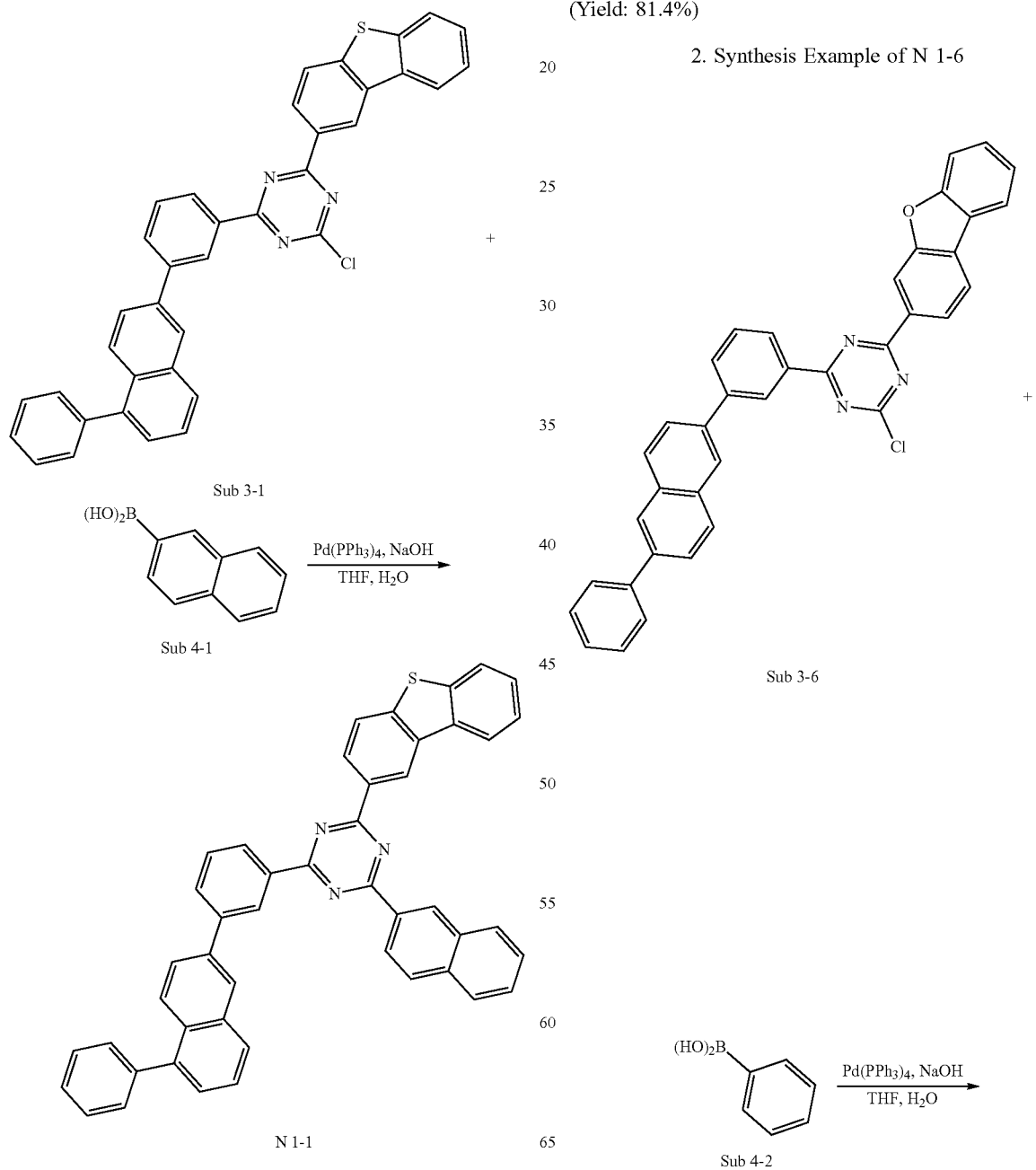

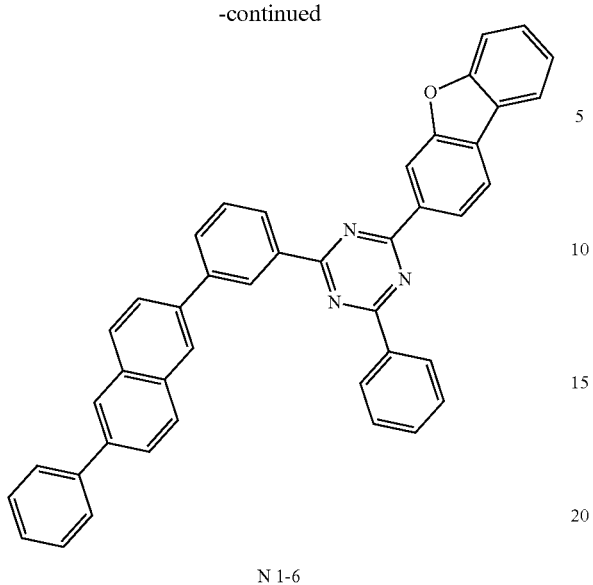

N 1-6

After putting Sub 3-6 (50.0 g, 89.3 mmol) in a round bottom flask and dissolving in THF (446 ml), Sub 4-2 (10.9 g, 89.3 mmol), Pd(PPh$_3$)$_4$ (6.2 g, 5.4 mmol), NaOH (10.7 g, 267.8 mmol), Water (223 ml) were added and tested in the same manner as in Sub 3-1-2 to obtain 44.5 g of product. (Yield: 82.8%)

3. Synthesis Example of N 1-15

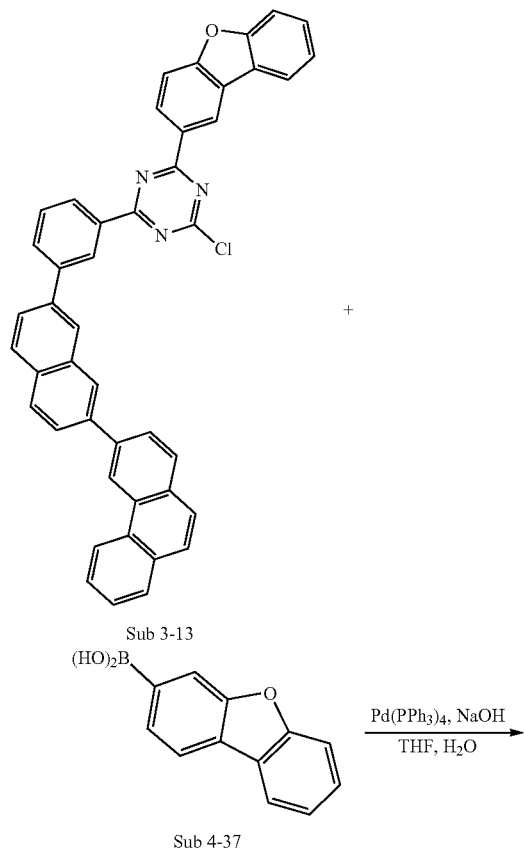

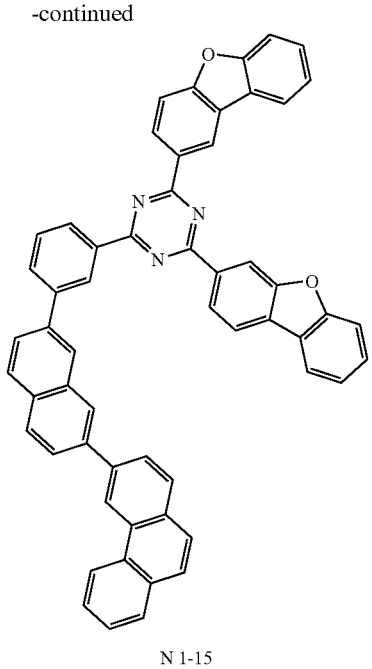

N 1-15

After putting Sub 3-13 (50.0 g, 75.7 mmol) in a round bottom flask and dissolving in THF (379 ml), Sub 4-37 (16.1 g, 75.7 mmol), Pd(PPh$_3$)$_4$ (5.3 g, 4.5 mmol), NaOH (9.1 g, 227.2 mmol), Water (189 ml) were added and tested in the same manner as in Sub 3-1-2 to obtain 48.4 g of product. (Yield: 80.7%)

4. Synthesis Example of N 1-49

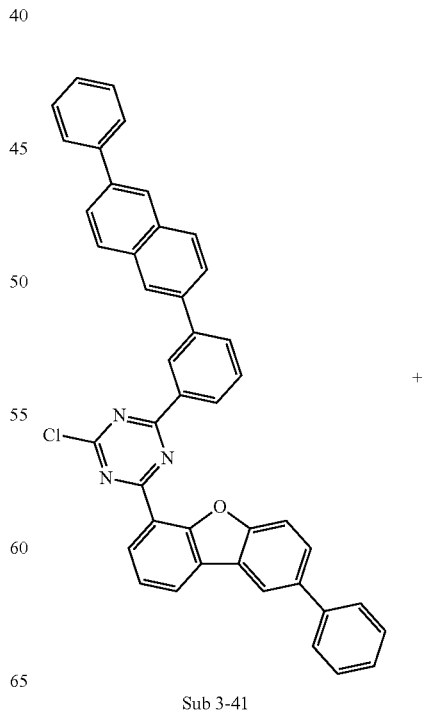

Sub 3-41

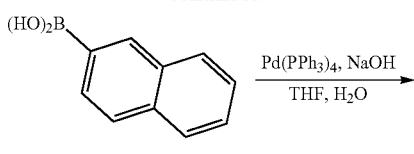

Sub 4-1

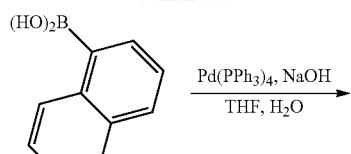

Sub 4-15

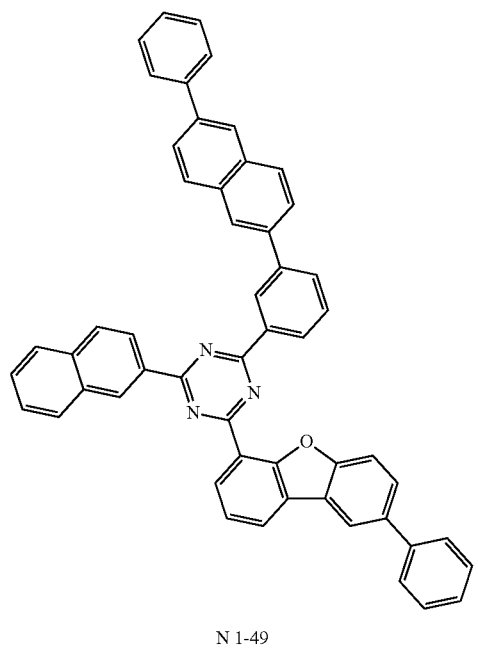

N 1-49

After putting Sub 3-41 (50.0 g, 78.6 mmol) in a round bottom flask and dissolving in THF (393 ml), Sub 4-1 (13.5 g, 78.6 mmol), Pd(PPh$_3$)$_4$ (5.5 g, 4.7 mmol), NaOH (9.4 g, 235.8 mmol), Water (196 ml) were added and tested in the same manner as in Sub 3-1-2 to obtain 46.9 g of product. (Yield: 81.9%)

5. Synthesis Example of N 1-50

N 1-50

After putting Sub 3-42 (50.0 g, 82.0 mmol) in a round bottom flask and dissolving in THF (410 ml), Sub 4-15 (14.1 g, 82.0 mmol), Pd(PPh$_3$)$_4$ (5.7 g, 4.9 mmol), NaOH (9.8 g, 245.9 mmol), Water (205 ml) were added and tested in the same manner as in Sub 3-1-2 to obtain 46.4 g of product. (Yield: 80.7%)

6. Synthesis Example of N 1-56

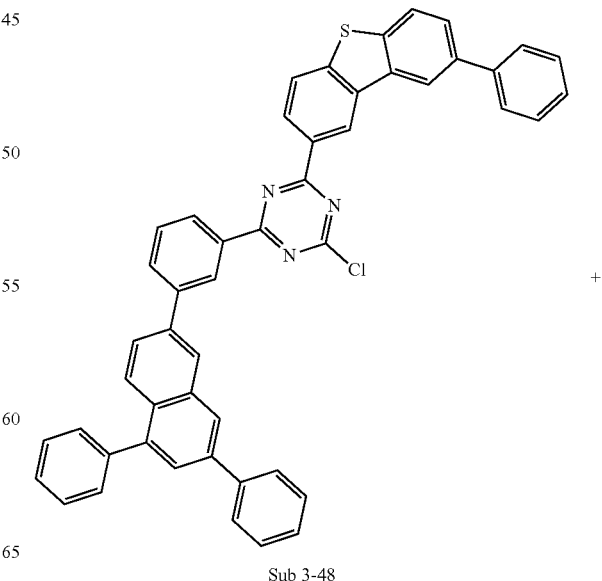

Sub 3-42

Sub 3-48

7. Synthesis Example of N 1-60

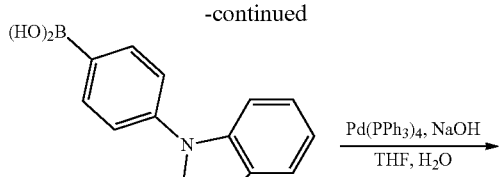

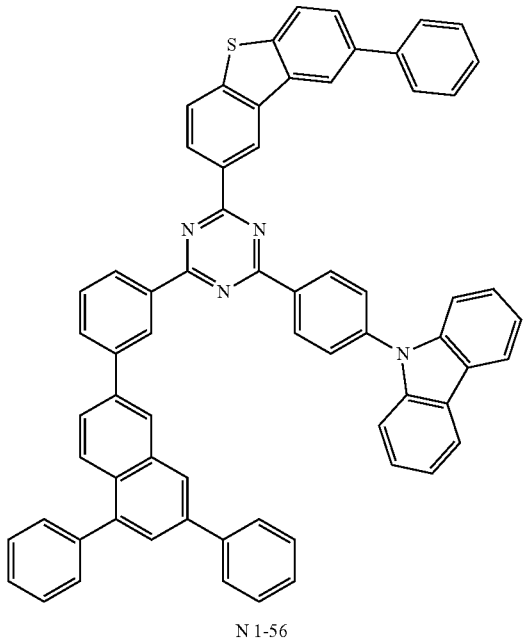

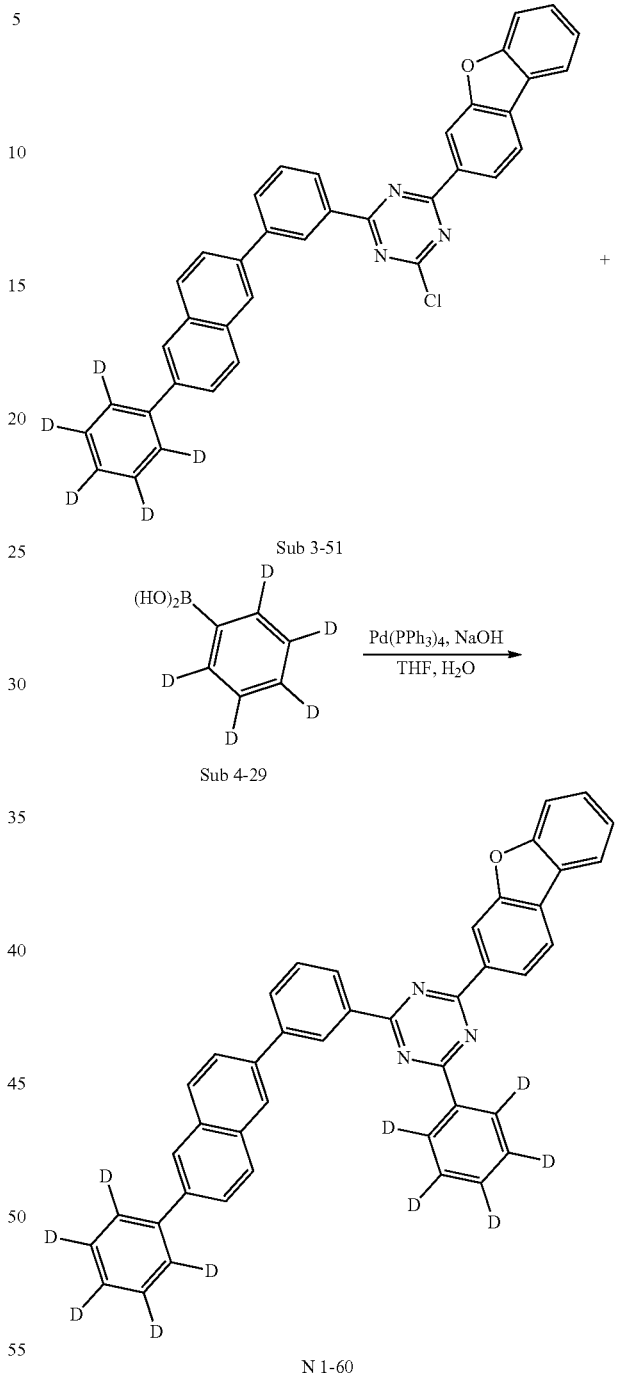

After putting Sub 3-48 (50.0 g, 68.7 mmol) in a round bottom flask and dissolving in THF (343 ml), Sub 4-28 (19.7 g, 68.7 mmol), Pd(PPh$_3$)$_4$ (4.8 g, 4.1 mmol), NaOH (8.2 g, 206.0 mmol), Water (172 ml) were added and tested in the same manner as in Sub 3-1-2 to obtain 51.4 g of product. (Yield: 80.0%)

After putting Sub 3-51 (50.0 g, 88.5 mmol) in a round bottom flask and dissolving in THF (442 ml), Sub 4-29 (11.2 g, 88.5 mmol), Pd(PPh$_3$)$_4$ (6.1 g, 5.3 mmol), NaOH (10.6 g, 265.4 mmol), Water (221 ml) were added and tested in the same manner as in Sub 3-1-2 to obtain 45.5 g of product. (Yield: 84.1%)

8. Synthesis Example of N 1-74

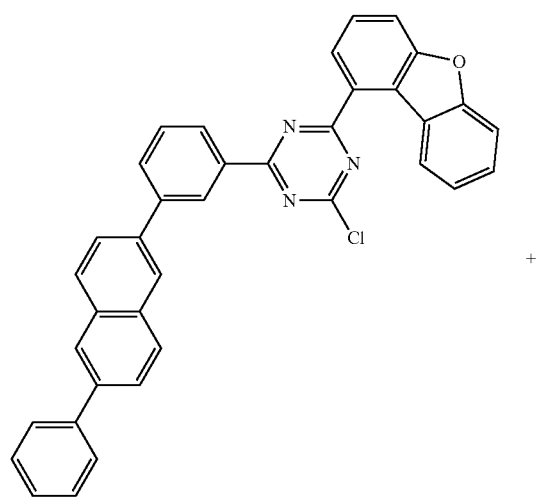
Sub 3-64

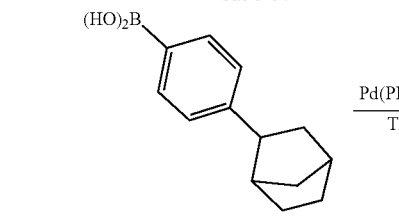
Sub 4-40

Pd(PPh₃)₄, NaOH
THF, H₂O

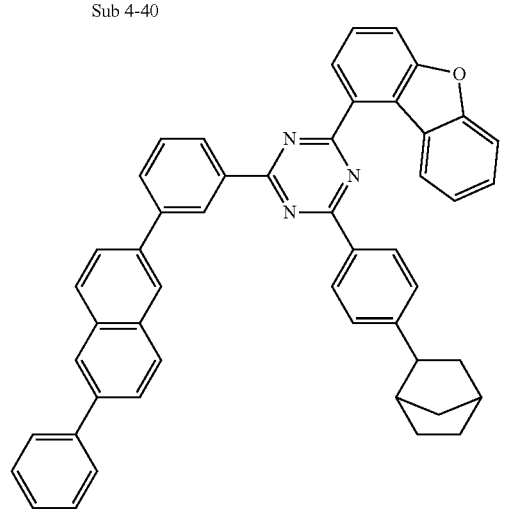
N 1-74

After putting Sub 3-64 (50.0 g, 89.3 mmol) in a round bottom flask and dissolving in THF (446 ml), Sub 4-40 (19.3 g, 89.3 mmol), Pd(PPh₃)₄ (6.2 g, 5.4 mmol), NaOH (10.7 g, 267.8 mmol), Water (223 ml) were added and tested in the same manner as in Sub 3-1-2 to obtain 51.8 g of product. (Yield: 83.4%)

9. Synthesis Example of N 1-78

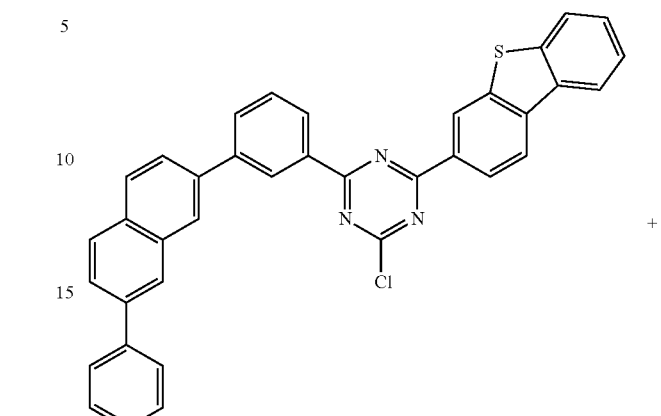
Sub 3-9

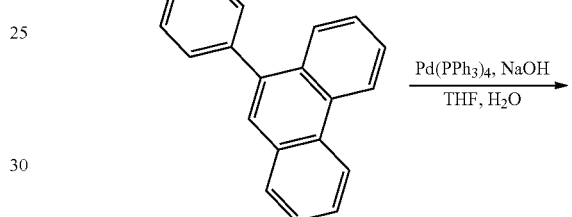
Sub 4-24

Pd(PPh₃)₄, NaOH
THF, H₂O

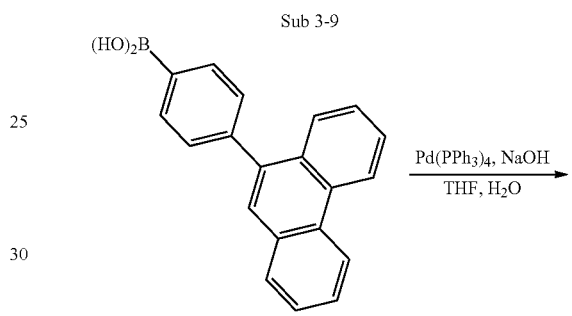
N 1-78

After putting Sub 3-9 (50.0 g, 86.8 mmol) in a round bottom flask and dissolving in THF (434 ml), Sub 4-24 (25.9 g, 86.8 mmol), Pd(PPh₃)₄ (6.0 g, 5.2 mmol), NaOH (10.4 g, 260.4 mmol), Water (217 ml) were added and tested in the same manner as in Sub 3-1-2 to obtain 55.5 g of product. (Yield: 80.5%)

Table 7 shows the FD-MS (Field Desorption-Mass Spectrometry) values of the compounds N 1-1 to N 1-100 of the present invention prepared according to the Synthesis Example as described.

TABLE 7

| compound | FD-MS | compound | FD-MS |
| --- | --- | --- | --- |
| N 1-1 | m/z = 667.21($C_{47}H_{29}N_3S$ = 667.83) | N 1-2 | m/z = 667.21($C_{47}H_{29}N_3S$ = 667.83) |
| N 1-3 | m/z = 693.22($C_{49}H_{31}N_3S$ = 693.87) | N 1-4 | m/z = 617.19($C_{43}H_{27}N_3S$ = 617.77) |
| N 1-5 | m/z = 601.22($C_{43}H_{27}N_3O$ = 601.71) | N 1-6 | m/z = 601.22($C_{43}H_{27}N_3O$ = 601.71) |
| N 1-7 | m/z = 651.23($C_{47}H_{29}N_3O$ = 651.77) | N 1-8 | m/z = 651.23($C_{47}H_{29}N_3O$ = 651.77) |
| N 1-9 | m/z = 667.21($C_{47}H_{29}N_3S$ = 667.83) | N 1-10 | m/z = 717.22($C_{51}H_{31}N_3S$ = 717.89) |
| N 1-11 | m/z = 793.26($C_{57}H_{35}N_3S$ = 793.99) | N 1-12 | m/z = 693.22($C_{49}H_{31}N_3S$ = 693.87) |
| N 1-13 | m/z = 717.28($C_{52}H_{35}N_3O$ = 717.87) | N 1-14 | m/z = 701.25($C_{51}H_{31}N_3O$ = 701.83) |
| N 1-15 | m/z = 791.26($C_{57}H_{33}N_3O_2$ = 791.91) | N 1-16 | m/z = 677.25($C_{49}H_{31}N_3O$ = 677.81) |
| N 1-17 | m/z = 769.26($C_{55}H_{35}N_3S$ = 769.97) | N 1-18 | m/z = 693.22($C_{49}H_{31}N_3S$ = 693.87) |
| N 1-19 | m/z = 845.29($C_{61}H_{39}N_3S$ = 846.06) | N 1-20 | m/z = 717.22($C_{51}H_{31}N_3S$ = 717.89) |
| N 1-21 | m/z = 601.22($C_{43}H_{27}N_3O$ = 601.71) | N 1-22 | m/z = 677.25($C_{49}H_{31}N_3O$ = 677.81) |
| N 1-23 | m/z = 677.25($C_{49}H_{31}N_3O$ = 677.81) | N 1-24 | m/z = 677.25($C_{49}H_{31}N_3O$ = 677.81) |
| N 1-25 | m/z = 617.19($C_{43}H_{27}N_3S$ = 617.77) | N 1-26 | m/z = 667.21($C_{47}H_{29}N_3S$ = 667.83) |
| N 1-27 | m/z = 743.24($C_{53}H_{33}N_3S$ = 743.93) | N 1-28 | m/z = 769.26($C_{55}H_{35}N_2S$ = 769.97) |
| N 1-29 | m/z = 651.23($C_{47}H_{29}N_3O$ = 651.77) | N 1-30 | m/z = 701.25($C_{51}H_{31}N_3O$ = 701.83) |
| N 1-31 | m/z = 803.29($C_{59}H_{37}N_3O$ = 803.97) | N 1-32 | m/z = 803.29($C_{59}H_{37}N_3O$ = 803.97) |
| N 1-33 | m/z = 667.21($C_{47}H_{29}N_3S$ = 667.83) | N 1-34 | m/z = 717.22($C_{51}H_{31}N_3S$ = 717.89) |
| N 1-35 | m/z = 793.26($C_{57}H_{35}N_3S$ = 793.99) | N 1-36 | m/z = 793.26($C_{57}H_{35}N_3S$ = 793.99) |
| N 1-37 | m/z = 777.28($C_{57}H_{35}N_3O$ = 777.93) | N 1-38 | m/z = 777.28($C_{57}H_{35}N_3O$ = 777.93) |
| N 1-39 | m/z = 879.32($C_{65}H_{41}N_3O$ = 880.06) | N 1-40 | m/z = 777.28($C_{57}H_{35}N_3O$ = 777.93) |
| N 1-41 | m/z = 767.24($C_{55}H_{33}N_3S$ = 767.95) | N 1-42 | m/z = 869.29($C_{63}H_{39}N_3S$ = 870.09) |
| N 1-43 | m/z = 843.27($C_{61}H_{37}N_3S$ = 844.05) | N 1-44 | m/z = 767.24($C_{55}H_{33}N_3S$ = 767.95) |
| N 1-45 | m/z = 701.25($C_{51}H_{31}N_3O$ = 701.83) | N 1-46 | m/z = 601.22($C_{43}H_{27}N_3O$ = 601.71) |
| N 1-47 | m/z = 651.23($C_{47}H_{29}N_3O$ = 651.77) | N 1-48 | m/z = 601.22($C_{43}H_{27}N_3O$ = 601.71) |
| N 1-49 | m/z = 727.26($C_{53}H_{33}N_3O$ = 727.87) | N 1-50 | m/z = 701.25($C_{51}H_{31}N_3O$ = 701.83) |
| N 1-51 | m/z = 727.26($C_{53}H_{33}N_3O$ = 727.87) | N 1-52 | m/z = 751.26($C_{55}H_{33}N_3O$ = 751.89) |
| N 1-53 | m/z = 793.26($C_{57}H_{35}N_3S$ = 793.99) | N 1-54 | m/z = 667.21($C_{47}H_{29}N_3S$ = 667.83) |
| N 1-55 | m/z = 959.33($C_{70}H_{45}N_3S$ = 960.21) | N 1-56 | m/z = 934.31($C_{67}H_{42}N_4S$ = 935.16) |
| N 1-57 | m/z = 606.25($C_{43}H_{22}D_5N_3O$ = 606.74) | N 1-58 | m/z = 606.25($C_{43}H_{22}D_5N_3O$ = 606.74) |
| N 1-59 | m/z = 655.26($C_{47}H_{25}D4N_3O$ = 655.79) | N 1-60 | m/z = 611.28($C_{43}H_{17}D_{10}N_3O$ = 611.77) |
| N 1-61 | m/z = 699.26($C_{49}H_{25}D_5N_3S$ = 699.90) | N 1-62 | m/z = 774.29($C_{55}H_{30}D_5N_3S$ = 775.00) |
| N 1-63 | m/z = 971.33($C_{71}H_{45}N_3S$ = 972.22) | N 1-64 | m/z = 895.30($C_{65}H_{41}N_3S$ = 896.12) |
| N 1-65 | m/z = 841.31($C_{62}H_{39}N_3O$ = 842.01) | N 1-66 | m/z = 691.23($C_{49}H_{29}N_3O_2$ = 691.79) |
| N 1-67 | m/z = 766.27($C_{55}H_{34}N_4O$ = 766.90) | N 1-68 | m/z = 843.29($C_{61}H_{37}N_3O_2$ = 843.99) |
| N 1-69 | m/z = 809.29($C_{58}H_{39}NS$ = 810.03) | N 1-70 | m/z = 847.30($C_{61}H_{41}N_3S$ = 848.08) |
| N 1-71 | m/z = 735.23($C_{51}H_{33}N_3OS$ = 735.90) | N 1-72 | m/z = 875.24($C_{61}H_{37}N_3S_2$ = 876.11) |
| N 1-73 | m/z = 735.32($C_{53}H_{41}N_3O$ = 735.93) | N 1-74 | m/z = 695.29($C_{50}H_{37}N_3O$ = 695.87) |
| N 1-75 | m/z = 767.39($C_{55}H_{49}N_3O$ = 768.02) | N 1-76 | m/z = 885.37($C_{65}H_{47}N_3O$ = 886.11) |
| N 1-77 | m/z = 763.30($C_{54}H_{41}N_3S$ = 764.00) | N 1-78 | m/z = 793.26($C_{57}H_{35}N_3S$ = 793.99) |
| N 1-79 | m/z = 722.26($C_{51}H_{26}D_5N_3S$ = 722.92) | N 1-80 | m/z = 743.24($C_{53}H_{33}N_3S$ = 743.93) |
| N 1-81 | m/z = 727.26($C_{53}H_{33}N_3O$ = 727.87) | N 1-82 | m/z = 757.22($C_{53}H_{31}N_3OS$ = 757.91) |
| N 1-83 | m/z = 791.26($C_{57}H_{33}N_3O_2$ = 791.91) | N 1-84 | m/z = 767.29($C_{56}H_{37}N_3O$ = 767.93) |
| N 1-85 | m/z = 767.24($C_{55}H_{33}N_3S$ = 767.95) | N 1-86 | m/z = 783.23($C_{55}H_{33}N_3OS$ = 783.95) |
| N 1-87 | m/z = 9O8.3O($C_{65}H_{40}N_4S$ = 9O9.12) | N 1-88 | m/z = 805.35($C_{57}H_{47}N_3S$ = 806.08) |
| N 1-89 | m/z = 829.31($C_{61}H_{39}N_3O$ = 830.00) | N 1-90 | m/z = 803.29($C_{59}H_{37}N_3O$ = 803.97) |
| N 1-91 | m/z = 803.29($C_{59}H_{37}N_3O$ = 803.97) | N 1-92 | m/z = 827.29($C_{61}H_{37}N_3O$ = 827.99) |
| N 1-93 | m/z = 799.30($C_{57}H_{41}N_3S$ = 800.04) | N 1-94 | m/z = 895.30($C_{65}H_{41}N_3S$ = 896.12) |
| N 1-95 | m/z = 693.22($C_{49}H_{31}N_3S$ = 693.87) | N 1-96 | m/z = 804.47($C_{55}H_{35}N_3S$ = 805.18) |
| N 1-97 | m/z = 691.23($C_{49}H_{29}N_3O_2$ = 691.79) | N 1-98 | m/z = 677.25($C_{49}H_{31}N_3O$ = 677.81) |
| N 1-99 | m/z = 799.30($C_{57}H_{41}N_3S$ = 800.04) | N 1-100 | m/z = 808.33($C_{59}D_{32}N_3O$ = 809.00) |

[Synthesis Example 3] A Compound Represented by Formula 4 or Formula 5

1. Synthesis Example of H-12

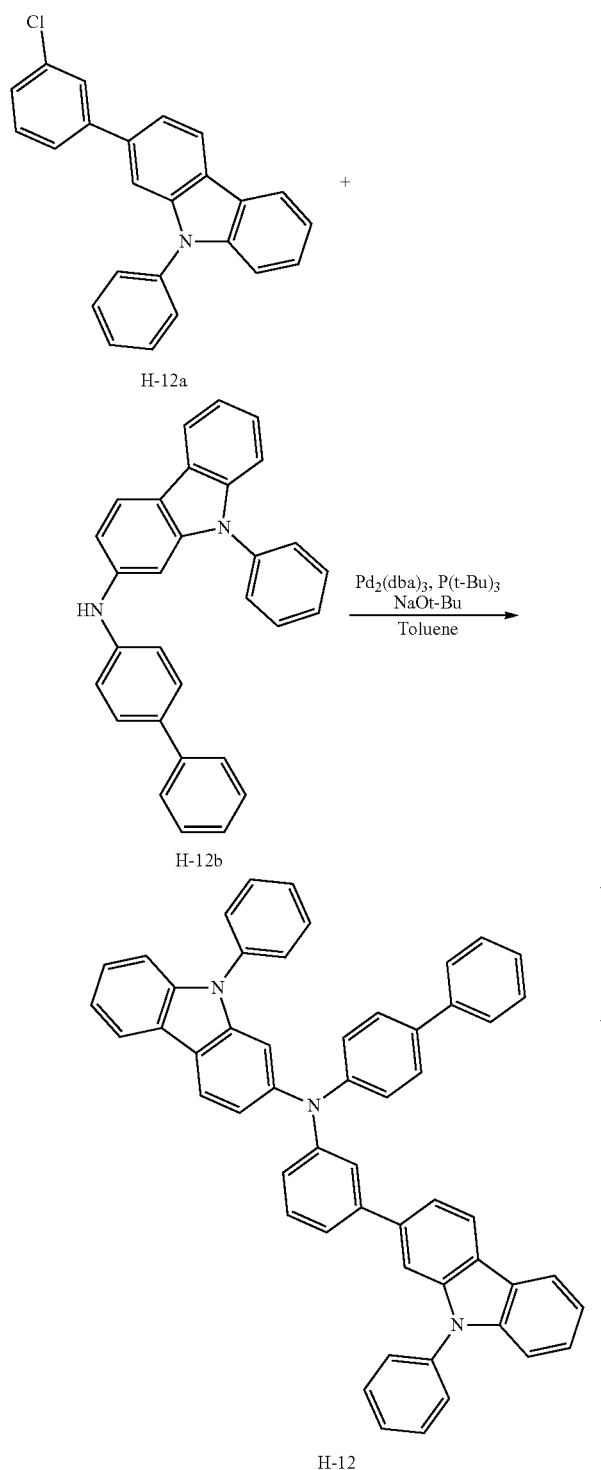

2. Synthesis Example of H-19

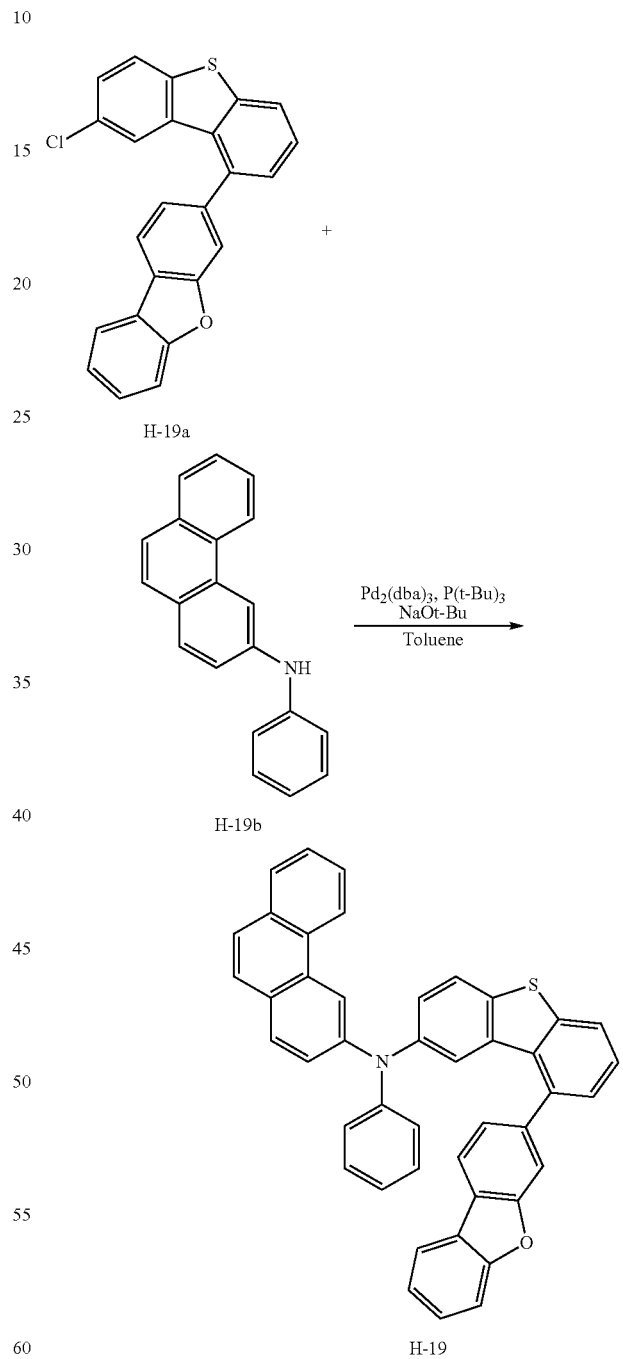

C. for 6 hours. When the reaction was completed, the reactant was extracted with $CH_2Cl_2$ and water, and the organic layer was dried over $MgSO_4$, concentrated, and the resulting compound was recrystallized using a silicagel column to obtain 53 g of the product. (Yield: 85.8%)

After dissolving H-12a (30 g, 0.08 mol) in Toluene (170 mL) in a round bottom flask, H-12b (34.8 g, 0.08 mol), $Pd_2(dba)_3$ (2.3 g, 0.003 mol), NaOt-Bu (24.5 g, 0.25 mol), P(t-Bu)$_3$ (2.1 g, 0.005 mol) were added and stirred at 135°

H-19a (50 g, 0.13 mol), H-19b (35 g, 0.13 mol), $Pd_2(dba)_3$ (3.6 g, 0.004 mol), NaOt-Bu (37.6 g, 0.40 mol), P(t-Bu)$_3$ (3.2 g, 0.008 mol), Toluene (260 mL) were added to a round bottom flask in the same manner as in H-12 to obtain 67 g of product. (Yield: 83.4%)

3. Synthesis Example of S-32

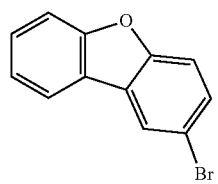

S-32a

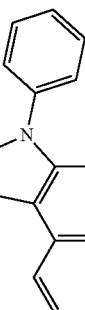

S-32b

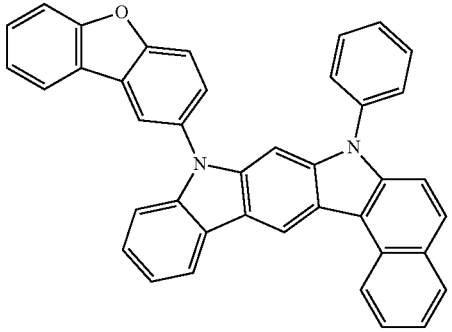

S-32

S-32a (10 g, 0.04 mol), S-32b (15.6 g, 0.04 mol), Pd$_2$(dba)$_3$ (1.1 g, 0.001 mol), NaOt-Bu (11.7 g, 0.12 mol), P(t-Bu)$_3$ (1.0 g, 0.002 mol), Toluene (80 mL) were added to a round bottom flask in the same manner as in H-12 to obtain 18 g of product. (Yield: 80.8%)

4. Synthesis Example of S-74

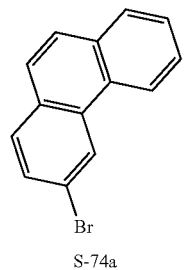

S-74a

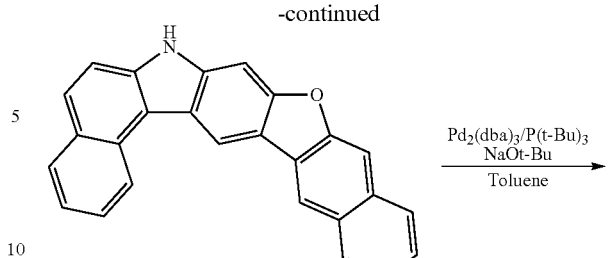

S-74b

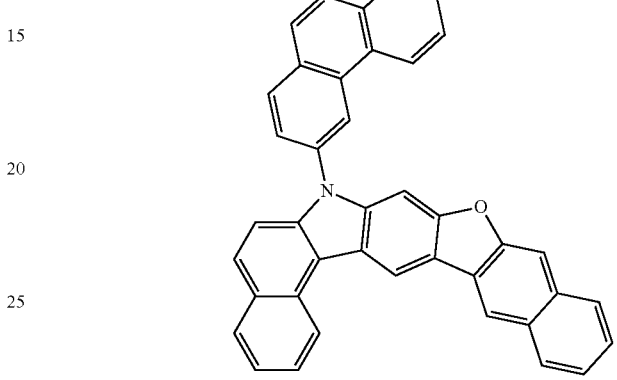

S-74

S-74a (15 g, 0.06 mol), S-74b (20.9 g, 0.06 mol), Pd$_2$(dba)$_3$ (1.6 g, 0.002 mol), NaOt-Bu (16.9 g, 0.18 mol), P(t-Bu)$_3$ (1.4 g, 0.004 mol), Toluene (120 mL) were tested in the same manner as in H-12 to obtain 27 g of product. (Yield: 86.4%)

5. Synthesis Example of S-104

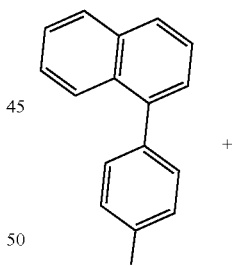

S-104a

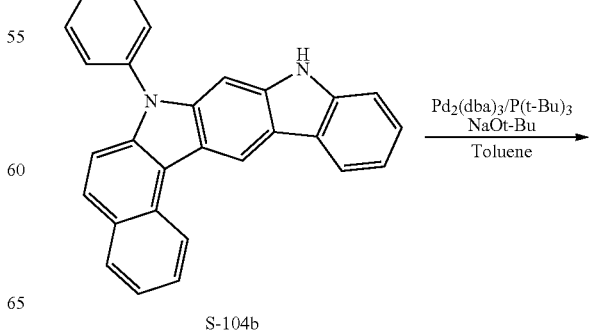

S-104b

-continued

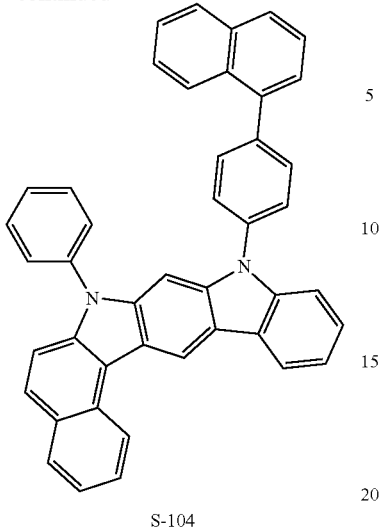

S-104

S-104a (30 g, 0.13 mol), S-104b (48.2.9 g, 0.13 mol), Pd$_2$(dba)$_3$ (3.5 g, 0.004 mol), NaOt-Bu (36.4 g, 0.38 mol), P(t-Bu)$_3$ (3.1 g, 0.008 mol), Toluene (120 mL) were tested in the same manner as in H-12 to obtain 60 g of product. (Yield: 81.5%)

Otherwise, the FD-MS values of the compounds H-1 to H-100 and S-1 to S-108 of the present invention prepared according to the synthesis examples as described above are shown in Tables 8 and 9.

TABLE 8

| compound | FD-MS | compound | FD-MS |
|---|---|---|---|
| H-1 | m/z = 487.19(C$_{36}$H$_{25}$NO = 487.6) | H-2 | m/z = 553.19(C$_{40}$H$_{27}$NS = 553.72) |
| H-3 | m/z = 563.26(C$_{43}$H$_{33}$N = 563.74) | H-4 | m/z = 602.27(C$_{45}$H$_{34}$N$_2$ = 602.78) |
| H-5 | m/z = 517.15(C$_{36}$H$_{23}$NOS = 517.65) | H-6 | m/z = 603.2(C$_{44}$H$_{29}$NS = 603.78) |
| H-7 | m/z = 735.29(C$_{57}$H$_{37}$N = 735.93) | H-8 | m/z = 562.24(C$_{42}$H$_{30}$N$_2$ = 562.72) |
| H-9 | m/z = 565.17(C$_{40}$H$_{23}$NO$_3$ = 565.63) | H-10 | m/z = 581.14(C$_{42}$H$_{23}$NO$_2$S = 581.69) |
| H-11 | m/z = 823.24(C$_{59}$H$_{37}$NS$_2$ = 824.07) | H-12 | m/z = 727.3(C$_{54}$H$_{37}$N$_3$ = 727.91) |
| H-13 | m/z = 627.22(C$_{46}$H$_{29}$NO$_2$ = 627.74) | H-14 | m/z = 633.16(C$_{44}$H$_{27}$NS$_2$ = 633.83) |
| H-15 | m/z = 675.29(C$_{52}$H$_{37}$N = 675.88) | H-16 | m/z = 678.3(C$_{51}$H$_{38}$N$_2$ = 678.88) |
| H-17 | m/z = 669.21(C$_{48}$H$_{31}$NOS = 669.84) | H-18 | m/z = 785.22(C$_{56}$H$_{35}$NS$_2$ = 786.02) |
| H-19 | m/z = 617.18(C$_{44}$H$_{27}$NOS = 617.77) | H-20 | m/z = 601.2(C$_{44}$H$_{27}$NO$_2$ = 601.71) |
| H-21 | m/z = 779.32(C$_{59}$H$_{41}$NO = 779.98) | H-22 | m/z = 583.23(C$_{42}$H$_{33}$NS = 583.79) |
| H-23 | m/z = 679.32(C$_{52}$H$_{41}$N = 679.91) | H-24 | m/z = 726.27(C$_{54}$H$_{34}$N$_2$O = 726.88) |
| H-25 | m/z = 593.18(C$_{42}$H$_{27}$NOS = 593.74) | H-26 | m/z = 774.22(C$_{54}$H$_{34}$N$_2$S$_2$ = 775) |
| H-27 | m/z = 557.24(C$_{40}$H$_{31}$NO$_2$ = 557.69) | H-28 | m/z = 652.25(C$_{48}$H$_{32}$N$_2$O = 652.8) |
| H-29 | m/z = 619.29(C$_{46}$H$_{37}$NO = 619.81) | H-30 | m/z = 603.2(C$_{44}$H$_{29}$NS = 603.78) |
| H-31 | m/z = 813.3(C6$_2$H$_{39}$NO = 814) | H-32 | m/z = 784.29(C$_{57}$H$_{40}$N$_2$S = 785.02) |
| H-33 | m/z = 577.2(C$_{42}$H$_{27}$NO$_2$ = 577.68) | H-34 | m/z = 607.14(C$_{42}$H$_{25}$NS$_2$ = 607.79) |
| H-35 | m/z = 801.34(C6$_2$H$_{43}$N = 802.03) | H-36 | m/z = 575.24(C$_{42}$H$_{29}$N$_3$ = 575.72) |
| H-37 | m/z = 577.2(C$_{42}$H$_{27}$NO$_2$ = 577.68) | H-38 | m/z = 607.14(C$_{42}$H$_{25}$NS$_2$ = 607.79) |
| H-39 | m/z = 801.34(C6$_2$H$_{43}$N = 802.03) | H-40 | m/z = 575.24(C$_{42}$H$_{29}$N$_3$ = 575.72) |
| H-41 | m/z = 601.2(C$_{44}$H$_{27}$NO$_2$ = 601.71) | H-42 | m/z = 471.11(C$_{31}$H$_{21}$NS$_2$ = 471.64) |
| H-43 | m/z = 675.29(C$_{52}$H$_{37}$N = 675.88) | H-44 | m/z = 727.3(C$_{54}$H$_{37}$N$_3$ = 727.91) |
| H-45 | m/z = 603.2(C$_{44}$H$_{29}$NS = 603.78) | H-46 | m/z = 561.16(C$_{38}$H$_{27}$NS$_2$ = 561.76) |
| H-47 | m/z = 799.32(C6$_2$H$_{41}$N = 800.02) | H-48 | m/z = 702.27(C$_{52}$H$_{34}$N$_2$O = 702.86) |
| H-49 | m/z = 729.27(C$_{54}$H$_{35}$NO$_2$ = 729.88) | H-50 | m/z = 785.22(C$_{56}$H$_{35}$NS$_2$ = 786.02) |
| H-51 | m/z = 812.32(C6$_2$H$_{40}$N$_2$ = 813.02) | H-52 | m/z = 681.22(C$_{48}$H$_{31}$N$_3$S = 681.86) |
| H-53 | m/z = 615.18(C$_{44}$H$_{25}$NO$_3$ = 615.69) | H-54 | m/z = 763.15(C$_{52}$H$_{29}$NS$_3$ = 763.99) |
| H-55 | m/z = 593.31(C$_{45}$H$_{39}$N = 593.81) | H-56 | m/z = 840.33(C6$_2$H$_{40}$N$_4$ = 841.03) |
| H-57 | m/z = 657.18(C$_{46}$H$_{27}$NO$_2$S = 657.79) | H-58 | m/z = 824.23(C$_{58}$H$_{36}$N$_2$S$_2$ = 825.06) |
| H-59 | m/z = 1195.42(C$_{91}$H$_{57}$NS = 1196.52) | H-60 | m/z = 656.19(C$_{46}$H$_{28}$N$_2$OS = 656.8) |
| H-61 | m/z = 607.16(C$_{42}$H$_{25}$NO$_2$S = 607.73) | H-62 | m/z = 773.2(C$_{54}$H$_{31}$NO$_3$S = 773.91) |
| H-63 | m/z = 1013.4(C$_{79}$H$_{51}$N = 1014.28) | H-64 | m/z = 758.24(C$_{54}$H$_{34}$N$_2$OS = 758.94) |
| H-65 | m/z = 623.14(C$_{42}$H$_{25}$NOS$_2$ = 623.79) | H-66 | m/z = 763.16(C$_{52}$H$_{29}$NO$_2$S$_2$ = 763.93) |
| H-67 | m/z = 799.2(C$_{56}$H$_{33}$NOS$_2$ = 800.01) | H-68 | m/z = 743.23(C$_{54}$H$_{33}$NOS = 743.92) |
| H-69 | m/z = 872.25(C6$_2$H$_{36}$NO$_2$S = 873.04) | H-70 | m/z = 772.22(C$_{54}$H$_{32}$N$_2$O$_2$S = 772.92) |
| H-71 | m/z = 830.28(C$_{61}$H$_{38}$N$_2$S = 831.05) | H-72 | m/z = 808.25(C$_{58}$H$_{33}$FN$_2$O$_2$ = 808.91) |
| H-73 | m/z = 929.21(C$_{64}$H$_{35}$NO$_3$S$_2$ = 930.11) | H-74 | m/z = 963.27(C$_{68}$H$_{41}$N$_3$S$_2$ = 964.22) |
| H-75 | m/z = 809.24(C$_{58}$H$_{35}$NO$_2$S = 809.98) | H-76 | m/z = 893.29(C$_{66}$H$_{39}$NO$_3$ = 894.04) |
| H-77 | m/z = 794.28(C$_{58}$H$_{38}$N$_2$S = 795.02) | H-78 | m/z = 900.26(C$_{64}$H$_{40}$N$_2$S$_2$ = 901.16) |

TABLE 8-continued

| compound | FD-MS | compound | FD-MS |
| --- | --- | --- | --- |
| H-79 | m/z = 758.28($C_{55}H_{38}N_2S$ = 758.98) | H-80 | m/z = 1082.37($C_{81}H_{50}N_2S$ = 1083.37) |
| H-81 | m/z = 573.25($C_{44}H_{31}N$ = 573.74) | H-82 | m/z = 649.28($C_{50}H_{35}N$ = 649.84) |
| H-83 | m/z = 699.29($C_{54}H_{37}N$ = 699.9) | H-84 | m/z = 699.29($C_{54}H_{37}N$ = 699.9) |
| H-85 | m/z = 673.28($C_{52}H_{35}N$ = 673.86) | H-86 | m/z = 649.28($C_{50}H_{35}N$ = 649.84) |
| H-87 | m/z = 625.28($C_{48}H_{35}N$ = 625.82) | H-88 | m/z = 673.28($C_{52}H_{35}N$ = 673.86) |
| H-89 | m/z = 773.31($C_{60}H_{39}N$ = 773.98) | H-90 | m/z = 749.31($C_{58}H_{39}N$ = 749.96) |
| H-91 | m/z = 699.29($C_{54}H_{37}N$ = 699.9) | H-92 | m/z = 599.26($C_{45}H_{33}N$ = 599.78) |
| H-93 | m/z = 639.26($C_{48}H_{33}NO$ = 639.8) | H-94 | m/z = 765.25($C_{57}H_{35}NS$ = 765.97) |
| H-95 | m/z = 677.31($C_{52}H_{39}N$ = 677.89) | H-96 | m/z = 727.3($C_{54}H_{37}N_3$ = 727.91) |
| H-97 | m/z = 552.18($C_{39}H_{24}N_2O_2$ = 552.63) | H-98 | m/z = 628.22($C_{45}H_{28}N_2O_2$ = 628.73) |
| H-99 | m/z = 614.24($C_{45}H_{30}N_2O$ = 614.75) | H-100 | m/z = 614.24($C_{45}H_{30}N_2O$ = 614.75) |

TABLE 9

| compound | FD-MS | compound | FD-MS |
| --- | --- | --- | --- |
| S-1 | m/z = 408.16($C_{30}H_{20}N_2$ = 408.5) | S-2 | m/z = 534.21($C_{40}H_{26}N_2$ = 534.66) |
| S-3 | m/z = 560.23($C_{42}H_{28}N_2$ = 560.7) | S-4 | m/z = 584.23($C_{44}H_{28}N_2$ = 584.72) |
| S-5 | m/z = 560.23($C_{42}H_{28}N_2$ = 560.7) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.2($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.2($C_{46}H_{28}N_2S$ = 640.8) | S-14 | m/z = 560.23($C_{42}H_{28}N_2$ = 560.7) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.7) | S-18 | m/z = 564.17($C_{40}H_{24}N_2S$ = 564.71) |
| S-19 | m/z = 574.2($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.2($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.2($C_{46}H_{29}NS$ = 627.81) | S-38 | m/z = 505.1($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.2($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.2($C_{36}H_{25}N$ = 471.6) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |

Otherwise, the synthesis examples of the present invention represented by the Formulas 2 to 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh$_3$-mediated reductive cyclization reaction (*J. Org. Chem.* 2005, 70, 5014.), and It will be easily understood by those skilled in the art that the reaction proceeds even when other substituents defined in Formulas 2 to 5 are bonded in addition to the substituents specified in the specific synthesis examples.

Manufacturing Evaluation of Organic Electronic Elements

[Example 31] Red Organic Light Emitting Device (Phosphorescent Host)

After vacuum depositing N$^1$-(naphthalen-2-yl)-N$^4$,N$^4$-bis(4-(naphthalen-2-yl(phenyl)amino)phenyl)-N$^1$-phenylbenzene-1,4-diamine (hereinafter abbreviated as 2-TNATA) on the ITO layer (anode) formed on the glass substrate to form a hole injection layer with a thickness of 60 nm, a hole transport layer was formed by vacuum depositing N,N'-bis(1-naphthalenyl)-N,N'-bis-phenyl-(1,1'-biphenyl)-4,4'-diamine (hereinafter abbreviated as NPB) to a thickness of 60 nm on the hole injection layer.

Subsequently, tris(4-(9H-carbazol-9-yl)phenyl)amine (hereinafter abbreviated as TCTA) was vacuum-deposited to a thickness of 10 nm on the hole transport layer to form an emitting-auxiliary layer. Then, the host of the emitting layer uses N 1-1, the compound of the present invention as a first host and H-17, the compound of the present invention as a second host, but a mixture obtained by mixing the first host and the second host in a weight ratio of 5:5 is used, and bis-(1-phenylisoquinolypiridium(111)acetylacetonate (hereinafter abbreviated as '(piq)$_2$Ir(acac)') was used as a dopant, but the dopant was doped so that the weight ratio of the host and the dopant was 95:5 to form an emitting layer having a thickness of 30 nm.

Next, (1,1'-biphenyl-4-olato)bis(2-methyl-8-quinolinolato)aluminum (hereinafter abbreviated as BAlq) was vacuum deposited on the emitting layer to form a hole blocking layer having a thickness of 10 nm, Tris(8-hydroxyquinolinato)aluminium (hereinafter abbreviated as Alq$_3$) was vacuum deposited on the hole blocking layer to a thickness of 40 nm to form an electron transport layer. Thereafter, 8-quinolinolato lithium (hereinafter abbreviated as Liq) was deposited on the electron transport layer to form an electron injection layer having a thickness of 0.2 nm, and then Al was deposited to form a cathode having a thickness of 150 nm.

[Example 32] to [Example 70]

An organic light emitting device was manufactured in the same manner as in Example 31, except that the compound of the present invention described in Table 10 was used as the host material of the emitting layer.

[Comparative Example 7] and [Comparative Example 8]

An organic light emitting device was manufactured in the same manner as in Example 31, except that Comparative Compound A or Comparative Compound B was used as the first host as the host material of the emitting layer.

[Comparative Compound A]

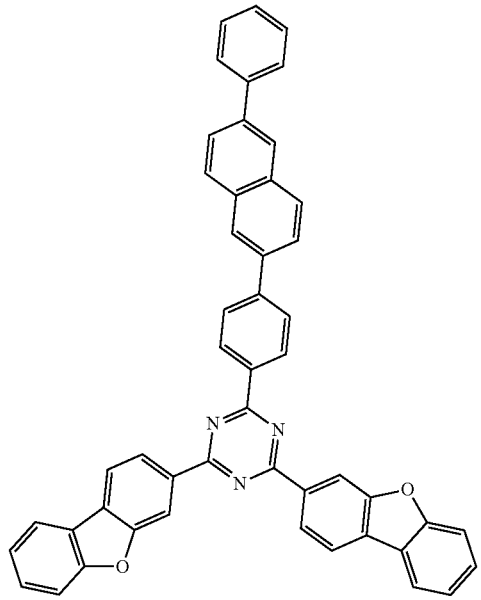

[Comparative Compound B]

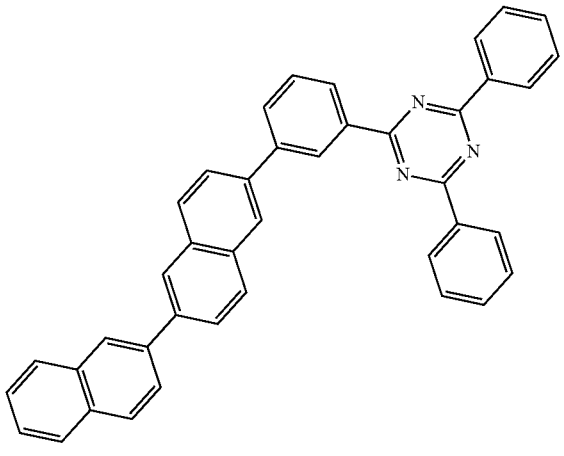

To the organic electroluminescent device manufactured by Examples 31 to 70, Comparative Examples 7 and 8 of the present invention, Electroluminescence (EL) characteristics were measured with a PR-650 of Photoresearch Co., by applying a forward bias DC voltage. As a result of the measurement, T95 life was measured at a standard luminance of 2,500 cd/m 2 through life measuring apparatus manufactured by McScience. Table 10 shows the results of device fabrication and evaluation.

This measuring device is independent form possible day-to-day variations of deposition rates, vacuum quality or other tool performance parameters, and allows assessing performance of new material in comparison with comparative compound under the same conditions.

At the time of assessment, each field contained 4 identically prepared OLEDs including a comparative compound, and since the performance of each of a total of 12 OLEDs in 3 fields is evaluated, the statistical evaluation of the obtained experimental results unequivocally showed the statistical significance.

TABLE 10

| | Frist host | Second host | Voltage | Current Density (mA/cm$^2$) | Brightness (cd/m$^2$) | Efficiency (cd/A) | T(95) |
|---|---|---|---|---|---|---|---|
| Comparative example7 | Comparative compound A | H-17 | 5.5 | 10.1 | 2500.0 | 24.7 | 107.7 |
| Comparative example8 | Comparative compound B | H-17 | 5.6 | 10.9 | 2500.0 | 23.0 | 104.5 |
| Example 31 | N 1-1 | H-17 | 5.0 | 8.3 | 2500.0 | 30.3 | 125.1 |
| Example 32 | N 1-6 | H-17 | 4.7 | 7.4 | 2500.0 | 33.7 | 128.7 |
| Example 33 | N 1-13 | H-17 | 4.9 | 8.9 | 2500.0 | 28.1 | 123.0 |
| Example 34 | N 1-22 | H-17 | 4.9 | 7.9 | 2500.0 | 31.8 | 126.8 |
| Example 35 | N 1-36 | H-17 | 5.1 | 8.8 | 2500.0 | 28.5 | 123.4 |
| Example 36 | N 1-47 | H-17 | 4.8 | 7.8 | 2500.0 | 32.2 | 120.3 |
| Example 37 | N 1-52 | H-17 | 5.0 | 8.2 | 2500.0 | 30.6 | 120.6 |
| Example 38 | N 1-53 | H-17 | 5.1 | 7.8 | 2500.0 | 31.9 | 125.3 |
| Example 39 | N 1-60 | H-17 | 4.8 | 7.4 | 2500.0 | 34.0 | 129.4 |
| Example 40 | N 1-63 | H-17 | 5.0 | 8.2 | 2500.0 | 30.6 | 120.7 |
| Example 41 | N 1-67 | H-17 | 4.8 | 8.8 | 2500.0 | 28.3 | 121.7 |
| Example 42 | N 1-73 | H-17 | 4.8 | 7.9 | 2500.0 | 31.7 | 124.6 |
| Example 43 | N 1-75 | H-17 | 4.9 | 8.4 | 2500.0 | 29.7 | 121.6 |
| Example 44 | N 1-97 | H-17 | 4.8 | 8.1 | 2500.0 | 30.9 | 123.1 |
| Example 45 | N 1-98 | H-17 | 5.1 | 8.4 | 2500.0 | 29.7 | 123.4 |
| Example 46 | N 1-1 | H-84 | 5.1 | 8.2 | 2500.0 | 30.4 | 120.5 |
| Example 47 | N 1-22 | H-84 | 5.0 | 8.1 | 2500.0 | 30.9 | 125.5 |
| Example 48 | N 1-52 | H-84 | 5.1 | 8.7 | 2500.0 | 28.6 | 120.7 |
| Example 49 | N 1-67 | H-84 | 4.9 | 8.3 | 2500.0 | 30.0 | 120.4 |
| Example 50 | N 1-75 | H-84 | 5.0 | 8.4 | 2500.0 | 29.6 | 121.6 |
| Example 51 | N 1-98 | H-84 | 5.2 | 7.8 | 2500.0 | 32.0 | 125.4 |
| Example 52 | N 1-6 | H-98 | 4.7 | 7.3 | 2500.0 | 34.3 | 130.7 |
| Example 53 | N 1-47 | H-98 | 4.8 | 8.9 | 2500.0 | 28.1 | 128.4 |
| Example 54 | N 1-53 | H-98 | 5.0 | 8.3 | 2500.0 | 30.1 | 127.6 |
| Example 55 | N 1-60 | H-98 | 4.9 | 7.2 | 2500.0 | 34.6 | 131.1 |
| Example 56 | N 1-67 | H-98 | 4.8 | 8.0 | 2500.0 | 31.2 | 126.1 |
| Example 57 | N 1-97 | H-98 | 4.9 | 8.6 | 2500.0 | 29.0 | 129.7 |
| Example 58 | N 1-13 | S-16 | 5.1 | 8.5 | 2500.0 | 29.4 | 135.8 |
| Example 59 | N 1-36 | S-16 | 5.3 | 8.0 | 2500.0 | 31.4 | 135.1 |
| Example 60 | N 1-60 | S-16 | 5.0 | 7.9 | 2500.0 | 31.8 | 136.5 |
| Example 61 | N 1-63 | S-16 | 5.2 | 8.1 | 2500.0 | 30.7 | 134.9 |
| Example 62 | N 1-75 | S-16 | 5.1 | 8.2 | 2500.0 | 30.5 | 138.2 |
| Example 63 | N 1-98 | S-16 | 5.1 | 8.6 | 2500.0 | 29.0 | 135.7 |
| Example 64 | N 1-6 | S-108 | 4.8 | 7.0 | 2500.0 | 35.7 | 140.9 |
| Example 65 | N 1-13 | S-108 | 5.0 | 8.8 | 2500.0 | 28.3 | 138.8 |
| Example 66 | N 1-47 | S-108 | 4.9 | 8.3 | 2500.0 | 30.2 | 140.3 |
| Example 67 | N 1-53 | S-108 | 5.2 | 8.6 | 2500.0 | 29.2 | 137.6 |
| Example 68 | N 1-60 | S-108 | 4.9 | 7.1 | 2500.0 | 35.1 | 141.2 |
| Example 69 | N 1-73 | S-108 | 4.9 | 8.0 | 2500.0 | 31.2 | 139.7 |
| Example 70 | N 1-97 | S-108 | 4.9 | 8.1 | 2500.0 | 30.9 | 138.5 |

As can be seen from the results of Table 10, when a red organic light emitting device is manufactured using the material for an organic light emitting device of the present invention as a host material of an emitting layer, it is possible to improve the driving voltage, luminous efficiency and lifespan of the organic light emitting device, compared to the comparative example using Comparative Compound A or Comparative Compound B having a similar basic skeleton to the compound of the present invention.

Comparative Compound A and Comparative Compound B are similar to the compounds of the present invention in that they are triazine compounds in which the group represented by the phenyl-naphthyl-aryl group in the molecule is substituted, but in the case of Comparative Compound A, it is different from the compound of the present invention in that the phenyl group between triazine and naphthyl forms a para bond, and in the case of Comparative compound B, it is different from the compound of the present invention in that all triazine substituents are aryl groups.

In order to confirm the Reorganization Energy (hereinafter abbreviated as RE) of a compound that changes due to such a structural difference, the data measured using the DFT method (B3LYP/6-31g(D)) of the Gaussian program of the compound N 1-97 of the present invention having high similarity to the comparative compound A are shown in Table 11.

TABLE 11

| compound | Reorganization Energy (RE) |
|---|---|
| N 1-97 | 0.187 |
| Comparative compound A | 0.232 |

As can be seen from the results of Table 11, it can be seen that the RE value of the compound N 1-97 of the present invention having high structural similarity with Comparative compound A is significantly different.

Due to this difference, the compound of the present invention having a low RE value has higher mobility and faster EOD than Comparative Compound A, so electron transfer and electron injection are remarkably improved, and as a result, the electron injection of the dopant is increased as the driving voltage is reduced and the emitting layer is enriched with electrons, so that the efficiency and lifespan are also significantly improved.

Table 12 shows the data measured using the DFT method (B3LYP/6-31g(D)) of the Gaussian program in order to confirm the energy level of the compound N 1-47 of the present invention, which has a high similarity to the Comparative Compound B.

TABLE 12

| compound | N 1-47 | Comparative compound B |
|---|---|---|
| LUMO(eV) | −1.784 | −1.671 |

From the results of Table 12, it can be seen that the energy levels of Comparative Compound B and Compound N 1-47 of the present invention are significantly different. More specifically, it is judged that as the LUMO level of the compound of the present invention is deeper than that of Comparative Compound B, injection of electrons from the electron transport region is performed more smoothly, and the performance of the element is also remarkably improved as the charge balance of the element is formed by increasing the formation of Exition in the emitting layer.

That is, as can be seen from the results of Tables 10 to 12, it can be confirmed that the compound of the present invention, which satisfies a specific configuration, exhibits a more significant effect in organic electronic elements than Comparative Compound A or Comparative Compound B, and that the compound of the present invention, which satisfies a specific structure, exhibits a significant effect compared to other comparative compounds not described herein.

These results suggests that even for compounds with similar molecular components, the properties of compounds such as hole properties, light efficiency properties, energy level, hole injection and mobility properties of molecules, Charge balance between holes and electrons, volume density and distance between molecules, etc. can vary significantly to the extent that it is difficult to predict, depending on the type and position of the substituent to be substituted, and also the performance of the device may vary due to complex factors, rather than one configuration affecting the overall result of the device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:
1. A compound represented by Formula 3-2 or Formula 3-3:

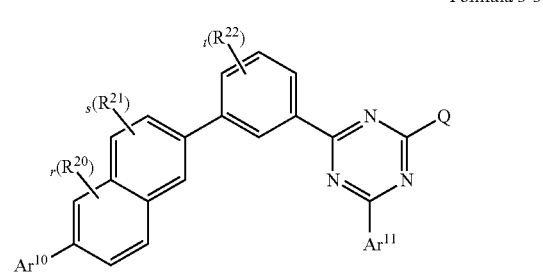

Formula 3-2

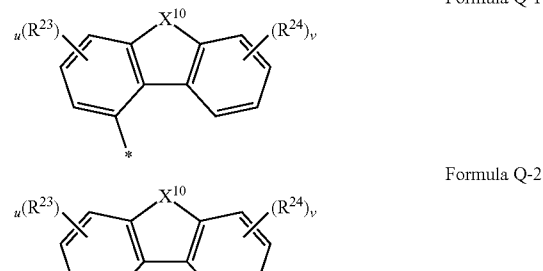

Formula 3-3

Formula Q-1

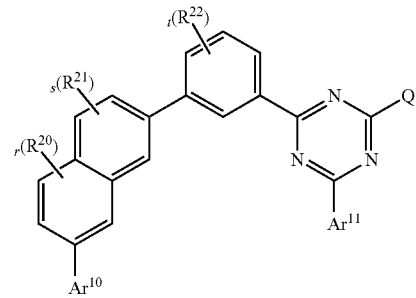

Formula Q-2 wherein:
1) Q is a substituent represented by Formula Q-1 or Formula Q-2,
2) $Ar^{10}$ is a $C_6$-$C_{60}$ aryl group,
3) $Ar^{11}$ is a $C_6$-$C_{60}$ aryl group; or a $C_2$-$C_{60}$ heterocyclic group including at least one heteroatom of O, N, S, Si or P,
4) $R^{20}$, $R^{21}$ and $R^{22}$ are the same or different, and each independently hydrogen; or deuterium,
5) $R^{23}$ and $R^{24}$ are the same or different, and each independently selected from the group consisting of hydrogen; deuterium; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or an adjacent plurality of $R^{23}$s or a plurality of $R^{24}$s may be bonded to each other to form a ring,
6) $X^{10}$ is O or S,
7) r, s and u are each independently an integer of 0 to 3, t and v are each independently an integer of 0 to 4,
8) * means a position for binding to Formula 3-2 or Formula 3-3, wherein the aryl group, heterocyclic group, fluorenyl group, aliphatic ring group, fused ring group, alkyl group, alkenyl group, alkynyl group, alkoxy group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring and a $C_6$-$C_{60}$ aromatic ring, or a $C_2$-$C_{60}$ heterocyclic group or a fused ring formed by the combination thereof.

2. The compound of claim 1, wherein $Ar^{10}$ and $Ar^{11}$ are represented by one of Formulas Ar-1 to Ar-7:

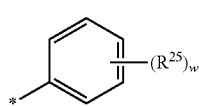

Formula Ar-1

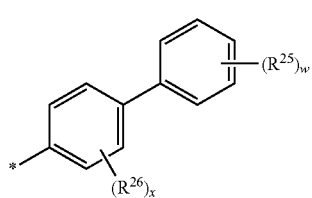

Formula Ar-2

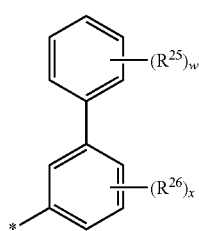

Formula Ar-3

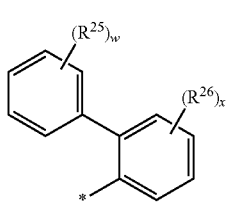

Formula Ar-4

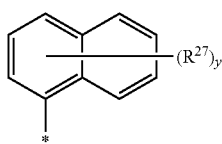

Formula Ar-5

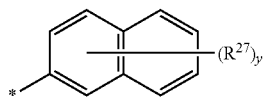

Formula Ar-6

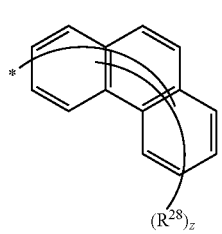

Formula Ar-7 wherein:
1) $R^{25}$, $R^{26}$, $R^{27}$ and $R^{28}$ are the same as the definition of $R^{23}$ in claim 1, or an adjacent plurality of $R^{25}$s, a plurality of $R^{26}$s, a plurality of $R^{27}$s, or a plurality of $R^{28}$s may be bonded to each other to form a ring,
2) W is an integer from 0 to 5, x is an integer from 0 to 4, y is an integer from 0 to 7, z is an integer from 0 to 9,
3) * means a moiety bonded to Formula 3-2 or Formula 3-3.

3. The compound of claim 1, wherein $Ar^{11}$ is represented by Formula Ar-8:

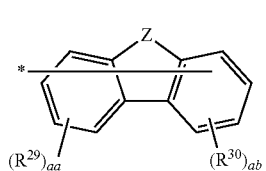

Formula Ar-8 wherein:
1) Z is O, S, $C(R^{31})(R^{32})$, $NR^{33}$ or N, wherein Z is N in the case where Z is combined with Formula 3-2 or Formula 3-3,
2) $R^{29}$, $R^{39}$, $R^{31}$, $R^{32}$ and $R^{33}$ are the same as definition of $R^{23}$ in claim 1, or an adjacent plurality of $R^{29}$s, a plurality of $R^{30}$s, a plurality of $R^{31}$s, a plurality of $R^{32}$s may be bonded to each other to form a ring,
3) Aa and ab are independently an integer of 0 to 4;
4) * means a moiety bonded to Formula 3-2 or Formula 3-3.

4. The compound of claim 1, wherein Formula 3-2 or Formula 3-3 is represented by any one of the following compounds:

N1-5
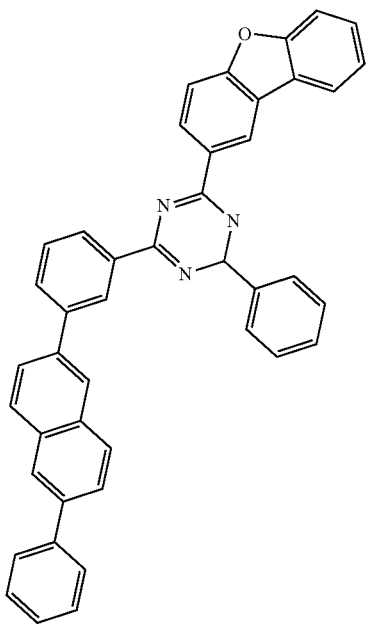
N1-10
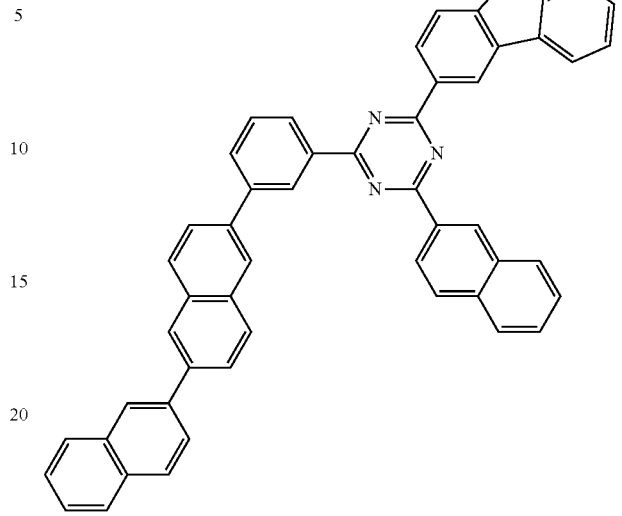
N1-13
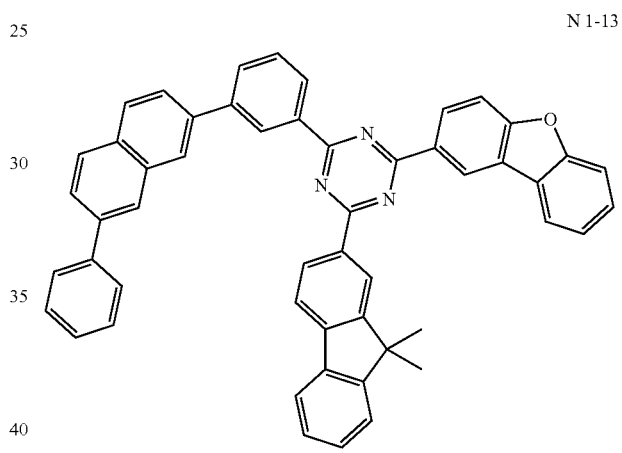
N1-8
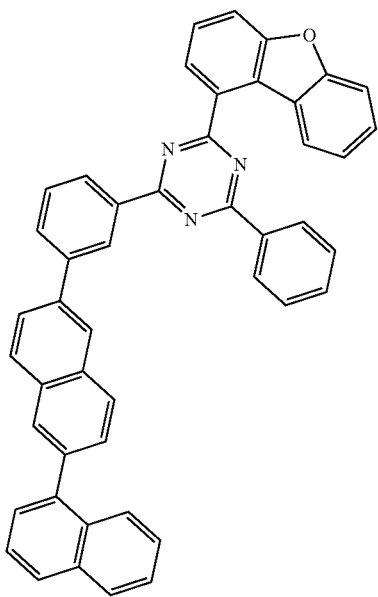
N1-14
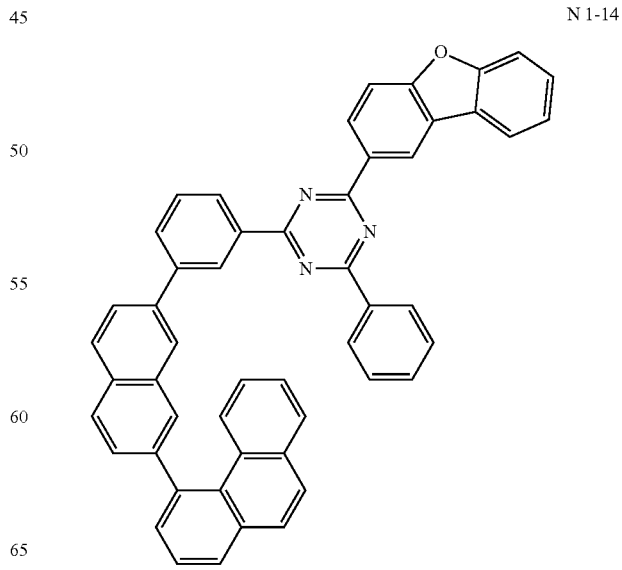

N 1-15
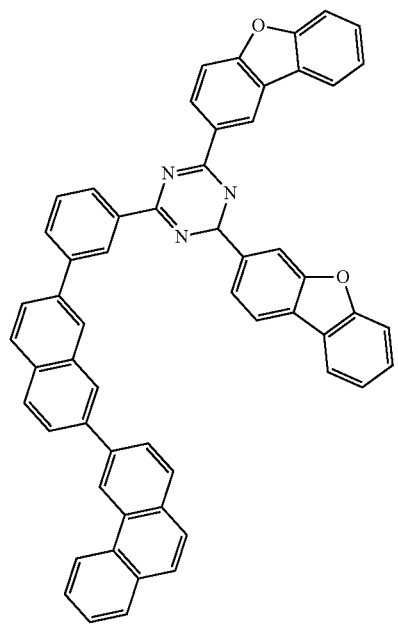
N 1-16
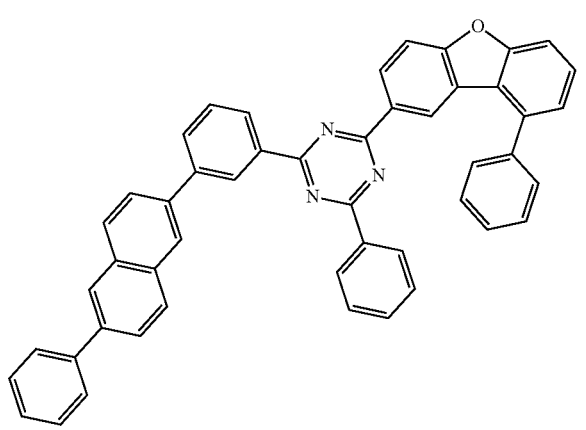
N 1-17
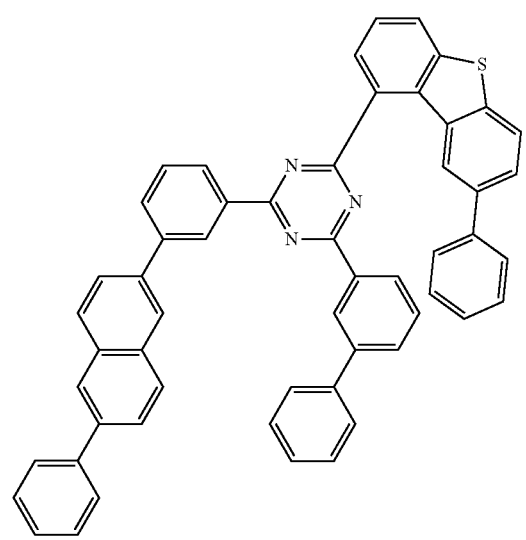
N 1-22
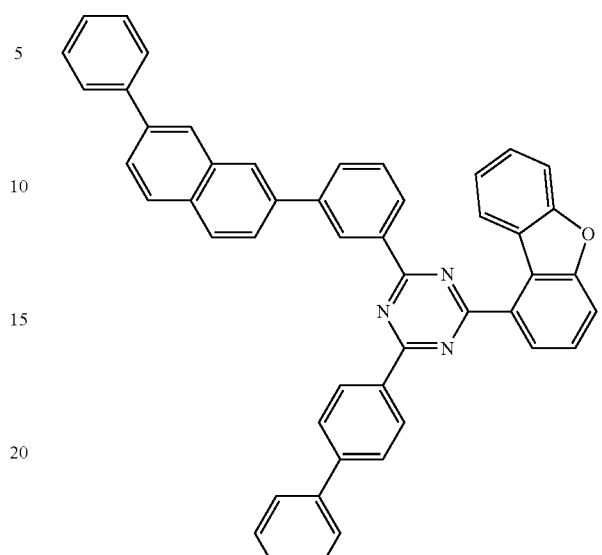
N 1-32
N 1-35
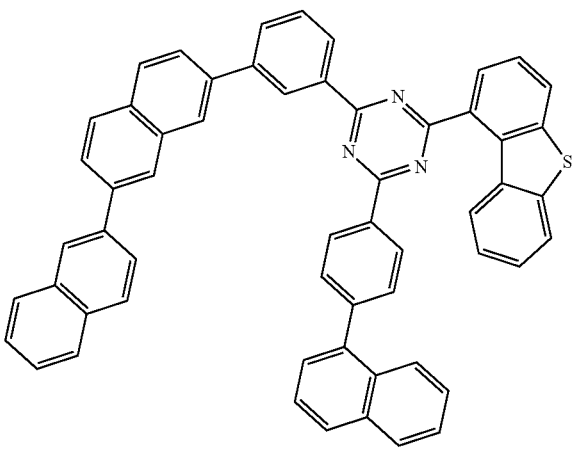

N1-37
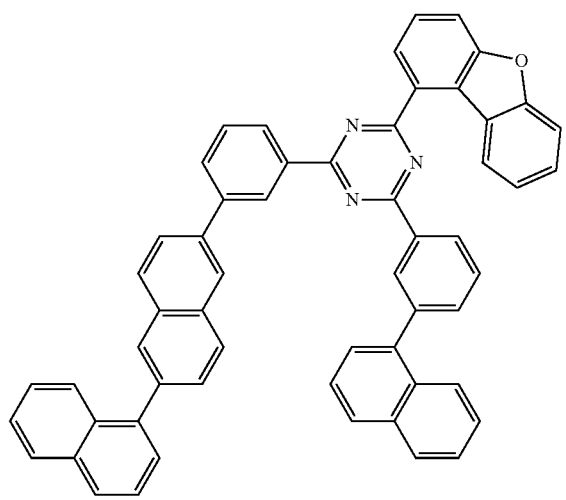
N1-48
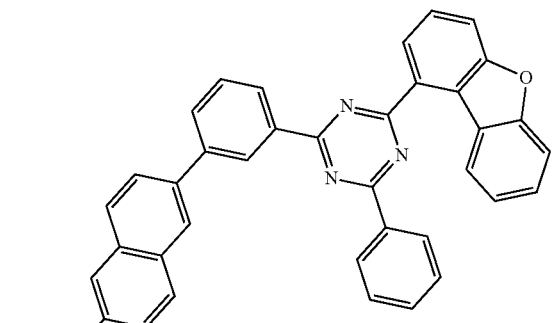
N1-41
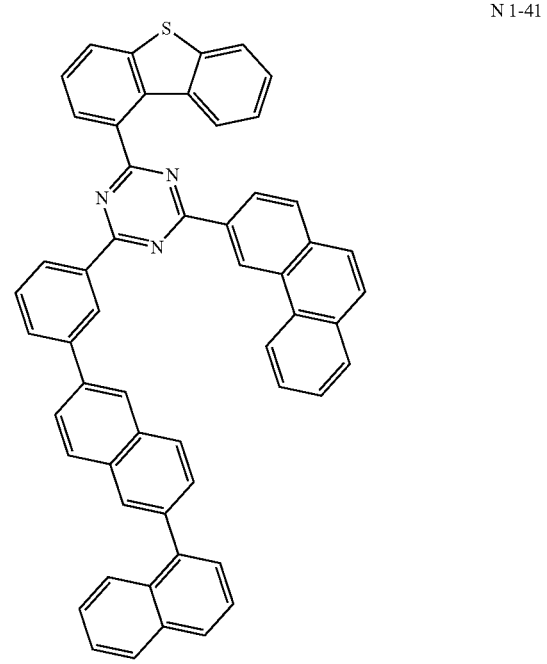
N1-51
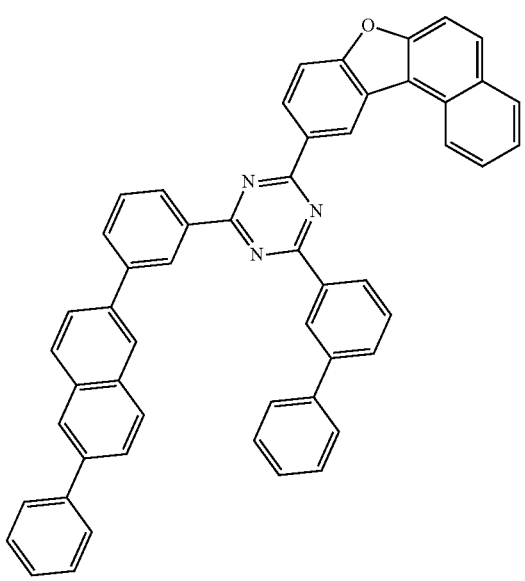
N1-47
N1-52
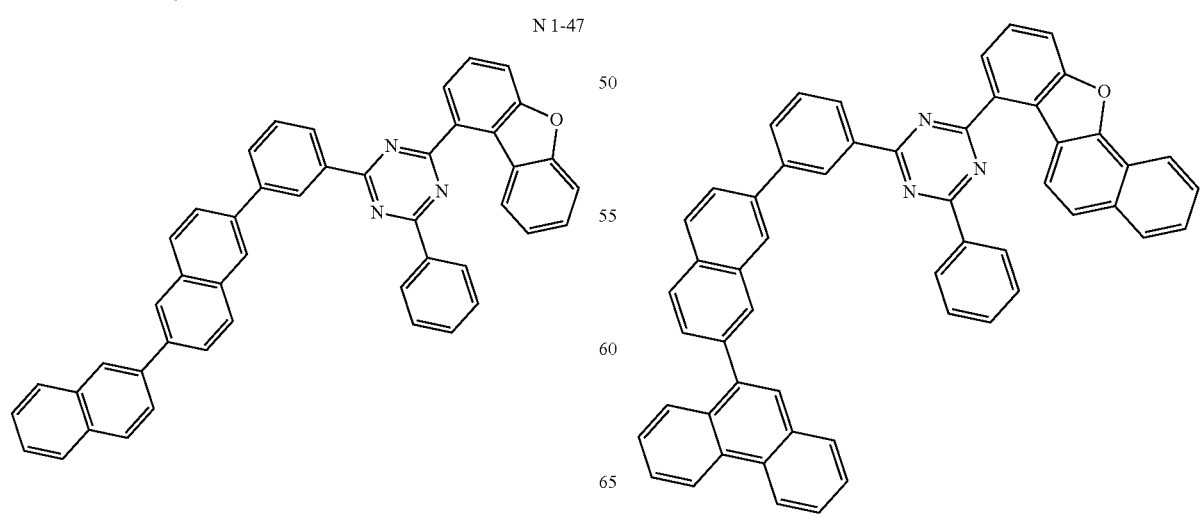

299
-continued
N 1-54
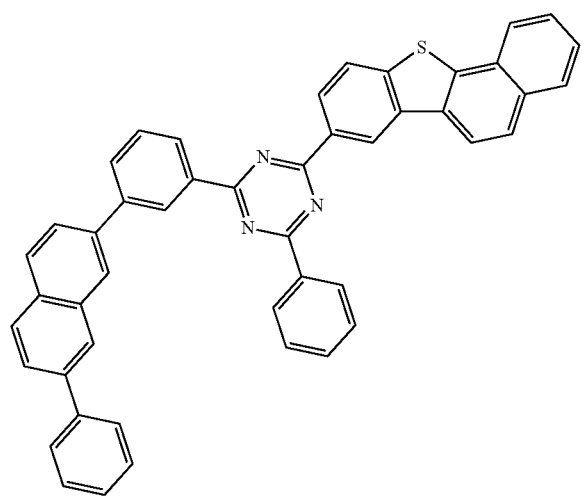
N 1-58
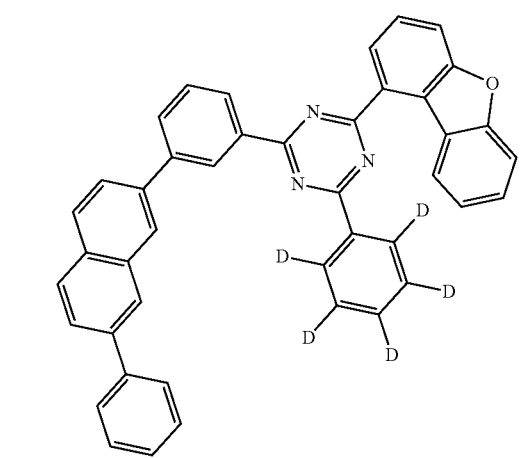
N 1-59
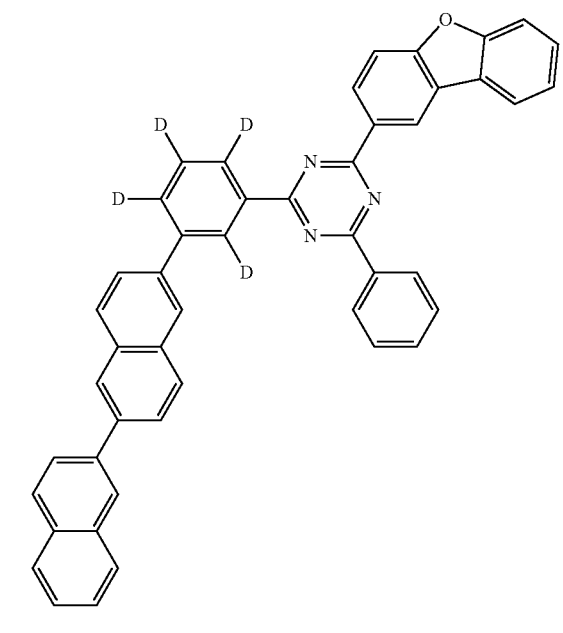
300
-continued
N 1-69
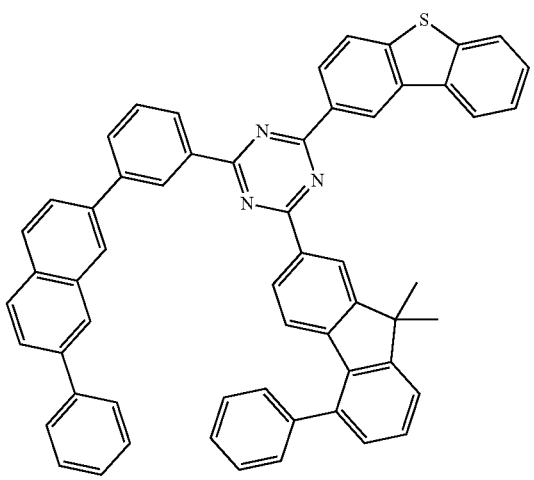
N 1-74
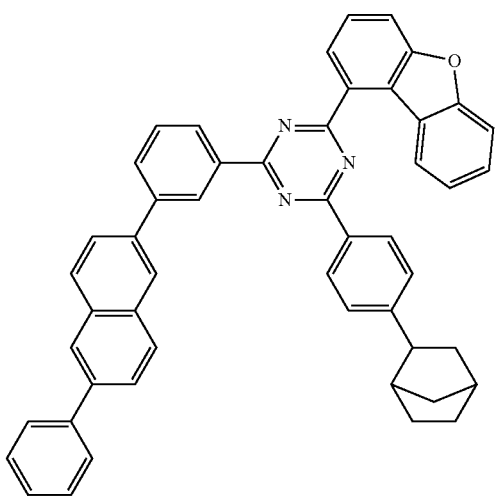
N 1-80
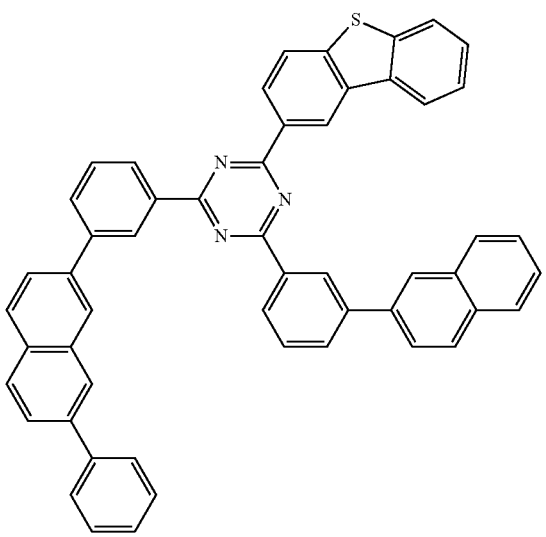

N 1-81
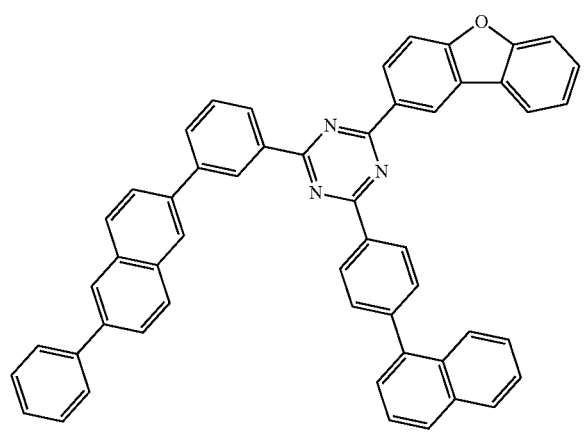
N 1-82
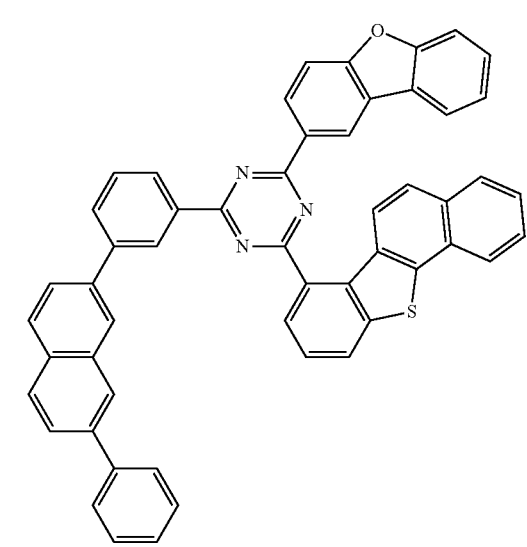
N 1-83
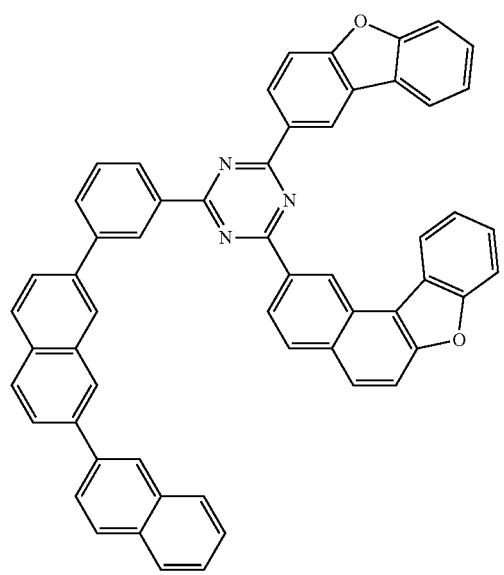
N 1-85
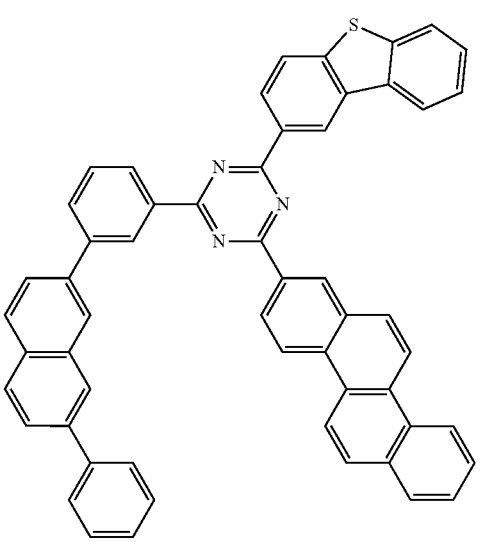
N 1-86
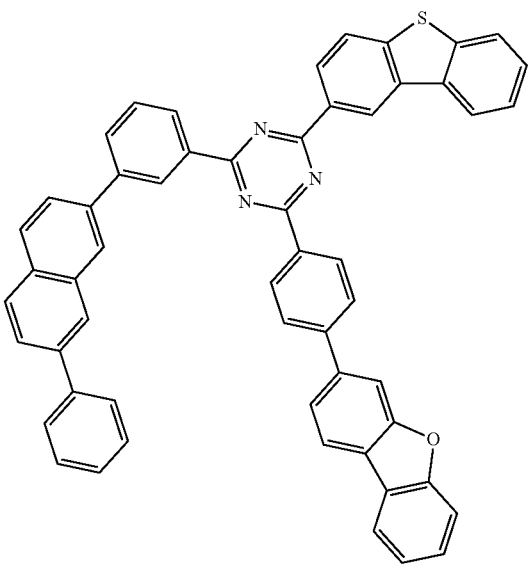

-continued

N 1-90
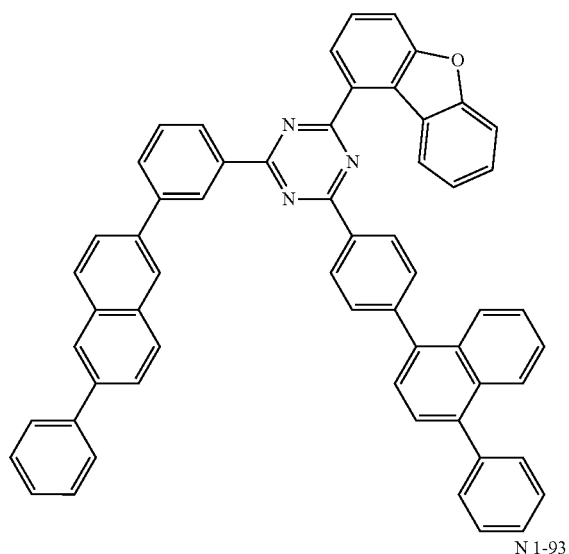

N 1-93

N 1-100
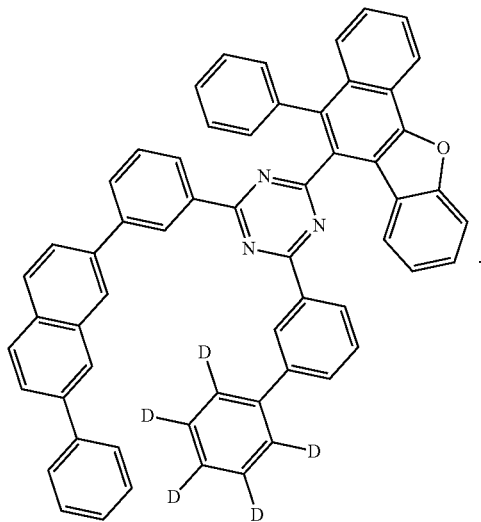

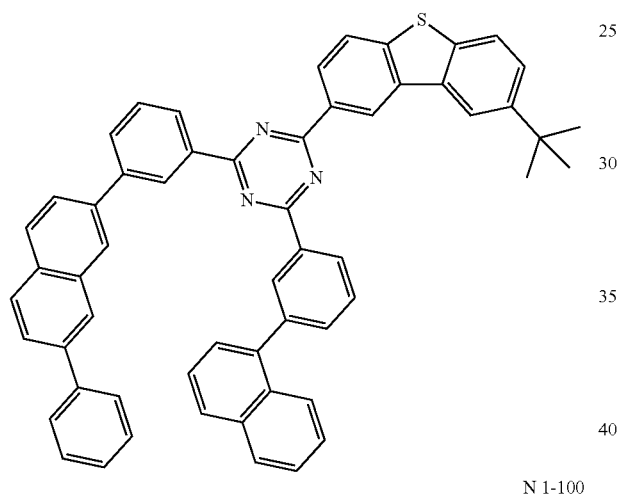

5. An organic electronic element comprising a first electrode; a second electrode; and an organic material layer formed between the first electrode and the second electrode, wherein the organic material layer includes an emitting layer, and the emitting layer is a phosphorescent emitting layer and comprises a first host compound represented by Formula 3-2 or Formula 3-3 in claim 1 and a second host compound represented by Formula 4 or Formula 5;

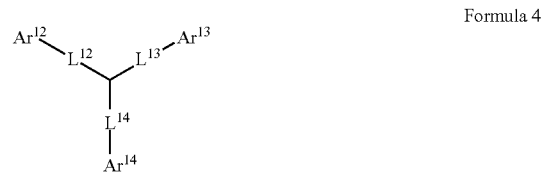

Formula 4

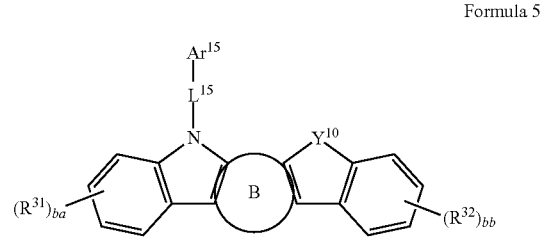

Formula 5 wherein:
$Ar^{12}$, $Ar^{13}$ and $Ar^{14}$ are each independently selected from the group consisting of a $C_6$-$C_{60}$ aryl group; a fluorenyl group; a $C_2$-$C_{60}$ heterocyclic group including at least one heteroatom of O, N, S, Si or a fused ring group of a $C_3$-$C_{60}$ aliphatic ring and a $C_6$-$C_{60}$ aromatic ring;

$Ar^{15}$ is each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L"-$NR^fR^g$, $L^{12}$, $L^{13}$ $L^{14}$, $L^{15}$ and L" are each independently selected from the group consisting of single bond; a $C_6$-$C_{60}$ arylene group; a fluorenylene group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P;

$R^f$ and $R^g$ are each independently selected from the group consisting of a $C_6$-$C_{60}$ aryl group; a fluorenyl group; a $C_2$-$C_{60}$ heterocyclic group including at least one heteroatom of O, N, S, Si or P; a $C_3$-$C_{60}$ aliphatic ring;

$Y^{10}$ is O, $CR^{51}R^{52}$ or $NR^{53}$,

B ring is a $C_6$-$C_{20}$ aryl group, $R^{31}$ and $R^{32}$ are the same or different, and each independently selected from the group consisting of a hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_6$-$C_{60}$ aryloxy group; or a plurality of adjacent $R^{31}$s or a plurality of $R^{32}$s may be bonded to each other to form a ring, $R^{51}$, $R^{52}$ and $R^{53}$ are each independently selected from the group consisting of a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_6$-$C_{60}$ aryloxy group; or $R^{51}$ and $R^{52}$ may be bonded to each other to form a spiro, ba and bb are independently an integer of 0 to 4;

wherein the aryl group, arylene group, heterocyclic group, fluorenyl group, fluorenylene group, aliphatic ring group, fused ring group, alkyl group, alkenyl group, alkynyl group, alkoxyl group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

6. The compound according to claim 5, wherein the compound represented by Formula 4 is any one of the following compounds H-1 to H-100:

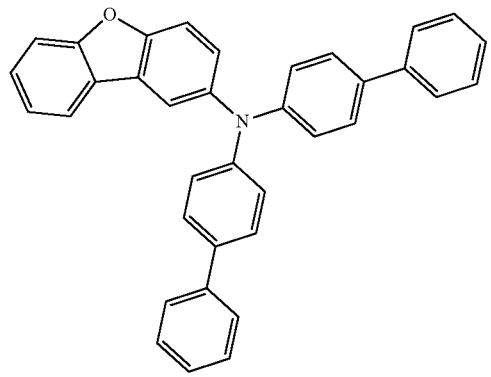

H-1

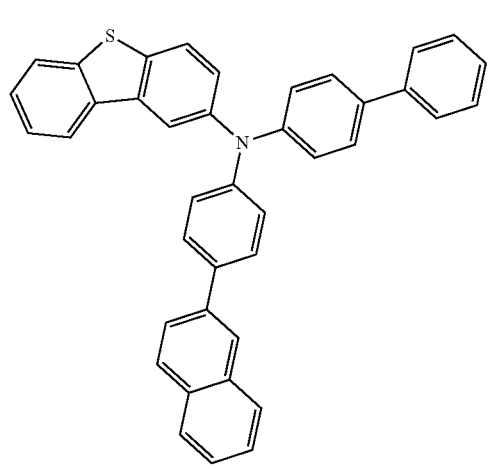

H-2

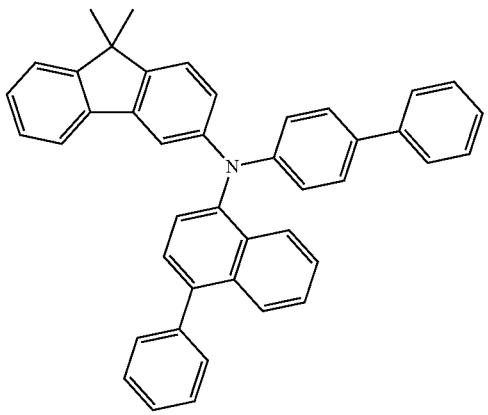

H-3

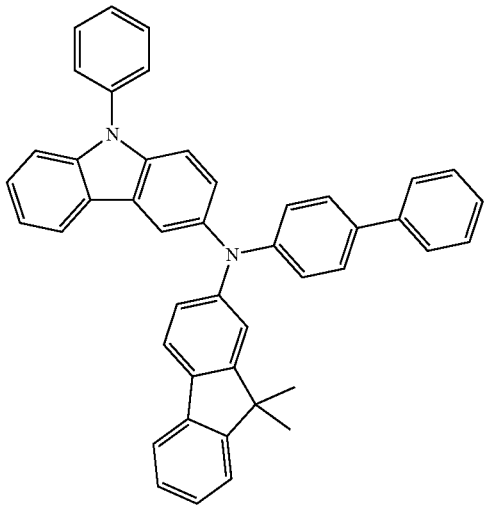

H-4

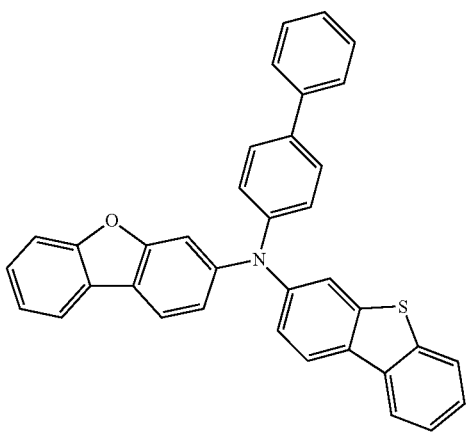

H-5

-continued
H-6
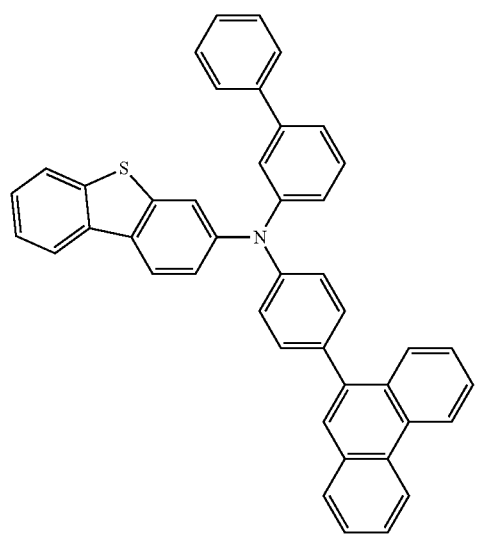
H-7
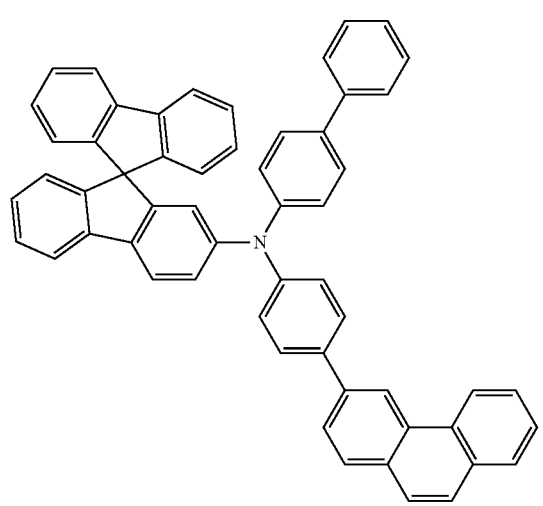
H-8
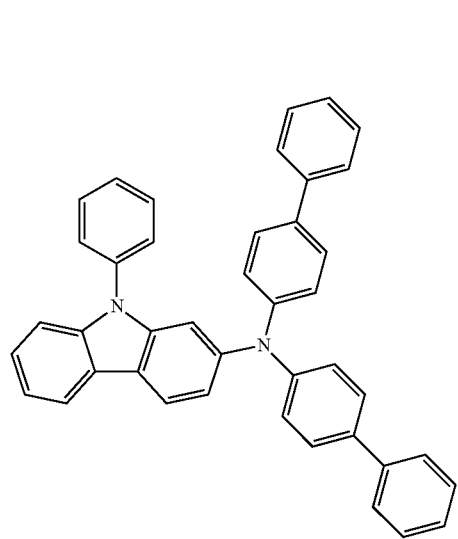
-continued
H-9
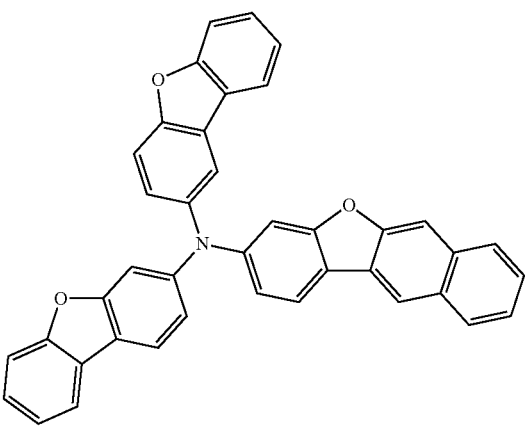
H-10
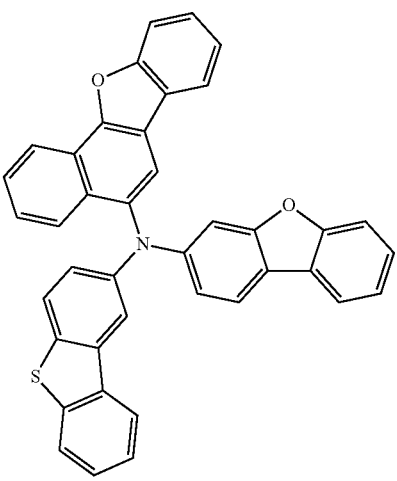
H-11
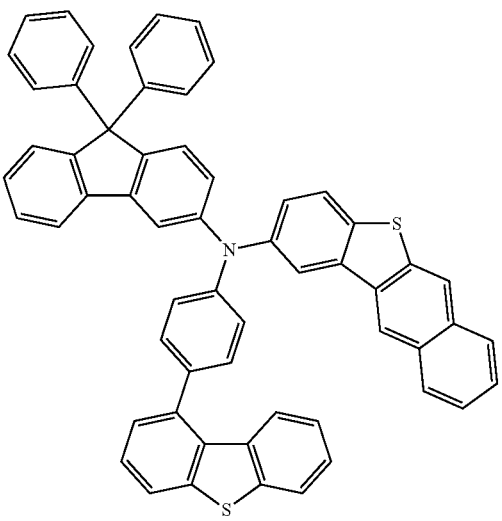

H-12
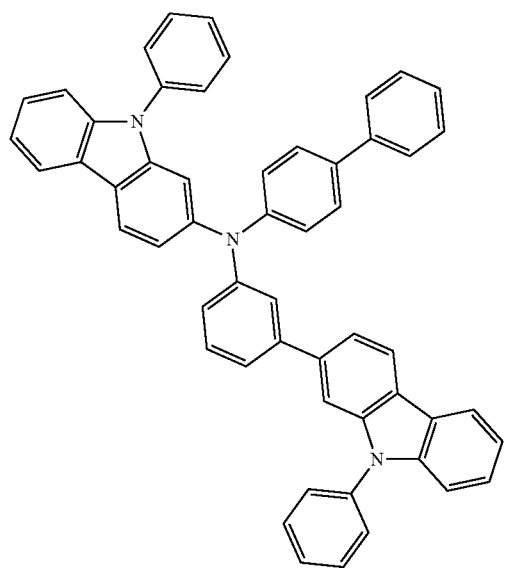
H-13
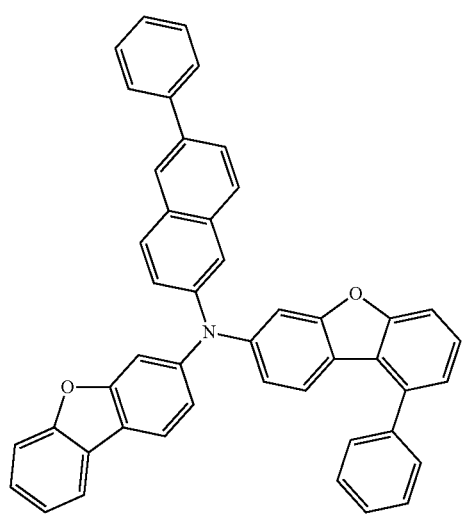
H-14
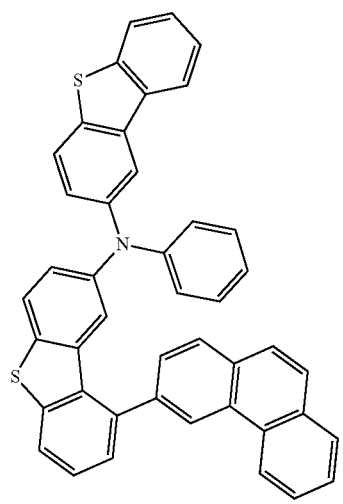
H-15
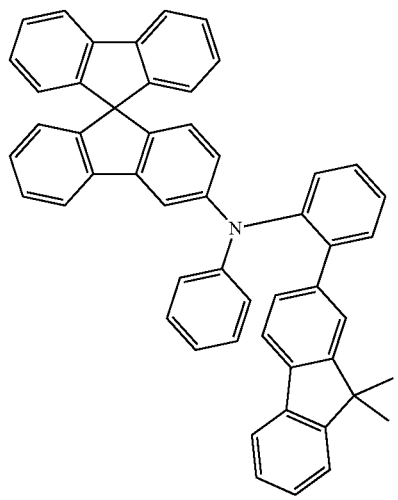
H-16
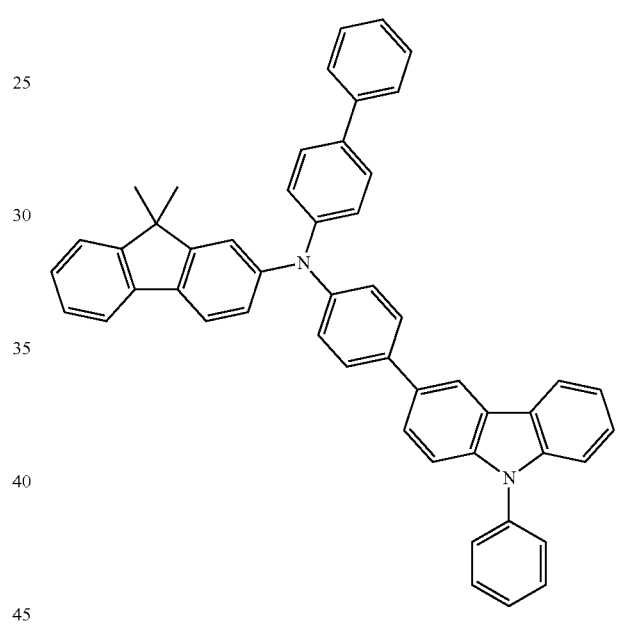
H-17
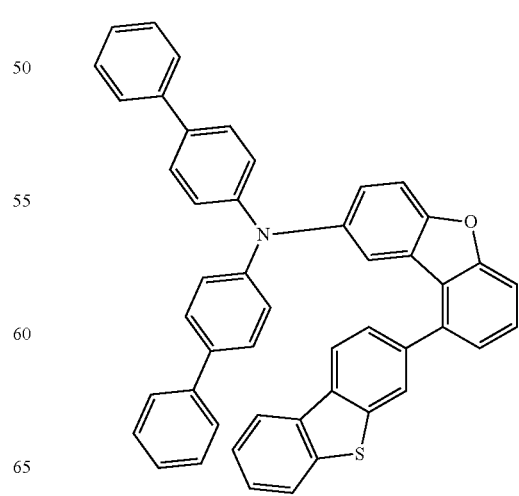

-continued
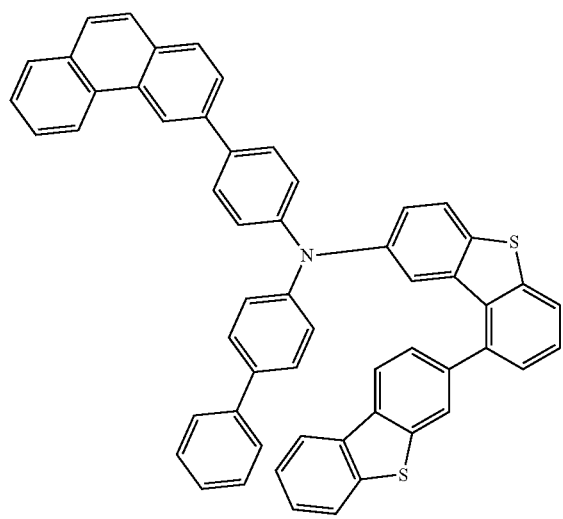
H-18
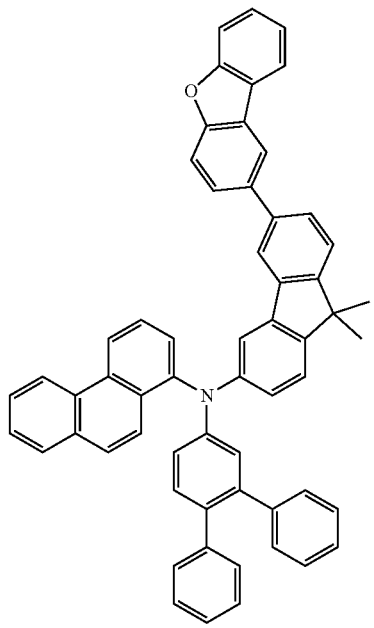
H-21
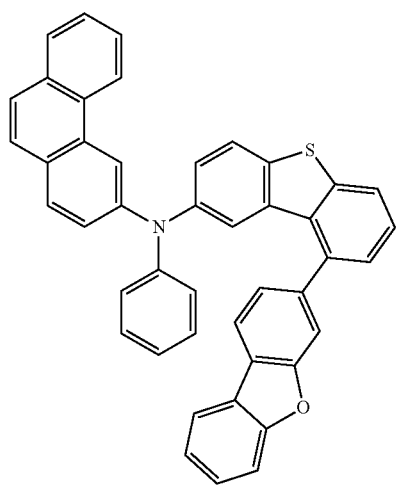
H-19
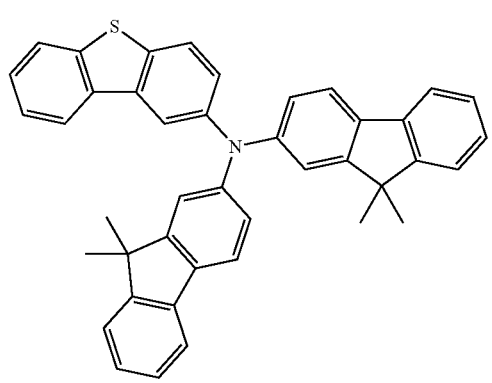
H-22
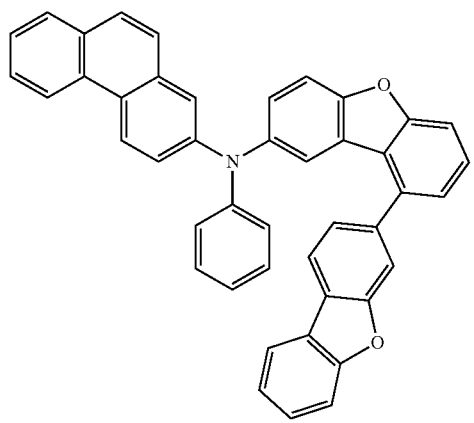
H-20
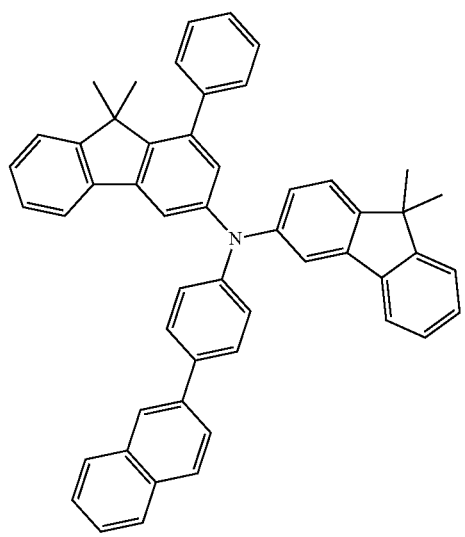
H-23

H-24
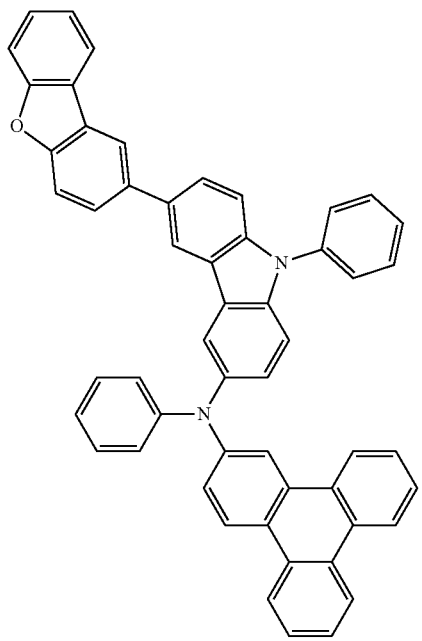
H-25
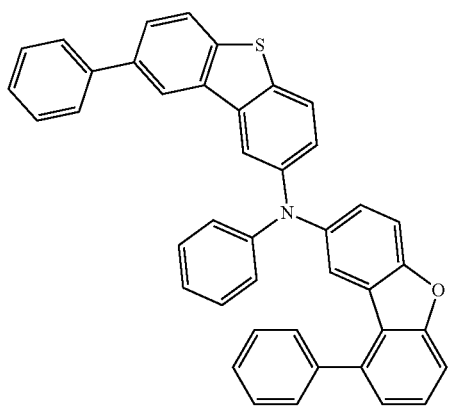
H-26
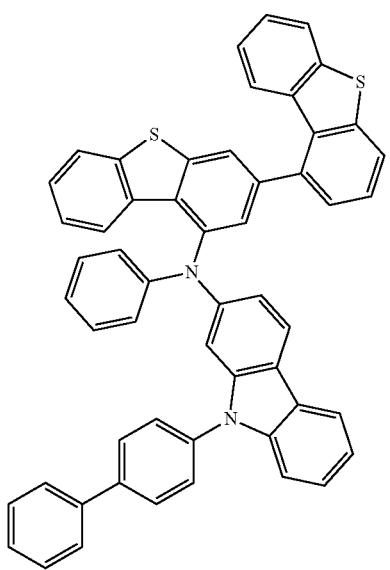
H-27
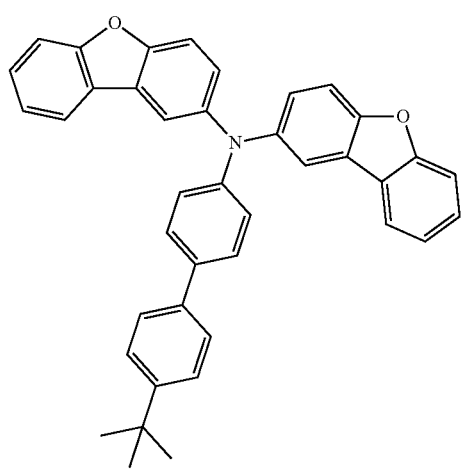
H-28
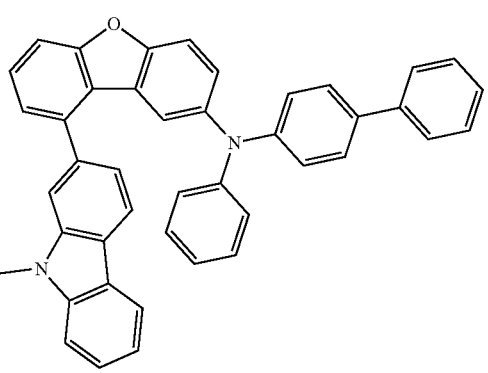
H-29
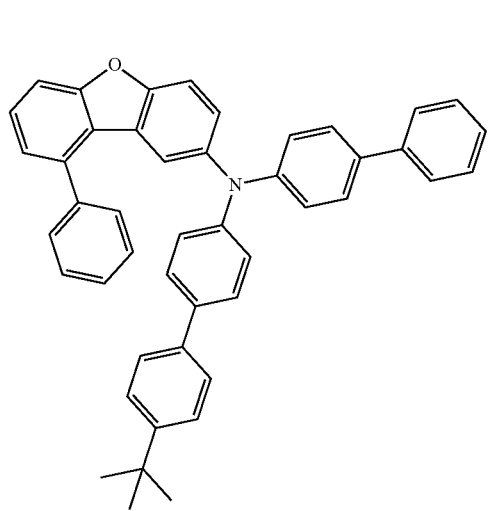

H-30
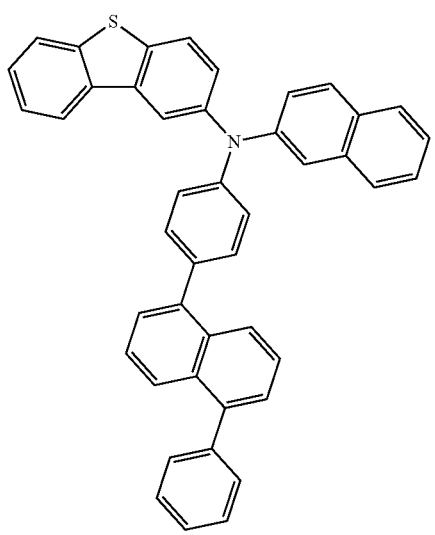
H-31
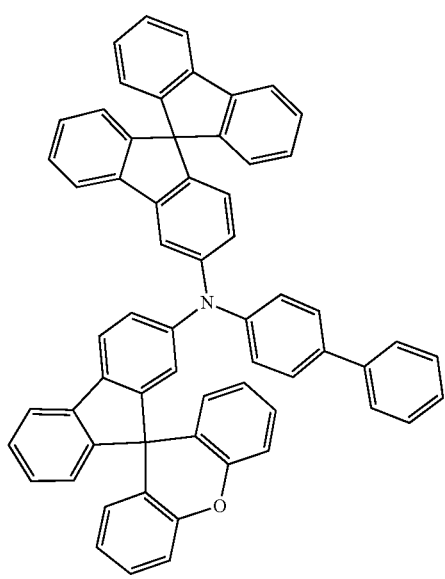
H-32
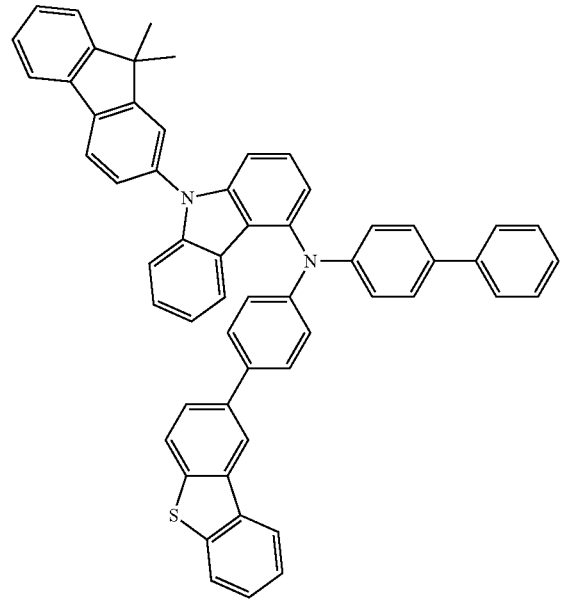
H-33
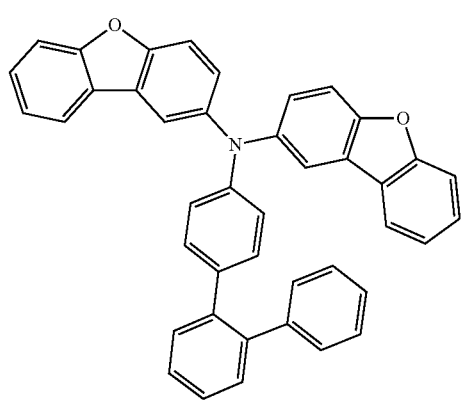
H-34
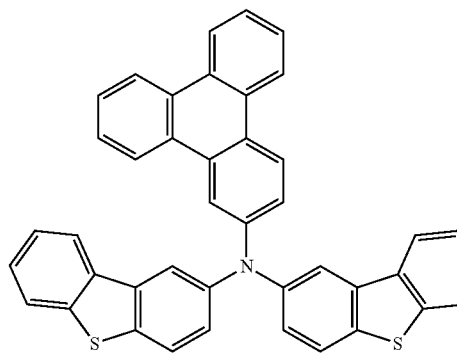

H-35
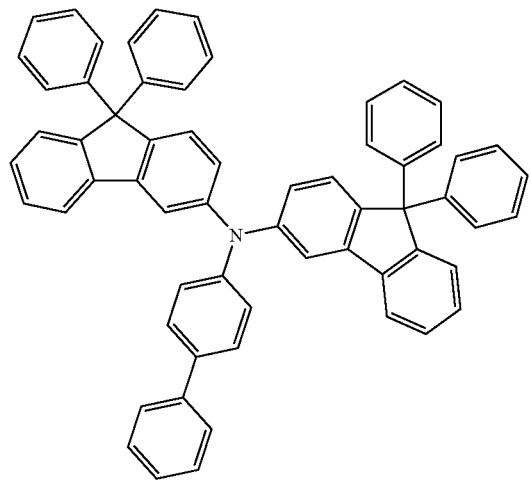
H-36
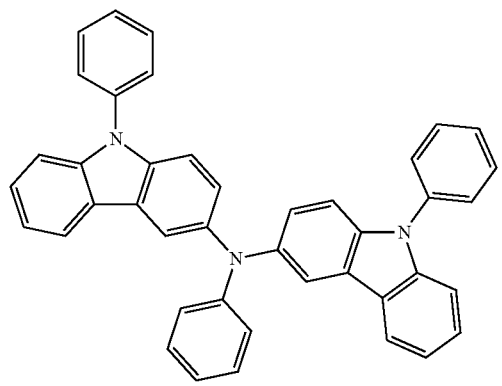
H-37
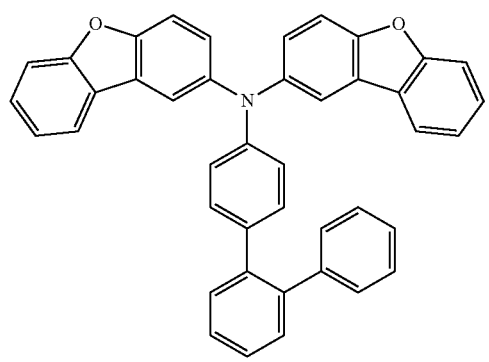
H-38
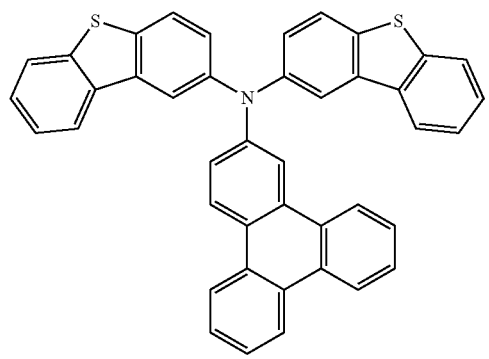
H-39
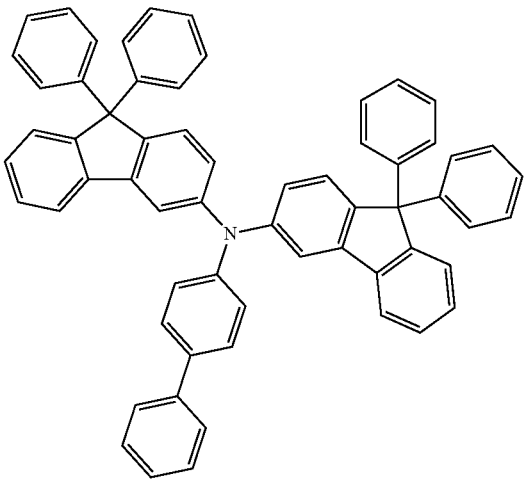
H-40
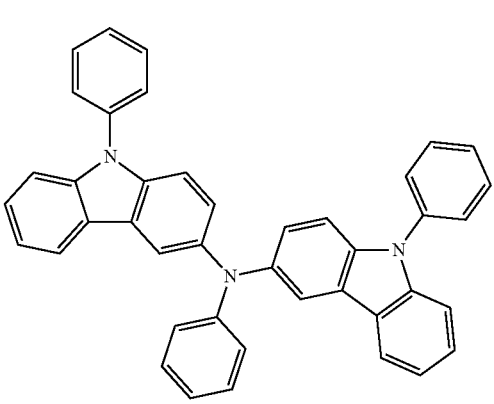
H-41
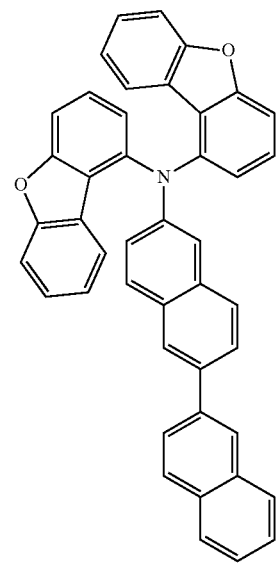

319
-continued
H-42
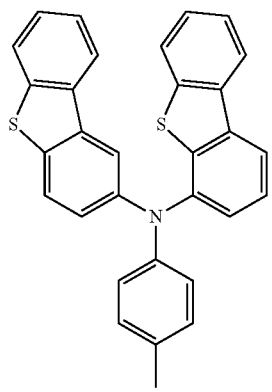
H-43
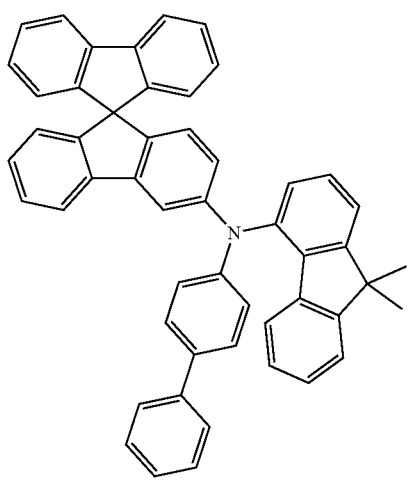
H-44
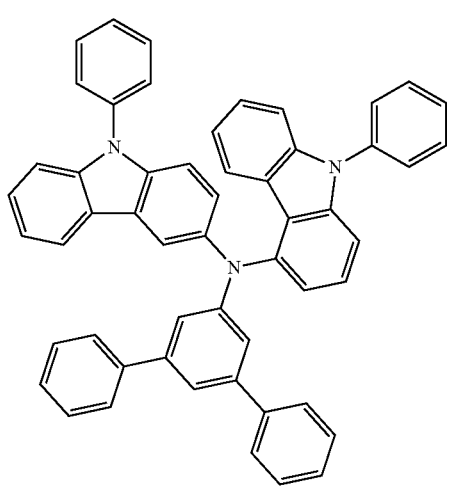
320
-continued
H-45
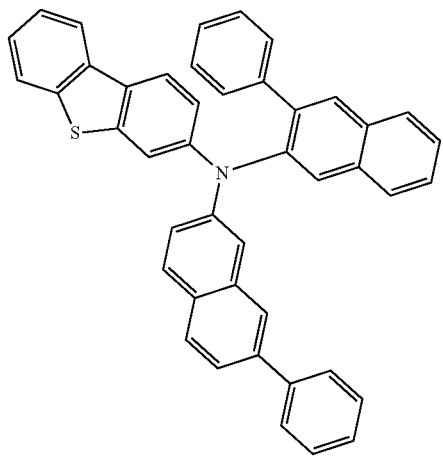
H-46
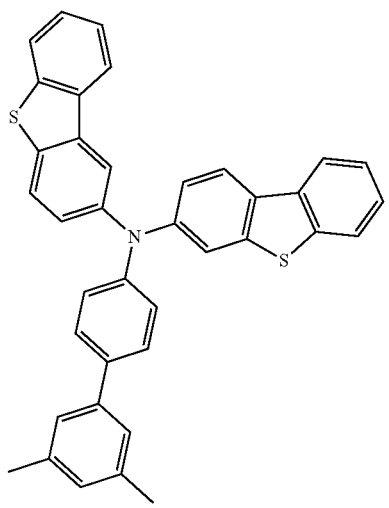
H-47
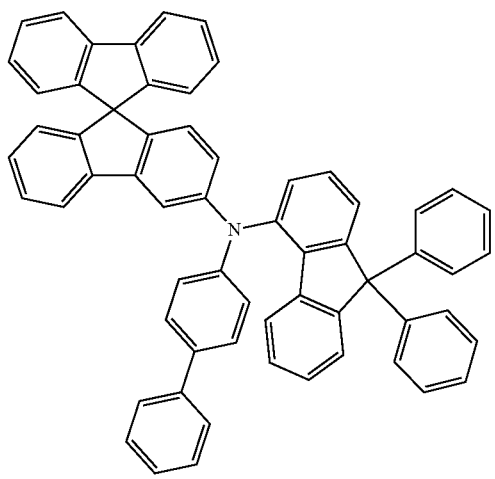

-continued
H-48
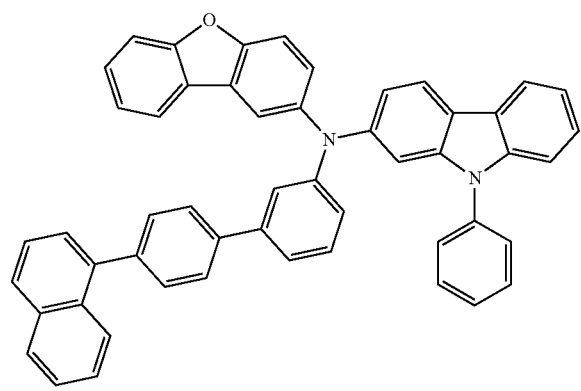
H-49
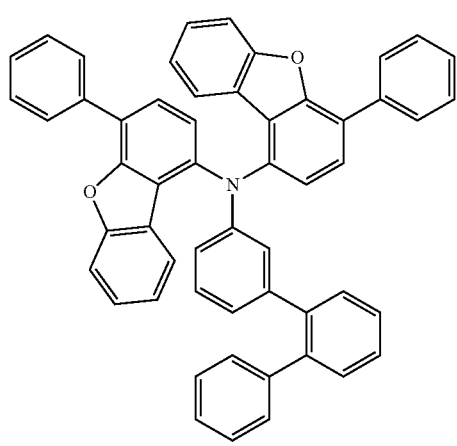
H-50
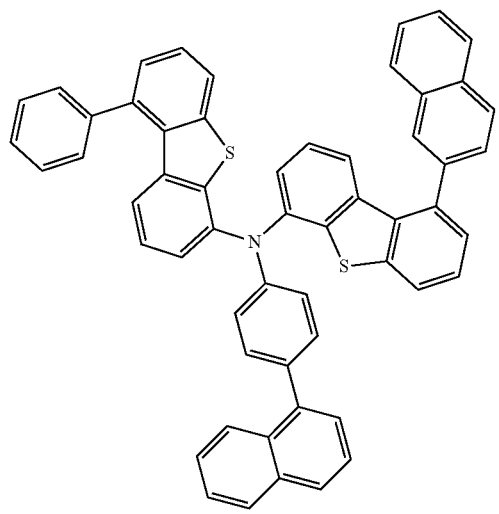
-continued
H-51
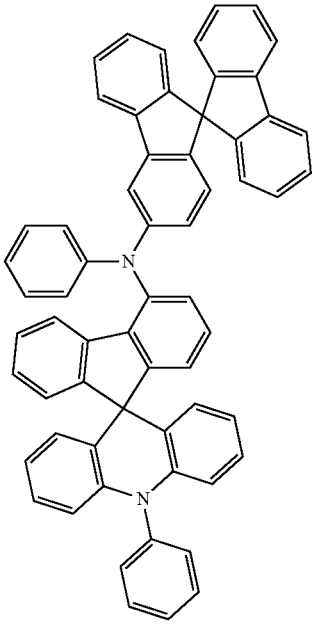
H-52
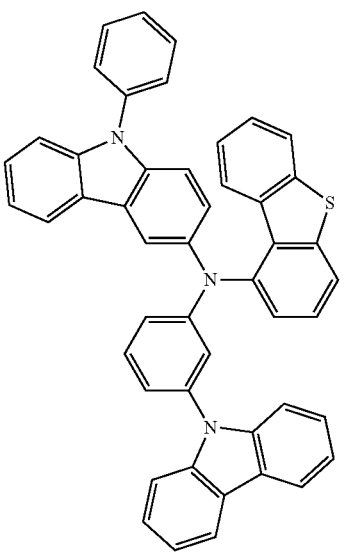
H-53
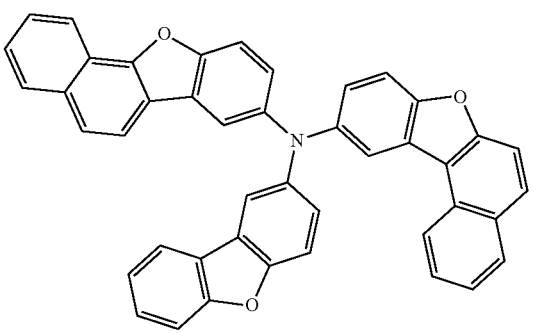

H-54
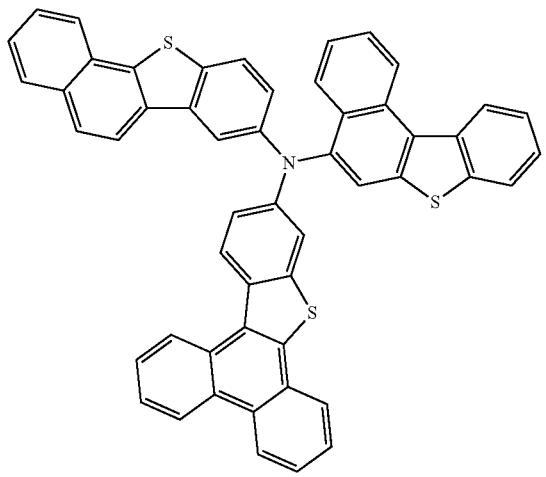
H-57
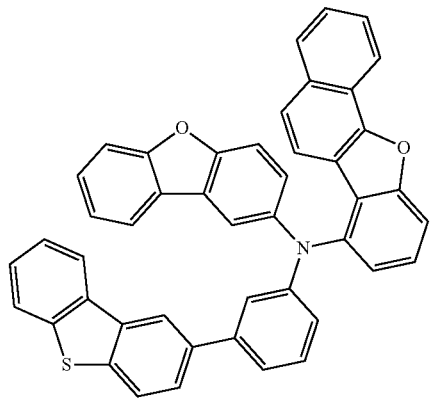
H-55
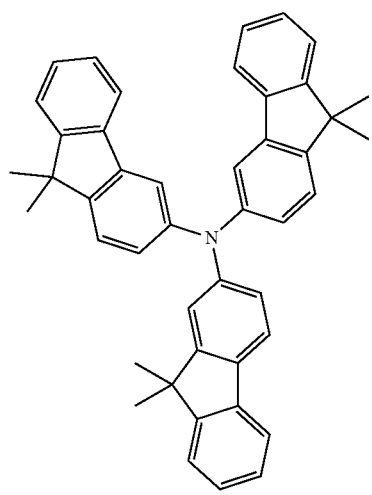
H-58
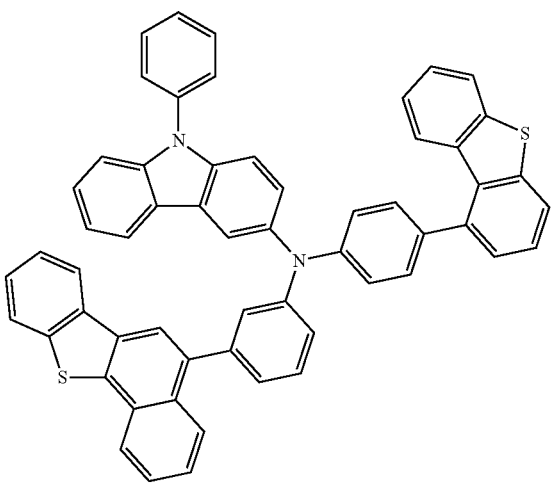
H-56
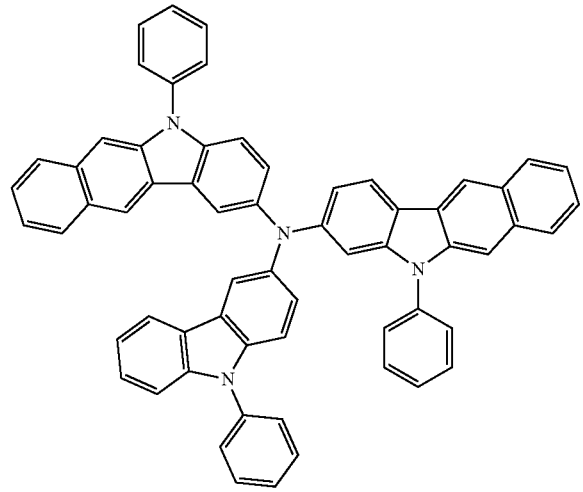
H-59
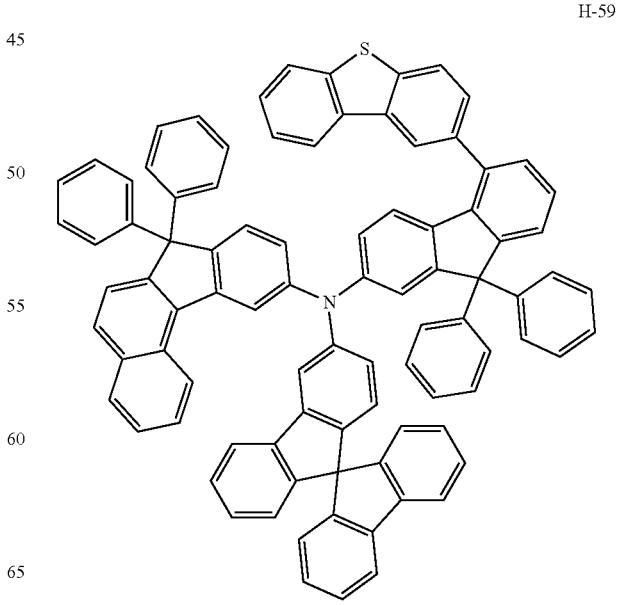

H-60
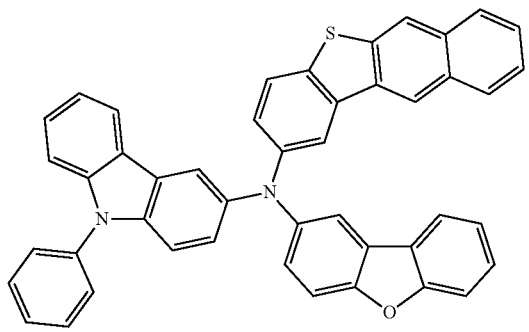
H-63
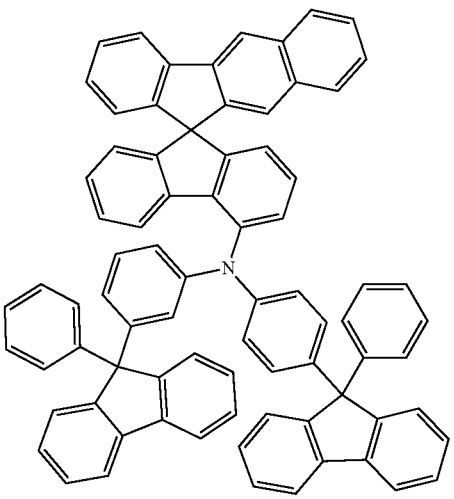
H-61
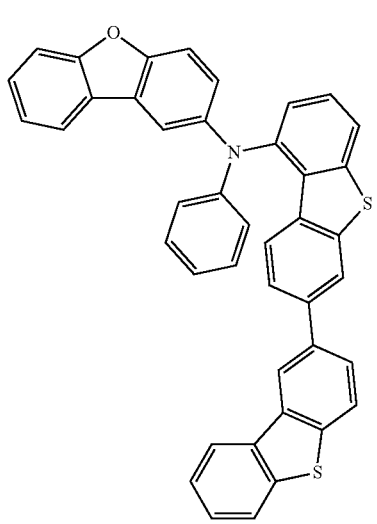
H-64
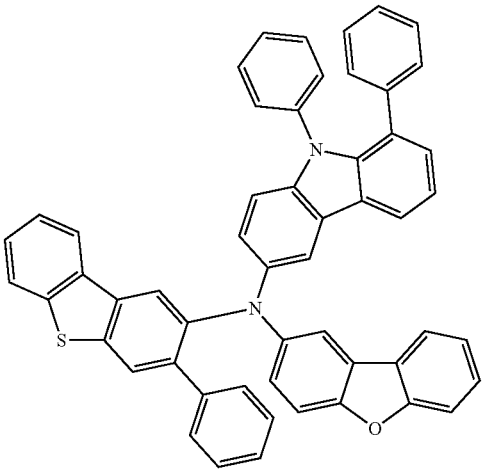
H-62
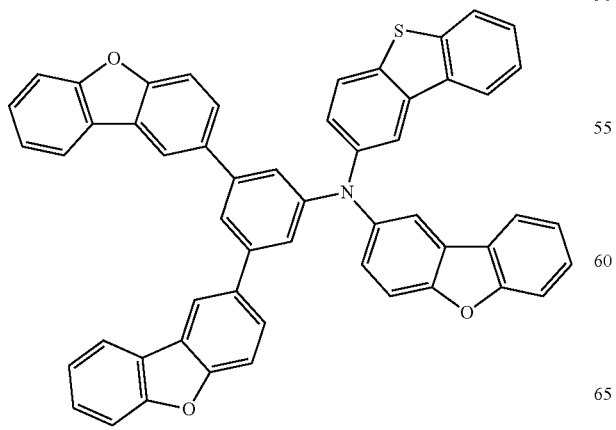
H-65
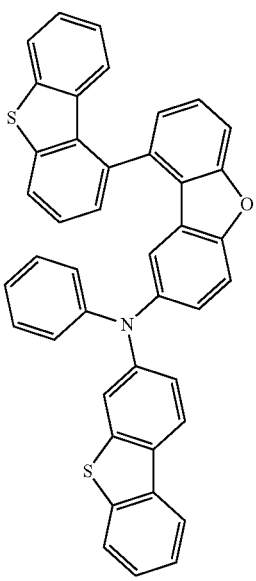

-continued
H-66
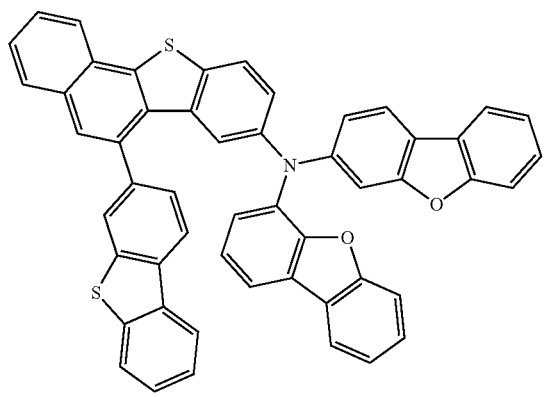
H-67
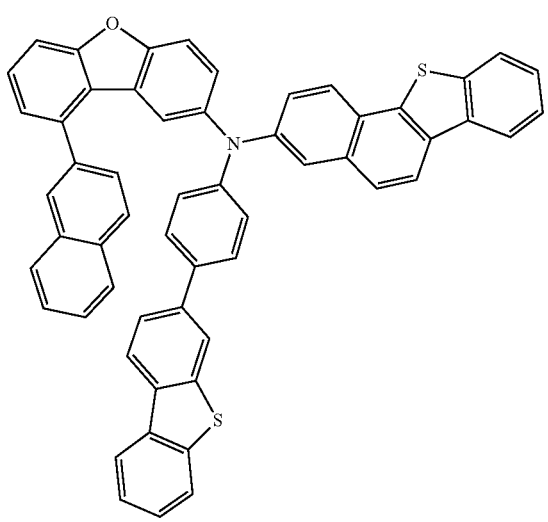
H-68
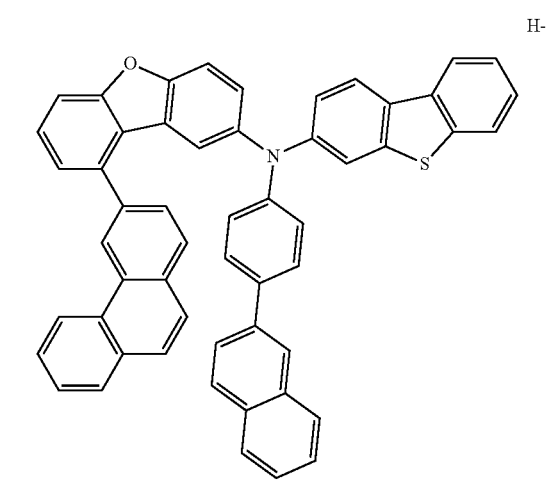
-continued
H-69
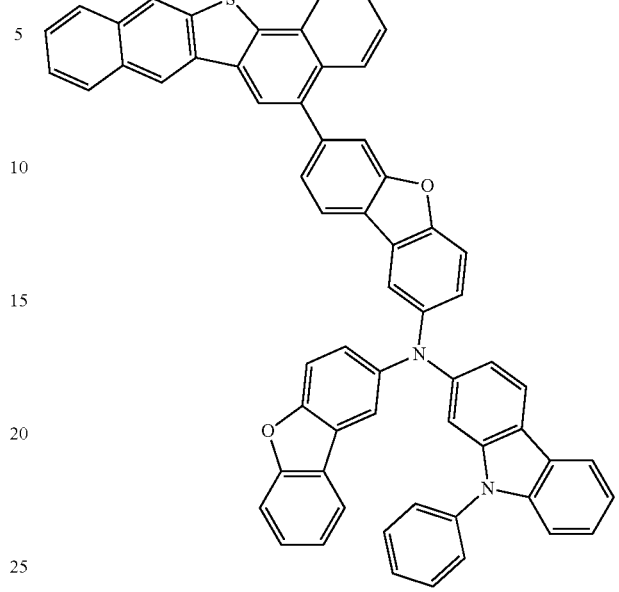
H-70
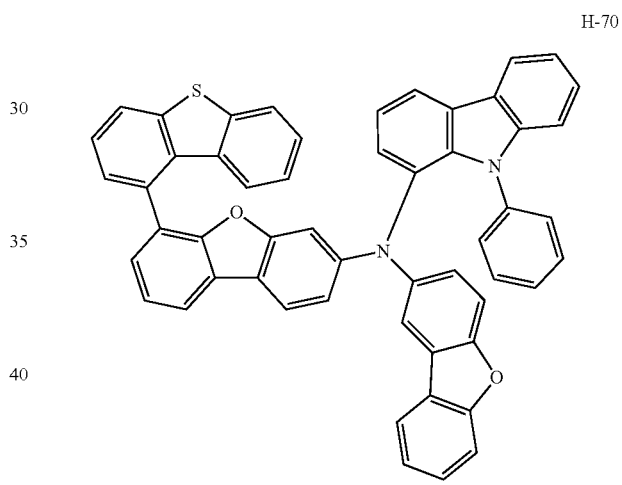
H-71
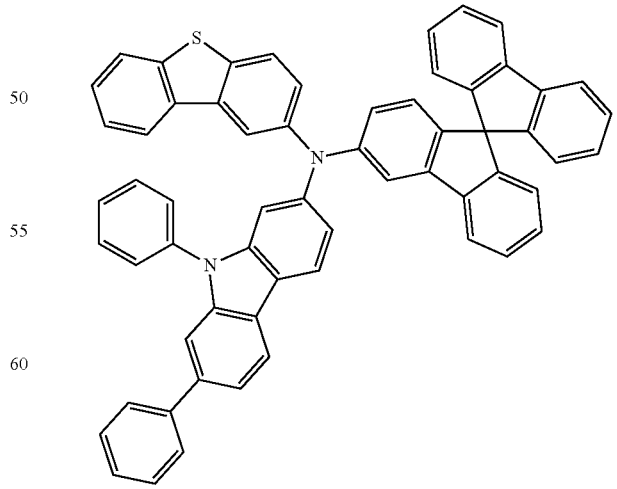

329
-continued
H-72
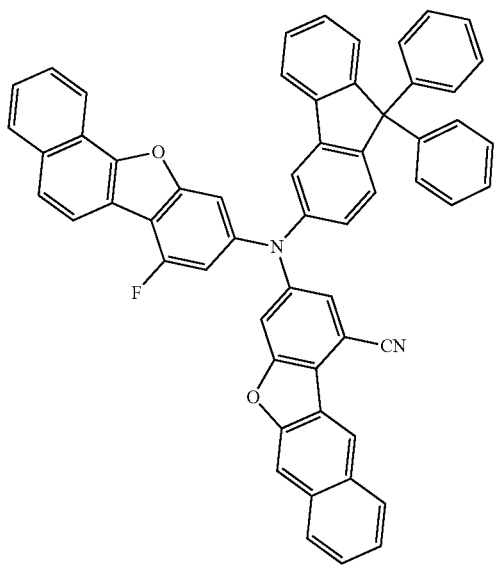
H-73
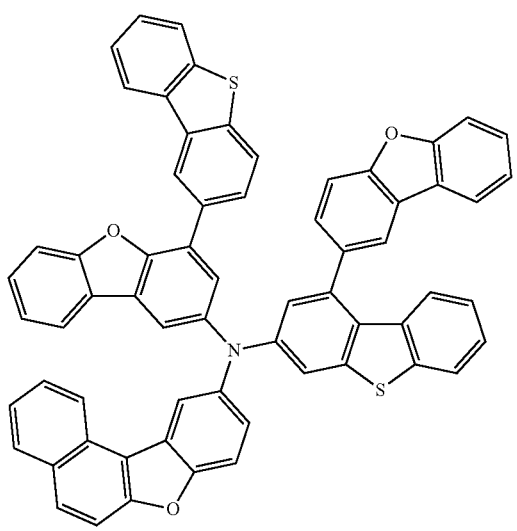
330
-continued
H-74
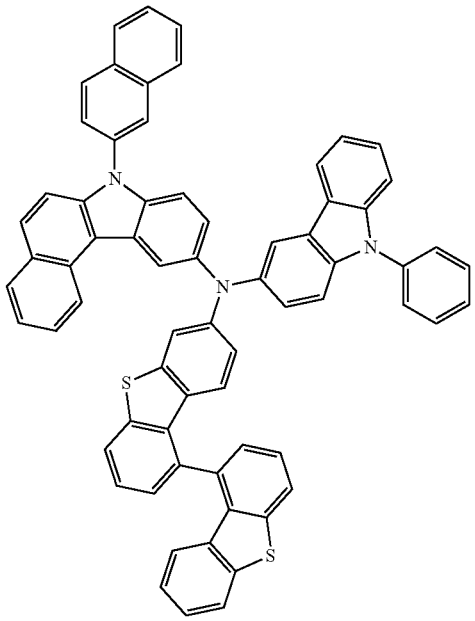
H-75
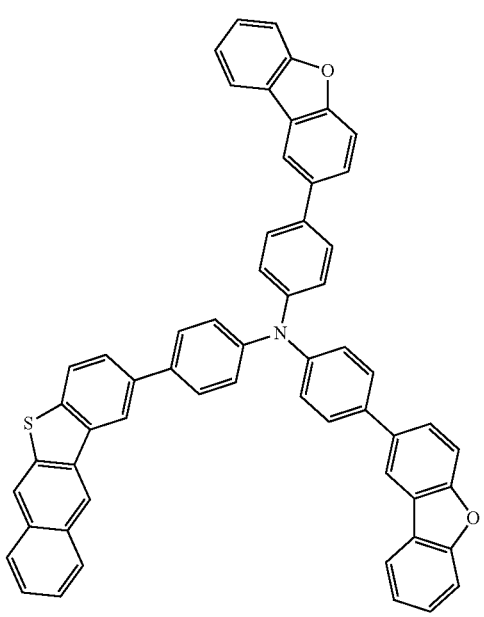

H-76
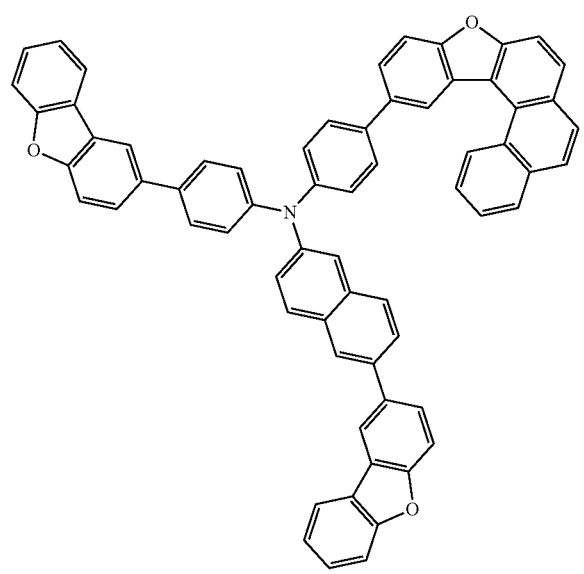
H-78
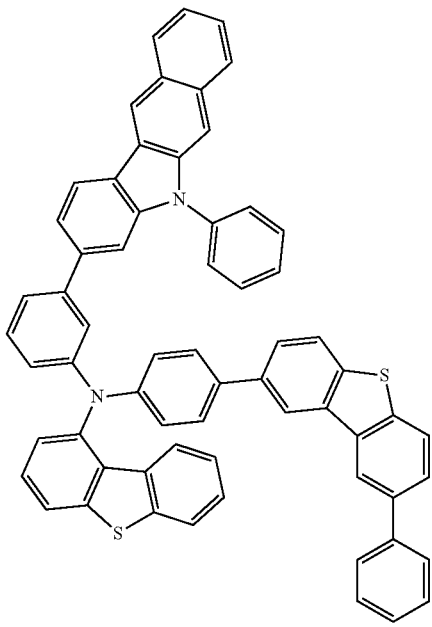
H-77
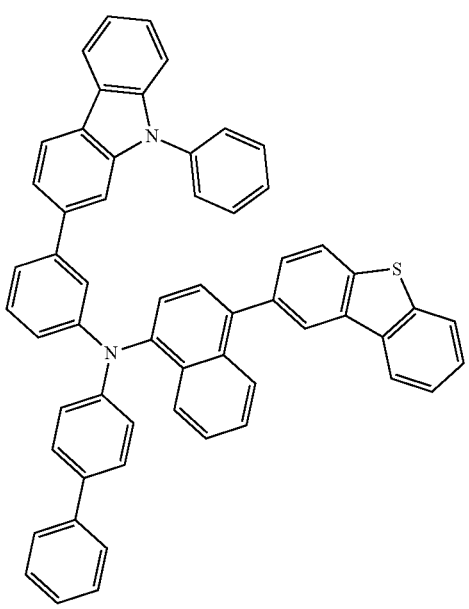
H-79
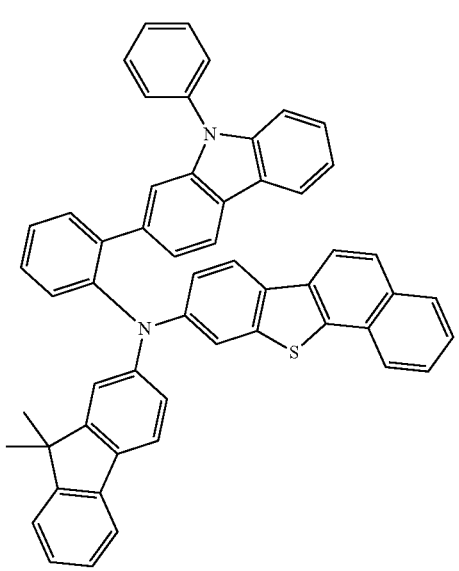

-continued
H-80
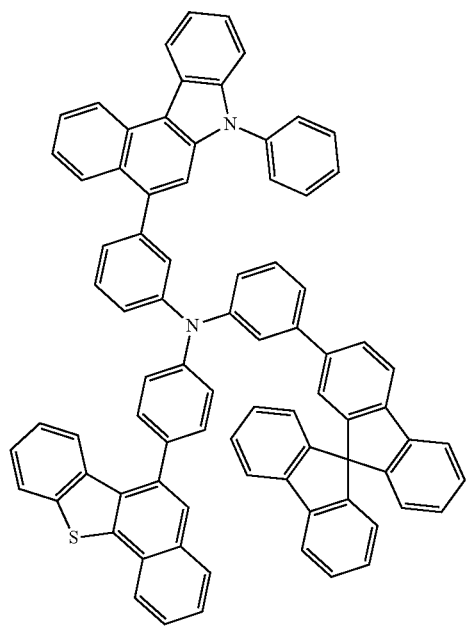
H-81
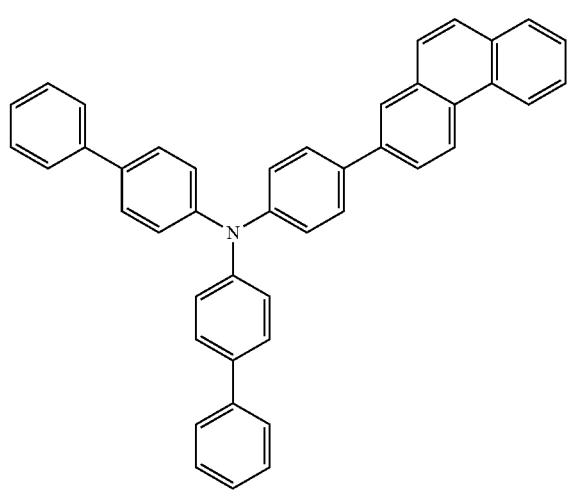
H-82
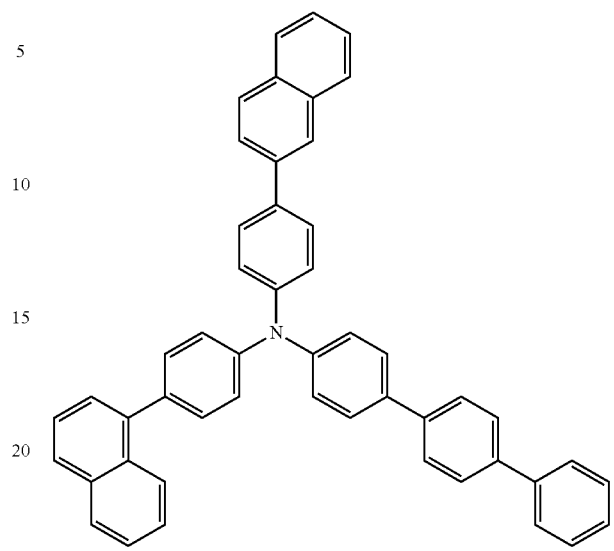
H-83
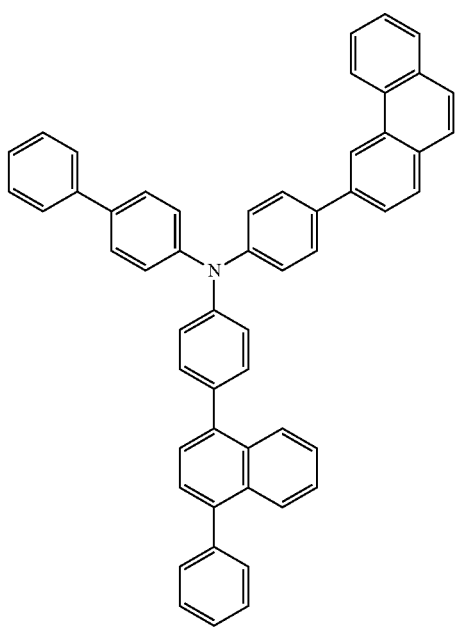

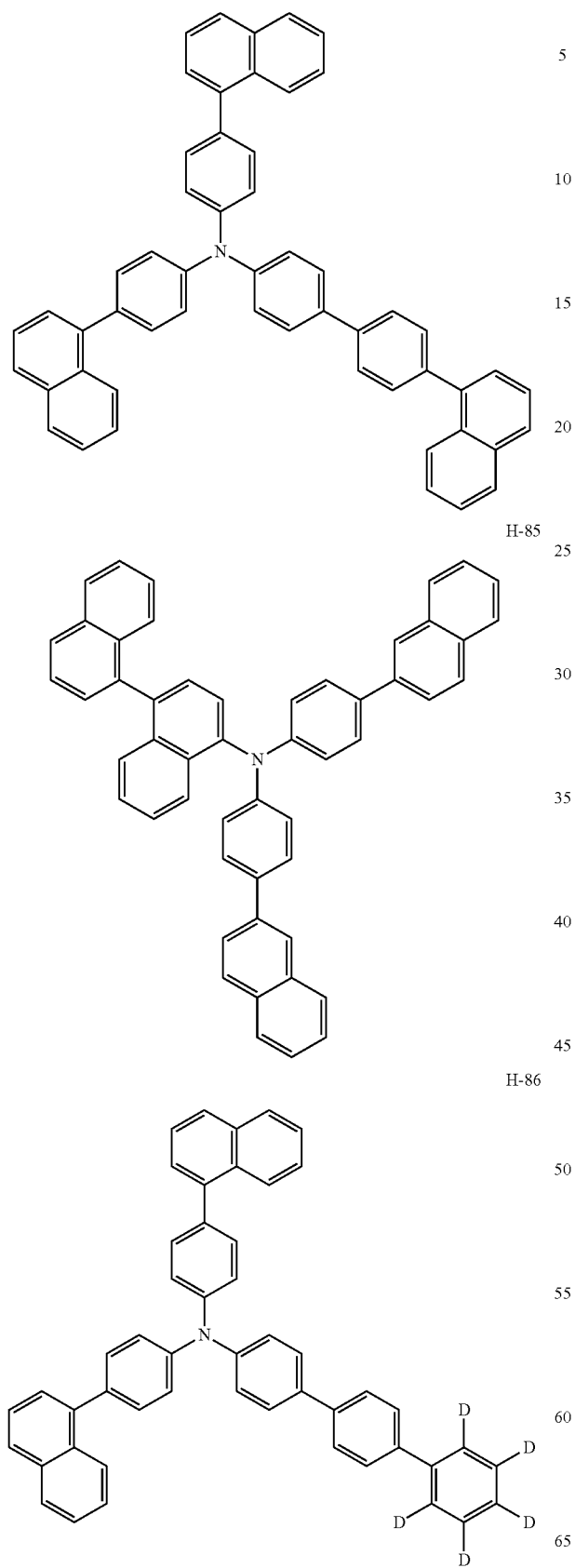
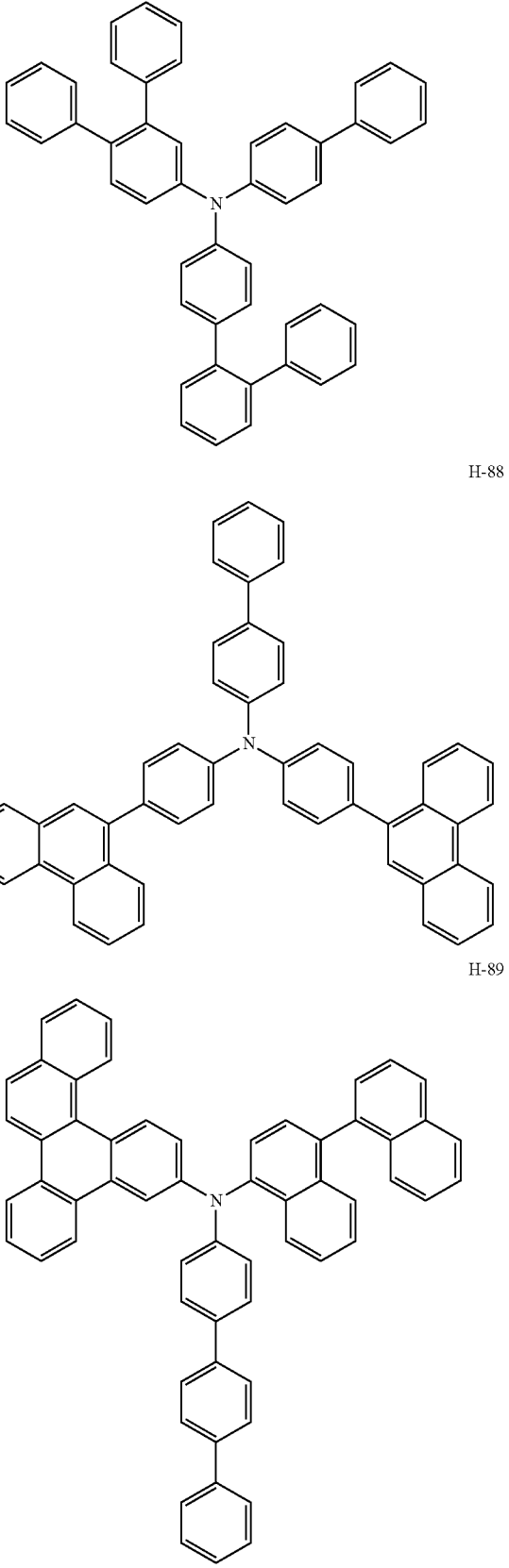

-continued
H-90
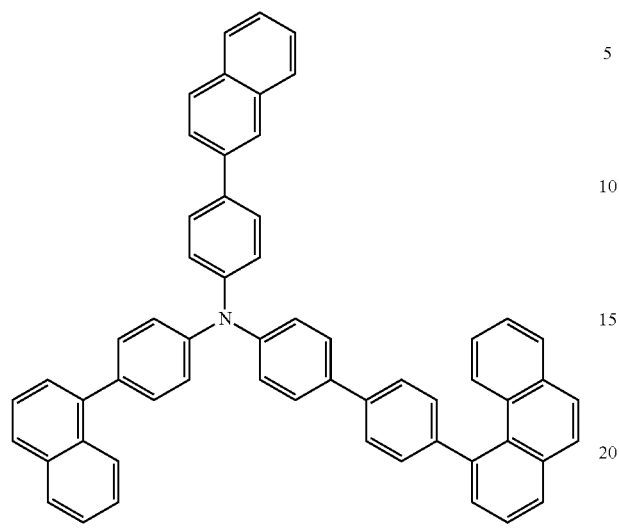
H-91
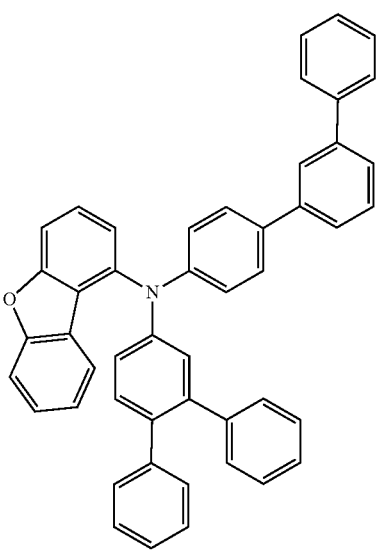
H-92
-continued
H-93
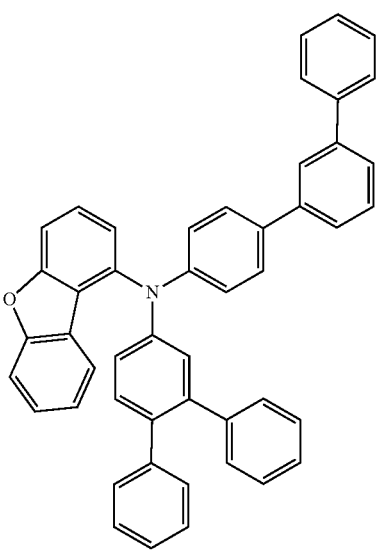
H-94
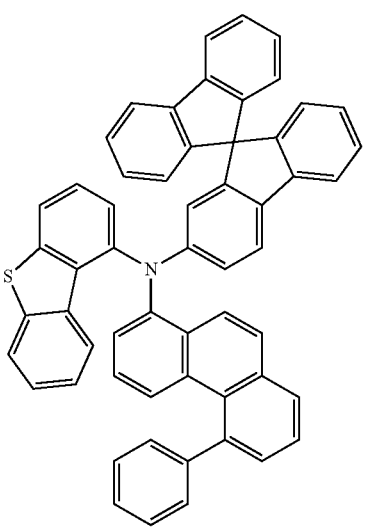
H-95
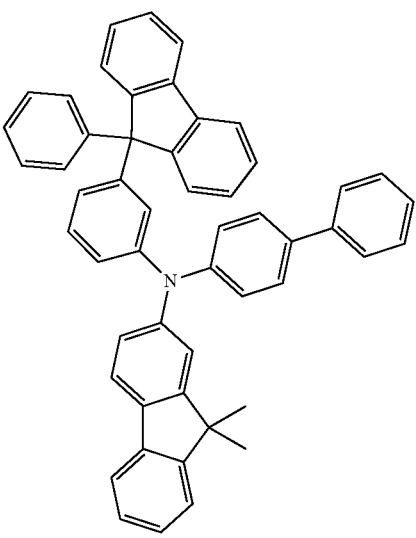

H-96
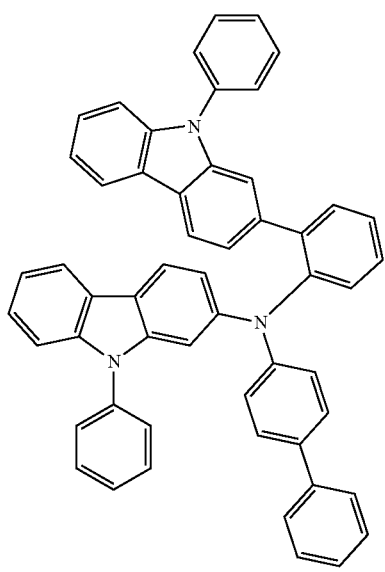
H-97
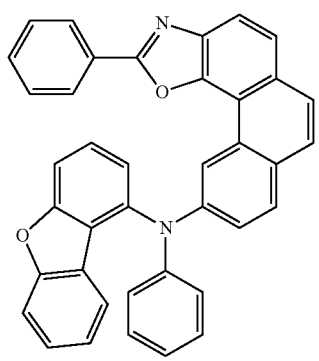
H-98
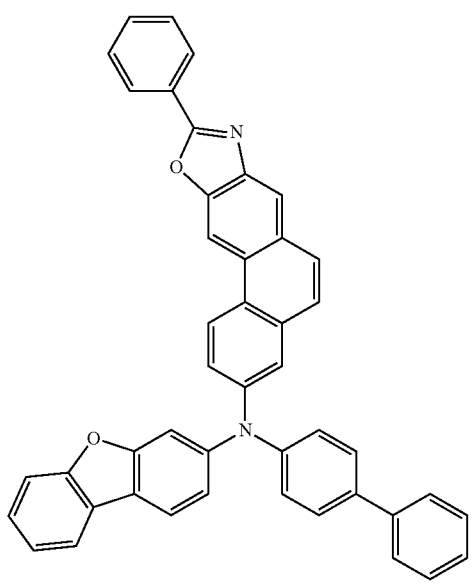
H-99
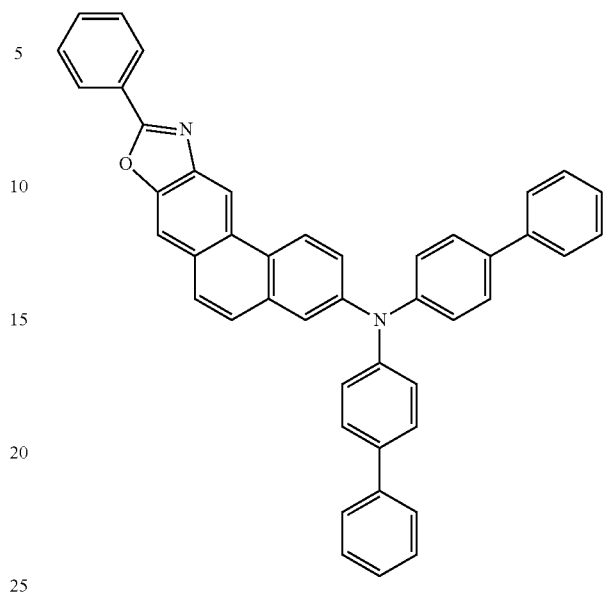
H-100
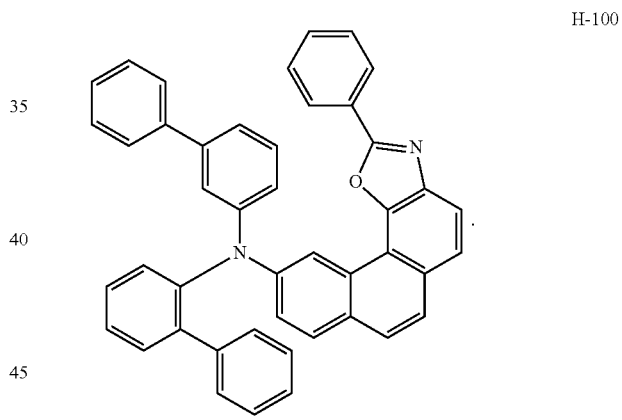
7. The compound according to claim 5, wherein the compound represented by Formula 5 is any one of the following compounds S-1 to S-108:
S-1
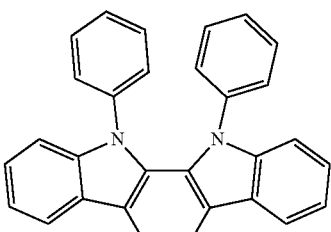

-continued
S-2
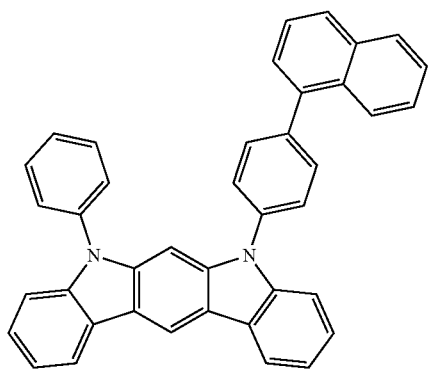
S-3
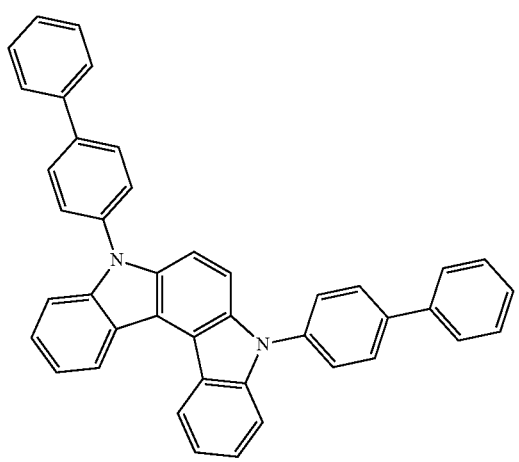
S-4
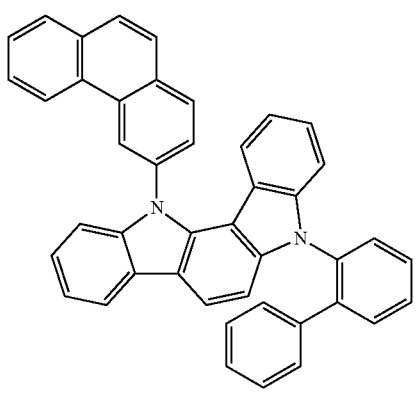
-continued
S-5
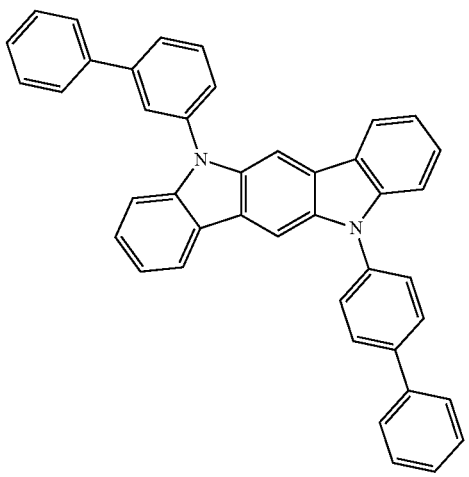
S-6
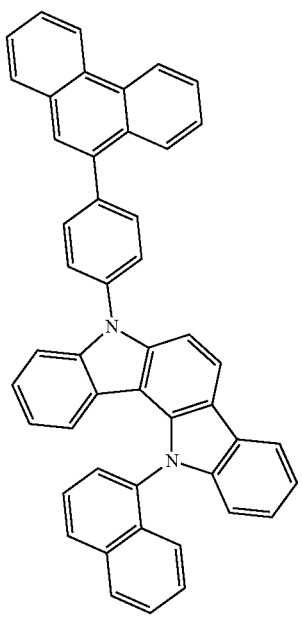
S-7
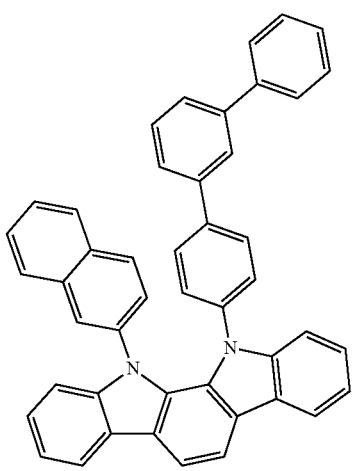

-continued
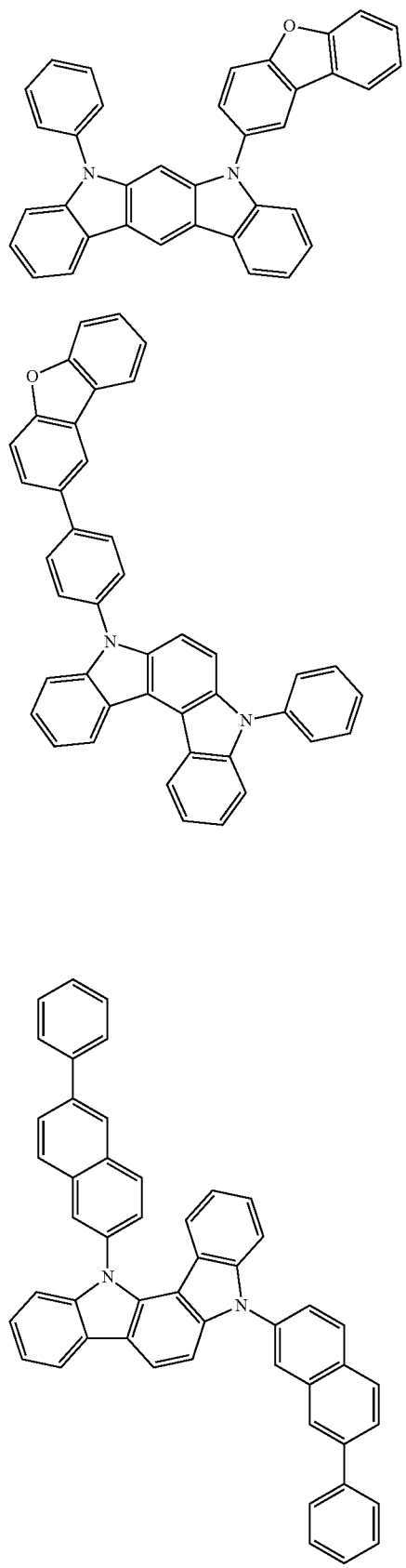
S-8
S-9
S-10
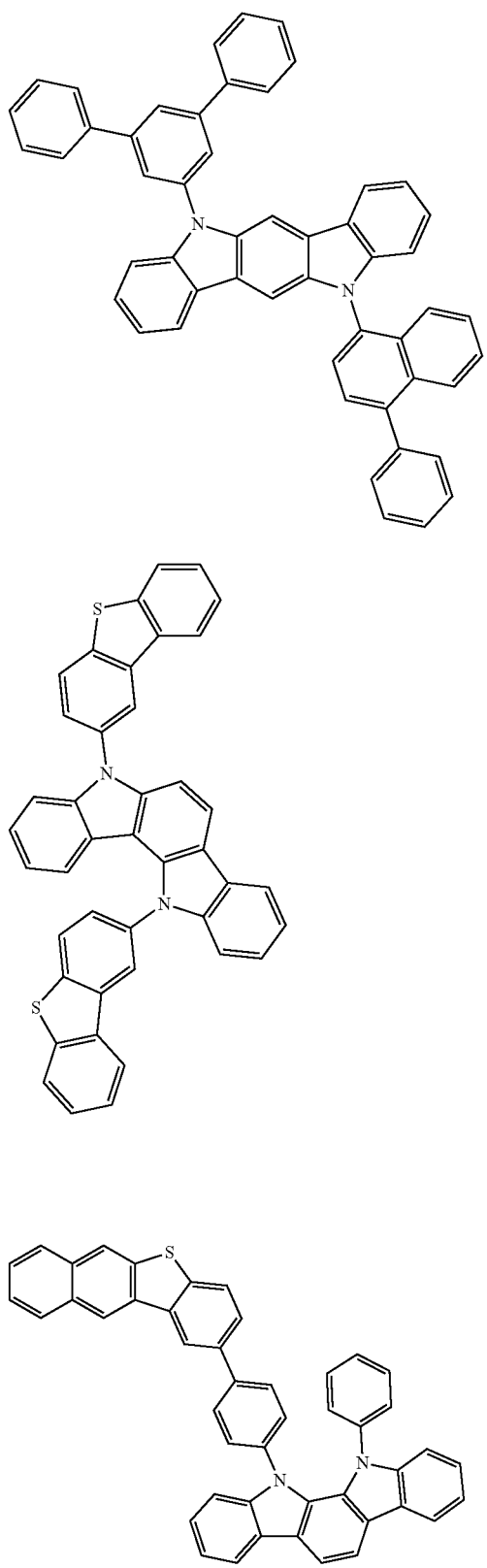
S-11
S-12
S-13

-continued
S-14
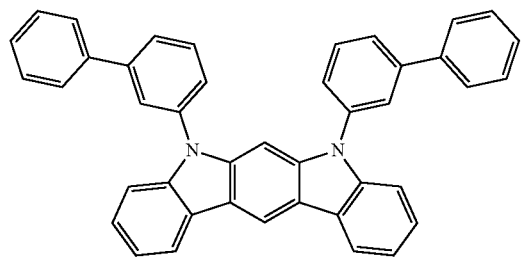
S-15
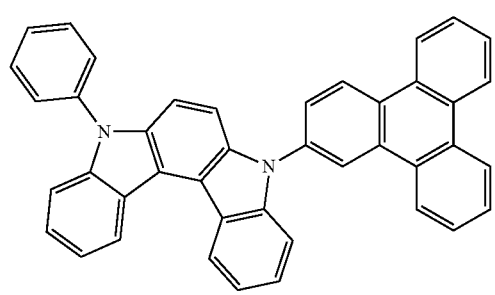
S-16
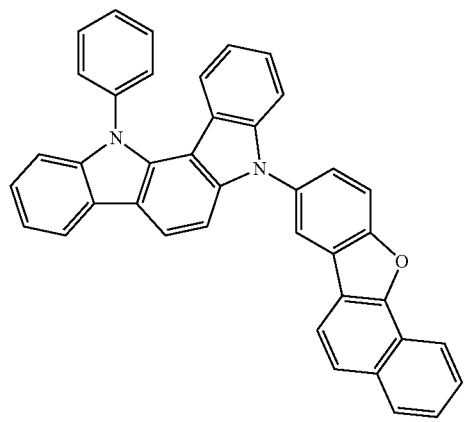
S-17
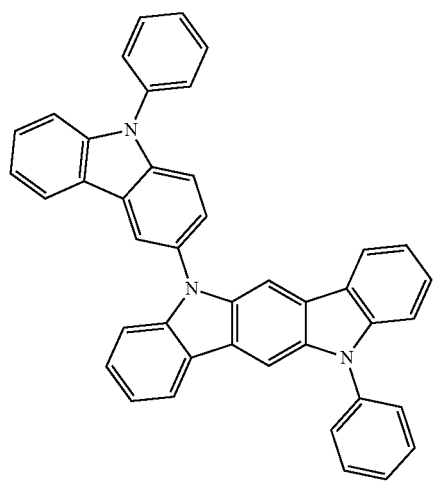
-continued
S-18
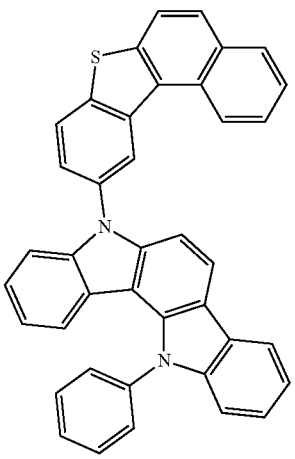
S-19
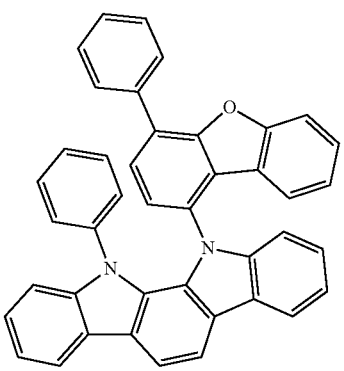
S-20
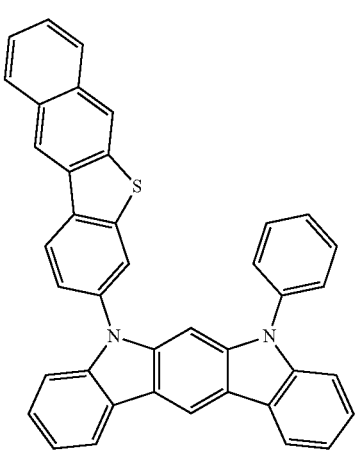

S-21
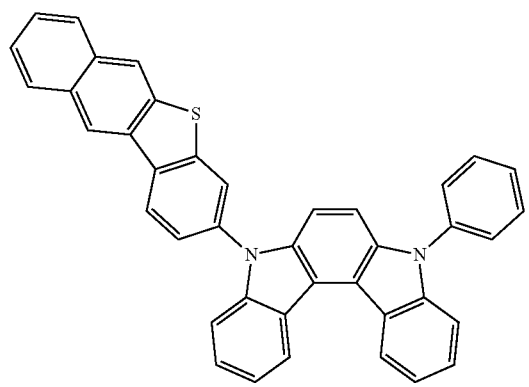
S-22
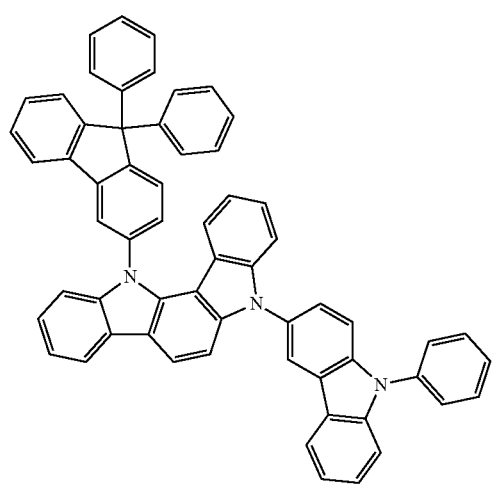
S-23
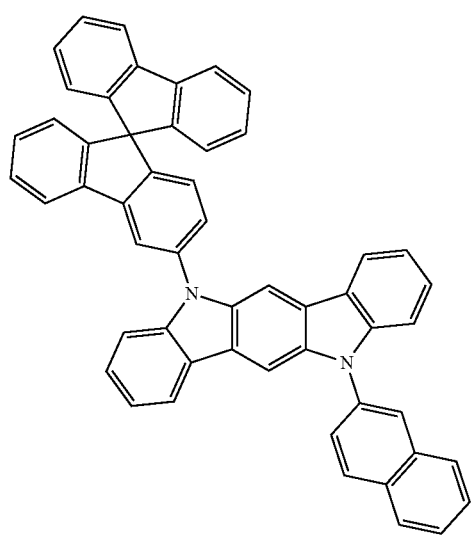
S-24
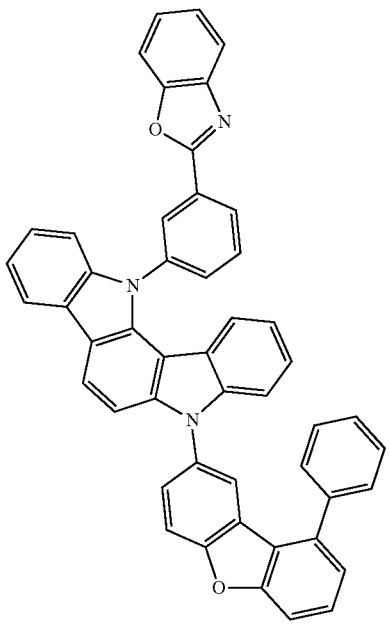
S-25
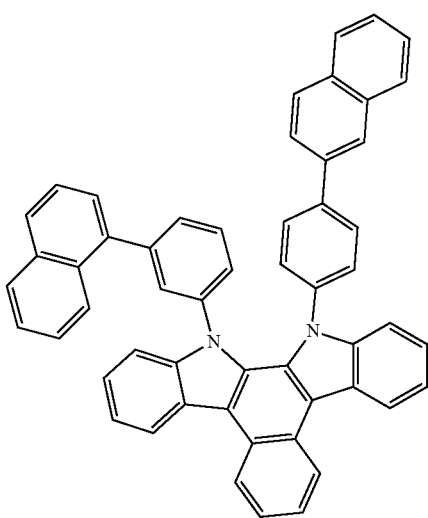
S-26
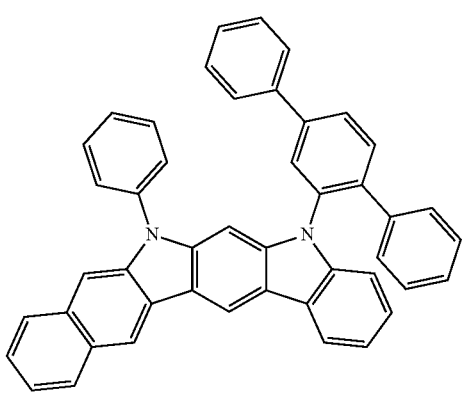

S-27
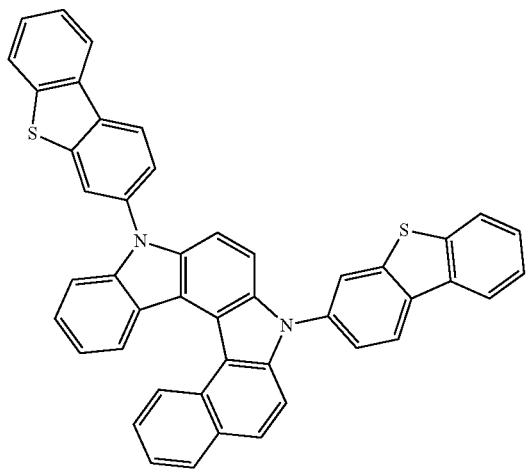
S-28
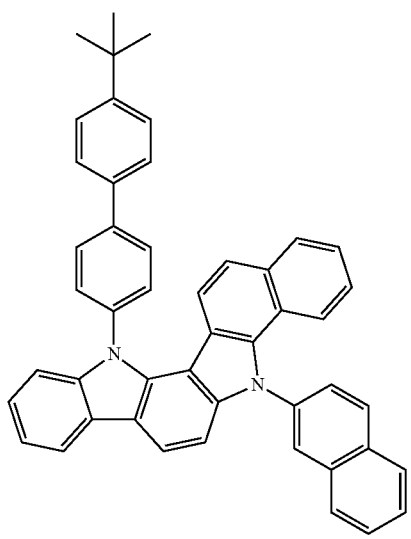
S-29
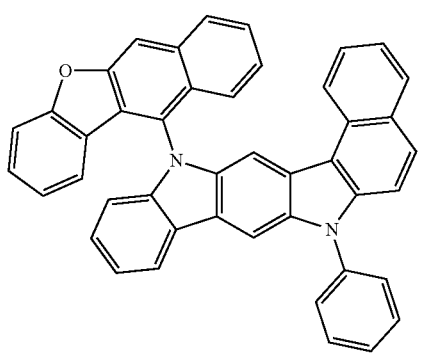
S-30
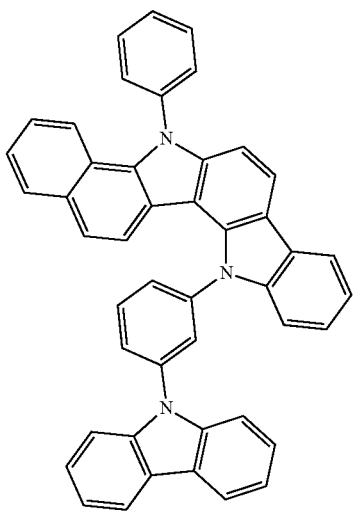
S-31
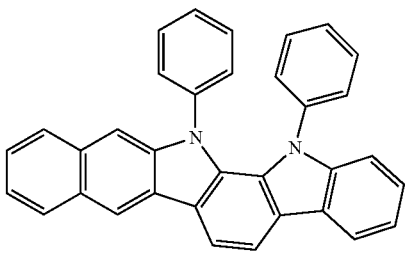
S-32
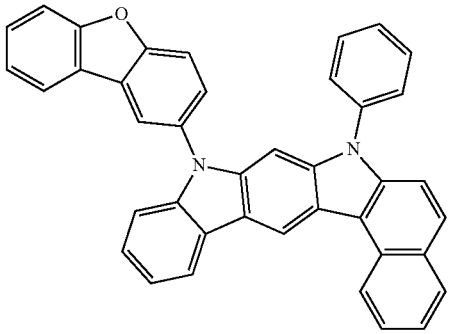
S-33
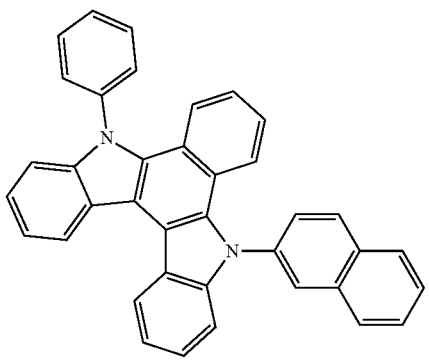

S-34
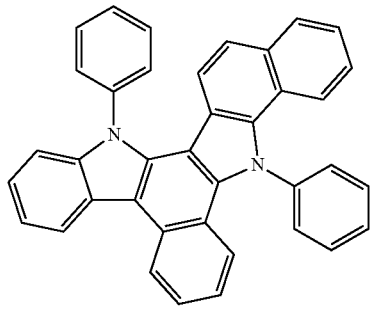
S-35
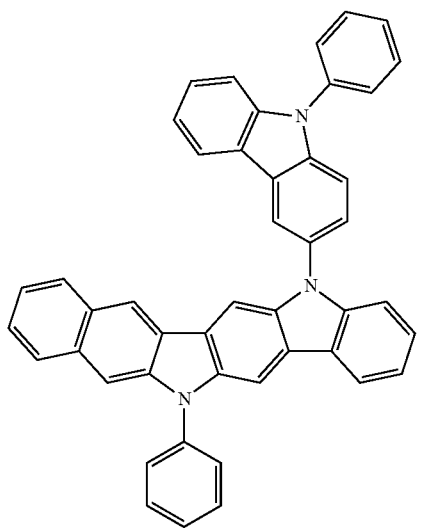
S-36
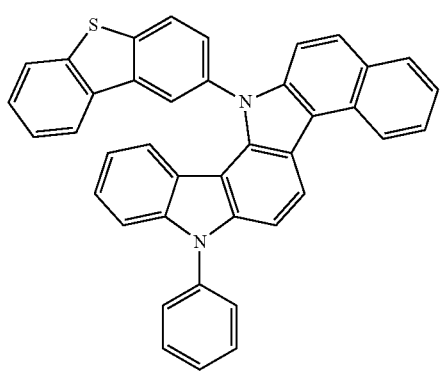
S-37
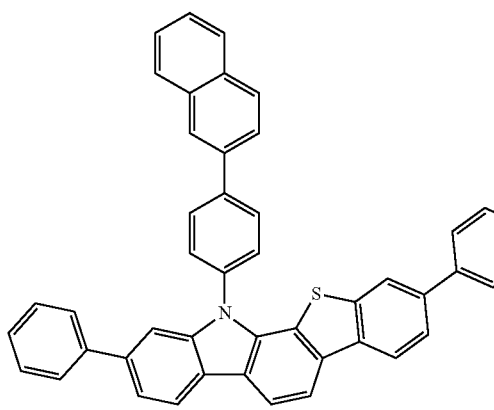
S-38
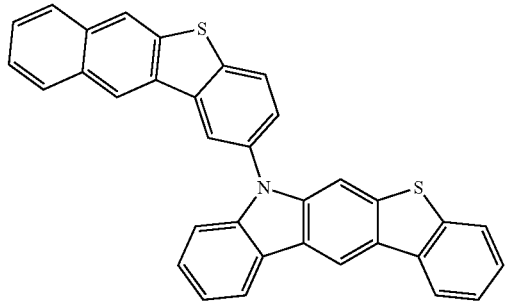
S-39
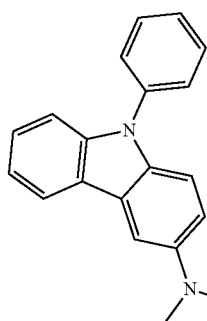
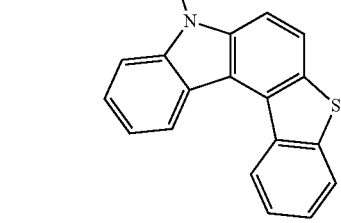
S-40
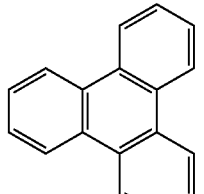
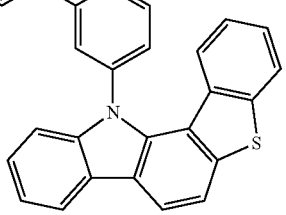

S-41
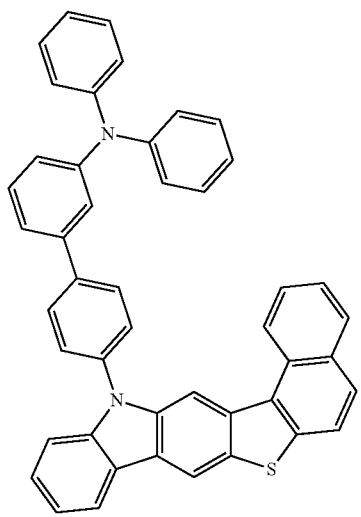
S-44
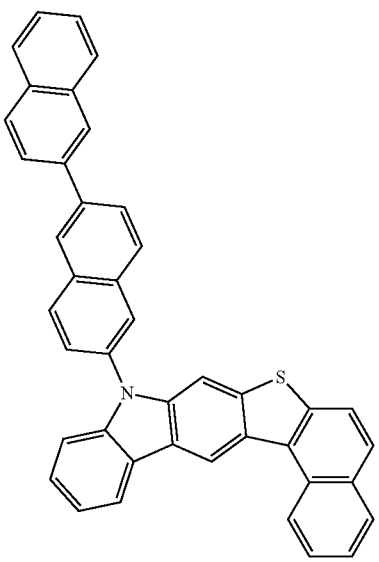
S-42
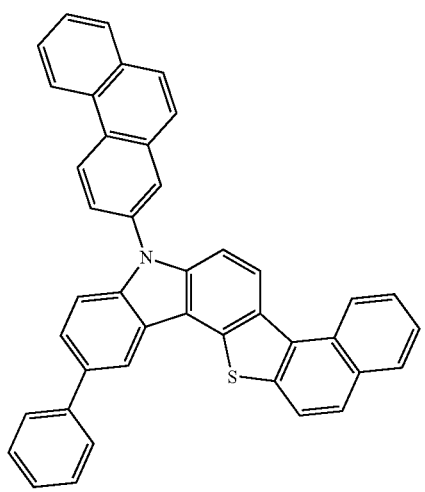
S-45
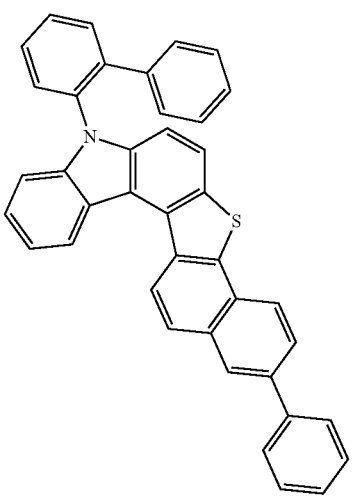
S-43
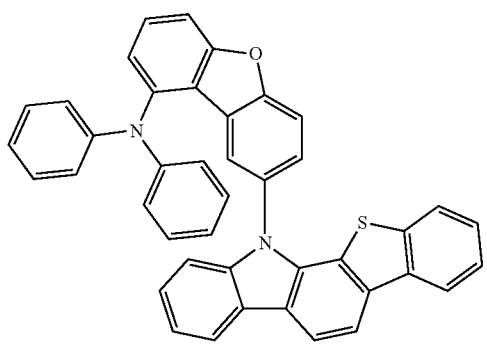
S-46
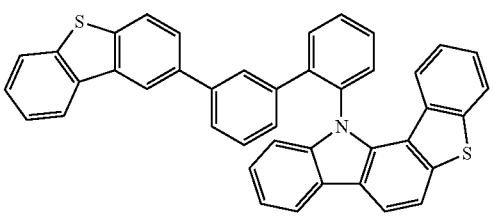

S-47
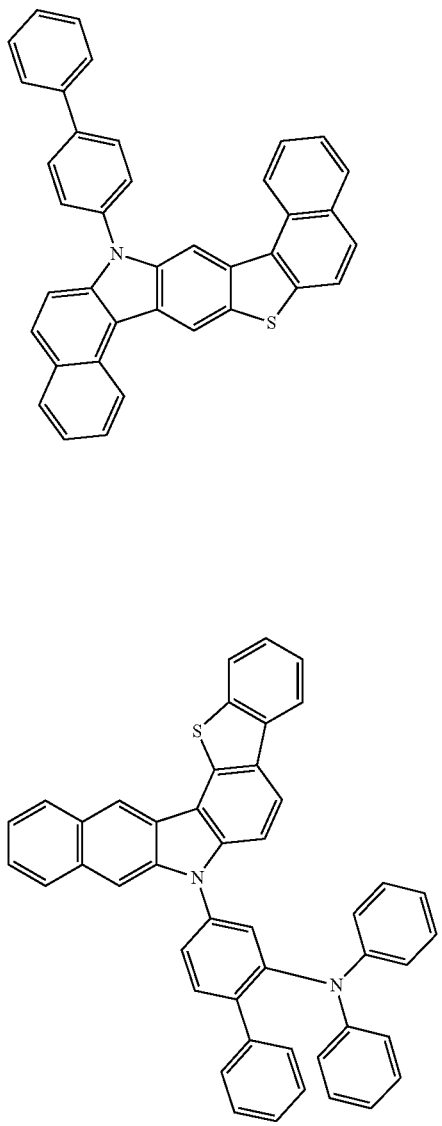
S-48
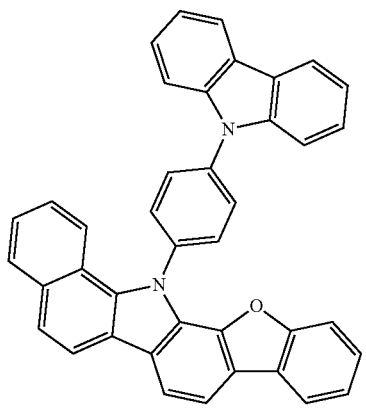
S-49
S-50
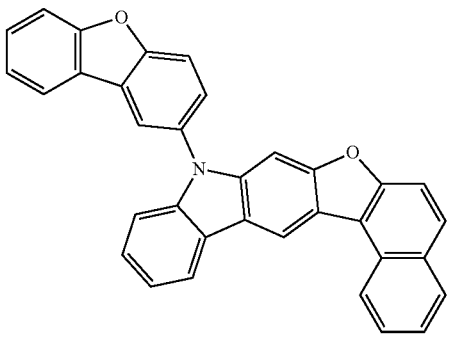
S-51
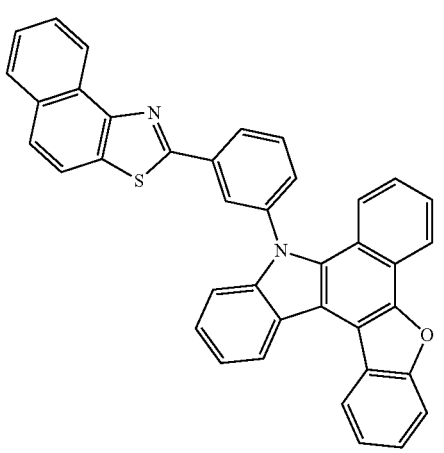
S-52
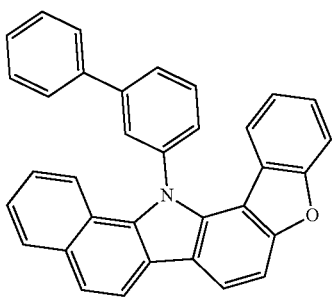
S-53
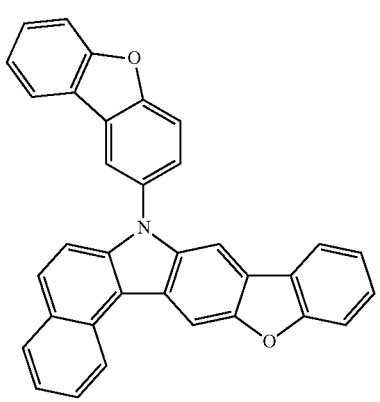

US 11,917,914 B1
-continued
S-54
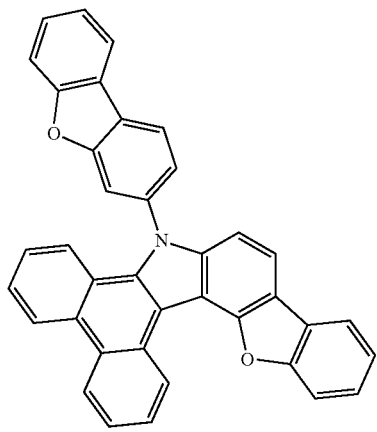
S-55
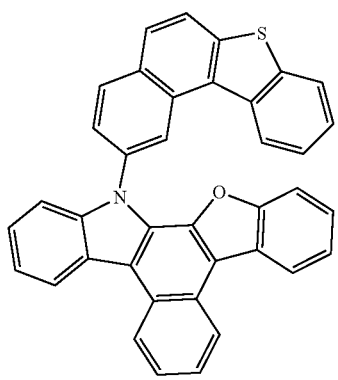
S-56
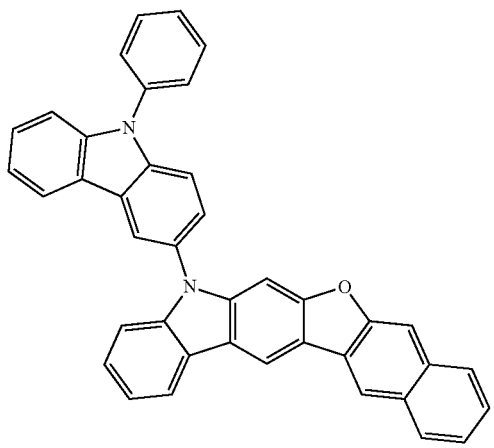
S-57
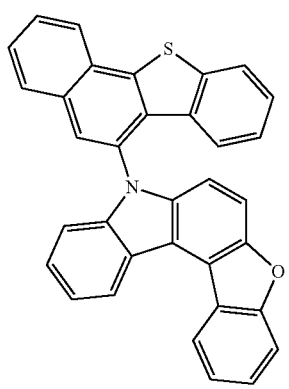
-continued
S-58
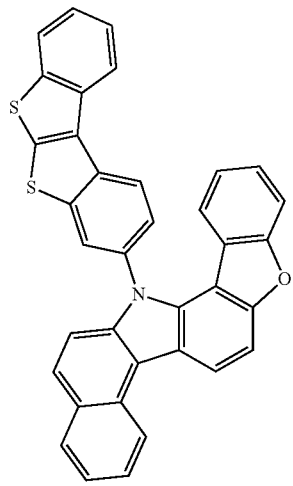
S-59
S-60

-continued
S-61
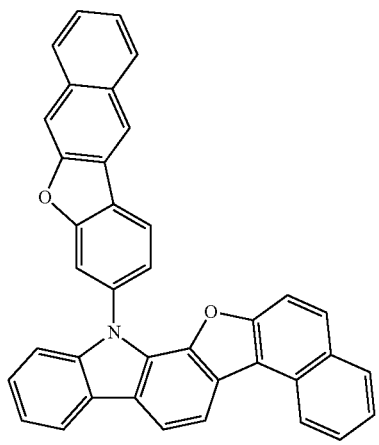
S-62
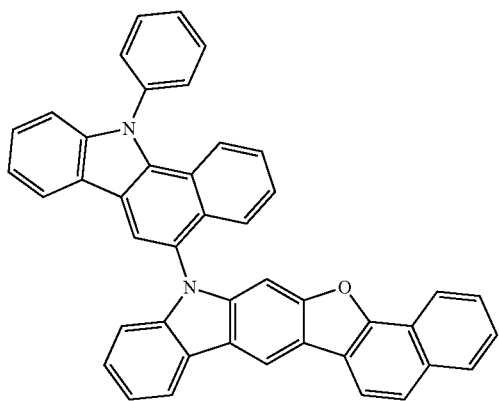
S-63
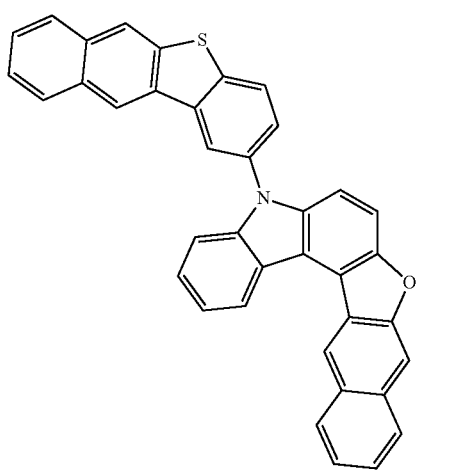
-continued
S-64
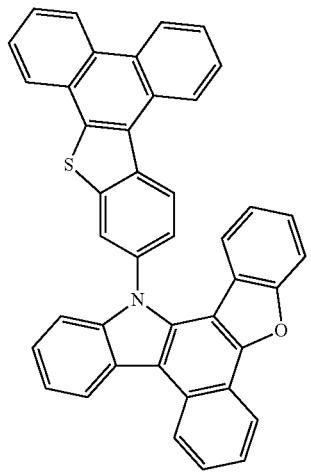
S-65
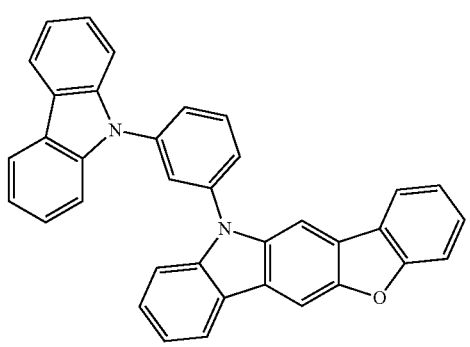
S-66
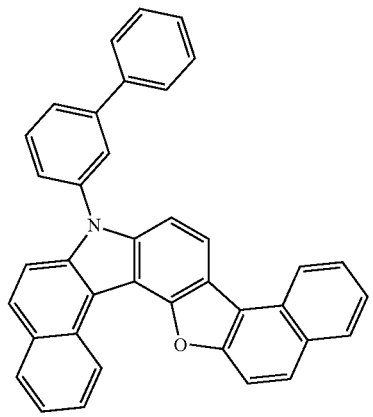
S-67
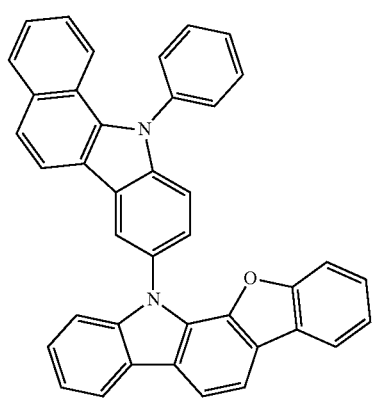

-continued
S-68
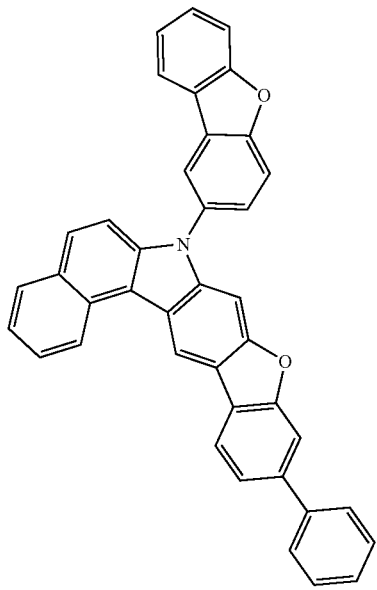
S-69
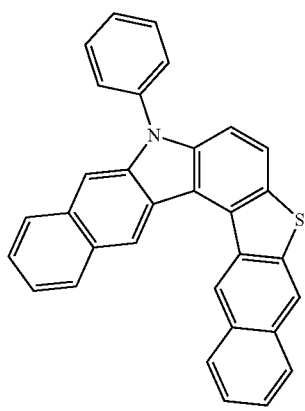
S-70
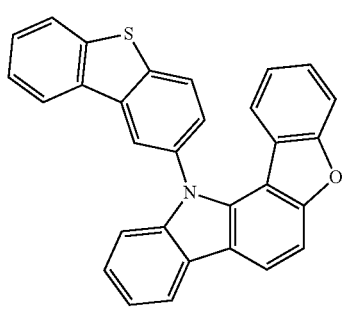
-continued
S-71
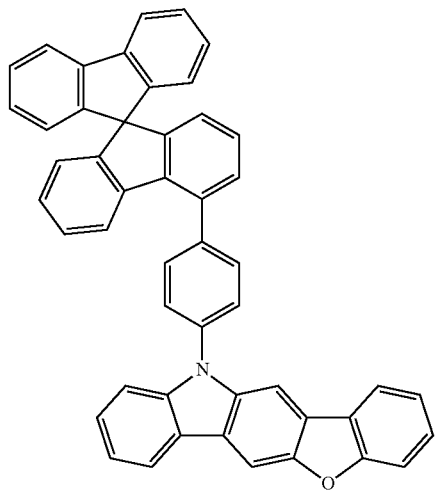
S-72
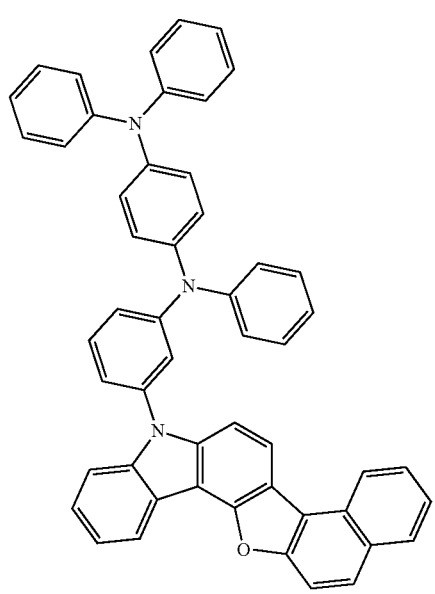
S-73
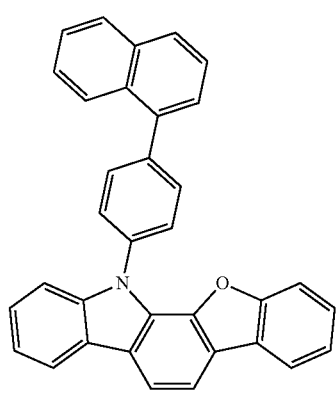

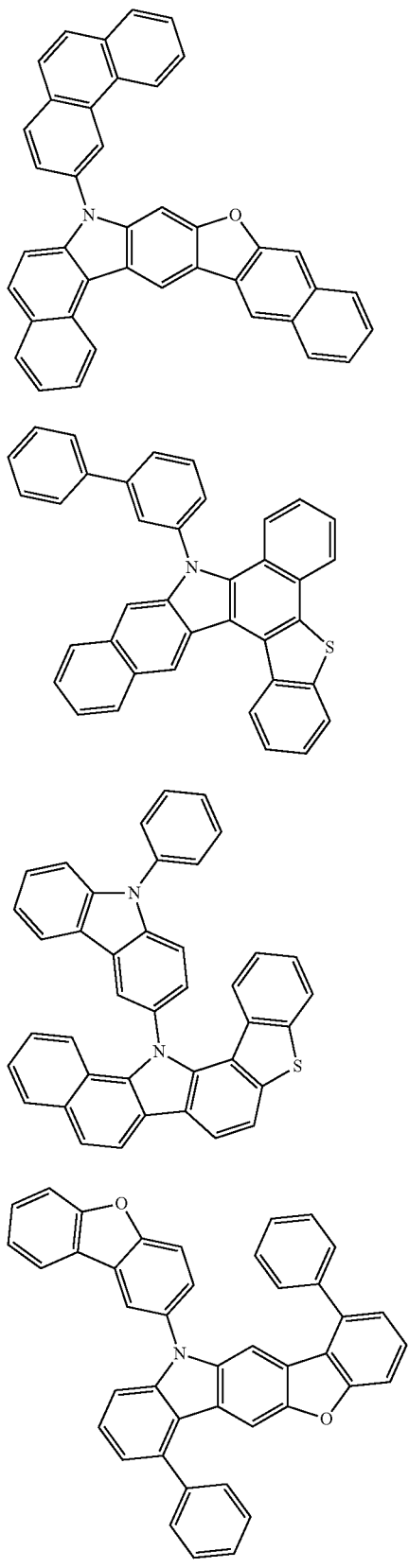
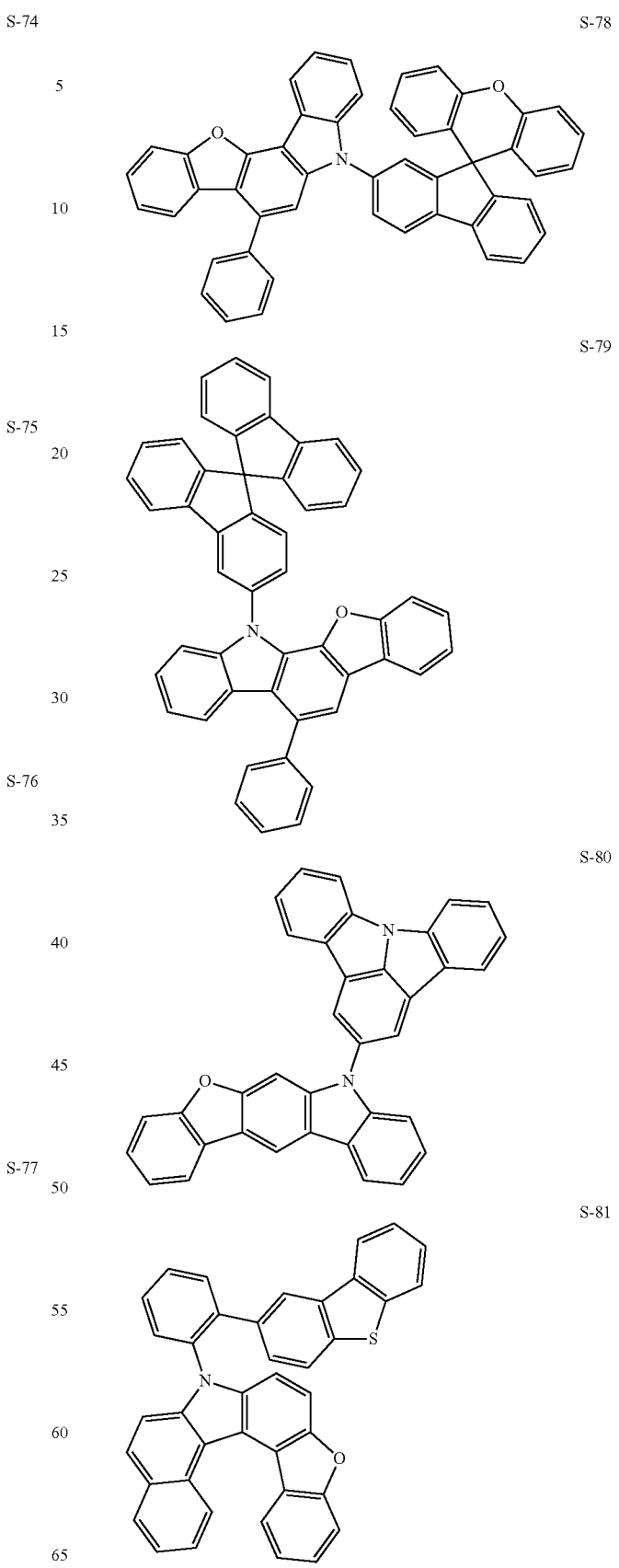

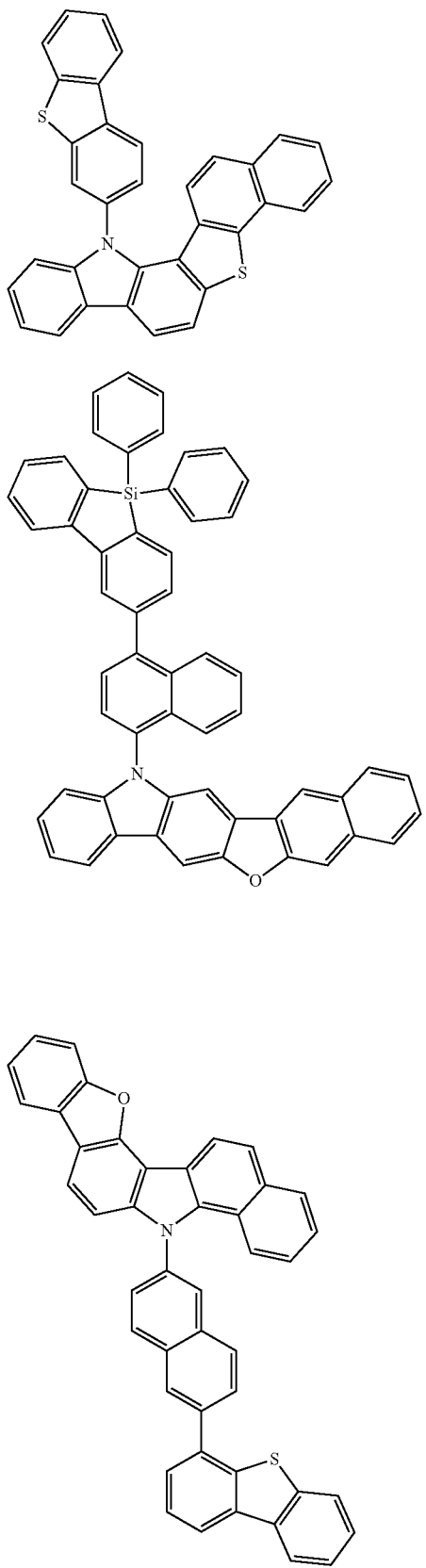
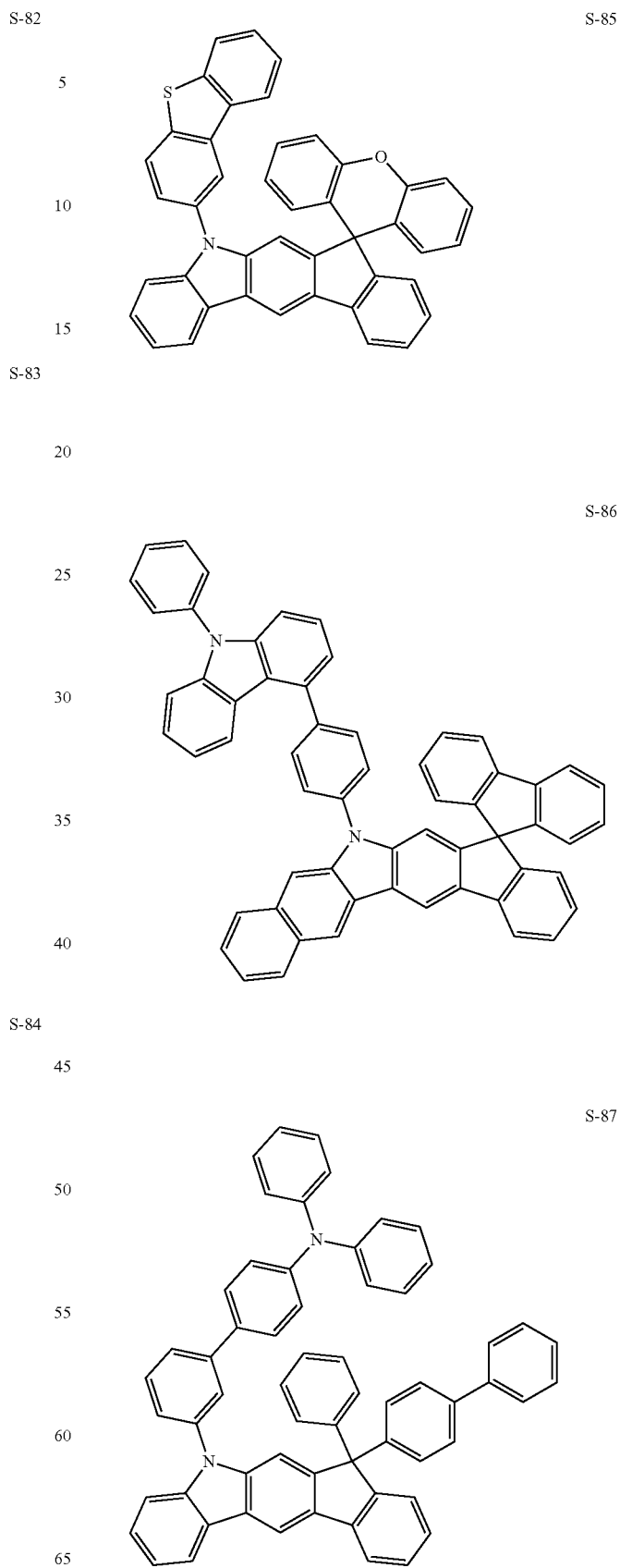

-continued
S-88
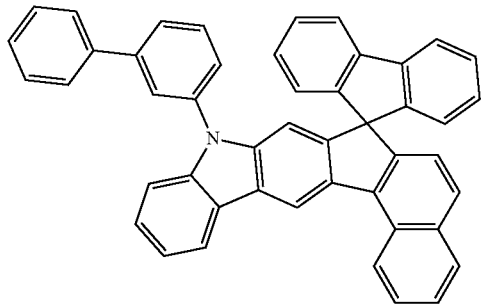
S-89
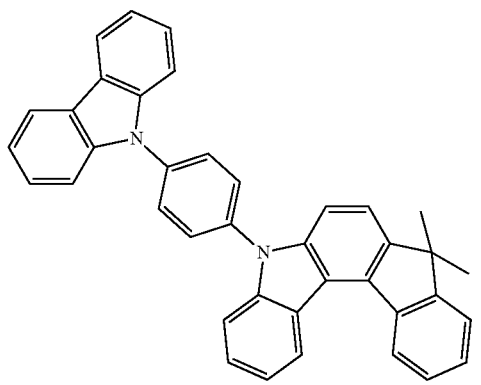
S-90
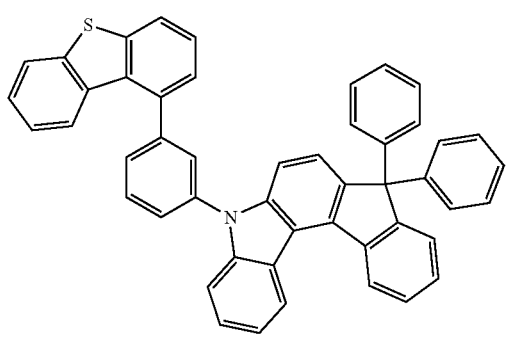
S-91
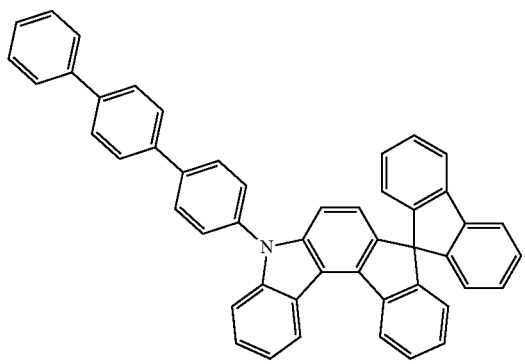
S-92
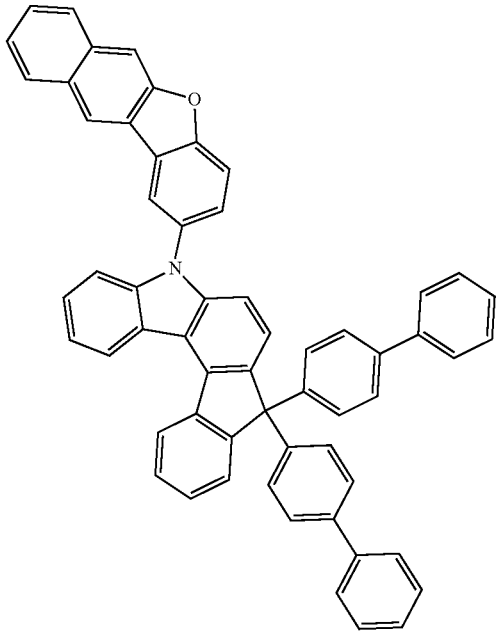
S-93
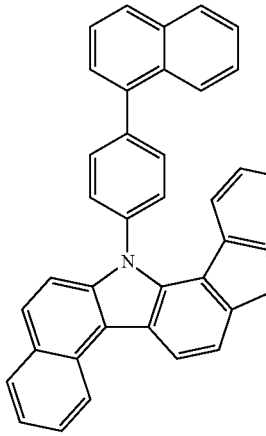
S-94
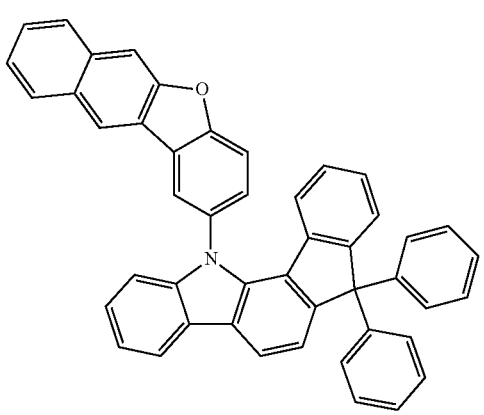

-continued
S-95
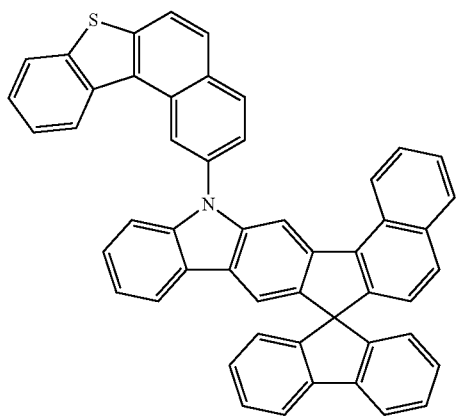
S-96
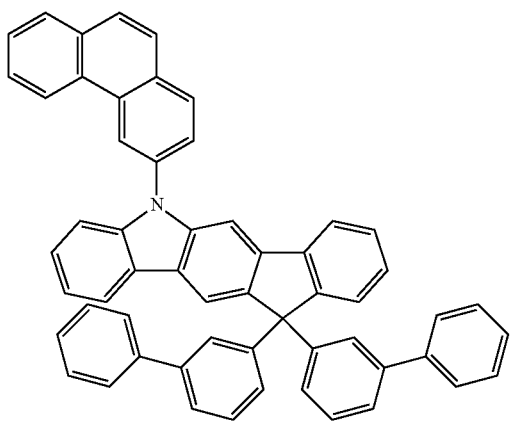
S-97
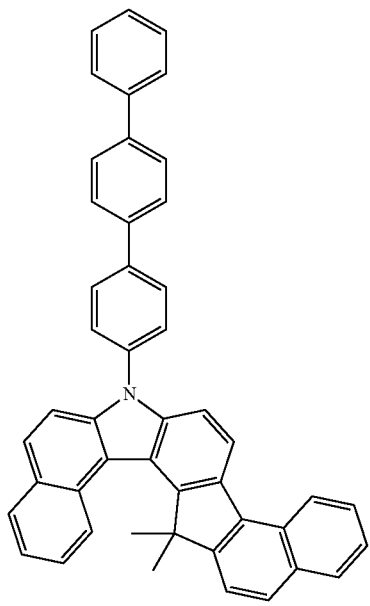
-continued
S-98
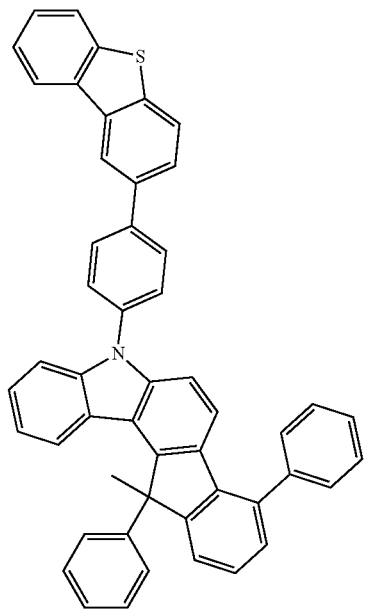
S-99
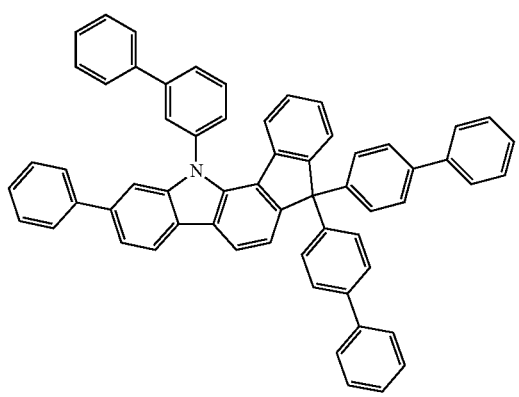
S-100
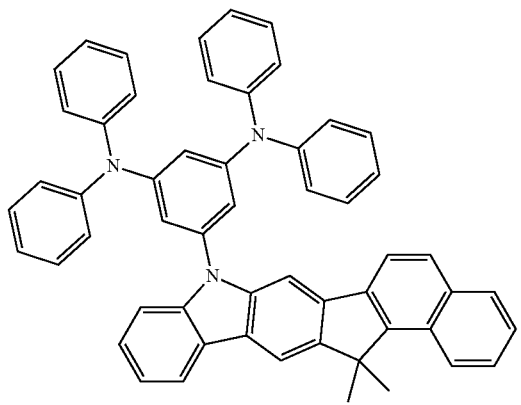

S-101
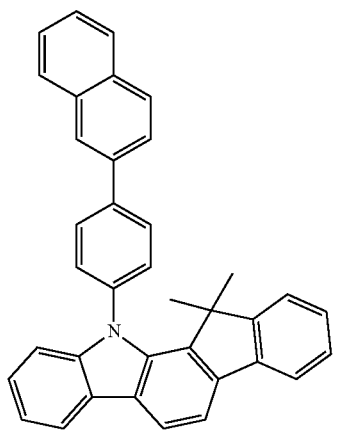
S-102
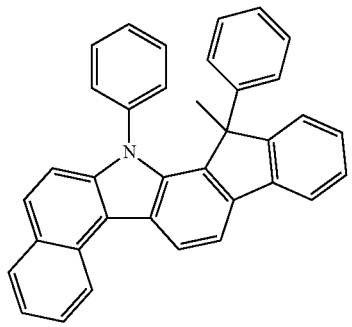
S-103
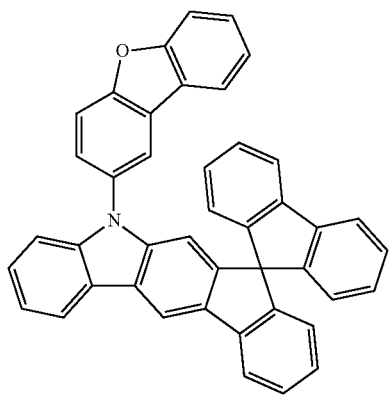
S-104
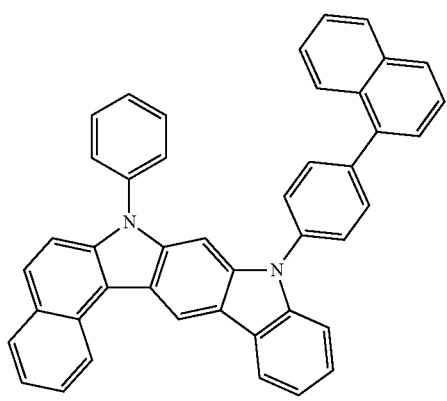
S-105
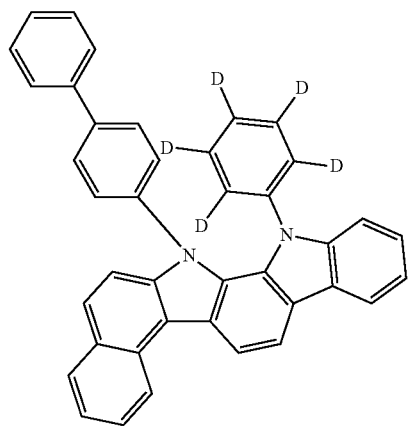
S-106
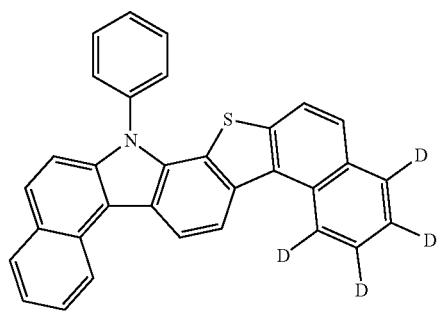
S-107
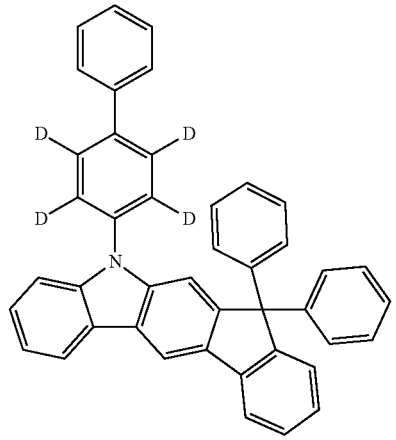
S-108
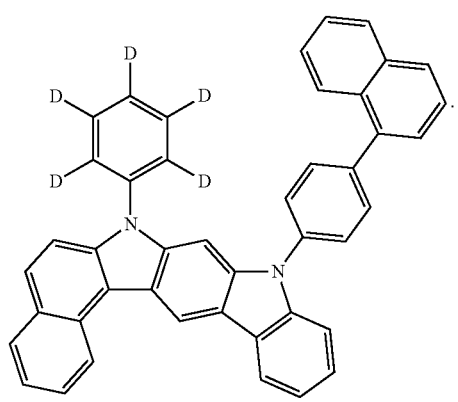
8. The organic electronic element of claim 5, further comprising a light efficiency enhancing layer formed on at least one surface of the first electrode and the second electrode, the surface being opposite to the organic material layer.

9. The organic electronic element of claim 5, wherein the organic material layer comprises 2 or more stacks comprising a hole transport layer, an emitting layer, and an electron transport layer sequentially formed on the first electrode.

10. The organic electronic element of claim 9, wherein the organic material layer further comprises a charge generation layer formed between the 2 or more stacks.

11. An electronic device comprising a display device comprising the organic electronic element of claim 5; and a control unit for driving the display device.

12. An electronic device according to claim 11, wherein the organic electronic element is at least one of an OLED, an organic solar cell, an organic photo conductor (OPC), organic transistor (organic TFT) and an element for monochromic or white illumination.

13. A method for reusing the compound represented by Formula 3-2 or Formula 3-3 according to claim 1 comprising:
- a step of depositing an organic emitting material comprising the compound represented by Formula 3-2 or Formula 3-3 in claim 1 in a manufacturing process of an organic light emitting device;
- a step of removing impurities from the crude organic light emitting material recovered from the deposition apparatus;
- a step of recovering the removed impurities; and
- a step of purifying the recovered impurities to a purity of 99.9% or higher.

\* \* \* \* \*

UNITED STATES PATENT AND TRADEMARK OFFICE
CERTIFICATE OF CORRECTION

PATENT NO. : 11,917,914 B1  
APPLICATION NO. : 18/355252  
DATED : February 27, 2024  
INVENTOR(S) : Lee et al.

Page 1 of 4

It is certified that error appears in the above-identified patent and that said Letters Patent is hereby corrected as shown below:

In the Claims

Column 292, Claim 3, Line 56:  
Please delete "$R^{39}$" and replace with -- $R^{30}$ --

Column 293, Claim 4, Formula N 1-5:

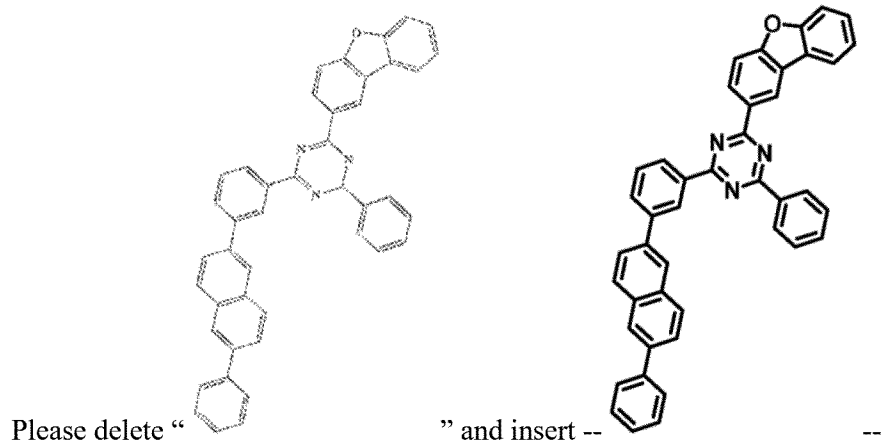

Please delete " " and insert -- --

Signed and Sealed this  
Fourth Day of June, 2024

Katherine Kelly Vidal  
*Director of the United States Patent and Trademark Office*

CERTIFICATE OF CORRECTION (continued)
U.S. Pat. No. 11,917,914 B1

Page 2 of 4

Column 294, Claim 4, Formula N 1-10:

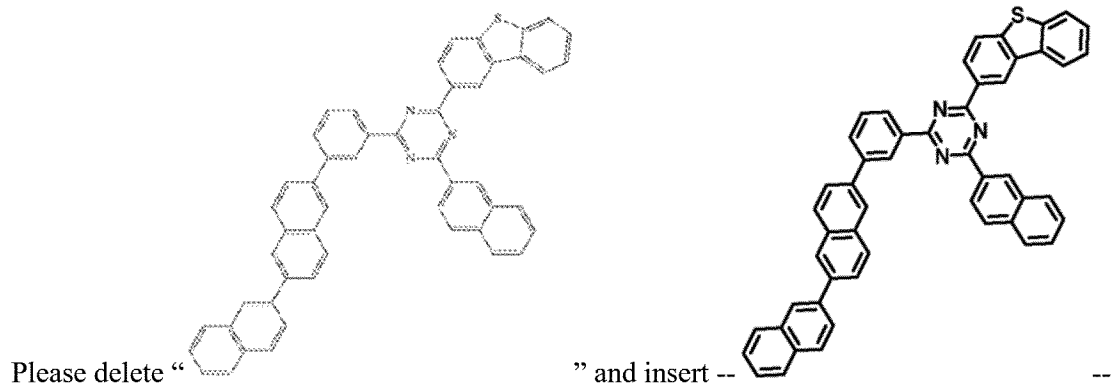

Column 294, Claim 4, Formula N 1-13:

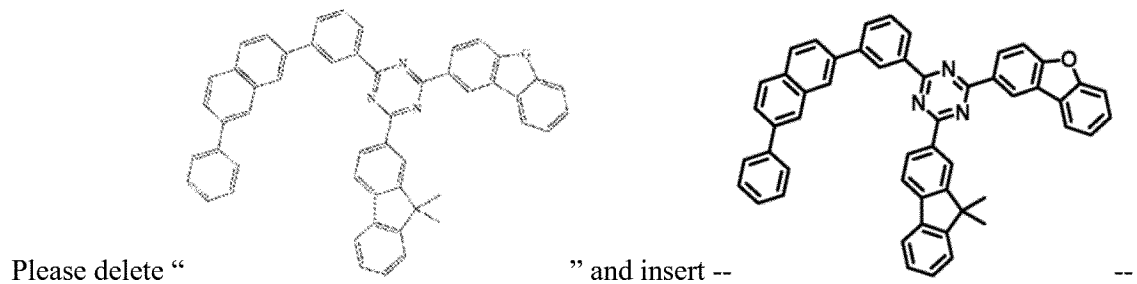

Column 294, Claim 4, Formula N 1-14:

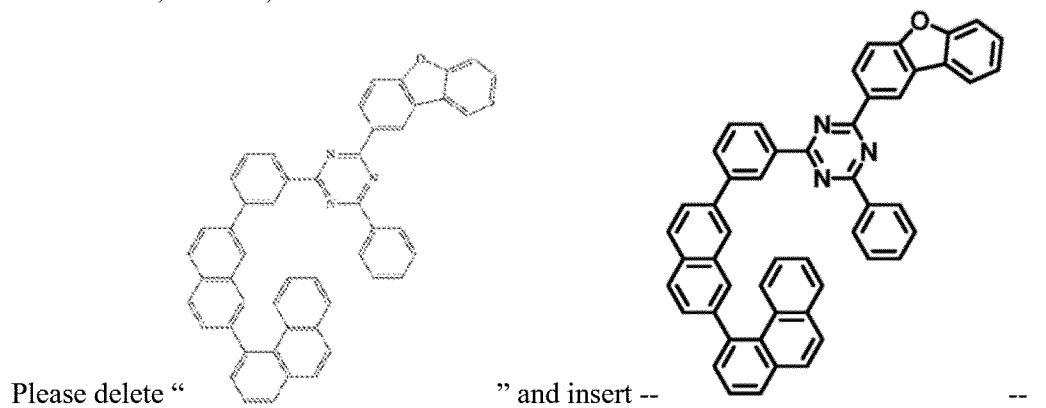

CERTIFICATE OF CORRECTION (continued)
U.S. Pat. No. 11,917,914 B1

Page 3 of 4

Column 295, Claim 4, Formula N 1-15:

Please delete " " and insert -- --

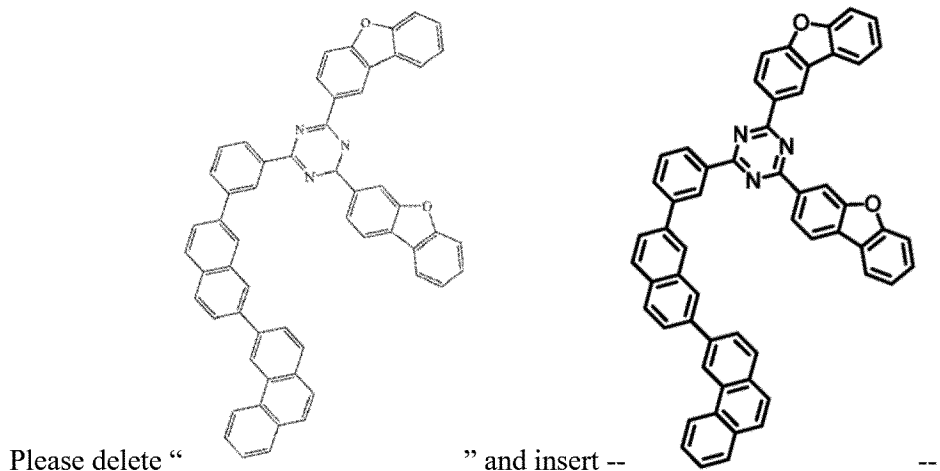

Column 301, Claim 4, Formula N 1-82:

Please delete " " and insert -- --

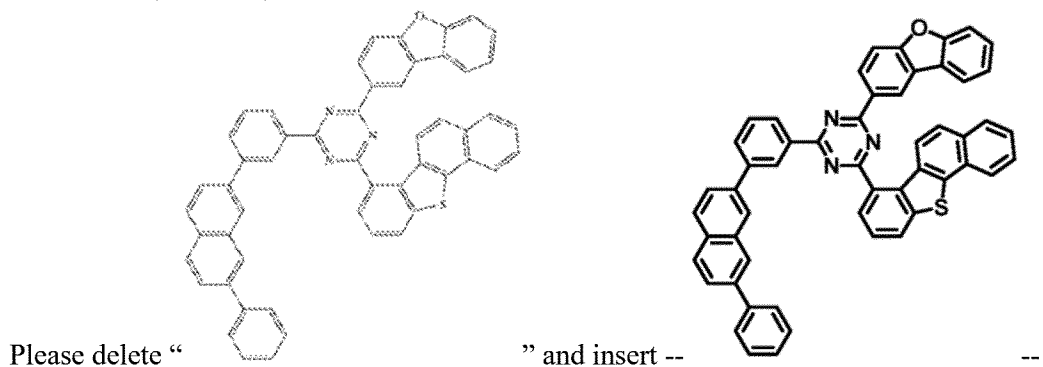

Column 304, Claim 5, Formula 4:

Please delete " " and insert -- --

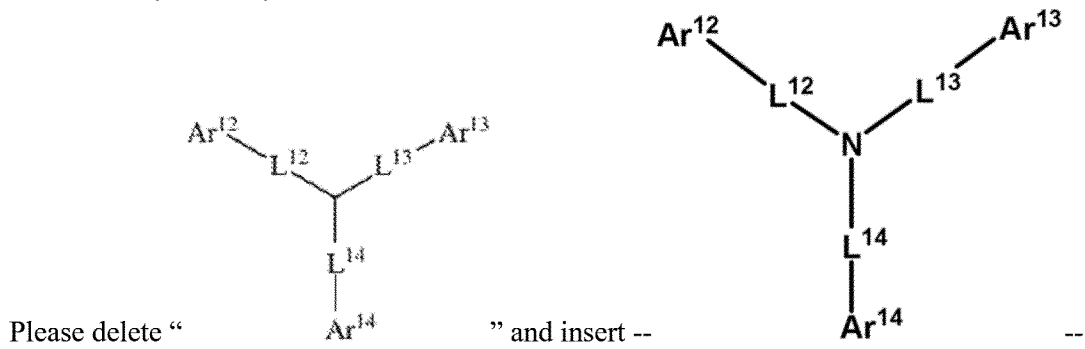

CERTIFICATE OF CORRECTION (continued)
U.S. Pat. No. 11,917,914 B1

Column 308, Claim 6, Formula H-9:

Please delete " 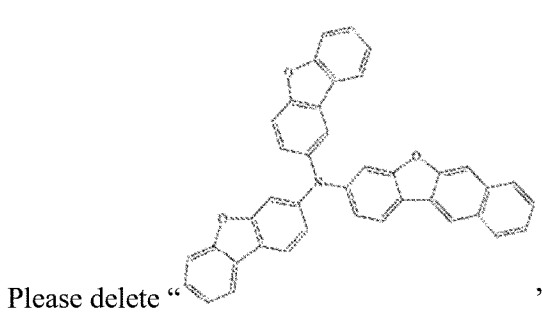 " and insert -- 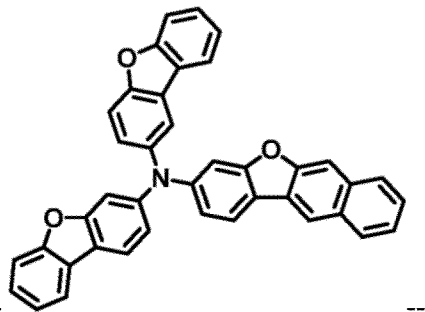 --

Column 312, Claim 6, Formula H-23:

Please delete " 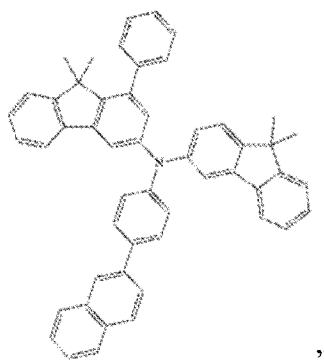 " and insert -- 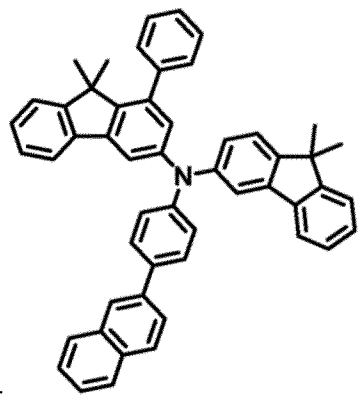 --